(12) United States Patent
Zask et al.

(10) Patent No.: US 8,129,371 B2
(45) Date of Patent: Mar. 6, 2012

(54) THIENOPYRIMIDINE AND PYRAZOLOPYRIMIDINE COMPOUNDS AND THEIR USE AS MTOR KINASE AND PI3 KINASE INHIBITORS

(75) Inventors: Arie Zask, New York, NY (US); Joshua Aaron Kaplan, Nyack, NY (US); Jeroen Cunera Verheijen, Highland Mills, NY (US); Kevin J. Curran, Congers, NY (US); David James Richard, Warwick, NY (US); Semiramis Ayral-Kaloustian, Tarrytown, NY (US)

(73) Assignee: Wyeth LLC, Madison, NJ (US)

( * ) Notice: Subject to any disclaimer, the term of this patent is extended or adjusted under 35 U.S.C. 154(b) by 618 days.

(21) Appl. No.: 12/251,712

(22) Filed: Oct. 15, 2008

(65) Prior Publication Data
US 2009/0098086 A1    Apr. 16, 2009

Related U.S. Application Data

(60) Provisional application No. 60/980,332, filed on Oct. 16, 2007, provisional application No. 61/027,595, filed on Feb. 11, 2008.

(51) Int. Cl.
C07D 265/36 (2006.01)
C07D 265/28 (2006.01)
A61K 31/537 (2006.01)
A61P 37/06 (2006.01)
A61P 35/00 (2006.01)
C07D 487/04 (2006.01)
C07D 495/04 (2006.01)

(52) U.S. Cl. .............. 514/230.5; 514/260.1; 514/262.1; 544/262; 544/278; 544/105

(58) Field of Classification Search ................ 544/105; 514/230.5
See application file for complete search history.

(56) References Cited

FOREIGN PATENT DOCUMENTS
EP    1 277 738 A1    1/2003

OTHER PUBLICATIONS

Fan et al., "A dual PI3 kinase/mTOR inhibitor reveals emergent efficacy in glioma" *Cancer Cell* May 2006 vol. 9, No. 5 pp. 341-349.

*Primary Examiner* — Susanna Moore
(74) *Attorney, Agent, or Firm* — David A. Rubin

(57) ABSTRACT

The invention relates to thienopyrimidine and pyrazolopyrimidine compounds of the Formulas (Ia) and (IIa),

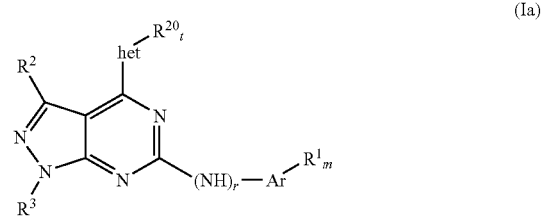

(Ia)

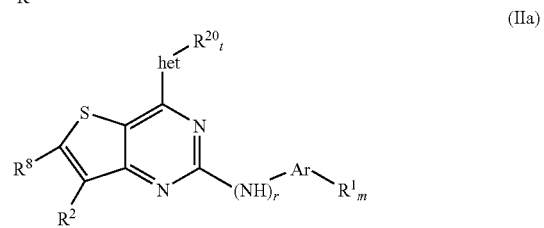

(IIa)

or a pharmaceutically acceptable salt thereof, wherein the constituent variables are as defined herein compositions comprising the compounds, and methods for making and using the compounds.

46 Claims, 2 Drawing Sheets

4 Cycle therapy:
• Ex. 105, bid x5
•Ex. 105 dx5 + Avastin

THIENOPYRIMIDINE AND PYRAZOLOPYRIMIDINE COMPOUNDS AND THEIR USE AS MTOR KINASE AND PI3 KINASE INHIBITORS

CROSS REFERENCE TO RELATED APPLICATIONS

This application claims the benefit of U.S. Provisional Application Nos. 60/980,332, filed Oct. 16, 2007 and 61/027,595, filed Feb. 11, 2008, the contents of which are hereby incorporated by reference in their entireties.

FIELD OF THE INVENTION

The invention relates to thienopyrimidine and pyrazolopyrimidine compounds, compositions comprising a thienopyrimidine or pyrazolopyrimidine compound, and methods for treating mTOR-related diseases comprising the administration of an effective amount of a thienopyrimidine or pyrazolopyrimidine compound. The invention also relates to methods for treating PI3K-related diseases comprising the administration of an effective amount of a thienopyrimidine or pyrazolopyrimidine compound.

BACKGROUND OF THE INVENTION

Mammalian Target of Rapamycin, mTOR, is a cell-signaling protein that regulates the response of tumor cells to nutrients and growth factors, as well as controlling tumor blood supply through effects on Vascular Endothelial Growth Factor, VEGF. Inhibitors of mTOR starve cancer cells and shrink tumors by inhibiting the effect of mTOR. All mTOR inhibitors bind to the mTOR kinase. This has at least two important effects. First, mTOR is a downstream mediator of the PI3K/Akt pathway. The PI3K/Akt pathway is thought to be over activated in numerous cancers and may account for the widespread response from various cancers to mTOR inhibitors. The over-activation of the upstream pathway would normally cause mTOR kinase to be over activated as well. However, in the presence of mTOR inhibitors, this process is blocked. The blocking effect prevents mTOR from signaling to downstream pathways that control cell growth. Over-activation of the PI3K/Akt kinase pathway is frequently associated with mutations in the PTEN gene, which is common in many cancers and may help predict what tumors will respond to mTOR inhibitors. The second major effect of mTOR inhibition is anti-angiogenesis, via the lowering of VEGF levels.

In lab tests, certain chemotherapy agents were found to be more effective in the presence of mTOR inhibitors. George, J. N., et al., Cancer Research, 61, 1527-1532, 2001. Additional lab results have shown that some rhabdomyosarcoma cells die in the presence of mTOR inhibitors. The complete functions of the mTOR kinase and the effects of mTOR inhibition are not completely understood.

Phosphatidylinositol (hereinafter abbreviated as "PI") is one of the phospholipids in cell membranes. In recent years it has become clear that PI plays an important role also in intracellular signal transduction. It is well recognized in the art that especially PI (4,5) bisphosphate (PI(4,5)P2) is degraded into diacylglycerol and inositol (1,4,5) triphosphate by phospholipase C to induce activation of protein kinase C and intracellular calcium mobilization, respectively [M. J. Berridge et al., Nature, 312, 315 (1984); Y. Nishizuka, Science, 225, 1365 (1984)].

In the late 1980s, phosphatidylinositol-3 kinase ("PI3K") was found to be an enzyme that phosphorylates the 3-position of the inositol ring of phosphatidylinositol [D. Whitman et al., Nature, 332, 664 (1988)].

When PI3K was discovered, it was originally considered to be a single enzyme. Recently however, it was clarified that a plurality of subtypes are present in PI3K. Three major classes of PI3Ks have now been identified on the basis of their in vitro substrate specificity [B. Vanhaesebroeck, Trend in Biol. Sci., 22, 267 (1997)].

Substrates for class I PI3Ks are PI, PI(4)P and PI(4,5)P2. In these substrates, PI(4,5)P2 is the most advantageous substrate in cells. Class I PI3Ks are further divided into two groups, class Ia and class Ib, in terms of their activation mechanism. Class Ia PI3Ks, which include PI3K p110α, p110β and p100δ subtypes, are activated in the tyrosine kinase system. Class Ib PI3K is a p110γ subtype activated by a G protein-coupled receptor.

PI and PI(4)P are known as substrates for class II PI3Ks but PI(4,5)P2 is not a substrate for the enzymes of this class. Class II PI3Ks include PI3K C2α, C2β and C2γ subtypes, which are characterized by containing C2 domains at the C terminus, implying that their activity will be regulated by calcium ions.

The substrate for class III PI3Ks is PI only. A mechanism for activation of the class III PI3Ks is not clarified yet. Because each subtype has its own mechanism for the regulating activity, it is considered that the respective subtypes will be activated depending on their respective stimuli specific to each of them.

In the PI3K subtypes, the class Ia subtype has been most extensively investigated to date. The three subtypes of class Ia are hetero dimers of a catalytic 110 kDa subunit and regulatory subunits of 85 kDa and 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit. Thus, the class Ia subtypes are considered to be associated with cell proliferation and carcinogenesis. Furthermore, the class Ia PI3K subtypes bind to activated ras oncogene to express their enzyme activity. It has been confirmed that the activated ras oncogene is present in many cancers, suggesting a role of class Ia PI3Ks in carcinogenesis.

There are three mTOR inhibitors, which have progressed into clinical trials. These compounds are Wyeth's Torisel, also known as 42-(3-hydroxy-2-(hydroxymethyl)-rapamycin 2-methylpropanoate, CCI-779 or Temsirolimus; Novartis' Everolimus, also known as 42-O-(2-hydroxyethyl)-rapamycin, or RAD 001; and Ariad's AP23573 also known as 42-(dimethylphopsinoyl)-rapamycin. The FDA has approved Torisel for the treatment of advanced renal cell carcinoma. In addition, Torisel is active in a NOS/SCID xenograft mouse model of acute lymphoblastic leukemia [Teachey et al, Blood, 107(3), 1149-1155, 2006]. Everolimus is in a phase II clinical study for patients with Stage 1V Malignant Melanoma. AP23573 has been given orphan drug and fast-track status by the FDA for treatment of soft-tissue and bone sarcomas.

The three mTOR inhibitors have non-linear, although reproducible pharmacokinetic profiles. Mean area under the curve (AUC) values for these drugs increase at a less than dose related way. The three compounds are all semi-synthetic derivatives of the natural macrolide antibiotic rapamycin. It would be desirable to find fully synthetic compounds, which inhibit mTOR that are more potent and exhibit improved pharmacokinetic behaviors.

As explained above, mTOR inhibitors and PI3K inhibitors are expected to be novel types of medicaments useful against cell proliferation disorders, especially as carcinostatic agents. Thus, it would be advantageous to have new mTOR inhibitors and PI3K inhibitors as potential treatment regimens for mTOR- and PI3K-related diseases. The instant invention is directed to these and other important ends.

SUMMARY OF THE INVENTION

In one aspect, the invention provides compounds of the Formula (Ia):

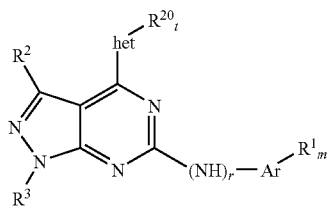

(Ia)

or pharmaceutically acceptable salts thereof, wherein the constituent variables are as defined below.

In another aspect, the invention provides compounds of Formula (IIa):

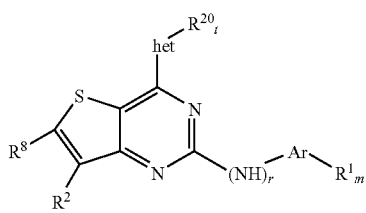

(IIa)

or a pharmaceutically acceptable salt thereof, wherein the constituent variables are as defined below.

In one aspect, the invention provides compounds of the Formula (Ib):

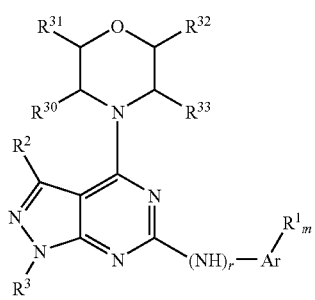

(Ib)

or pharmaceutically acceptable salts thereof, wherein the constituent variables are as defined below.

In another aspect, the invention provides compounds of Formula (IIb):

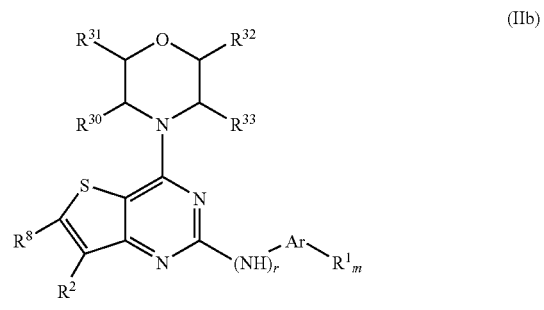

(IIb)

or a pharmaceutically acceptable salt thereof, wherein the constituent variables are as defined below.

In one aspect, the invention provides compounds of the Formula (I):

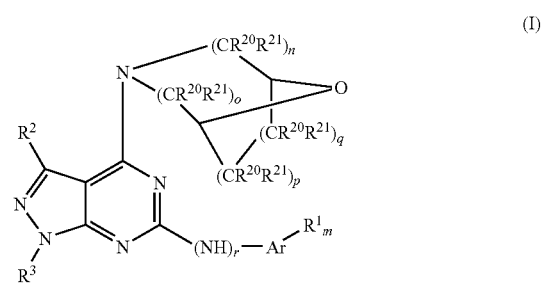

(I)

or pharmaceutically acceptable salts thereof, wherein the constituent variables are as defined below.

In another aspect, the invention provides compounds of Formula (II):

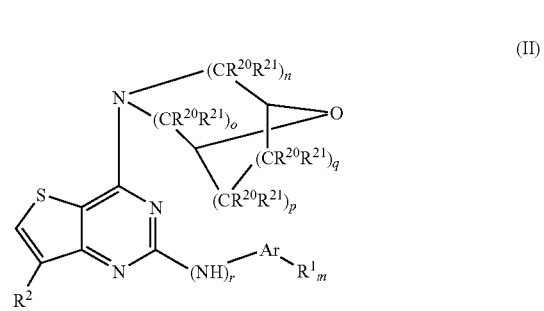

(II)

or a pharmaceutically acceptable salt thereof, wherein the constituent variables are as defined below.

In another aspect, the invention provides compounds of Formula (VIII):

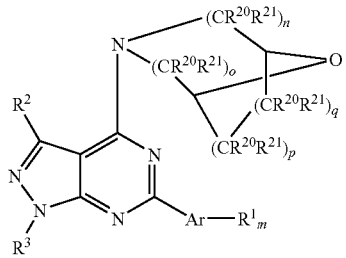

(VIII)

or a pharmaceutically acceptable salt thereof, wherein the constituent variables are as defined below.

In another aspect, the invention provides compounds of Formula (IX):

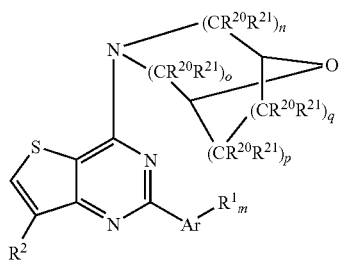

(IX)

or a pharmaceutically acceptable salt thereof, wherein the constituent variables are as defined below.

In another aspect, the invention provides compounds of Formula (X):

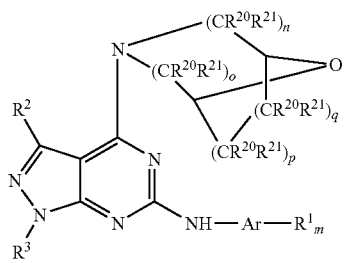

(X)

or a pharmaceutically acceptable salt thereof, wherein the constituent variables are as defined below.

In another aspect, the invention provides compounds of Formula (XI):

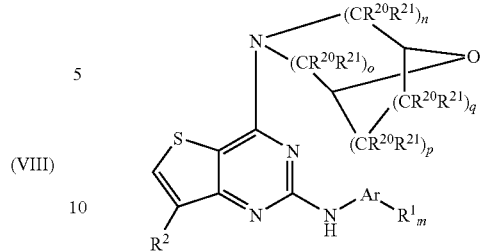

(XI)

or a pharmaceutically acceptable salt thereof, wherein the constituent variables are as defined below.

In other aspects, the invention provides pharmaceutical compositions comprising compounds or pharmaceutically acceptable salts of compounds of Formula (I), Formula (II), Formula (Ia), Formula (IIa), Formula (Ib), Formula (IIb), Formula (VIII), Formula (IX), Formula (X), or Formula (XI) and a pharmaceutically acceptable carrier.

In further aspects, the invention provides compounds or pharmaceutically acceptable salts of the compounds of Formula (I), Formula (II), Formula (Ia), Formula (Ia), Formula (Ib), Formula (IIb), Formula (VIII), Formula (IX), Formula (X), or Formula (XI) that are useful as mTOR inhibitors, and methods for inhibiting mTOR using the compounds or pharmaceutically acceptable salts thereof.

In further aspects, the invention provides compounds or pharmaceutically acceptable salts of the compounds of Formula (I), Formula (II), Formula (Ia), Formula (IIa), Formula (Ib), Formula (IIb), Formula (VIII), Formula (IX), Formula (X), or Formula (XI) that are useful as PI3K inhibitors, and methods for inhibiting PI3K using the compounds or pharmaceutically acceptable salts thereof.

In one embodiment, the invention provides methods for treating an mTOR-related disorder, comprising administering to a mammal in need thereof, the compounds or pharmaceutically acceptable salts of compounds of Formula (I), Formula (II), Formula (Ia), Formula (IIa), Formula (Ib), Formula (IIb), Formula (VIII), Formula (IX), Formula (X), or Formula (XI) in an amount effective to treat a mTOR-related disorder.

In one embodiment, the invention provides methods for treating a PI3K-related disorder, comprising administering to a mammal in need thereof the compounds or pharmaceutically acceptable salts of compounds of Formula (I), Formula (II), Formula (Ia), Formula (IIa), Formula (Ib), Formula (IIb), Formula (VIII), Formula (IX), Formula (X), or Formula (XI) in an amount effective to treat a PI3K-related disorder.

In other aspects, the invention provides further methods of synthesizing the compounds or pharmaceutically acceptable salts of compounds of Formula (I), Formula (II), Formula (Ia), Formula (IIa), Formula (Ib), Formula (IIb), Formula (VIII), Formula (IX), Formula (X), or Formula (XI).

DETAILED DESCRIPTION

Figure 1:
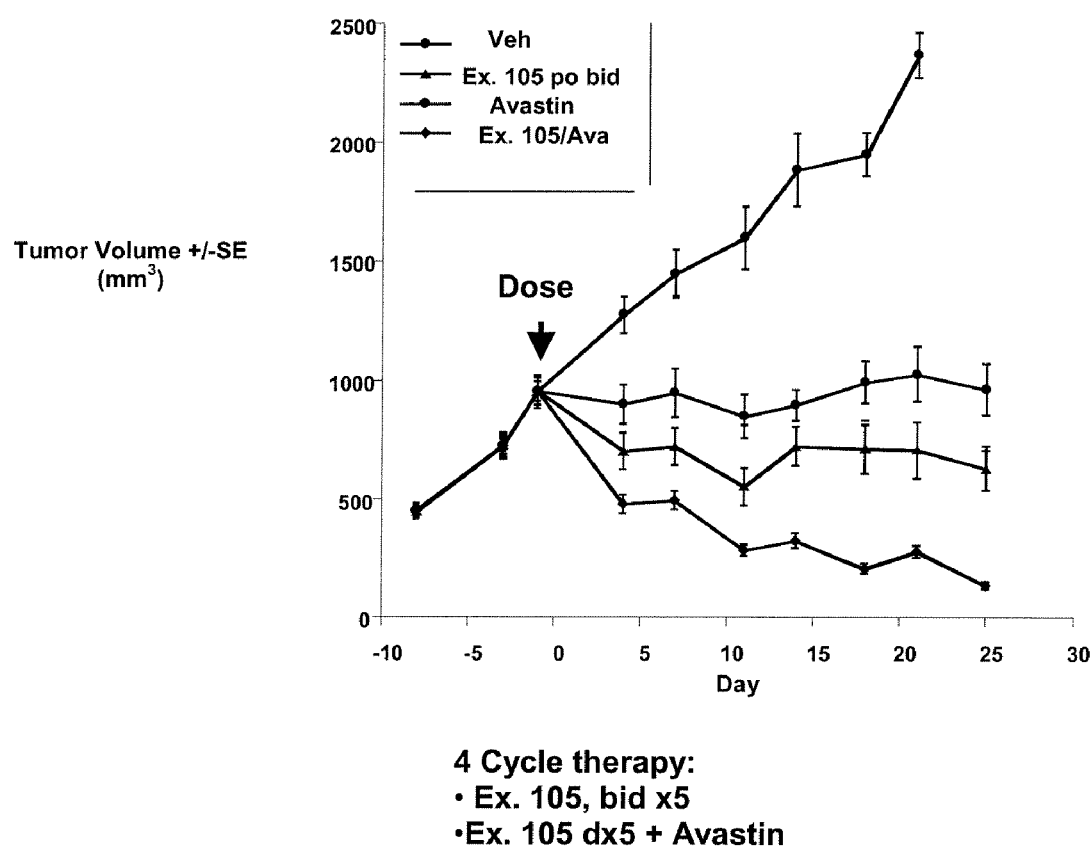
FIG. 1 shows the effect of Avastin (bevacizumab) individually, the Example 105 compound individually, and a combination of Avastin (bevacizumab) and the Example 105 compound, with specified dosing regimens, on tumor size in the A498 renal cell carcinoma model.

In one aspect, the invention provides compounds of the Formula (Ia) or of Formula (IIa):

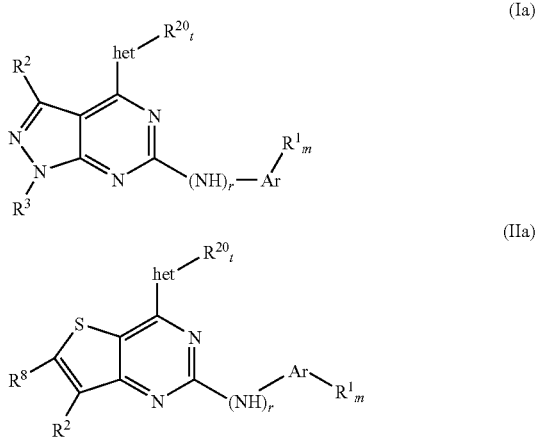

or pharmaceutically acceptable salts thereof, wherein:
het is a 5-10-membered bridged heterobicylyl-group containing at least one oxygen atom, at least one nitrogen atom, and optionally additional heteroatoms selected from oxygen, sulfur and nitrogen, and is connected to the thienopyrimidinyl or pyrazolopyrimidinyl group through one of the nitrogen atoms;
$R^{20}$ is independently selected from halogen, hydroxyl, $C_1$-$C_2$alkoxy, $NH_2$, $NH(C_1$-$C_2$alkyl), $N(C_1$-$C_2$alkyl)($C_1$-$C_2$alkyl), $NHC(O)(C_1$-$C_2$alkyl), $N(C_1$-$C_2$alkyl)$C(O)(C_1$-$C_2$alkyl), $NHC(O)H$, $C(O)NH_2$, $C(O)NH(C_1$-$C_2$alkyl), $C(O)N(C_1$-$C_2$alkyl)($C_1$-$C_2$alkyl), CN, C(O)OH, and $C_1$-$C_4$alkoxycarbonyl;
t is 0-16;
each $R^1$ is independently halogen; $C_1$-$C_6$alkyl optionally substituted with from 1 to 3 substituents independently selected from halogen, —$NH_2$, -alkylamino, -dialkylamino, —$N(C_1$-$C_3$alkyl)$C(O)(C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_1$-$C_6$alkoxy optionally substituted with from 1 to 3 substituents independently selected from halogen, —$NH_2$, -alkylamino, -dialkylamino, —$N(C_1$-$C_3$alkyl)$C(O)(C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, -alkylamino, -dialkylamino, —$N(C_1$-$C_3$alkyl)$C(O)(C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; $C_1$-$C_8$acyl; $C_1$-$C_8$alkoxycarbonyl; $C_1$-$C_8$alkylcarboxy; —N—($C_1$-$C_6$)alkylamido; hydroxyl; $NR^4R^5$; —NHC(O)$NR^4R^5$; —NHC(O)NHN$R^4R^5$; —NHC(O)$OR^6$; —NH(SO$_2$)NH—$C_1$-$C_6$alkyl; —NH(SO$_2$)NH—$C_6$-$C_{14}$aryl; —NHC(S)—$NR^4R^5$; —NHC(=N—CN)—$NR^4R^5$; —NHC(=$NR^4$)—$NR^4R^5$; —N=C(S—$C_1$-$C_6$alkyl)(NH—$C_1$-$C_6$alkyl); or —N(H)—C(=N—(CN))—(O—$C_6$-$C_{14}$aryl);
m is 0, 1, 2, 3, or 4;
r is 0 or 1;
each $R^4$ and $R^5$ is independently —H; a 4- to 7-membered monocyclic heterocycle optionally substituted with from 1 to 3 substituents independently selected from $C_1$-$C_6$alkyl, heterocyclylalkyl, $C_7$-$C_{24}$arylalkyl, $C_1$-$C_8$acyl, $C_1$-$C_8$alkoxycarbonyl, $C_1$-$C_8$alkylcarboxy, halo, —$C_1$-$C_8$haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; $C_6$-$C_{14}$aryl optionally substituted with from 1 to 3 substituents independently selected from $C_1$-$C_6$alkyl optionally substituted with —$NH_2$, -alkylamino, or -dialkylamino, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido optionally substituted with —$NH_2$, -alkylamino, or -dialkylamino, —C(O)$NH_2$, -alkylcarboxamido, heterocycle optionally substituted with $C_1$-$C_6$alkyl, —S(O)$_2$-heterocyclylalkyl optionally substituted with $C_1$-$C_6$alkyl, heterocyclylalkyl optionally substituted with $C_1$-$C_6$alkyl, $C_1$-$C_6$alkoxy optionally substituted with —$NH_2$, -alkylamino, -dialkylamino, heterocycle, or hydroxyl, —C(O)NH—$NH_2$, —C(O)NH—NH($C_1$-$C_6$alkyl), —C(O)NH—N($C_1$-$C_6$alkyl)($C_1$-$C_6$alkyl), —C(O)NH-heterocycle, —SO$_2$($C_1$-$C_6$alkyl), —CN, and —$NO_2$; heteroaryl optionally substituted with from 1 to 3 substituents independently selected from $C_1$-$C_6$alkyl optionally substituted with —$NH_2$, -alkylamino, or -dialkylamino, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —($C_1$-$C_6$alkyl)carboxyl, —N—($C_1$-$C_6$)alkylamido optionally substituted with —$NH_2$, -alkylamino, or -dialkylamino, —C(O)$NH_2$, -alkylcarboxamido, heterocycle optionally substituted with $C_1$-$C_6$alkyl, —S(O)$_2$-heterocyclylalkyl optionally substituted with $C_1$-$C_6$alkyl, heterocyclylalkyl optionally substituted with $C_1$-$C_6$alkyl, $C_1$-$C_6$alkoxy optionally substituted with —$NH_2$, -alkylamino, -dialkylamino, heterocycle optionally substituted with $C_1$-$C_6$alkyl, or hydroxyl, —C(O)NH—$NH_2$, —C(O)NH—NH($C_1$-$C_6$alkyl), —C(O)NH—N($C_1$-$C_6$alkyl)($C_1$-$C_6$alkyl), —C(O)NH-heterocycle, —SO$_2$($C_1$-$C_6$alkyl), —CN, and —$NO_2$; —$C_3$-$C_8$carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$, wherein any two hydrogen atoms on the same carbon atom of the carbocyclic ring can be replaced by an oxygen atom to form an oxo (═O) substituent, and wherein any two hydrogen atoms on the same carbon atom of the carbocyclic ring can be replaced by an alkylenedioxy group so that the alkylenedioxy group, when taken together with the carbon atom to which it is attached, forms a 5- to 7-membered heterocycle containing two oxygen atoms; heterocyclylalkyl optionally substituted with $C_1$-$C_6$alkyl; $C_6$-$C_{10}$carbocycle; bicyclic heterocycle; or $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy optionally substituted with —$NH_2$, $C_1$-$C_6$alkyl, —C(O)OH, —$C_1$-$C_6$alkoxycarbonyl, —$C_1$-$C_8$acyl, $C_6$-$C_{14}$aryl, heteroaryl, -alkylcarboxamido optionally substituted with —$NH_2$, -alkylamino, or -dialkylamino, —C(O)-heterocycle optionally substituted with $C_1$-$C_6$alkyl, and $C_3$-$C_8$carbocycle;

or $R^4$ and $R^5$ when taken together with the nitrogen to which they are attached can form a 3- to 7-membered heterocycle wherein up to two of the carbon atoms of the heterocycle can be independently replaced with —N($R^7$)—, —O—, —C(O)—, or —S(═O)$_s$—;

each s is independently 1 or 2;

$R^6$ is $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl optionally substituted with —$NH_2$, -alkylamino, or -dialkylamino, heteroaryl, and $C_3$-$C_8$carbocycle; heterocyclylalkyl optionally substituted with $C_1$-$C_6$alkyl; $C_6$-$C_{10}$carbocycle; bicyclic heterocycle; or $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$;

$R^7$ is hydrogen; $C_1$-$C_8$acyl; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_3$-$C_8$carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; alkylamino; or arylamino optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle;

with the proviso that when m>1, two $R^1$ groups attached to adjacent carbon atoms can be taken together with the two carbons to which they are attached to form a fused 5- to 7-membered aromatic ring wherein up to 2 of the carbon atoms of the fused ring can be replaced with —N═, —N($R^7$)—, —O—, or —S(═O)$_s$—;

$R^2$ is hydrogen; halogen; $C_1$-$C_8$acyl; heterocycle; heterocyclylalkyl; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkynyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_6$-$C_{14}$aryl optionally substituted with from 1 to 3 substituents independently selected from $C_1$-$C_6$alkyl, halo, haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; or heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$;

$R^3$ is hydrogen; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkynyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_1$-C$_8$acyl; C$_6$-C$_{14}$aryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; heteroaryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; C$_7$-C$_{24}$arylalkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; heterocyclylalkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_1$-C$_6$hydroxyalkyl-; alkylcarboxy; alkoxycarbonyl; C$_1$-C$_6$ perfluoroalkyl; —S(O)$_s$—C$_1$-C$_6$alkyl wherein the C$_1$-C$_6$alkyl of —S(O)$_s$—C$_1$-C$_6$alkyl is optionally substituted with from 1 to 3 substituents independently selected from C$_1$-C$_6$alkyl, halo, -haloalkyl, hydroxyl, C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$; —S(O)$_s$-aryl wherein the aryl of —S(O)$_s$-aryl is optionally substituted with from 1 to 3 substituents independently selected from C$_1$-C$_6$alkyl, halo, -haloalkyl, hydroxyl, C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$; C$_3$-C$_8$carbocycle optionally substituted with from 1 to 3 substituents independently selected from C$_1$-C$_6$alkyl, halo, -haloalkyl, hydroxyl, C$_1$-C$_6$alkoxy, —NH$_2$, -alkylamino optionally substituted by hydroxyl, -dialkylamino, heterocycle optionally substituted with C$_1$-C$_6$alkyl, —NH—N(C$_1$-C$_6$alkyl)$_2$, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$, wherein any two hydrogen atoms on the same carbon atom of the C$_3$-C$_8$carbocycle ring can be replaced by an oxygen atom to form an oxo (═O) substituent, wherein any two hydrogen atoms on the same carbon atom of the C$_3$-C$_8$carbocycle ring can be replaced by an alkyleneoxy group so that the alkyleneoxy group, when taken together with the carbon atom to which it is attached, forms a spiro-fused 5- to 7-membered heterocycle containing an oxygen atom, and wherein any two hydrogen atoms on the same carbon atom of the C$_3$-C$_8$carbocycle ring can be replaced by an alkylenedioxy group so that the alkylenedioxy group, when taken together with the carbon atom to which it is attached, forms a 5- to 7-membered heterocycle containing two oxygen atoms wherein the 5- to 7-membered heterocycle containing two oxygen atoms is optionally substituted with from 1 to 3 C$_1$-C$_6$alkyl substituents; a 6- to 10-membered bicyclic carbocycle optionally substituted with from 1 to 3 substituents independently selected from C$_1$-C$_6$alkyl, halo, -haloalkyl, hydroxyl, C$_1$-C$_6$alkoxy, —NH$_2$, -aminoalkyl, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$, wherein any two hydrogen atoms on the same carbon atom of the bicyclic carbocycle rings can be replaced by an oxygen atom to form an oxo (═O) substituent, and wherein any two hydrogen atoms on the same carbon atom of the bicyclic carbocycle rings can be replaced by an alkylenedioxy group so that the alkylenedioxy group, when taken together with the carbon atom to which it is attached, forms a 5- to 7-membered heterocycle containing two oxygen atoms; a 4- to 7-membered monocyclic heterocycle optionally substituted with from 1 to 3 substituents independently selected from C$_1$-C$_6$alkyl, heterocyclylalkyl, arylalkyl, (C$_1$-C$_9$heteroaryl)alkyl-, C$_1$-C$_8$acyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, S(O)$_s$—C$_1$-C$_6$alkyl, —S(O)$_s$-aryl, -alkylcarboxamido, and —NO$_2$; or a 6- to 10-membered bicyclic heterocycle optionally substituted with from 1 to 3 substituents independently selected from C$_1$-C$_6$alkyl, heterocyclylalkyl, arylalkyl, (C$_1$-C$_9$heteroaryl)alkyl-, C$_1$-C$_8$acyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; and R$^8$ is hydrogen; halogen; C$_1$-C$_8$acyl; C$_1$-C$_6$alkyl; C$_2$-C$_6$alkenyl; C$_2$-C$_6$alkynyl; C$_6$-C$_{14}$aryl; heterocyclylalkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, —S(O)$_2$—C$_1$-C$_6$alkyl, and C$_3$-C$_8$carbocycle; or heteroaryl;

Ar is phenyl, naphthyl, or a monocyclic or bicyclic ring system having from 5 to 14 ring members, and containing at least one ring nitrogen atom, wherein the phenyl, naphthyl, and monocyclic or bicyclic ring system is optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$.

In one aspect, the invention provides compounds of the Formula (Ib) or of Formula (IIb):

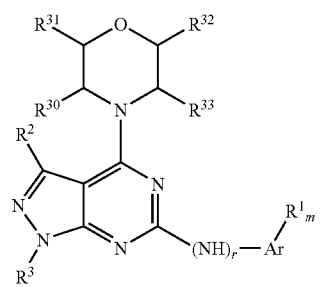

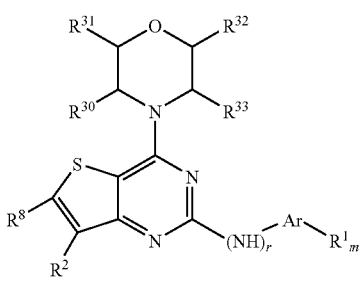

(IIb)

or pharmaceutically acceptable salts thereof, wherein:

$R^{30}$, $R^{31}$, $R^{32}$, and $R^{33}$ are each independently selected from hydrogen, halogen, hydroxyl, $C_1$-$C_2$alkoxy, $C(O)NH_2$, $C(O)NH(C_1$-$C_2$alkyl), $C(O)N(C_1$-$C_2$alkyl)($C_1$-$C_2$alkyl), CN, $C(O)OH$, and $C_1$-$C_4$alkoxycarbonyl;

provided that one of $R^{30}$ and $R^{32}$, $R^{30}$ and $R^{33}$, or $R^{31}$ and $R^{32}$ together are —$CH_2$—, —$CH_2CH_2$—, —$CH_2CH_2CH_2$—, —$CH_2$—O—, —$CH_2CH_2$—O—, —$CH_2OCH_2$—, $CH_2$—NH—, —$CH_2CH_2$—NH—, —$CH_2NHCH_2$—, —$CH_2$—N($CH_3$)—, —$CH_2CH_2$—N($CH_3$)—, or —$CH_2N(CH_3)CH_2$—, and with the two carbon atoms to which they are attached formed a bridged ring;

wherein the bridged ring formed by $R^{32}$, $R^{30}$ and $R^{33}$, or $R^{31}$ and $R^{32}$ is optionally substituted with halogen, hydroxyl, methyl, or ethyl or one $CH_2$ group is optionally replaced with —C(O)—;

each $R^1$ is independently halogen; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_1$-$C_6$alkoxy optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_2$-$C_6$alkynyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl) carboxyl, —N—($C_1$-$C_6$)alkylamido, —C(O)$NH_2$, -alkylcarboxamido and —$NO_2$; $C_1$-$C_8$acyl; $C_1$-$C_8$alkoxycarbonyl; $C_1$-$C_8$alkylcarboxy; —N—($C_1$-$C_6$)alkylamido; hydroxyl; $NR^4R^5$; —NHC(O)$NR^4R^5$; —NHC(O)NHN$R^4R^5$; —NHC(O)$OR^6$; —NH($SO_2$)NH—$C_1$-$C_6$alkyl; —NH($SO_2$)NH—$C_6$-$C_{14}$aryl; —NHC(S)—$NR^4R^5$; —NHC(=N—CN)—$NR^4R^5$; —NHC(=$NR^4$)—$NR^4R^5$; —N=C(S—$C_1$-$C_6$alkyl)(NH—$C_1$-$C_6$alkyl); or —N(H)—C(=N—(CN))—(O—$C_6$-$C_{14}$aryl);

m is 0, 1, 2, 3, or 4;

r is 0 or 1;

each $R^4$ and $R^5$ is independently —H; a 4- to 7-membered monocyclic heterocycle optionally substituted with from 1 to 3 substituents independently selected from $C_1$-$C_6$alkyl, heterocyclylalkyl, $C_7$-$C_{24}$arylalkyl, $C_1$-$C_8$acyl, $C_1$-$C_8$alkoxycarbonyl, $C_1$-$C_8$alkylcarboxy, halo, —$C_1$-$C_8$haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; $C_6$-$C_{14}$aryl optionally substituted with from 1 to 3 substituents independently selected from $C_1$-$C_6$alkyl optionally substituted with —$NH_2$, -alkylamino, or -dialkylamino, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido optionally substituted with —$NH_2$, -alkylamino, or -dialkylamino, —C(O)$NH_2$, -alkylcarboxamido, heterocycle optionally substituted with $C_1$-$C_6$alkyl, —S(O)$_2$-heterocyclylalkyl optionally substituted with $C_1$-$C_6$alkyl, heterocyclylalkyl optionally substituted with $C_1$-$C_6$alkyl, $C_1$-$C_6$alkoxy optionally substituted with —$NH_2$, -alkylamino, -dialkylamino, heterocycle, or hydroxyl, —C(O)NH—$NH_2$, —C(O)NH—NH($C_1$-$C_6$alkyl), —C(O)NH—N($C_1$-$C_6$alkyl)($C_1$-$C_6$alkyl), —C(O)NH-heterocycle, —$SO_2$($C_1$-$C_6$alkyl), —CN, and —$NO_2$; heteroaryl optionally substituted with from 1 to 3 substituents independently selected from $C_1$-$C_6$alkyl optionally substituted with —$NH_2$, -alkylamino, or -dialkylamino, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —($C_1$-$C_6$alkyl)carboxyl, —N—($C_1$-$C_6$)alkylamido optionally substituted with —$NH_2$, -alkylamino, or -dialkylamino, —C(O)$NH_2$, -alkylcarboxamido, heterocycle optionally substituted with $C_1$-$C_6$alkyl, —S(O)$_2$-heterocyclylalkyl optionally substituted with $C_1$-$C_6$alkyl, heterocyclylalkyl optionally substituted with $C_1$-$C_6$alkyl, $C_1$-$C_6$alkoxy optionally substituted with —$NH_2$, -alkylamino, -dialkylamino, heterocycle optionally substituted with $C_1$-$C_6$alkyl, or hydroxyl, —C(O)NH—$NH_2$, —C(O)NH—NH($C_1$-$C_6$alkyl), —C(O)NH—N($C_1$-$C_6$alkyl)($C_1$-$C_6$alkyl), —C(O)NH-heterocycle, —$SO_2$($C_1$-$C_6$alkyl), —CN, and —$NO_2$; —$C_3$-$C_8$carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$, wherein any two hydrogen atoms on the same carbon atom of the carbocyclic ring can be replaced by an oxygen atom to form an oxo (=O) substituent, and wherein any two hydrogen atoms on the same carbon atom of the carbocyclic ring can be replaced by an alkylenedioxy group so that the alkylenedioxy group, when taken together with the carbon atom to which it is attached, forms a 5- to 7-membered heterocycle containing two oxygen atoms; heterocyclylalkyl optionally substituted with $C_1$-$C_6$alkyl; $C_6$-$C_{10}$carbocycle; bicyclic heterocycle; or $C_1$-$C_6$alkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy optionally substituted with —NH$_2$, C$_1$-C$_6$alkyl, —C(O)OH, —C$_1$-C$_6$alkoxycarbonyl, —C$_1$-C$_8$acyl, C$_6$-C$_{14}$aryl, heteroaryl, -alkylcarboxamido optionally substituted with —NH$_2$, -alkylamino, or -dialkylamino, —C(O)-heterocycle optionally substituted with C$_1$-C$_6$alkyl, and C$_3$-C$_8$carbocycle; or R$^4$ and R$^5$ when taken together with the nitrogen to which they are attached can form a 3- to 7-membered heterocycle wherein up to two of the carbon atoms of the heterocycle can be independently replaced with —N(R$^7$)—, —O—, —C(O)—, or —S(=O)$_s$; each s is independently 1 or 2;

R$^6$ is C$_1$-C$_6$alkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl optionally substituted with —NH$_2$, -alkylamino, or -dialkylamino, heteroaryl, and C$_3$-C$_8$carbocycle; heterocyclylalkyl optionally substituted with C$_1$-C$_6$alkyl; C$_6$-C$_{10}$carbocycle; bicyclic heterocycle; or C$_6$-C$_{14}$aryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$;

R$^7$ is hydrogen; C$_1$-C$_8$acyl; C$_1$-C$_6$alkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_3$-C$_8$carbocycle optionally substituted with from 1 to 3 substituents independently selected from C$_1$-C$_6$alkyl, halo, -haloalkyl, hydroxyl, C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$; C$_6$-C$_{14}$aryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; heteroaryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; alkylamino; or arylamino optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C(O)C$_1$-C$_6$alkyl, C$_6$-C$_{14}$aryl, heteroaryl, and C$_3$-C$_8$carbocycle;

with the proviso that when m>1, two R$^1$ groups attached to adjacent carbon atoms can be taken together with the two carbons to which they are attached to form a fused 5- to 7-membered aromatic ring wherein up to 2 of the carbon atoms of the fused ring can be replaced with —N=, —N(R$^7$)—, —O—, or —S(=O)$_s$—;

R$^2$ is hydrogen; halogen; C$_1$-C$_8$acyl; heterocycle; heterocyclylalkyl; C$_1$-C$_6$alkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_2$-C$_6$alkenyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_2$-C$_6$alkynyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_6$-C$_{14}$aryl optionally substituted with from 1 to 3 substituents independently selected from C$_1$-C$_6$alkyl, halo, haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; or heteroaryl optionally substituted with from 1 to 3 substituents independently selected from C$_1$-C$_6$alkyl, halo, -haloalkyl, hydroxyl, C$_1$-C$_6$hydroxyalkyl, —NH$_2$, -aminoalkyl, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$;

R$^3$ is hydrogen; C$_1$-C$_6$alkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_2$-C$_6$alkenyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_2$-C$_6$alkynyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_1$-C$_8$acyl; C$_6$-C$_{14}$aryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; $C_7$-$C_{24}$arylalkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; heterocyclylalkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_1$-$C_6$hydroxyalkyl-; alkylcarboxy; alkoxycarbonyl; $C_1$-$C_6$ perfluoroalkyl; —S(O)$_s$—$C_1$-$C_6$alkyl wherein the $C_1$-$C_6$alkyl of —S(O)$_s$—$C_1$-$C_6$alkyl is optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$; —S(O)$_s$-aryl wherein the aryl of —S(O)$_s$-aryl is optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$; $C_3$-$C_8$carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino optionally substituted by hydroxyl, -dialkylamino, heterocycle optionally substituted with $C_1$-$C_6$alkyl, —NH—N($C_1$-$C_6$alkyl)$_2$, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$, wherein any two hydrogen atoms on the same carbon atom of the $C_3$-$C_8$carbocycle ring can be replaced by an oxygen atom to form an oxo (=O) substituent, wherein any two hydrogen atoms on the same carbon atom of the $C_3$-$C_8$carbocycle ring can be replaced by an alkyleneoxy group so that the alkyleneoxy group, when taken together with the carbon atom to which it is attached, forms a spiro-fused 5- to 7-membered heterocycle containing an oxygen atom, and wherein any two hydrogen atoms on the same carbon atom of the $C_3$-$C_8$carbocycle ring can be replaced by an alkylenedioxy group so that the alkylenedioxy group, when taken together with the carbon atom to which it is attached, forms a 5- to 7-membered heterocycle containing two oxygen atoms wherein the 5- to 7-membered heterocycle containing two oxygen atoms is optionally substituted with from 1 to 3 $C_1$-$C_6$alkyl substituents; a 6- to 10-membered bicyclic carbocycle optionally substituted with from 1 to 3 substituents independently selected from $C_1$-$C_6$alkyl, halo, -haloalkyl, hydroxyl, $C_1$-$C_6$alkoxy, —$NH_2$, -aminoalkyl, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$, wherein any two hydrogen atoms on the same carbon atom of the bicyclic carbocycle rings can be replaced by an oxygen atom to form an oxo (=O) substituent, and wherein any two hydrogen atoms on the same carbon atom of the bicyclic carbocycle rings can be replaced by an alkylenedioxy group so that the alkylenedioxy group, when taken together with the carbon atom to which it is attached, forms a 5- to 7-membered heterocycle containing two oxygen atoms; a 4- to 7-membered monocyclic heterocycle optionally substituted with from 1 to 3 substituents independently selected from $C_1$-$C_6$alkyl, heterocyclylalkyl, arylalkyl, ($C_1$-$C_9$heteroaryl)alkyl-, $C_1$-$C_8$acyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, S(O)$_s$—$C_1$-$C_6$alkyl, —S(O)$_s$-aryl, -alkylcarboxamido, and —$NO_2$; or a 6- to 10-membered bicyclic heterocycle optionally substituted with from 1 to 3 substituents independently selected from $C_1$-$C_6$alkyl, heterocyclylalkyl, arylalkyl, ($C_1$-$C_9$heteroaryl)alkyl-, $C_1$-$C_8$acyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; and $R^8$ is hydrogen; halogen; $C_1$-$C_8$acyl; $C_1$-$C_6$alkyl; $C_2$-$C_6$alkenyl; $C_2$-$C_6$alkynyl; $C_6$-$C_{14}$aryl; heterocyclylalkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, —S(O)$_2$—$C_1$-$C_6$alkyl, and $C_3$-$C_8$carbocycle; or heteroaryl;

Ar is phenyl, naphthyl, or a monocyclic or bicyclic ring system having from 5 to 14 ring members, and containing at least one ring nitrogen atom, wherein the phenyl, naphthyl, and monocyclic or bicyclic ring system is optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$.

In one aspect, the invention provides compounds of the Formula (I) or of Formula (II):

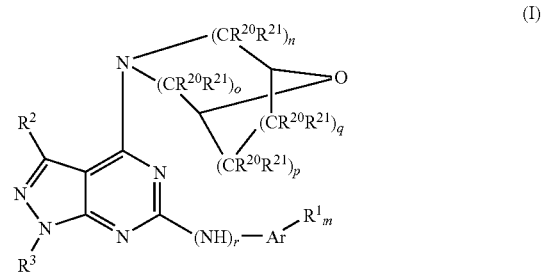

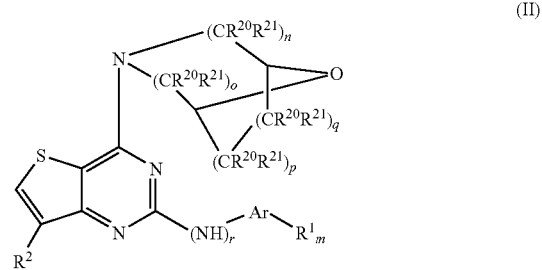

or pharmaceutically acceptable salts thereof, wherein:

each $R^1$ is independently halogen; $C_1$-$C_6$alkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_1$-$C_6$alkoxy optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_2$-$C_6$alkynyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; $C_1$-$C_8$acyl; $C_1$-$C_8$alkoxycarbonyl; $C_1$-$C_8$alkylcarboxy; —N—($C_1$-$C_6$)alkylamido; hydroxyl; $NR^4R^5$; —NHC(O)$NR^4R^5$; —NHC(O)$OR^6$; —NH($SO_2$)NH—$C_1$-$C_6$alkyl; —NH($SO_2$)NH—$C_6$-$C_{14}$aryl; —NHC(S)—NH—$C_1$-$C_6$alkyl; —N═C(S—$C_1$-$C_6$alkyl)(NH—$C_1$-$C_6$alkyl); or —N(H)—C(═N—(CN))—(O—$C_6$-$C_{14}$aryl);

m is 0, 1 or 2;
n is 1 or 2;
o is 1 or 2;
p and q are each independently 0, 1, or 2;
with the two provisos that at least one of n and o must be 1; and the sum of p and q must be greater than zero;
r is 0 or 1;
each $R^{20}$ and $R^{21}$ is independently selected from halogen, hydroxyl, $C_1$-$C_2$alkoxy, $NH_2$, $NH(C_1$-$C_2$alkyl), $N(C_1$-$C_2$alkyl)($C_1$-$C_2$alkyl), $NHC(O)(C_1$-$C_2$alkyl), $N(C_1$-$C_2$alkyl)C(O)($C_1$-$C_2$alkyl), NHC(O)H, C(O)$NH_2$, C(O)NH($C_1$-$C_2$alkyl), C(O)N($C_1$-$C_2$alkyl)($C_1$-$C_2$alkyl), CN, C(O)OH, and C(O)O$C_1$-$C_2$alkyl;
each $R^4$ and $R^5$ is independently —H; a 4- to 7-membered monocyclic heterocycle optionally substituted with from 1 to 3 substituents independently selected from $C_1$-$C_6$alkyl, heterocyclylalkyl, $C_7$-$C_{24}$arylalkyl, $C_1$-$C_8$acyl, $C_1$-$C_8$alkoxycarbonyl, $C_1$-$C_8$alkylcarboxy, halo, —$C_1$-$C_8$haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; —$C_3$-$C_8$carbocycle optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$, wherein any two hydrogen atoms on the same carbon atom of the carbocyclic ring can be replaced by an oxygen atom to form an oxo (═O) substituent, and wherein any two hydrogen atoms on the same carbon atom of the carbocyclic ring can be replaced by an alkylenedioxy group so that the alkylenedioxy group, when taken together with the carbon atom to which it is attached, forms a 5- to 7-membered heterocycle containing two oxygen atoms; or $C_1$-$C_6$alkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle;

or $R^4$ and $R^5$ when taken together with the nitrogen to which they are attached can form a 3- to 7-membered heterocycle wherein up to two of the carbon atoms of the heterocycle can be independently replaced with —$N(R^7)$—, —O—, or —$S(═O)_s$;
each s is independently 1 or 2;
$R^6$ is $C_1$-$C_6$alkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; or $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$;
$R^7$ is hydrogen; $C_1$-$C_8$acyl; $C_1$-$C_6$alkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_3$-$C_8$carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; alkylamino; or aminoaryl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; with the proviso that when m=2, any two adjacent $R^1$ groups can be taken together with the two carbons to which they are attached to form a 5- to 7-membered aromatic ring wherein up to 2 of the carbon atoms of the fused ring can be replaced with —N=, —N($R^7$)—, —O—, or —S(=O)$_s$;

$R^2$ is hydrogen; halogen; $C_1$-$C_8$acyl; $C_1$-$C_6$alkyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_2$-$C_6$alkynyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_6$-$C_{14}$aryl optionally substituted with from 1 to 3 substituents independently selected from $C_1$-$C_6$alkyl, halo, haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; or heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$;

$R^3$ is hydrogen; $C_1$-$C_6$alkyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_2$-$C_6$alkenyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_2$-$C_6$alkynyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; $C_1$-$C_8$acyl; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; $C_7$-$C_{24}$arylalkyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; heterocyclylalkyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle; hydroxyl($C_1$-$C_6$alkyl)-; alkylcarboxy; alkoxycarbonyl; $C_1$-$C_6$ perfluoroalkyl; —S(O)$_s$—$C_1$-$C_6$alkyl wherein the $C_1$-$C_6$alkyl of —S(O)$_s$—$C_1$-$C_6$alkyl is optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$; —S(O)$_s$-aryl wherein the aryl of —S(O)$_s$-aryl is optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$; a $C_3$-$C_8$carbocycle optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-

$C_1$-$C_6$alkylcarboxyl, —N—($C_1$-$C_6$)alkylamido, —C(O)NH$_2$, and —NO$_2$, wherein any two hydrogen atoms on the same carbon atom of the carbocycle ring can be replaced by an oxygen atom to form an oxo (=O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms; a 6- to 10-membered bicyclic carbocycle optionally substituted with from 1 to 3 substituents independently selected from $C_1$-$C_6$alkyl, halo, -haloalkyl, hydroxyl, —$C_1$-$C_6$alkoxy, —NH$_2$, -aminoalkyl, -dialkylamino, —COOH, —$C_1$-$C_6$alkoxycarbonyl, —$C_1$-$C_6$alkylcarboxyl, —N—($C_1$-$C_6$)alkylamido, —C(O)NH$_2$, and —NO$_2$, wherein any two hydrogen atoms on the same carbon atom of the bicyclic carbocycle rings can be replaced by an oxygen atom to form an oxo (=O) substituent, and wherein any two hydrogen atoms on the same carbon atom of the bicyclic carbocycle rings can be replaced by an alkylenedioxy group so that the alkylenedioxy group, when taken together with the carbon atom to which it is attached, forms a 5- to 7-membered heterocycle containing two oxygen atoms; a 4- to 7-membered monocyclic heterocycle optionally substituted with from 1 to 3 substituents independently selected from $C_1$-$C_6$alkyl, heterocyclylalkyl, arylalkyl, $C_1$-$C_8$acyl, halo, -haloalkyl, hydroxyl, $C_1$-$C_6$hydroxyalkyl, —NH$_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH$_2$, -alkylcarboxamido and —NO$_2$; or a 6- to 10-membered bicyclic heterocycle optionally substituted with from 1 to 3 substituents independently selected from $C_1$-$C_6$alkyl, heterocyclylalkyl, arylalkyl, $C_1$-$C_8$acyl, halo, -haloalkyl, hydroxyl, $C_1$-$C_6$hydroxyalkyl, —NH$_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH$_2$, -alkylcarboxamido and —NO$_2$; and Ar is phenyl, naphthyl, or a monocyclic or bicyclic ring system having from 5 to 14 ring members, and containing at least one ring nitrogen atom, wherein the phenyl, naphthyl, and monocyclic or bicyclic ring system is optionally substituted with from 1 to 3 substituents independently selected from $C_1$-$C_6$alkyl, halo, -haloalkyl, hydroxyl, $C_1$-$C_6$hydroxyalkyl, —NH$_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH$_2$, -alkylcarboxamido and —NO$_2$.

In one embodiment, the pyrazolopyrimidine compounds of the invention have the Formula (I), below:

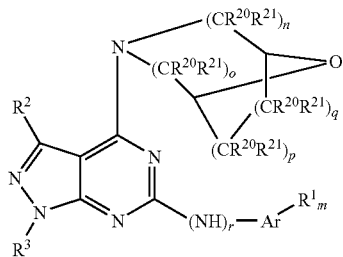

(I)

or pharmaceutically acceptable salts thereof, wherein the constituent variables are as defined above.

In some embodiments of the compounds of Formula (Ia) above, Ar is phenyl.

In some embodiments, m is 1.

In some embodiments of the compounds of Formula (Ia) and (Ia), $R^1$ is —NHC(O)NR$^4$R$^5$, —NHC(O)OR$^6$, —NH(SO$_2$)NH—($C_1$-$C_6$alkyl) or —NH(SO$_2$)NH—$C_6$-$C_{14}$aryl.

In some embodiments, $R^1$ is —NHC(O)NR$^4$R$^5$.

In another embodiment, $R^5$ is H.

In another embodiment, the —NHC(O)NR$^4$R$^5$ group is attached to the C4 of the phenyl ring.

In some further embodiments, $R^3$ is hydrogen.

In some further embodiments, $R^3$ is $C_1$-$C_6$alkyl optionally substituted with from 1 to 3 substituents independently selected from halogen, —NH$_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)NH$_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$carbocycle.

In some further embodiments, $R^3$ is $C_1$-$C_6$alkyl optionally substituted with from 1 to 3 independently selected halogens.

In some further embodiments, $R^3$ is 2,2,2-trifluoroethyl.

In some further embodiments, $R^3$ is a 4- to 7-membered monocyclic heterocycle optionally substituted with from 1 to 3 substituents independently selected from $C_1$-$C_6$alkyl, heterocyclylalkyl, arylalkyl, ($C_1$-$C_9$heteroaryl)alkyl-, $C_1$-$C_8$acyl, halo, -haloalkyl, hydroxyl, $C_1$-$C_6$hydroxyalkyl, —NH$_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)NH$_2$, S(O)$_s$—$C_1$-$C_6$alkyl, —S(O)$_s$-aryl, -alkylcarboxamido, and —NO$_2$.

In some further embodiments, the 4- to 7-membered monocyclic heterocycle is an optionally substituted piperidinyl.

In some embodiments, $R^3$ is optionally substituted piperidin-4-yl.

In some further embodiments, the 4- to 7-membered monocyclic heterocycle is an optionally substituted piperidinyl wherein the piperidinyl nitrogen is substituted with $C_1$-$C_6$alkyl, heterocyclylalkyl, arylalkyl, ($C_1$-$C_9$heteroaryl)alkyl-, $C_1$-$C_8$acyl, halo, -haloalkyl, hydroxyl, $C_1$-$C_6$hydroxyalkyl, —NH$_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)NH$_2$, S(O)$_s$—$C_1$-$C_6$alkyl, —S(O)$_s$-aryl, or -alkylcarboxamido.

In some further embodiments, the compound has the Formula (Ia), and $R^3$ is $C_7$-$C_{14}$arylalkyl.

In some further embodiments, the compound has the Formula (Ia), and $R^3$ is a 4- to 7-membered monocyclic heterocycle containing at least one ring oxygen atom. In some further embodiments, the compound has the Formula (Ia), and $R^3$ is a $C_3$-$C_8$carbocycle optionally substituted with from 1 to 3 substituents independently selected from $C_1$-$C_6$alkyl, halo, -haloalkyl, hydroxyl, —$C_1$-$C_6$alkoxy, —NH$_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)NH$_2$, and —NO$_2$, wherein any two hydrogen atoms on the same carbon atom of the carbocycle ring can be replaced by an oxygen atom to form an oxo (=O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms.

In some embodiments, het is selected from 8-oxa-3-azabicyclo[3.2.1]oct-3-yl, 3-oxa-8-azabicyclo[3.2.1]oct-8-yl, and 2-oxa-5-azabicyclo[2.2.1]hept-5-yl.

In some embodiments, t is 0.

In some embodiments, the compound has the Formula (II):

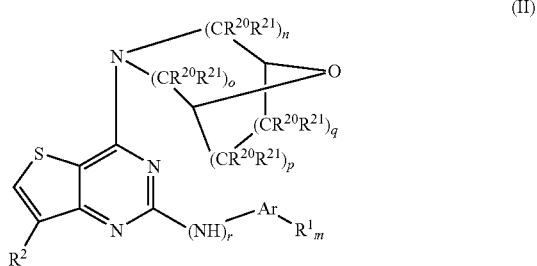

(II)

or a pharmaceutically acceptable salt thereof, wherein the constituent variables are as defined above.

In some further embodiments, the compound has the Formula (II), wherein Ar is phenyl, and $R^1$ is independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido, and —$NO_2$.

In some further embodiments, $R^1$ is —NHC(O)$NR^4R^5$.

In some further embodiments, $R^1$ is —NHC(O)$OR^6$.

In some further embodiments, $R^6$ is 2-hydroxyethyl.

In some further embodiments, Ar is indolyl, m is 0, 1, or 2, and $R^1$ is independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$.

In some further embodiments, Ar is pyridinyl, m is 0, 1, or 2, and $R^1$ is independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$.

In some further embodiments, Ar is pyrimidinyl, m is 0, 1, or 2, and $R^1$ is independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$.

In some further embodiments, Ar is phenyl.

In another embodiment, $R^1$ is —NHC(O)$NR^4R^5$.

In another embodiment, $R^5$ is H.

In another embodiment, the —NHC(O)$NR^4R^5$ group is attached to the C4 of the phenyl ring.

In another embodiment, $R^1$ is —NHC(O)$OR^6$.

In some such embodiments, the —NHC(O)$OR^6$ group is attached to the C4 of the phenyl ring.

In some embodiments of the compounds of Formula (I) and (II), n, o, p, and q are each 1.

In some embodiments of the compounds of Formula (I) and (II), $R^3$ is a $C_3$-$C_8$carbocycle, or a $C_5$-$C_7$ carbocycle, each of which can be optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, and —$NO_2$, wherein any two hydrogen atoms on the same carbon atom of the carbocycle ring can optionally be replaced by an oxygen atom to form an oxo (=O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms.

In some such embodiments, $R^3$ is a $C_6$carbocycle, wherein two hydrogen atoms on one of the carbon atoms of the carbocycle ring have been replaced by an alkylenedioxy group so that the alkylenedioxy group, when taken together with the carbon atom to which it is attached, forms a 5- to 7-membered heterocycle containing two oxygen atoms.

In some embodiments of the compounds of Formula (I) and (II), n, o, p, and q are each 1; r is 0; $R^3$ is a $C_5$-$C_7$ carbocycle, which can be optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, and —$NO_2$, wherein any two hydrogen atoms on the same carbon atom of the carbocycle ring can optionally be replaced by an oxygen atom to form an oxo (=O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms; $R^1$ is —NHC(O)$NR^4R^5$, —NHC(O)$OR^6$, —NH($SO_2$)NH—$C_1$-$C_6$alkyl or —NH($SO_2$)NH—$C_6$-$C_{14}$aryl, and Ar is phenyl.

In some embodiments of the compounds of Formula (I) and (II), n, o, p, and q are each 1; r is 0; $R^3$ is a $C_6$carbocycle, wherein two hydrogen atoms on one of the carbon atoms of the carbocycle ring have been replaced by an alkylenedioxy group so that the alkylenedioxy group, when taken together with the carbon atom to which it is attached, forms a 5- to 7-membered heterocycle containing two oxygen atoms; $R^1$ is —NHC(O)$NR^4R^5$ and Ar is phenyl.

Illustrative compounds of Formula (I) are exemplified by the following compounds:

3-[4-(8-oxa-3-azabicyclo[3.2.1]oct-3-yl)-1-phenyl-1H-pyrazolo[3,4-d]pyrimidin-6-yl]phenol;

1-methyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

methyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate;

1-ethyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-3-ylurea;

1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea;

1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea;

1-(2-fluoroethyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

methyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

tert-butyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[6-{4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

methyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;

methyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate.

methyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate;

methyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;

1-ethyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea;

1-(2-fluoroethyl)-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea;

1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-phenylurea;

1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-3-ylurea;

1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-4-ylurea;

tert-butyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

tert-butyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

tert-butyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

tert-butyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;

tert-butyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate.

tert-butyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;

1-methyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea;

1-methyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea;

1-ethyl-3-{4-[4-(8-oxa-3-azabicyclo[3.2.1]oct-3-yl)-1-piperidin-4-yl-1H-pyrazolo[3,4-d]pyrimidin-6-yl]phenyl}urea;

1-{4-[4-(8-oxa-3-azabicyclo[3.2.1]oct-3-yl)-1-piperidin-4-yl-1H-pyrazolo[3,4-d]pyrimidin-6-yl]phenyl}-3-phenylurea;

4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]aniline;

4-{[1-(1-benzylpiperidin-4-yl)-4-(8-oxa-3-azabicyclo[3.2.1]oct-3-yl)-1H-pyrazolo[3,4-d]pyrimidin-6-yl]amino}phenol;

ethyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

ethyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

ethyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;

ethyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate;

ethyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;

ethyl 4-[6-(4-{[(1-methylpiperidin-4-yl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate.

ethyl 4-{6-[4-({[1-(tert-butoxycarbonyl)piperidin-4-yl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;

ethyl 4-{6-[4-({[3-(methylamino)propyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;

ethyl 4-[4-(8-oxa-3-azabicyclo[3.2.1]oct-3-yl)-6-{4-[(1H-pyrazol-5-ylcarbamoyl)amino]phenyl}-1H-pyrazolo[3,4-d]pyrimidin-1-yl]piperidine-1-carboxylate;

1-{4-[1-ethyl-4-(8-oxa-3-azabicyclo[3.2.1]oct-3-yl)-1H-pyrazolo[3,4-d]pyrimidin-6-yl]phenyl}-3-methylurea;

1-ethyl-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(2-fluoroethyl)urea;

1-cyclopropyl-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(2-hydroxyethyl)urea;

2-hydroxyethyl{4-[1-ethyl-4-(8-oxa-3-azabicyclo[3.2.1]oct-3-yl)-1H-pyrazolo[3,4-d]pyrimidin-6-yl]phenyl}carbamate;

1-{4-[1-ethyl-4-(8-oxa-3-azabicyclo[3.2.1]oct-3-yl)-1H-pyrazolo[3,4-d]pyrimidin-6-yl]phenyl}-3-phenylurea;

1-{4-[1-ethyl-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-ethyl-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-ethyl-4-(8-oxa-3-azabicyclo[3.2.1]oct-3-yl)-1H-pyrazolo[3,4-d]pyrimidin-6-yl]phenyl}-3-[3-(methylamino)propyl]urea;

1-methyl-3-{4-[1-methyl-4-(8-oxa-3-azabicyclo[3.2.1]oct-3-yl)-1H-pyrazolo[3,4-d]pyrimidin-6-yl]phenyl}urea;

1-ethyl-3-{4-[1-methyl-4-(8-oxa-3-azabicyclo[3.2.1]oct-3-yl)-1H-pyrazolo[3,4-d]pyrimidin-6-yl]phenyl}urea.

1-(2-fluoroethyl)-3-{4-[1-methyl-4-(8-oxa-3-azabicyclo[3.2.1]oct-3-yl)-1H-pyrazolo[3,4-d]pyrimidin-6-yl]phenyl}urea;

1-cyclopropyl-3-{4-[1-methyl-4-(8-oxa-3-azabicyclo[3.2.1]
oct-3-yl)-1H-pyrazolo[3,4-d]pyrimidin-6-yl]
phenyl}urea;
1-(2-hydroxyethyl)-3-{4-[1-methyl-4-(8-oxa-3-azabicyclo
[3.2.1]oct-3-yl)-1H-pyrazolo[3,4-d]pyrimidin-6-yl]
phenyl}urea;
1-{4-[1-methyl-4-(8-oxa-3-azabicyclo[3.2.1]oct-3-yl)-1H-
pyrazolo[3,4-d]pyrimidin-6-yl]phenyl}-3-phenylurea;
1-{4-[1-methyl-4-(8-oxa-3-azabicyclo[3.2.1]oct-3-yl)-1H-
pyrazolo[3,4-d]pyrimidin-6-yl]phenyl}-3-pyridin-3-
ylurea;
1-{4-[1-methyl-4-(8-oxa-3-azabicyclo[3.2.1]oct-3-yl)-1H-
pyrazolo[3,4-d]pyrimidin-6-yl]phenyl}-3-pyridin-4-
ylurea;
1-[2-(dimethylamino)ethyl]-3-{4-[1-methyl-4-(8-oxa-3-
azabicyclo[3.2.1]oct-3-yl)-1H-pyrazolo[3,4-d]pyrimidin-
6-yl]phenyl}urea;
1-[3-(dimethylamino)propyl]-3-{4-[1-methyl-4-(8-oxa-3-
azabicyclo[3.2.1]oct-3-yl)-1H-pyrazolo[3,4-d]pyrimidin-
6-yl]phenyl}urea;
methyl{4-[1-methyl-4-(8-oxa-3-azabicyclo[3.2.1]oct-3-yl)-
1H-pyrazolo[3,4-d]pyrimidin-6-yl]phenyl}carbamate;
3-[1-methyl-4-(8-oxa-3-azabicyclo[3.2.1]oct-3-yl)-1H-
pyrazolo[3,4-d]pyrimidin-6-yl]phenol;
1-{4-[1-(1,4-dioxaspiro[4.5]dec-8-yl)-4-(8-oxa-3-azabicy-
clo[3.2.1]oct-3-yl)-1H-pyrazolo[3,4-d]pyrimidin-6-yl]
phenyl}-3-methylurea;
1-methyl-3-{4-[4-(8-oxa-3-azabicyclo[3.2.1]oct-3-yl)-1-(4-
oxocyclohexyl)-1H-pyrazolo[3,4-d]pyrimidin-6-yl]
phenyl}urea;
1-{4-[1-(4-hydroxycyclohexyl)-4-(8-oxa-3-azabicyclo
[3.2.1]oct-3-yl)-1H-pyrazolo[3,4-d]pyrimidin-6-yl]phe-
nyl}-3-methylurea;
ethyl 4-[4-(8-oxa-3-azabicyclo[3.2.1]oct-3-yl)-6-{4-[(pip-
eridin-4-ylcarbamoyl)amino]phenyl}-1H-pyrazolo[3,4-d]
pyrimidin-1-yl]piperidine-1-carboxylate;
isopropyl 4-[6-(4-aminophenyl)-4-(8-oxa-3-azabicyclo
[3.2.1]oct-3-yl)-1H-pyrazolo[3,4-d]pyrimidin-1-yl]pip-
eridine-1-carboxylate;
isopropyl 4-[6-{4-[(methylcarbamoyl)amino]phenyl}-4-(8-
oxa-3-azabicyclo[3.2.1]oct-3-yl)-1H-pyrazolo[3,4-d]py-
rimidin-1-yl]piperidine-1-carboxylate.
1-[4-(1-{1-[(6-bromopyridin-3-yl)methyl]piperidin-4-yl}-
4-morpholin-4-yl-1H-pyrazolo[3,4-d]pyrimidin-6-yl)
phenyl]-3-methylurea;
1-methyl-3-(4-{4-morpholin-4-yl-1-[(pyridin-3-ylmethyl)
piperidin-4-yl]-1H-pyrazolo[3,4-d]pyrimidin-6-
yl}phenyl)urea;
1-methyl-3-[4-(1-{1-[(2-methylpyridin-3-yl)carbonyl]pip-
eridin-4-yl}-4-morpholin-4-yl-1H-pyrazolo[3,4-d]pyri-
midin-6-yl)phenyl]urea;
1-methyl-3-[4-(1-{1-[(4-methylpyridin-3-yl)carbonyl]pip-
eridin-4-yl}-4-morpholin-4-yl-1H-pyrazolo[3,4-d]pyri-
midin-6-yl)phenyl]urea;
1-methyl-3-(4-{4-morpholin-4-yl-1-[1-(pyridin-2-ylmethyl)
piperidin-4-yl]-1H-pyrazolo[3,4-d]pyrimidin-6-
yl}phenyl)urea;
1-(4-{1'-[1-(2-methoxybenzoyl)piperidin-4-yl]-4-morpho-
lin-4-yl-1H-pyrazolo[3,4-d]pyrimidin-6-yl}phenyl)-3-
methylurea;
1-(4-{1'-[1-(3-acetylbenzoyl)piperidin-4-yl]-4-morpholin-
4-yl-1H-pyrazolo[3,4-d]pyrimidin-6-yl}phenyl)-3-me-
thylurea;
1-(2-fluoro-4-{4-morpholin-4-yl-1-[1-(pyridin-3-ylmethyl)
piperidin-4-yl]-1H-pyrazolo[3,4-d]pyrimidin-6-
yl}phenyl)-3-pyridin-3-ylurea;
2-[4-(6-{4-[(methylcarbamoyl)amino]phenyl}-4-morpho-
lin-4-yl-1H-pyrazolo[3,4-d]pyrimidin-1-yl)piperidin-1-
yl]acetamide;
Methyl 4-(6-{4-[(methylcarbamoyl)amino]phenyl}-4-mor-
pholin-4-yl-1H-pyrazolo[3,4-d]pyrimidin-1-yl)piperi-
dine-1-carboxylate.
isopropyl 4-[6-{4-[(ethylcarbamoyl)amino]phenyl}-4-(8-
oxa-3-azabicyclo[3.2.1]oct-3-yl)-1H-pyrazolo[3,4-d]py-
rimidin-1-yl]piperidine-1-carboxylate;
isopropyl 4-[6-(4-{[(2-fluoroethyl)carbamoyl]
amino}phenyl)-4-(8-oxa-3-azabicyclo[3.2.1]oct-3-yl)-
1H-pyrazolo[3,4-d]pyrimidin-1-yl]piperidine-1-carboxy-
late;
isopropyl 4-[6-(4-{[(2-hydroxyethyl)carbamoyl]
amino}phenyl)-4-(8-oxa-3-azabicyclo[3.2.1]oct-3-yl)-
1H-pyrazolo[3,4-d]pyrimidin-1-yl]piperidine-1-carboxy-
late;
isopropyl 4-[6-{4-[(cyclopropylcarbamoyl)amino]phenyl}-
4-(8-oxa-3-azabicyclo[3.2.1]oct-3-yl)-1H-pyrazolo[3,4-
d]pyrimidin-1-yl]piperidine-1-carboxylate;
isopropyl 4-[4-(8-oxa-3-azabicyclo[3.2.1]oct-3-yl)-6-{4-
[(phenylcarbamoyl)amino]phenyl}-1H-pyrazolo[3,4-d]
pyrimidin-1-yl]piperidine-1-carboxylate;
isopropyl 4-[4-(8-oxa-3-azabicyclo[3.2.1]oct-3-yl)-6-{4-
[(pyridin-3-ylcarbamoyl)amino]phenyl}-1H-pyrazolo[3,
4-d]pyrimidin-1-yl]piperidine-1-carboxylate;
isopropyl 4-[4-(8-oxa-3-azabicyclo[3.2.1]oct-3-yl)-6-{4-
[(pyridin-4-ylcarbamoyl)amino]phenyl}-1H-pyrazolo[3,
4-d]pyrimidin-1-yl]piperidine-1-carboxylate;
isopropyl 4-[6-{4-[(methoxycarbonyl)amino]phenyl}-4-(8-
oxa-3-azabicyclo[3.2.1]oct-3-yl)-1H-pyrazolo[3,4-d]py-
rimidin-1-yl]piperidine-1-carboxylate;
3-[1-ethyl-4-(8-oxa-3-azabicyclo[3.2.1]oct-3-yl)-1H-pyra-
zolo[3,4-d]pyrimidin-6-yl]phenol;
1-ethyl-6-(1H-indol-5-yl)-4-(8-oxa-3-azabicyclo[3.2.1]oct-
3-yl)-1H-pyrazolo[3,4-d]pyrimidine;
1-{4-[1-benzyl-4-(8-oxa-3-azabicyclo[3.2.1]oct-3-yl)-1H-
pyrazolo[3,4-d]pyrimidin-6-yl]phenyl}-3-methylurea;
1-{4-[1-benzyl-4-(8-oxa-3-azabicyclo[3.2.1]oct-3-yl)-1H-
pyrazolo[3,4-d]pyrimidin-6-yl]phenyl}-3-ethylurea;
1-{4-[1-benzyl-4-(8-oxa-3-azabicyclo[3.2.1]oct-3-yl)-1H-
pyrazolo[3,4-d]pyrimidin-6-yl]phenyl}-3-pyridin-4-
ylurea;
4-[1-(1-isobutyrylpiperidin-4-yl)-4-(8-oxa-3-azabicyclo
[3.2.1]oct-3-yl)-1H-pyrazolo[3,4-d]pyrimidin-6-yl]
aniline.
1-{4-[1-(1-isobutyrylpiperidin-4-yl)-4-(8-oxa-3-azabicyclo
[3.2.1]oct-3-yl)-1H-pyrazolo[3,4-d]pyrimidin-6-yl]phe-
nyl}-3-methylurea;
1-ethyl-3-{4-[1-(1-isobutyrylpiperidin-4-yl)-4-(8-oxa-3-
azabicyclo[3.2.1]oct-3-yl)-1H-pyrazolo[3,4-d]pyrimidin-
6-yl]phenyl}urea;
1-(2-hydroxyethyl)-3-{4-[1-(1-isobutyrylpiperidin-4-yl)-4-
(8-oxa-3-azabicyclo[3.2.1]oct-3-yl)-1H-pyrazolo[3,4-d]
pyrimidin-6-yl]phenyl}urea;
1-(2-fluoroethyl)-3-{4-[1-(1-isobutyrylpiperidin-4-yl)-4-(8-
oxa-3-azabicyclo[3.2.1]oct-3-yl)-1H-pyrazolo[3,4-d]py-
rimidin-6-yl]phenyl}urea;
1-cyclopropyl-3-{4-[1-(1-isobutyrylpiperidin-4-yl)-4-(8-
oxa-3-azabicyclo[3.2.1]oct-3-yl)-1H-pyrazolo[3,4-d]py-
rimidin-6-yl]phenyl}urea;
1-{4-[1-(1-isobutyrylpiperidin-4-yl)-4-(8-oxa-3-azabicyclo
[3.2.1]oct-3-yl)-1H-pyrazolo[3,4-d]pyrimidin-6-yl]phe-
nyl}-3-phenylurea;
1-{4-[1-(1-isobutyrylpiperidin-4-yl)-4-(8-oxa-3-azabicyclo
[3.2.1]oct-3-yl)-1H-pyrazolo[3,4-d]pyrimidin-6-yl]phe-
nyl}-3-pyridin-3-ylurea;

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-4-ylurea;
1-{4-[4-(8-oxa-3-azabicyclo[3.2.1]oct-3-yl)-1-(tetrahydro-2H-pyran-2-yl)-1H-pyrazolo[3,4-d]pyrimidin-6-yl]phenyl}-3-pyridin-3-ylurea;
1-{4-[4-(8-oxa-3-azabicyclo[3.2.1]oct-3-yl)-1H-pyrazolo[3,4-d]pyrimidin-6-yl]phenyl}-3-pyridin-3-ylurea;
1-(4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea;
1-(4-(4-(8-oxa-3-azabicyclo[3.2.1]octan-3-yl)-1-(4-oxocyclohexyl)-1H-pyrazolo[3,4-d]pyrimidin-6-yl)phenyl)-3-methylurea;
1-(4-(4-(8-oxa-3-azabicyclo[3.2.1]octan-3-yl)-1-(4-hydroxycyclohexyl)-1H-pyrazolo[3,4-d]pyrimidin-6-yl)phenyl)-3-methylurea;
1-(4-(4-(8-oxa-3-azabicyclo[3.2.1]octan-3-yl)-1-((1r,4r)-4-hydroxycyclohexyl)-1H-pyrazolo[3,4-d]pyrimidin-6-yl)phenyl)-3-methylurea; and
1-(4-(4-(8-oxa-3-azabicyclo[3.2.1]octan-3-yl)-1-((1s,4s)-4-hydroxycyclohexyl)-1H-pyrazolo[3,4-d]pyrimidin-6-yl)phenyl)-3-methylurea; and
2-hydroxyethyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate.

Illustrative compounds of Formula (Ia) are exemplified by the following compounds:

methyl 4-[6-{4-[(ethoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate;
methyl 4-[6-(4-{[(2-hydroxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;
methyl 4-[6-(4-{[(2-methoxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;
methyl 4-[6-(4-{[(2-aminoethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;
methyl 4-{6-[4-({[2-(dimethylamino)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-[4-(8-oxa-3-azabicyclo[3.2.1]oct-3-yl)-6-(4-{[(2-pyrrolidin-1-ylethoxy)carbonyl]amino}phenyl)-1H-pyrazolo[3,4-d]pyrimidin-1-yl]piperidine-1-carboxylate;
methyl 4-[6-(4-{[(2-morpholin-4-ylethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;
methyl 4-{6-[4-({[2-(4-methylpiperazin-1-yl)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-[6-{4-[(methoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate;
methyl 4-[6-(4-aminophenyl)-4-(8-oxa-3-azabicyclo[3.2.1]oct-3-yl)-1H-pyrazolo[3,4-d]pyrimidin-1-yl]piperidine-1-carboxylate;
2-hydroxyethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;
3-hydroxypropyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-ethylurea;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-fluoroethyl)urea;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-hydroxyethyl)urea;
1-cyclopropyl-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-phenylurea;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-4-ylurea;
2,2,2-trifluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;
2-fluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;
3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-1,3-oxazolidin-2-one;
2-({4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}amino)ethanol;
1-[2-(dimethylamino)ethyl]-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
methyl{4-[4-(8-oxa-3-azabicyclo[3.2.1]oct-3-yl)-1-(4-oxocyclohexyl)-1H-pyrazolo[3,4-d]pyrimidin-6-yl]phenyl}carbamate;
methyl{4-[1-(4-hydroxycyclohexyl)-4-(8-oxa-3-azabicyclo[3.2.1]oct-3-yl)-1H-pyrazolo[3,4-d]pyrimidin-6-yl]phenyl}carbamate;
methyl{4-[1-isopropyl-4-(8-oxa-3-azabicyclo[3.2.1]oct-3-yl)-1H-pyrazolo[3,4-d]pyrimidin-6-yl]phenyl}carbamate;
1-{4-[1-isopropyl-4-(8-oxa-3-azabicyclo[3.2.1]oct-3-yl)-1H-pyrazolo[3,4-d]pyrimidin-6-yl]phenyl}-3-methylurea;
1-ethyl-3-{4-[1-isopropyl-4-(8-oxa-3-azabicyclo[3.2.1]oct-3-yl)-1H-pyrazolo[3,4-d]pyrimidin-6-yl]phenyl}urea;
1-(2-fluoroethyl)-3-{4-[1-isopropyl-4-(8-oxa-3-azabicyclo[3.2.1]oct-3-yl)-1H-pyrazolo[3,4-d]pyrimidin-6-yl]phenyl}urea;
1-cyclopropyl-3-{4-[1-isopropyl-4-(8-oxa-3-azabicyclo[3.2.1]oct-3-yl)-1H-pyrazolo[3,4-d]pyrimidin-6-yl]phenyl}urea;
1-(2-hydroxyethyl)-3-{4-[1-isopropyl-4-(8-oxa-3-azabicyclo[3.2.1]oct-3-yl)-1H-pyrazolo[3,4-d]pyrimidin-6-yl]phenyl}urea;

2-hydroxyethyl{4-[1-isopropyl-4-(8-oxa-3-azabicyclo [3.2.1]oct-3-yl)-1H-pyrazolo[3,4-d]pyrimidin-6-yl] phenyl}carbamate;
3-hydroxypropyl{4-[1-isopropyl-4-(8-oxa-3-azabicyclo [3.2.1]oct-3-yl)-1H-pyrazolo[3,4-d]pyrimidin-6-yl] phenyl}carbamate;
2,3-dihydroxypropyl{4-[1-isopropyl-4-(8-oxa-3-azabicyclo [3.2.1]oct-3-yl)-1H-pyrazolo[3,4-d]pyrimidin-6-yl] phenyl}carbamate;
1-{4-[1-isopropyl-4-(8-oxa-3-azabicyclo[3.2.1]oct-3-yl)-1H-pyrazolo[3,4-d]pyrimidin-6-yl]phenyl}-3-phenylurea;
1-{4-[1-isopropyl-4-(8-oxa-3-azabicyclo[3.2.1]oct-3-yl)-1H-pyrazolo[3,4-d]pyrimidin-6-yl]phenyl}-3-pyridin-3-ylurea;
1-{4-[1-isopropyl-4-(8-oxa-3-azabicyclo[3.2.1]oct-3-yl)-1H-pyrazolo[3,4-d]pyrimidin-6-yl]phenyl}-3-pyridin-4-ylurea;
1-{4-[1-(4,4-dimethoxycyclohexyl)-4-(8-oxa-3-azabicyclo [3.2.1]oct-3-yl)-1H-pyrazolo[3,4-d]pyrimidin-6-yl]phenyl}-3-methylurea;
1-{4-[1-(1,5-dioxaspiro[5.5]undec-9-yl)-4-(8-oxa-3-azabicyclo[3.2.1]oct-3-yl)-1H-pyrazolo[3,4-d]pyrimidin-6-yl] phenyl}-3-methylurea;
1-{4-[1-(3,3-dimethyl-1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-methylurea;
methyl(4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-[4-(2-hydroxyethyl)phenyl]urea;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-phenylurea;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-pyridin-3-ylurea;
2-hydroxyethyl(4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-[4-(4-methylpiperazin-1-yl)phenyl]urea;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-ethylurea;
1-cyclopropyl-3-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)urea;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-pyridin-4-ylurea;
1-(4-{1-[2-(dimethylamino)ethyl]-4-(8-oxa-3-azabicyclo [3.2.1]oct-3-yl)-1H-pyrazolo[3,4-d]pyrimidin-6-yl}phenyl)-3-[4-(hydroxymethyl)phenyl]urea;
methyl 4-{6-[4-({[4-(hydroxymethyl)phenyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-{6-[4-({[4-(2-hydroxyethyl)phenyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-{6-[4-({[4-(4-methylpiperazin-1-yl)phenyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-{6-[4-({[6-(4-methylpiperazin-1-yl)pyridin-3-yl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-[6-(4-{[(2-aminoethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;
methyl 4-{6-[4-({[2-(dimethylamino)ethyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-{6-[4-({[2-(4-methylpiperazin-1-yl)ethyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-{6-[4-({[3-(hydroxymethyl)phenyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
methyl 4-{6-[4-({[2-(hydroxymethyl)phenyl] carbamoyl}amino)phenyl]-4-(8-oxa-3-azabicyclo[3.2.1] oct-3-yl)-1H-pyrazolo[3,4-d]pyrimidin-1-yl}piperidine-1-carboxylate;
1-(2-aminoethyl)-3-{4-[1-ethyl-4-(8-oxa-3-azabicyclo [3.2.1]oct-3-yl)-1H-pyrazolo[3,4-d]pyrimidin-6-yl] phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[2-(methylamino)ethyl]urea;
1-[2-(dimethylamino)ethyl]-3-{4-[1-ethyl-4-(8-oxa-3-azabicyclo[3.2.1]oct-3-yl)-1H-pyrazolo[3,4-d]pyrimidin-6-yl]phenyl}urea;
1-(3-aminopropyl)-3-{4-[1-ethyl-4-(8-oxa-3-azabicyclo [3.2.1]oct-3-yl)-1H-pyrazolo[3,4-d]pyrimidin-6-yl] phenyl}urea;
1-[3-(dimethylamino)propyl]-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea;
1-{4-[1-ethyl-4-(8-oxa-3-azabicyclo[3.2.1]oct-3-yl)-1H-pyrazolo[3,4-d]pyrimidin-6-yl]phenyl}-3-(2-morpholin-4-ylethyl)urea;
1-{4-[1-ethyl-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-{4-[1-ethyl-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;
1-{4-[1-ethyl-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;
1-{4-[1-ethyl-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea;
1-{4-[1-ethyl-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;

1-{4-[1-ethyl-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;
1-{4-[2-(dimethylamino)ethoxy]phenyl}-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-(4-methoxyphenyl)urea;
1-(4-chlorophenyl)-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-(4-methylphenyl)urea;
1-(4-cyanophenyl)-3-{4-[1-ethyl-4-(8-oxa-3-azabicyclo[3.2.1]oct-3-yl)-1H-pyrazolo[3,4-d]pyrimidin-6-yl]phenyl}urea;
2-hydroxypropyl{4-[1-ethyl-4-(8-oxa-3-azabicyclo[3.2.1]oct-3-yl)-1H-pyrazolo[3,4-d]pyrimidin-6-yl]phenyl}carbamate;
methyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-methylurea;
1-ethyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea;
2-hydroxyethyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate;
1-(2-hydroxyethyl)-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea;
1-cyclopropyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-phenylurea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-3-ylurea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-4-ylurea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;
1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;
2-[6-(4-aminophenyl)-4-(8-oxa-3-azabicyclo[3.2.1]oct-3-yl)-1H-pyrazolo[3,4-d]pyrimidin-1-yl]ethanol;
ethyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate;
2-hydroxyethyl(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)carbamate;
2-hydroxyethyl(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)carbamate;
2-hydroxyethyl{4-[4-(8-oxa-3-azabicyclo[3.2.1]oct-3-yl)-1-(4-oxocyclohexyl)-1H-pyrazolo[3,4-d]pyrimidin-6-yl]phenyl}carbamate;
2-hydroxyethyl{4-[1-(4-hydroxycyclohexyl)-4-(8-oxa-3-azabicyclo[3.2.1]oct-3-yl)-1H-pyrazolo[3,4-d]pyrimidin-6-yl]phenyl}carbamate;
2-hydroxyethyl{4-[1-(2-cyanoethyl)-4-(8-oxa-3-azabicyclo[3.2.1]oct-3-yl)-1H-pyrazolo[3,4-d]pyrimidin-6-yl]phenyl}carbamate;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-methylurea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-cyclopropylurea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-3-ylurea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-4-ylurea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-{4-[2-(dimethylamino)ethoxy]phenyl}urea;
1-[2-(2-aminoethoxy)ethyl]-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[(1-methylpiperidin-4-yl)methyl]urea;
1-cyclohexyl-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-(1-methylpiperidin-4-yl)urea;

1-(cis-4-aminocyclohexyl)-3-{4-[1-ethyl-4-(8-oxa-3-azabicyclo[3.2.1]oct-3-yl)-1H-pyrazolo[3,4-d]pyrimidin-6-yl]phenyl}urea;

1-(trans-4-aminocyclohexyl)-3-{4-[1-ethyl-4-(8-oxa-3-azabicyclo[3.2.1]oct-3-yl)-1H-pyrazolo[3,4-d]pyrimidin-6-yl]phenyl}urea;

1-[4-(hydroxymethyl)phenyl]-3-{4-[1-methyl-4-(8-oxa-3-azabicyclo[3.2.1]oct-3-yl)-1H-pyrazolo[3,4-d]pyrimidin-6-yl]phenyl}urea;

1-[4-(2-hydroxyethyl)phenyl]-3-{4-[1-methyl-4-(8-oxa-3-azabicyclo[3.2.1]oct-3-yl)-1H-pyrazolo[3,4-d]pyrimidin-6-yl]phenyl}urea;

1-[4-(dimethylamino)phenyl]-3-{4-[1-methyl-4-(8-oxa-3-azabicyclo[3.2.1]oct-3-yl)-1H-pyrazolo[3,4-d]pyrimidin-6-yl]phenyl}urea;

1-(4-aminophenyl)-3-{4-[1-methyl-4-(8-oxa-3-azabicyclo[3.2.1]oct-3-yl)-1H-pyrazolo[3,4-d]pyrimidin-6-yl]phenyl}urea;

1-{4-[1-methyl-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;

1-{4-[1-methyl-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[1-methyl-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;

1-{4-[1-methyl-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;

1-{4-[1-methyl-4-(8-oxa-3-azabicyclo[3.2.1]oct-3-yl)-1H-pyrazolo[3,4-d]pyrimidin-6-yl]phenyl}-3-[4-(methylsulfonyl)phenyl]urea;

1-{4-[1-methyl-4-(8-oxa-3-azabicyclo[3.2.1]oct-3-yl)-1H-pyrazolo[3,4-d]pyrimidin-6-yl]phenyl}-3-{4-[(2-piperidin-1-ylethyl)sulfonyl]phenyl}urea;

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-methylurea;

1-[4-(dimethylamino)phenyl]-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;

1-{4-[2-(dimethylamino)ethoxy]phenyl}-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;

2-hydroxyethyl{4-[1-(2-fluoroethyl)-4-(8-oxa-3-azabicyclo[3.2.1]oct-3-yl)-1H-pyrazolo[3,4-d]pyrimidin-6-yl]phenyl}carbamate;

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-ethyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;

1-(4-morpholin-4-ylphenyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-(6-morpholin-4-ylpyridin-3-yl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-[4-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

3-aminobenzyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate;

1-[3-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

3-(dimethylamino)phenyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate;

1-[3-(dimethylamino)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

N~2~,N~2~-dimethyl-N-{4-[({4-[1-methyl-4-(8-oxa-3-azabicyclo[3.2.1]oct-3-yl)-1H-pyrazolo[3,4-d]pyrimidin-6-yl]phenyl}carbamoyl)amino]phenyl}glycinamide;

N-{4-[({4-[1-methyl-4-(8-oxa-3-azabicyclo[3.2.1]oct-3-yl)-1H-pyrazolo[3,4-d]pyrimidin-6-yl]phenyl}carbamoyl)amino]phenyl}acetamide;

1-[4-(2-hydroxyethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-[4-(4-methylpiperazin-1-yl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-[6-(4-methylpiperazin-1-yl)pyridin-3-yl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-[4-(2-hydroxyethoxy)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

2-hydroxyethyl{4-[1-(1-benzylpiperidin-4-yl)-4-(8-oxa-3-azabicyclo[3.2.1]oct-3-yl)-1H-pyrazolo[3,4-d]pyrimidin-6-yl]phenyl}carbamate;

1-cyclopropyl-3-(4-{4-[(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea;

2-hydroxyethyl{4-[4-(3-oxa-8-azabicyclo[3.2.1]oct-8-yl)-1-(2,2,2-trifluoroethyl)-1H-pyrazolo[3,4-d]pyrimidin-6-yl]phenyl}carbamate;

1-methyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-pyridin-3-ylurea;

1-[4-(hydroxymethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-[4-(4-methylpiperazin-1-yl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-cyclopropyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-[4-(2-hydroxyethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-(4-morpholin-4-ylphenyl)-3-{4-[4-(3-oxa-8-azabicyclo [3.2.1]oct-8-yl)-1-(2,2,2-trifluoroethyl)-1H-pyrazolo[3,4-d]pyrimidin-6-yl]phenyl}urea;

1-(6-morpholin-4-ylpyridin-3-yl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-{4-[2-(dimethylamino)ethoxy]phenyl}-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-[2-(4-methylpiperazin-1-yl)-2-oxoethyl]urea;

1-{4-[1-ethyl-4-(8-oxa-3-azabicyclo[3.2.1]oct-3-yl)-1H-pyrazolo[3,4-d]pyrimidin-6-yl]phenyl}-3-[3-(4-methylpiperazin-1-yl)-3-oxopropyl]urea;

N-[2-(dimethylamino)ethyl]-N-2~-({4-[1-ethyl-4-(8-oxa-3-azabicyclo[3.2.1]oct-3-yl)-1H-pyrazolo[3,4-d]pyrimidin-6-yl]phenyl}carbamoyl)glycinamide;

N-[2-(dimethylamino)ethyl]-N-3~-({4-[1-ethyl-4-(8-oxa-3-azabicyclo[3.2.1]oct-3-yl)-1H-pyrazolo[3,4-d]pyrimidin-6-yl]phenyl}carbamoyl)-beta-alaninamide;

1-{4-[1-ethyl-4-(8-oxa-3-azabicyclo[3.2.1]oct-3-yl)-1H-pyrazolo[3,4-d]pyrimidin-6-yl]phenyl}-3-(4-pyrrolidin-1-ylphenyl)urea;

1-{4-[1-ethyl-4-(8-oxa-3-azabicyclo[3.2.1]oct-3-yl)-1H-pyrazolo[3,4-d]pyrimidin-6-yl]phenyl}-3-[4-(2-hydroxyethoxy)phenyl]urea;

1-{4-[1-ethyl-4-(8-oxa-3-azabicyclo[3.2.1]oct-3-yl)-1H-pyrazolo[3,4-d]pyrimidin-6-yl]phenyl}-3-[6-(2-hydroxyethoxy)pyridin-3-yl]urea;

1-{4-[1-ethyl-4-(8-oxa-3-azabicyclo[3.2.1]oct-3-yl)-1H-pyrazolo[3,4-d]pyrimidin-6-yl]phenyl}-3-[6-(2-morpholin-4-ylethoxy)pyridin-3-yl]urea;

1-[6-(dimethylamino)pyridin-3-yl]-3-{4-[1-ethyl-4-(8-oxa-3-azabicyclo[3.2.1]oct-3-yl)-1H-pyrazolo[3,4-d]pyrimidin-6-yl]phenyl}urea;

4-[({4-[1-ethyl-4-(8-oxa-3-azabicyclo[3.2.1]oct-3-yl)-1H-pyrazolo[3,4-d]pyrimidin-6-yl]phenyl}carbamoyl)amino]benzamide;

1-{4-[1-ethyl-4-(8-oxa-3-azabicyclo[3.2.1]oct-3-yl)-1H-pyrazolo[3,4-d]pyrimidin-6-yl]phenyl}-3-[6-(methylamino)pyridin-3-yl]urea;

1-(6-aminopyridin-3-yl)-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(4-piperazin-1-ylphenyl)urea;

1-{4-[(2,2-dimethylhydrazino)carbonyl]phenyl}-3-{4-[1-ethyl-4-(8-oxa-3-azabicyclo[3.2.1]oct-3-yl)-1H-pyrazolo[3,4-d]pyrimidin-6-yl]phenyl}urea;

4-[({4-[1-ethyl-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-ylbenzamide;

2-hydroxyethyl(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)carbamate;

1-methyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea;

1-[4-(hydroxymethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-[4-(4-methylpiperazin-1-yl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-cyclopropyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-[4-(2-hydroxyethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-(4-morpholin-4-ylphenyl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-(6-morpholin-4-ylpyridin-3-yl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-{4-[2-(dimethylamino)ethoxy]phenyl}-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-ethyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-(4-piperazin-1-ylphenyl)urea;

4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]benzamide;

4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-ylbenzamide;

1-[4-(hydroxymethyl)phenyl]-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;

1-{4-[2-(dimethylamino)ethoxy]phenyl}-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

2-hydroxyethyl{4-[1-(4-methoxycyclohexyl)-4-(8-oxa-3-azabicyclo[3.2.1]oct-3-yl)-1H-pyrazolo[3,4-d]pyrimidin-6-yl]phenyl}carbamate;

1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-pyridin-4-ylurea;

1-[4-(4-methylpiperazin-1-yl)phenyl]-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea;

1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-(4-piperazin-1-ylphenyl)urea;

2-hydroxyethyl(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)carbamate;

1-cyclopropyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea;

1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-(4-piperazin-1-ylphenyl)urea;
1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-(4-piperazin-1-ylphenyl)urea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-methylurea;
1-ethyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
1-cyclopropyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
1-(2-hydroxyethyl)-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
2-hydroxyethyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-phenylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-4-ylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-3-ylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea;
methyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate;
1-methyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;
1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-pyridin-3-ylurea;
1-methyl-3-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}urea;
1-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}-3-pyridin-3-ylurea;
1-(4-{1-[4-(2,2-dimethylhydrazino)cyclohexyl]-4-(8-oxa-3-azabicyclo[3.2.1]oct-3-yl)-1H-pyrazolo[3,4-d]pyrimidin-6-yl}phenyl)-3-methylurea;
1-{4-[1-{4-[(2-hydroxyethyl)amino]cyclohexyl}-4-(8-oxa-3-azabicyclo[3.2.1]oct-3-yl)-1H-pyrazolo[3,4-d]pyrimidin-6-yl]phenyl}-3-methylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-(4-piperazin-1-ylphenyl)urea;
1-{4-[(2,2-dimethylhydrazino)carbonyl]phenyl}-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea;
1-{4-[4-(7-formyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea;
1-{4-[4-(7-acetyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea;
tert-butyl 7-[6-{4-[(pyridin-4-ylcarbamoyl)amino]phenyl}-1-(2,2,2-trifluoroethyl)-1H-pyrazolo[3,4-d]pyrimidin-4-yl]-9-oxa-3,7-diazabicyclo[3.3.1]nonane-3-carboxylate;
1-methyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea;
1-cyclopropyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea;
2-hydroxyethyl(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)carbamate;
1-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea;
1-[4-(4-methylpiperazin-1-yl)phenyl]-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea;
1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-pyridin-3-ylurea;
1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-methylurea;
1-{4-[1-ethyl-3-(4-methylpiperazin-1-yl)-4-(8-oxa-3-azabicyclo[3.2.1]oct-3-yl)-1H-pyrazolo[3,4-d]pyrimidin-6-yl]phenyl}-3-methylurea;
1-{4-[1-ethyl-4-(8-oxa-3-azabicyclo[3.2.1]oct-3-yl)-3-pyridin-3-yl-1H-pyrazolo[3,4-d]pyrimidin-6-yl]phenyl}-3-methylurea;
1-{4-[1-ethyl-4-(8-oxa-3-azabicyclo[3.2.1]oct-3-yl)-3-vinyl-1H-pyrazolo[3,4-d]pyrimidin-6-yl]phenyl}-3-methylurea;
1-{4-[3-(1,2-dihydroxyethyl)-1-ethyl-4-(8-oxa-3-azabicyclo[3.2.1]oct-3-yl)-1H-pyrazolo[3,4-d]pyrimidin-6-yl]phenyl}-3-methylurea;
1-{4-[1-ethyl-3-formyl-4-(8-oxa-3-azabicyclo[3.2.1]oct-3-yl)-1H-pyrazolo[3,4-d]pyrimidin-6-yl]phenyl}-3-methylurea;
1-(4-{1-ethyl-3-[(4-methylpiperazin-1-yl)methyl]-4-(8-oxa-3-azabicyclo[3.2.1]oct-3-yl)-1H-pyrazolo[3,4-d]pyrimidin-6-yl}phenyl)-3-methylurea;
1-{4-[1-ethyl-4-(8-oxa-3-azabicyclo[3.2.1]oct-3-yl)-3-(pyrrolidin-1-ylmethyl)-1H-pyrazolo[3,4-d]pyrimidin-6-yl]phenyl}-3-methylurea;
methyl 4-[6-(4-{[(2-hydroxyethoxy)carbonyl]amino}phenyl)-4-(3-oxa-8-azabicyclo[3.2.1]oct-8-yl)-1H-pyrazolo[3,4-d]pyrimidin-1-yl]piperidine-1-carboxylate;
methyl 4-[6-{4-[(methylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate;
methyl 4-[6-{4-[(ethylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate;
methyl 4-[6-(4-{[(2-fluoroethyl)carbamoyl]amino}phenyl)-4-(3-oxa-8-azabicyclo[3.2.1]oct-8-yl)-1H-pyrazolo[3,4-d]pyrimidin-1-yl]piperidine-1-carboxylate;
methyl 4-[6-{4-[(cyclopropylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate;
methyl 4-[4-(3-oxa-8-azabicyclo[3.2.1]oct-8-yl)-6-{4-[(phenylcarbamoyl)amino]phenyl}-1H-pyrazolo[3,4-d]pyrimidin-1-yl]piperidine-1-carboxylate;

methyl 4-[4-(3-oxa-8-azabicyclo[3.2.1]oct-8-yl)-6-{4-[(pyridin-3-ylcarbamoyl)amino]phenyl}-1H-pyrazolo[3,4-d]pyrimidin-1-yl]piperidine-1-carboxylate;

methyl 4-[4-(3-oxa-8-azabicyclo[3.2.1]oct-8-yl)-6-{4-[(pyridin-4-ylcarbamoyl)amino]phenyl}-1H-pyrazolo[3,4-d]pyrimidin-1-yl]piperidine-1-carboxylate;

methyl 4-{6-[4-({[4-(4-methylpiperazin-1-yl)phenyl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate;

methyl 4-[4-(3-oxa-8-azabicyclo[3.2.1]oct-8-yl)-6-(4-{[(4-piperazin-1-ylphenyl)carbamoyl]amino}phenyl)-1H-pyrazolo[3,4-d]pyrimidin-1-yl]piperidine-1-carboxylate;

methyl 4-{6-[4-({[6-(4-methylpiperazin-1-yl)pyridin-3-yl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate;

methyl 4-[6-{4-[({4-[(dimethylamino)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[6-{4-[({4-[(4-methylpiperazin-1-yl)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[6-{4-[({4-[2-(dimethylamino)ethoxy]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

2-hydroxyethyl(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)carbamate;

1-ethyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;

1-(2-fluoroethyl)-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;

1-cyclopropyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;

1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-phenylurea;

4-[4-(8-oxa-3-azabicyclo[3.2.1]oct-3-yl)-1-(2,2,2-trifluoroethyl)-1H-pyrazolo[3,4-d]pyrimidin-6-yl]aniline;

methyl{4-[1-ethyl-4-(8-oxa-3-azabicyclo[3.2.1]oct-3-yl)-1H-pyrazolo[3,4-d]pyrimidin-6-yl]phenyl}carbamate;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-3-ylurea;

methyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;

3-[4-(3-oxa-8-azabicyclo[3.2.1]oct-8-yl)-1-phenyl-1H-pyrazolo[3,4-d]pyrimidin-6-yl]phenol;

2-hydroxyethyl(4-{4-[(6R)-6-hydroxy-8-oxa-3-azabicyclo[3.2.1]oct-3-yl]-1-(2,2,2-trifluoroethyl)-1H-pyrazolo[3,4-d]pyrimidin-6-yl}phenyl)carbamate;

1-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}-3-methylurea;

1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-methylurea;

3-{4-[(1S,4S)-2-oxa-5-azabicyclo[2.2.1]hept-5-yl]-1-phenyl-1H-pyrazolo[3,4-d]pyrimidin-6-yl}phenol;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-methylurea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-(1,3-dioxan-5-yl)-4-(8-oxa-3-azabicyclo[3.2.1]oct-3-yl)-1H-pyrazolo[3,4-d]pyrimidin-6-yl]phenyl}-3-methylurea;

1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-methylurea;

1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-methylurea;

1-(1,4-dioxaspiro[4.5]dec-8-yl)-6-(1H-indol-5-yl)-4-(8-oxa-3-azabicyclo[3.2.1]oct-3-yl)-1H-pyrazolo[3,4-d]pyrimidine;

1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea;

1-{4-[4-(6-hydroxy-3-oxa-8-azabicyclo[3.2.1]oct-8-yl)-1-(2,2,2-trifluoroethyl)-1H-pyrazolo[3,4-d]pyrimidin-6-yl]phenyl}-3-methylurea;

1-{4-[4-(6,8-dioxa-3-azabicyclo[3.2.1]oct-3-yl)-1-methyl-1H-pyrazolo[3,4-d]pyrimidin-6-yl]phenyl}-3-pyridin-3-ylurea;

1-{4-[4-(6,8-dioxa-3-azabicyclo[3.2.1]oct-3-yl)-1-methyl-1H-pyrazolo[3,4-d]pyrimidin-6-yl]phenyl}-3-methylurea;

1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-(4-piperazin-1-ylphenyl)urea;

6-(1H-indol-5-yl)-4-(8-oxa-3-azabicyclo[3.2.1]oct-3-yl)-1-[1-(pyridin-3-ylmethyl)piperidin-4-yl]-1H-pyrazolo[3,4-d]pyrimidine;

1-cyclopropyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[3-bromo-1-ethyl-4-(8-oxa-3-azabicyclo[3.2.1]oct-3-yl)-1H-pyrazolo[3,4-d]pyrimidin-6-yl]phenyl}-3-methylurea;

1-cyclopropyl-3-{4-[1-(cis-methoxycyclohexyl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}urea;

1-[4-(4-methylpiperazin-1-yl)phenyl]-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea;

1-cyclopropyl-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea;

1-cyclopropyl-3-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}urea;

1-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea; and 1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea.

Illustrative compounds of Formula (II) are exemplified by the following compounds:

1-methyl-3-{4-[4-(8-oxa-3-azabicyclo[3.2.1]oct-3-yl)thieno[3,2-d]pyrimidin-2-yl]phenyl}urea;
1-ethyl-3-{4-[4-(8-oxa-3-azabicyclo[3.2.1]oct-3-yl)thieno[3,2-d]pyrimidin-2-yl]phenyl}urea;
1-(2-fluoroethyl)-3-{4-[4-(8-oxa-3-azabicyclo[3.2.1]oct-3-yl)thieno[3,2-d]pyrimidin-2-yl]phenyl}urea;
1-(2-hydroxyethyl)-3-{4-[4-(8-oxa-3-azabicyclo[3.2.1]oct-3-yl)thieno[3,2-d]pyrimidin-2-yl]phenyl}urea;
1-cyclopropyl-3-{4-[4-(8-oxa-3-azabicyclo[3.2.1]oct-3-yl)thieno[3,2-d]pyrimidin-2-yl]phenyl}urea;
1-{4-[4-(8-oxa-3-azabicyclo[3.2.1]oct-3-yl)thieno[3,2-d]pyrimidin-2-yl]phenyl}-3-phenylurea;
1-{4-[4-(8-oxa-3-azabicyclo[3.2.1]oct-3-yl)thieno[3,2-d]pyrimidin-2-yl]phenyl}-3-pyridin-3-ylurea;
1-{4-[4-(8-oxa-3-azabicyclo[3.2.1]oct-3-yl)thieno[3,2-d]pyrimidin-2-yl]phenyl}-3-pyridin-4-ylurea;
4-[4-(8-oxa-3-azabicyclo[3.2.1]oct-3-yl)thieno[3,2-d]pyrimidin-2-yl]aniline;
N-{4-[4-(8-oxa-3-azabicyclo[3.2.1]oct-3-yl)thieno[3,2-d]pyrimidin-2-yl]phenyl}acetamide;
methyl{4-[4-(8-oxa-3-azabicyclo[3.2.1]oct-3-yl)thieno[3,2-d]pyrimidin-2-yl]phenyl}carbamate;
3-[4-(8-oxa-3-azabicyclo[3.2.1]oct-3-yl)thieno[3,2-d]pyrimidin-2-yl]phenol;
4-[4-(8-oxa-3-azabicyclo[3.2.1]oct-3-yl)thieno[3,2-d]pyrimidin-2-yl]phenol;
2-(1H-indol-5-yl)-4-(8-oxa-3-azabicyclo[3.2.1]oct-3-yl)thieno[3,2-d]pyrimidine;
5-[4-(8-oxa-3-azabicyclo[3.2.1]oct-3-yl)thieno[3,2-d]pyrimidin-2-yl]pyridin-2-amine;
5-[4-(8-oxa-3-azabicyclo[3.2.1]oct-3-yl)thieno[3,2-d]pyrimidin-2-yl]pyrimidin-2-amine; and
4-{[4-(8-oxa-3-azabicyclo[3.2.1]oct-3-yl)thieno[3,2-d]pyrimidin-2-yl]amino}phenol.

Illustrative compounds of Formula (IIa) are exemplified by the following compounds:

1-methyl-3-(4-{6-[(4-methylpiperazin-1-yl)methyl]-4-(8-oxa-3-azabicyclo[3.2.1]oct-3-yl)thieno[3,2-d]pyrimidin-2-yl}phenyl)urea;
1-cyclopropyl-3-(4-{6-[(4-methylpiperazin-1-yl)methyl]-4-(8-oxa-3-azabicyclo[3.2.1]oct-3-yl)thieno[3,2-d]pyrimidin-2-yl}phenyl)urea;
2,2-dimethyl-N-(4-{6-[(4-methylpiperazin-1-yl)methyl]-4-(8-oxa-3-azabicyclo[3.2.1]oct-3-yl)thieno[3,2-d]pyrimidin-2-yl}phenyl)hydrazinecarboxamide;
1-(4-{6-[(4-methylpiperazin-1-yl)methyl]-4-(8-oxa-3-azabicyclo[3.2.1]oct-3-yl)thieno[3,2-d]pyrimidin-2-yl}phenyl)-3-pyridin-3-ylurea;
1-(4-{6-[(4-methylpiperazin-1-yl)methyl]-4-(8-oxa-3-azabicyclo[3.2.1]oct-3-yl)thieno[3,2-d]pyrimidin-2-yl}phenyl)-3-pyridin-4-ylurea;
4-{[(4-{6-[(4-methylpiperazin-1-yl)methyl]-4-(8-oxa-3-azabicyclo[3.2.1]oct-3-yl)thieno[3,2-d]pyrimidin-2-yl}phenyl)carbamoyl]amino}benzamide;
1-methyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea;
1-ethyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea;
1-cyclopropyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea;
1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-phenylurea;
1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-3-ylurea; and
1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-4-ylurea.

Illustrative compounds of the invention are exemplified by the following compounds:

1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-3-ylurea;
1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-4-ylurea;
1-{4-[1-ethyl-4-(8-oxa-3-azabicyclo[3.2.1]oct-3-yl)-1H-pyrazolo[3,4-d]pyrimidin-6-yl]phenyl}-3-{4-[(4-methylpiperazin-1-yl)methyl]phenyl}urea;
1-[4-(aminomethyl)phenyl]-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[4-(pyrrolidin-1-ylmethyl)phenyl]urea;
1-{4-[(dimethylamino)methyl]phenyl}-3-{4-[1-ethyl-4-(8-oxa-3-azabicyclo[3.2.1]oct-3-yl)-1H-pyrazolo[3,4-d]pyrimidin-6-yl]phenyl}urea;
1-cyclopropyl-3-{4-[1-(4-ethoxycyclohexyl)-4-(8-oxa-3-azabicyclo[3.2.1]oct-3-yl)-1H-pyrazolo[3,4-d]pyrimidin-6-yl]phenyl}urea;
1-cyclopropyl-3-{4-[4-(8-oxa-3-azabicyclo[3.2.1]oct-3-yl)-1-(4-propoxycyclohexyl)-1H-pyrazolo[3,4-d]pyrimidin-6-yl]phenyl}urea;
1-[4-(4-methylpiperazin-1-yl)phenyl]-3-{4-[4-(8-oxa-3-azabicyclo[3.2.1]oct-3-yl)-1-(4-propoxycyclohexyl)-1H-pyrazolo[3,4-d]pyrimidin-6-yl]phenyl}urea;
1-{4-[1-(4-ethoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-cyclobutyl-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(3-oxa-8-azabicyclo[3.2.1]oct-8-yl)-1H-pyrazolo[3,4-d]pyrimidin-6-yl]phenyl}-3-methylurea;
1-cyclopentyl-3-{4-[1-ethyl-4-(3-oxa-8-azabicyclo[3.2.1]oct-8-yl)-1H-pyrazolo[3,4-d]pyrimidin-6-yl]phenyl}urea;
1-ethyl-3-{4-[1-ethyl-4-(3-oxa-8-azabicyclo[3.2.1]oct-8-yl)-1H-pyrazolo[3,4-d]pyrimidin-6-yl]phenyl}urea;
1-{4-[1-ethyl-4-(3-oxa-8-azabicyclo[3.2.1]oct-8-yl)-1H-pyrazolo[3,4-d]pyrimidin-6-yl]phenyl}-3-phenylurea;
tert-butyl 9-(6-(4-((2-hydroxyethoxy)carbonylamino)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate;
2-hydroxyethyl 4-(4-(3-oxa-7,9-diazabicyclo[3.3.1]nonan-9-yl)-1-(2,2,2-trifluoroethyl)-1H-pyrazolo[3,4-d]pyrimidin-6-yl)phenylcarbamate;
1-(4-{[2-(dimethylamino)ethyl] (methyl)amino}phenyl)-3-{4-[1-ethyl-4-(8-oxa-3-azabicyclo[3.2.1]oct-3-yl)-1H-pyrazolo[3,4-d]pyrimidin-6-yl]phenyl}urea;
2-hydroxyethyl{4-[1-ethyl-4-(3-oxa-8-azabicyclo[3.2.1]oct-8-yl)-1H-pyrazolo[3,4-d]pyrimidin-6-yl]phenyl}carbamate;

1-{4-[1-ethyl-4-(3-oxa-8-azabicyclo[3.2.1]oct-8-yl)-1H-pyrazolo[3,4-d]pyrimidin-6-yl]phenyl}-3-{4-[(4-methylpiperazin-1-yl)methyl]phenyl}urea;

1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-methylurea;

1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-cyclopentyl-3-{4-[1-ethyl-4-(8-oxa-3-azabicyclo[3.2.1]oct-3-yl)-1H-pyrazolo[3,4-d]pyrimidin-6-yl]phenyl}urea;

1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea;

1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-methylurea;

1-{4-[1-ethyl-4-(3-oxa-8-azabicyclo[3.2.1]oct-8-yl)-1H-pyrazolo[3,4-d]pyrimidin-6-yl]phenyl}-3-[4-(pyrrolidin-1-ylmethyl)phenyl]urea;

1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-methylurea;

1-{4-[1-ethyl-4-(3-oxa-8-azabicyclo[3.2.1]oct-8-yl)-1H-pyrazolo[3,4-d]pyrimidin-6-yl]phenyl}-3-pyridin-3-ylurea;

1-{4-[2-(dimethylamino)ethoxy]phenyl}-3-{4-[1-ethyl-4-(3-oxa-8-azabicyclo[3.2.1]oct-8-yl)-1H-pyrazolo[3,4-d]pyrimidin-6-yl]phenyl}urea;

1-(4-{[2-(dimethylamino)ethyl](methyl)amino}phenyl)-3-{4-[1-ethyl-4-(3-oxa-8-azabicyclo[3.2.1]oct-8-yl)-1H-pyrazolo[3,4-d]pyrimidin-6-yl]phenyl}urea;

1-{4-[1-ethyl-4-(3-oxa-8-azabicyclo[3.2.1]oct-8-yl)-1H-pyrazolo[3,4-d]pyrimidin-6-yl]phenyl}-3-[6-(4-methylpiperazin-1-yl)pyridin-3-yl]urea;

2-hydroxyethyl 4-(4-(2-oxa-5-azabicyclo[2.2.2]octan-5-yl)-1-(2,2,2-trifluoroethyl)-1H-pyrazolo[3,4-d]pyrimidin-6-yl)phenylcarbamate;

2-hydroxyethyl 4-(4-(3-oxa-9-azabicyclo[3.3.1]nonan-9-yl)-1-(2,2,2-trifluoroethyl)-1H-pyrazolo[3,4-d]pyrimidin-6-yl)phenylcarbamate;

1-(4-{[2-(dimethylamino)ethyl]amino}phenyl)-3-{4-[1-ethyl-4-(3-oxa-8-azabicyclo[3.2.1]oct-8-yl)-1H-pyrazolo[3,4-d]pyrimidin-6-yl]phenyl}urea;

1-{4-[(dimethylamino)methyl]phenyl}-3-{4-[1-ethyl-4-(3-oxa-8-azabicyclo[3.2.1]oct-8-yl)-1H-pyrazolo[3,4-d]pyrimidin-6-yl]phenyl}urea;

1-cyclopropyl-3-{4-[1-ethyl-4-(3-oxa-8-azabicyclo[3.2.1]oct-8-yl)-1H-pyrazolo[3,4-d]pyrimidin-6-yl]phenyl}urea;

2-hydroxyethyl 4-(4-(3,7-dioxa-9-azabicyclo[3.3.1]nonan-9-yl)-1-(2,2,2-trifluoroethyl)-1H-pyrazolo[3,4-d]pyrimidin-6-yl)phenylcarbamate;

tert-butyl 9-(6-(4-(3-methylureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate;

1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-methylurea;

1-(4-{[2-(dimethylamino)ethyl]amino}phenyl)-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(3-oxa-8-azabicyclo[3.2.1]oct-8-yl)-1H-pyrazolo[3,4-d]pyrimidin-6-yl]phenyl}-3-[4-(2-pyrrolidin-1-ylethoxy)phenyl]urea;

1-{4-[1-ethyl-4-(3-oxa-8-azabicyclo[3.2.1]oct-8-yl)-1H-pyrazolo[3,4-d]pyrimidin-6-yl]phenyl}-3-[4-(4-methylpiperazin-1-yl)phenyl]urea;

1-cyclobutyl-3-{4-[1-ethyl-4-(3-oxa-8-azabicyclo[3.2.1]oct-8-yl)-1H-pyrazolo[3,4-d]pyrimidin-6-yl]phenyl}urea;

1-[4-(aminomethyl)phenyl]-3-{4-[1-ethyl-4-(3-oxa-8-azabicyclo[3.2.1]oct-8-yl)-1H-pyrazolo[3,4-d]pyrimidin-6-yl]phenyl}urea;

1-{4-[1-ethyl-4-(3-oxa-8-azabicyclo[3.2.1]oct-8-yl)-1H-pyrazolo[3,4-d]pyrimidin-6-yl]phenyl}-3-pyridin-4-ylurea;

1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea;

1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(4-(2-(dimethylamino)ethoxy)phenyl)urea;

1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea; and tert-butyl9-(6-(3-(4-(2-(dimethylamino)ethoxy)phenyl)ureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate.

The invention also includes pharmaceutical compositions comprising an effective amount of a compound (1a) or (IIa) and a pharmaceutically acceptable carrier.

In one embodiment, methods are provided for synthesizing a compound of Formula (Ia) or Formula (IIa) comprising:
a) reacting a compound of the Formula $(R^{20})_t$-het-H wherein het, $R^{20}$, and t are as defined for Formulas (Ia) and (IIa) with a compound of the Formula (IV) or Formula (XII):

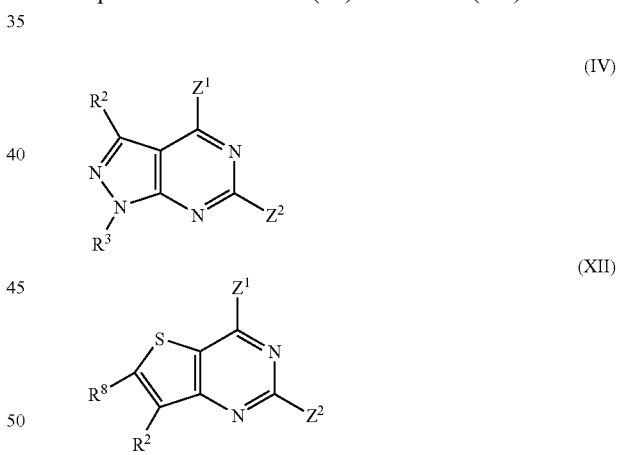

wherein $Z^1$ and $Z^2$ are each independently a halogen; and $R^2$, $R^3$, and $R^8$ are as defined for Formulas (Ia) and (IIa); thereby providing a compound having the Formula (XIII) or Formula (XIV):

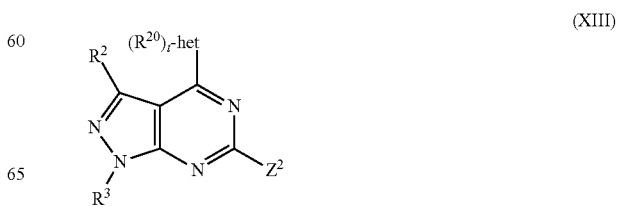

-continued

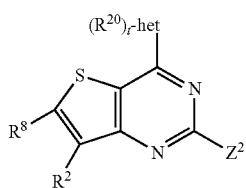
(XIV)

and either:
b) reacting the compound of Formula (XIII) or the compound of Formula (XIV), with a boronic acid of the structure $(R^1)_m$—Ar(OH)$_2$, with a boronic pinacol ester of the structure $(R^1)_m$—Ar(OC(CH$_3$)$_2$—)$_2$, or with a boronic ester of the structure $(R^1)_m$—Ar(OC$_1$-C$_6$alkyl)$_2$;
wherein each $R^1$, m, and r as defined for Formulas (Ia) and (IIa);
thereby providing a compound of the Formula (XV) or Formula (XVI):

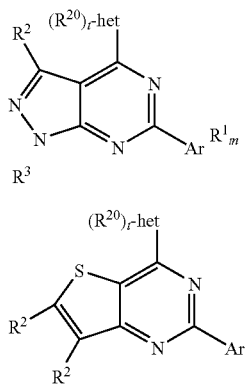
(XV)

(XVI)

or:
(c) reacting the compound of Formula (XIII) or of Formula (XIV) with an amine of Formula: $(R^1)_m$—Ar—NH$_2$, thereby providing a compound of the Formula (XVII) or of Formula (XVIII):

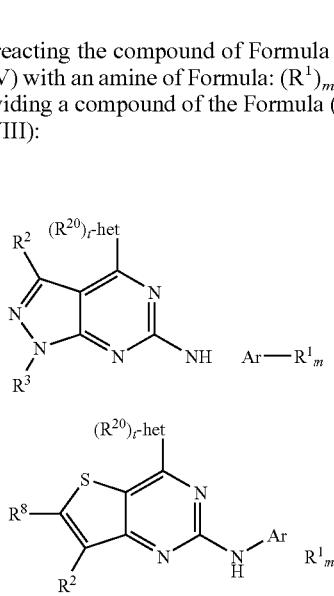
(XVII)

(XVIII)

or pharmaceutically acceptable salts thereof.

The invention further provides methods for preparing the compounds described herein. In one embodiment, methods are provided for synthesizing a compound of Formula (VIII), Formula (IX), Formula (X), or Formula (XI) comprising:

a) reacting a compound of the Formula (III):

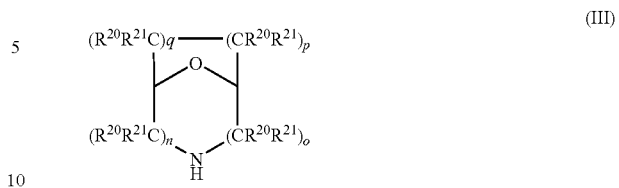
(III)

wherein, n, o, p, q, $R^{20}$ and $R^{21}$ as defined above for Formula (I) or Formula (II);
with a compound of the Formula (IV) or Formula (V):

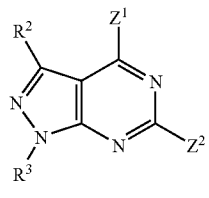
(IV)

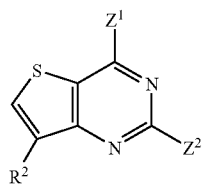
(V)

wherein $Z^1$ and $Z^2$ are each independently a halogen; and $R^2$ and $R^3$ are as defined above for Formula (I) or Formula (II);
thereby providing a compound having the Formula (VI) or Formula (VII):

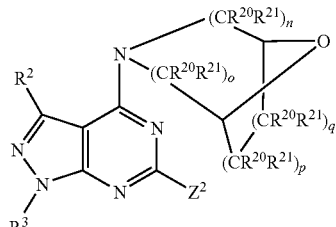
(VI)

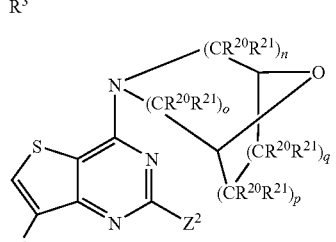
(VII)

and either:
b) reacting the compound of Formula (VI) or the compound of Formula (VII), with a boronic acid of the structure $(R^1)_m$—Ar(OH)$_2$, with a boronic pinacol ester of the structure $(R^1)_m$—Ar(OC(CH$_3$)$_2$—)$_2$, or with a boronic ester of the structure $(R^1)_m$—Ar(OC$_1$-C$_6$alkyl)$_2$;
wherein each $R^1$, m, and Ar as defined above for Formula (I) or Formula (II);

thereby providing a compound of the Formula (VIII) or Formula (IX):

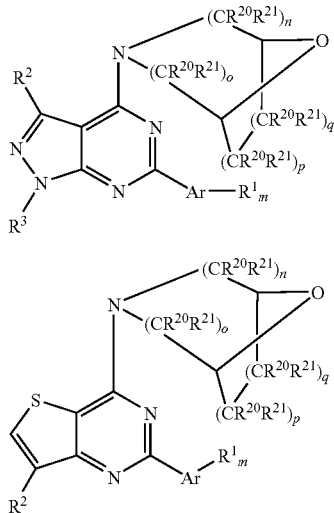

or:
(c) reacting the compound of Formula (VI) or of Formula (VII) with an amine of Formula: $(R^1)_m$—Ar—$NH_2$;
thereby providing a compound of the Formula (X) or of Formula (XI):

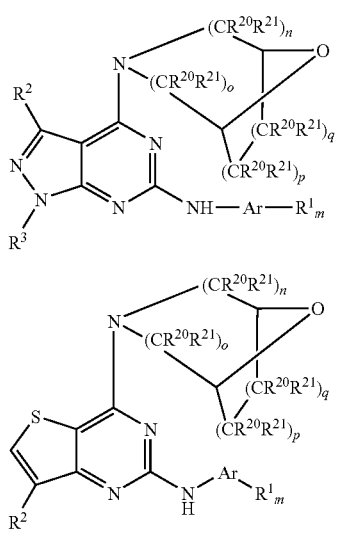

or pharmaceutically acceptable salts thereof.

The invention also includes pharmaceutical compositions comprising an effective amount of a pyrazolopyrimidine or thienopyrimidine compound and a pharmaceutically acceptable carrier. The invention includes a pyrazolopyrimidine or thienopyrimidine compound when provided as a pharmaceutically acceptable prodrug, hydrated salt, such as a pharmaceutically acceptable salt, or mixtures thereof.

Representative "pharmaceutically acceptable salts" include but are not limited to, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

An "effective amount" when used in connection a pyrazolopyrimidine or thienopyrimidine compound of this invention is an amount effective for treating or preventing a disease associated with mTOR.

The following abbreviations are used herein and have the indicated definitions: ACN is acetonitrile, AcOH is acetic acid, and ATP is adenosine triphosphate. Celite™ is flux-calcined diatomaceous earth. Celite™ is a registered trademark of World Minerals Inc. CHAPS is 3[(3-cholamidopropyl)dimethylammonio]-propanesulfonic acid, DEAD is diethyl azodicarboxylate, DIAD is diisopropylazodicarboxylate, DMAP is dimethyl aminopyridine, DMF is N,N-dimethylformamide, DMSO is dimethylsulfoxide, DPBS is Dulbecco's Phosphate Buffered Saline Formulation, EDTA is ethylenediaminetetraacetic acid, ESI is Electrospray Ionization, EtOAc is ethyl acetate, EtOH is ethanol, HEPES is 4-(2-hydroxyethyl)-1-piperazineethanesulfonic acid, GMF is Glass, Hunig's Base is diisopropylethylamine, HPLC is high pressure liquid chromatography, LPS is lipopolysaccharide. Magnesol™ is a hydrated, synthetic, amorphous magnesium silicate. Magnesol™ is a registered trademark of the Dallas Group of America Inc. MeCN is acetonitrile, MeOH is methanol, MS is mass spectrometry, $NEt_3$ is triethylamine, NMR is nuclear magnetic resonance, PBS is phosphate-buffered saline (pH 7.4), RPMI 1640 is a buffer (Sigma-Aldrich Corp., St. Louis, Mo., USA), SDS is dodecyl sulfate (sodium salt), SRB is Sulforhodamine B, TCA is tricholoroacetic acid, TFA is trifluoroacetic acid, THF is tetrahydrofuran, TLC is thin-layer chromatography, and TRIS is tris(hydroxymethyl) aminomethane.

The following definitions are used in connection with the pyrazolopyrimidine and thienopyrimidine compounds of the present invention. In general, the number of carbon atoms present in a given group is designated "$C_x$-$C_y$", where x and y are the lower and upper limits, respectively. For example, a group designated as "$C_1$-$C_6$" contains from 1 to 6 carbon atoms.

The term "acyl" refers to groups of formula —C(=O)—X, where X is straight, branched, or cyclic alkyl, straight, branched, or cyclic alkenyl, straight, branched, or cyclic alkynyl, $C_6$-$C_{14}$aryl, —C(=O)—($C_1$-$C_8$alkyl), a 5 to 7 membered aromatic or non-aromatic heterocyclic ring, or —C(=O)—OH, wherein each of the foregoing except —C(=O)—OH is optionally substituted with from one to three substituents independently selected from halogen, hydroxyl, $C_1$-$C_3$alkoxy, CN, $NH_2$, $C_1$-$C_6$mono-alkylamino and $C_1$-$C_6$di-alkylamino. The number of carbon atoms in the acyl group can be from 1 to 12 ("$C_1$-$C_{12}$acyl"), from 1 to 8 ("$C_1$-$C_8$acyl"), from 1 to 6 ("$C_1$-$C_6$acyl"), or from 1 to 4 ("$C_1$-$C_4$acyl"). Examples of acyl groups include, without limitation, acetyl-, benzoyl-, propionyl-, isobutyryl-, oxalyl-, morpholinylcarbonyl, and the like.

The term "alkoxy" refers to a group of formula —O-(alkyl). The number of carbon atoms in the alkoxy group can be from 1 to 12 ("$C_1$-$C_{12}$alkoxy"), from 1 to 8 ("$C_1$-$C_8$alkoxy"), from 1 to 6 ("$C_1$-$C_6$alkoxy"), or from 1 to 4 ("$C_1$-$C_4$alkoxy"). Examples of alkoxy groups include, without limitation, methoxy, ethoxy, n-propoxy, 1-propoxy, n-butoxy and t-butoxy.

The term "alkoxycarbonyl" refers to a group of formula —C(=O)-(alkoxy). The number of carbon atoms in the alkoxycarbonyl group can be from 1 to 12 ("$C_1$-$C_{12}$alkoxycarbonyl"), from 1 to 8 ("$C_1$-$C_8$alkoxycarbonyl"), from 1 to 6 ("$C_1$-$C_6$alkoxycarbonyl"), or from 1 to 4 ("$C_1$-$C_4$alkoxycarbonyl"). Examples of alkoxycarbonyl groups include, without limitation, t-butoxycarbonyl—(TBOC) and benzyloxycarbonyl (BOC).

The terms "alkylene", "alkenylene", and "alkynylene" are intended to mean the same residues as alkyl, alkenyl, and alkynyl, but having two points of attachment within a chemical structure. Examples of alkylene groups include, without limitation, ethylene (—$CH_2CH_2$—), propylene (—$CH_2CH_2CH_2$—), and dimethylpropylene (—$CH_2C(CH_3)_2CH_2$—). Likewise, examples of alkenylene groups include, without limitation, ethenylene (—CH=CH—) and propenylene (—CH=CH—$CH_2$—). Examples of alkynylene groups include, without limitation, ethynylene (—C≡C—) and propynylene (—CH≡CH—$CH_2$—).

The term "alkyl" refers to a hydrocarbon chain that may be a straight or branched, containing the indicated number of carbon atoms. For example, $C_1$-$C_{10}$ indicates that the group can have from 1 to 10 (inclusive) carbon atoms. In the absence of any numerical designation, "alkyl" is a chain (straight or branched) having 1 to 6 (inclusive) carbon atoms. In general, alkyl groups can have from 1-3 carbon atoms ($C_1$-$C_3$alkyl), from 1-5 carbon atoms ($C_1$-$C_5$ alkyl), from 1-6 carbon atoms ($C_1$-$C_6$alkyl), from 1-8 carbon atoms ($C_1$-$C_8$alkyl), or from 1-12 carbon atoms ($C_1$-$C_{12}$alkyl). Examples of alkyl groups include, without limitation, methyl, ethyl, propyl, butyl, pentyl, hexyl, isopropyl, isobutyl, sec-butyl, tert-butyl, isopentyl, neopentyl, and isohexyl.

The term "alkylcarboxy" refers to groups of formula —O—C(=O)-(alkyl) having the indicated number of carbon atoms, for example $C_1$-$C_6$alkylcarboxy. Examples of alkylcarboxy groups include but are not limited to acetoxy, ethylcarboxy, propylcarboxy, and isopentylcarboxy.

The term "alkenyl" refers to an alkyl group as defined above that contains the specified number of carbon atoms, and at least one carbon-carbon double bond. For example, "$C_2$-$C_6$alkenyl" indicates alkyl groups having from 2 to 6 carbon atoms, and at least one double bond. Examples of alkenyl groups include, without limitation, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene and 5-decene.

The term "alkynyl" refers to an alkyl group as defined above that contains at least one carbon-carbon triple bond. For example, "$C_2$-$C_{10}$alkenyl" and "$C_2$-$C_{10}$alkenyl" indicate alkyl groups having from 2 to 10, and from 2 to 6, carbon atoms, respectively, and at least one triple bond. Examples of alkynyl groups include, without limitation, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-decyne, 2-decyne, 3-decyne, 4-decyne and 5-decyne.

"Haloalkyl" refers to an alkyl group, as defined above, wherein 1, 2, 3, 4, 5 or 6 of the alkyl group's hydrogen atoms have been replaced independently with —F, —Cl, —Br or —I. Representative examples of haloalkyl groups include, but are not limited to —$CH_2F$, —$CCl_3$, —$CF_3$, —$CH_2CF_3$, —$CH_2Cl$, —$CH_2CH_2Br$, —$CH_2CH_2I$, —$CH_2CH_2CH_2F$, —$CH_2CH_2CH_2Cl$, —$CH_2CH_2CH_2CH_2Br$, —$CH_2CH_2CH_2CH_2$—I, —$CH_2CH_2CH_2CH_2CH_2Br$, —$CH_2CH_2CH_2CH_2CH_2I$, —$CH_2CH(Br)CH_3$, —$CH_2CH(Cl)CH_2CH_3$, —$CH(F)CH_2CH_3$ and —$C(CH_3)_2(CH_2Cl)$.

"Alkylamino" refers to a group of formula —NH(alkyl) where alkyl is as defined above. Representative examples of an aminoalkyl group include, but are not limited to —$NHCH_3$, —$NHCH_2CH_3$, —$NHCH_2CH_2CH_3$, —$NHCH_2CH_2CH_2CH_3$, —$NHCH(CH_3)_2$, —$NHCH_2CH(CH_3)_2$, —$NHCH(CH_3)CH_2CH_3$ and —NH—$C(CH_3)_3$.

"Arylamino" refers to a group of formula —NH-aryl, wherein "aryl" is as defined below. In some embodiments, the arylamino groups have from 6 to 14 carbon atoms. Examples of arylamino groups include, but are not limited to, phenylamino (anilido), naphth-1-yl-amino, naphth-2-yl-lamino and the like.

"Dialkylamino" refers to a group of formula —N(alkyl)(alkyl), wherein each alkyl group is independently selected and is as defined above. Representative examples of dialkylamino groups include, but are not limited to, —$N(CH_3)_2$, —$N(CH_2CH_3)(CH_3)$, —$N(CH_2CH_3)_2$, —$N(CH_2CH_2CH_3)_2$, —$N(CH_2CH_2CH_2CH_3)_2$, —$N(CH(CH_3)_2)_2$, —$N(CH(CH_3)_2)(CH_3)$, —$N(CH_2CH(CH_3)_2)_2$, —$NH(CH(CH_3)CH_2CH_3)_2$, —$N(C(CH_3)_3)_2$, —$N(C(CH_3)_3)(CH_3)$, and —$N(CH_3)(CH_2CH_3)$.

"Aryl" refers to a hydrocarbon ring system having the specified number of carbon atoms, which contains at least one aromatic ring. For example, "$C_6$-$C_{14}$aryl" indicates such a system having from 6 to 14 ring carbon atoms. Examples of aryl groups include, but are not limited to phenyl, naphthyl, biphenyl, anthryl, tetrahydronaphthyl, fluorenyl, indanyl, biphenylenyl, and acenaphthenyl groups. As used herein, "aryl" is intended to include such ring systems wherein two or more rings are joined by a single bond, such as biphenyl.

"Arylalkyl" refers to a group of formula -(alkyl)-aryl, where aryl and alkyl are as defined above. In some embodiments, the arylalkyl groups have from 7 to 20 carbon atoms. Examples of arylalkyl groups include benzyl, 1-phenylethyl, 2-phenylethyl, 3-phenylpropyl, 2-phenylpropyl, 1-naphthylmethyl, 2-naphthylmethyl and the like.

"N-alkylamido" refers to a group of formula —NHC(O)-(alkyl), wherein alkyl is as defined above. The term —N—($C_1$-$C_6$)alkylamido indicates such a group having from 1-6 carbon atoms in the alkyl portion thereof. Representative examples of a N—($C_1$-$C_6$)alkylamido groups include, but are not limited to, —$NHC(O)CH_3$, —$NHC(O)CH_2CH_3$, —$NHC(O)CH_2CH_2CH_3$, —$NHC(O)CH_2CH_2CH_2CH_3$, —$NHC(O)CH_2CH_2CH_2CH_2CH_3$, —$NHC(O)CH(CH_3)_2$, —$NHC(O)CH_2CH(CH_3)_2$, —$NHC(O)CH(CH_3)CH_2CH_3$, —$NHC(O)$—$C(CH_3)_3$ and —$NHC(O)CH_2C(CH_3)_3$.

"Alkylcarboxamido" or "alkylcarboxyamido" refer to a group of formula —C(O)NH-(alkyl), wherein alkyl is as defined above. Representative examples of such a group include, but are not limited to —$C(O)NHCH_3$, —$C(O)NHCH_2CH_3$, —$C(O)NHCH_2CH_2CH_3$, —$C(O)NHCH_2CH_2CH_2CH_3$, —$C(O)NHCH_2CH_2CH_2CH_2CH_3$, —C(O)NHCH(CH$_3$)$_2$, —C(O)NHCH$_2$CH(CH$_3$)$_2$, —C(O)NHCH(CH$_3$)CH$_2$CH$_3$, —C(O)NH—C(CH$_3$)$_3$ and —C(O)NHCH$_2$C(CH$_3$)$_3$.

The term "halo" or "halogen" is intended to denote —F, —Cl, —Br or —I.

The term "heteroaryl" refers to mono and bicyclic aromatic groups of 5 to 10 atoms containing 1-6 heteroatoms independently selected from oxygen, sulfur and nitrogen. Examples of monocyclic heteroaryl radicals include, but are not limited to, oxazinyl, thiazinyl, diazinyl, triazinyl, tetrazinyl, imidazolyl, tetrazolyl, isoxazolyl, furanyl, furazanyl, oxazolyl, thiazolyl, thiophenyl, pyrazolyl, triazolyl, pyrimidinyl, N-pyridyl, 2-pyridyl, 3-pyridyl and 4-pyridyl. Examples of bicyclic heteroaryl radicals include but are not limited to, benzimidazolyl, indolyl, isoquinolinyl, indazolyl, quinolinyl, quinazolinyl, purinyl, benzisoxazolyl, benzoxazolyl, benzthiazolyl, benzodiazolyl, benzotriazolyl, isoindolyl and indazolyl.

The term "heteroatom" as used herein designates a sulfur, nitrogen, or oxygen atom.

As used herein, the term "hydroxyalkyl" or "hydroxylalkyl" is intended to mean an alkyl group as defined herein, in which one, two or three hydrogen atoms thereof have been replaced with a hydroxyl (OH) group. The term "C$_1$-C$_6$hydroxyalkyl" or "C$_1$-C$_6$hydroxylalkyl" is intended to indicate such a group having from 1 to 6 carbon atoms. Examples of hydroxyalkyl groups include, for example, —CH$_2$OH, —CH$_2$CH$_2$OH, —CH$_2$CH$_2$CH$_2$OH, —CH$_2$CH(OH)CH$_2$OH, —CH$_2$CH(OH)CH$_3$, —CH(CH$_3$)CH$_2$OH and higher homologs.

A "subject" is a mammal, e.g., a human, mouse, rat, guinea pig, dog, cat, horse, cow, pig, or non-human primate, such as a monkey, chimpanzee, baboon or rhesus.

"Alkylcarboxyl-" refers to an alkyl group, defined above, attached to the parent structure through the oxygen atom of a carboxyl (C(O)—O—) functionality. Examples of (C$_1$-C$_6$alkyl)carboxyl- include acetoxy, propionoxy, propylcarboxyl, and isopentylcarboxyl.

The term "carbocycle" denotes a non-aromatic hydrocarbon ring. Additionally, any two hydrogen atoms on the same carbon atom of the carbocyclic ring may be replaced by an oxygen atom to form an oxo (=O) substituent, or the two hydrogen atoms may be replaced by an alkylenedioxy group so that the alkylenedioxy group, when taken together with the carbon atom to which it is attached, forms a 5- to 7-membered heterocycle containing two oxygen atoms. Representative examples of C$_3$-C$_8$carbocycles include, but are not limited to, cyclopropyl, cyclobutyl, cyclopentyl, cyclohexyl, cycloheptyl and cyclooctyl.

A "bicyclic carbocycle" is a non-aromatic hydrocarbon ring system containing two rings. Additionally, each of any two hydrogen atoms on the same carbon atom of the bicyclic carbocycle rings may be replaced by an oxygen atom to form an oxo (=O) substituent or the two hydrogen atoms may be replaced by an alkylenedioxy group so that the alkylenedioxy group, when taken together with the carbon atom to which it is attached, form a 5- to 7-membered heterocycle containing two oxygen atoms. Representative examples of a C$_6$-C$_{10}$carbocycles include, but are not limited to, cis-1-decalinyl, trans 2-decalinyl, cis-4-perhydroindanyl, 2,3-dihydro-1H-inden-1-yl, 1,2,3,4-tetrahydronaphthalen-1-yl, and trans-7-perhydroindanyl.

"(Heteroaryl)alkyl-" refers to an alkyl group, as defined above, wherein one or more of the alkyl group's hydrogen atoms has been replaced with a heteroaryl-group as defined above. Examples of (C$_1$-C$_9$heteroaryl)alkyl-moieties include 2-pyridylmethyl, 2-thiophenylethyl, 3-pyridylpropyl, 2-quinolinylmethyl, 2-indolylmethyl, and the like. A (heteroaryl)alkyl group can be unsubstituted or substituted with one or more of the following groups: halogen, H$_2$N—, hydroxyl, (C$_1$-C$_6$alkyl)amino-, di(C$_1$-C$_6$alkyl)amino-, (C$_1$-C$_6$alkyl)C(O)N(C$_1$-C$_3$alkyl)-, (C$_1$-C$_6$alkyl)carboxyamido-, HC(O)NH—, H$_2$NC(O)—, (C$_1$-C$_6$alkyl)NHC(O)—, di(C$_1$-C$_6$alkyl)NC(O)—, NC—, hydroxyl, C$_1$-C$_6$alkoxy-, C$_1$-C$_6$alkyl-, HO$_2$C—, (C$_1$-C$_6$alkoxy)carbonyl-, (C$_1$-C$_6$alkyl)C(O)—, C$_6$-C$_{14}$aryl-, C$_1$-C$_9$heteroaryl-, C$_3$-C$_8$cycloalkyl-, C$_1$-C$_6$haloalkyl-, C$_1$-C$_6$aminoalkyl-, (C$_1$-C$_6$alkyl)carboxyl-, C$_1$-C$_6$carboxyamidoalkyl-, or O$_2$N—.

"Heterocycle" or "heterocyclyl-" refers to 3-10-membered monocyclic, fused bicyclic, and bridged bicyclic groups containing at least one heteroatom selected from oxygen, sulfur and nitrogen. A heterocycle may be saturated or partially saturated. Exemplary C$_1$-C$_9$heterocyclyl-groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, oxazine, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane. The contemplated heterocycle rings or ring systems have a minimum of 3 members. Therefore, for example, C$_1$heterocyclyl-radicals would include but are not limited to oxaziranyl, diaziridinyl, and diazirinyl, C$_2$heterocyclyl-radicals include but are not limited to aziridinyl, oxiranyl, and diazetidinyl, C$_9$heterocyclyl-radicals include but are not limited to azecanyl, tetrahydroquinolinyl, and perhydroisoquinolinyl.

"Bridged heterobicyclyl-group containing at least one oxygen atom, at least one nitrogen atom, and optionally additional heteroatoms selected from oxygen, sulfur and nitrogen, and is connected to the thienopyrimidinyl or pyrazolopyrimidinyl group through one of the nitrogen atoms;" refers to 5-10-membered bridged bicyclic groups containing at least one nitrogen atom, one oxygen atom, and optionally additional heteroatom selected from oxygen, sulfur and nitrogen. A bridged heterobicyclyl-group containing at least one oxygen atom, at least one nitrogen atom, and optionally additional heteroatoms selected from oxygen, sulfur and nitrogen, and is connected to the thienopyrimidinyl or pyrazolopyrimidinyl group through one of the nitrogen atoms; may be saturated or partially saturated. Exemplary bridged heterobicyclyl-containing at least one oxygen atom, at least one nitrogen atom, and connected through one of the nitrogen atom include but are not limited to 2-oxa-5-azabicyclo[2.2.1]heptane, 2-oxa-5-azabicyclo[2.2.2]octane, 7-oxa-2,5-diazabicyclo[2.2.2]octane, 2,7-dioxa-5-azabicyclo[2.2.2]octane, 5,7-dioxa-2-azabicyclo[2.2.2]octane, 3-oxa-6-azabicyclo[3.1.1]heptane, 6-oxa-3-azabicyclo[3.1.1]heptane, 6-oxa-3,8- diazabicyclo[3.2.1]octane, 3,6-dioxa-8-azabicyclo[3.2.1]octane, 3-oxa-8-azabicyclo[3.2.1]octan-8-yl, 6,8-dioxa-3-azabicyclo[3.2.1]octane, 6,8-dioxa-3-azabicyclo[3.2.1]octane, 8-oxa-3-azabicyclo[3.2.1]octan-3-yl, 3-oxa-7,9-diazabicyclo[3.3.1]nonane, 7-methyl-3-oxa-7,9-diazabicyclo[3.3.1]nonan-9-yl, 9-oxa-3,7-diazabicyclo[3.3.1]non-3-yl, 9-oxa-3-azabicyclo[3.3.1]nonan-3-yl, 3-oxa-9-azabicyclo[3.3.1]nonan-9-yl, and 3,7-dioxa-9-azabicyclo[3.3.1]nonan-9-yl. The contemplated heterocycle rings or ring systems have a minimum of 5 members. Therefore, for example, $C_5$heterobicyclyl-radicals include but are not limited to 2-oxa-5-azabicyclo[2.2.1]heptan-5-yl and 6,8-dioxa-3-azabicyclo[3.2.1]octan-3-yl. $C_6$heterobicyclyl-radicals include but are not limited to 2-oxa-5-azabicyclo[2.2.2]octan-5-yl, 3-oxa-8-azabicyclo[3.2.1]octan-8-yl, 8-oxa-3-azabicyclo[3.2.1]octan-3-yl, 9-oxa-3,7-diazabicyclo[3.3.1]non-3-yl, 7-methyl-3-oxa-7,9-diazabicyclo[3.3.1]nonan-9-yl, 3-oxa-7,9-diazabicyclo[3.3.1]nonan-7-yl, 3-oxa-7,9-diazabicyclo[3.3.1]nonan-9-yl, and 3,7-dioxa-9-azabicyclo[3.3.1]nonan-9-yl. $C_7$heterobicyclyl-radicals include but are not limited to 9-oxa-3-azabicyclo[3.3.1]nonan-3-yl and 3-oxa-9-azabicyclo[3.3.1]nonan-9-yl.

"Heterocyclyl(alkyl)-" refers to an alkyl group, as defined above, wherein one or more of the alkyl group's hydrogen atoms has been replaced with a heterocycle group as defined above. Heterocyclyl($C_1$-$C_6$alkyl)-moieties include 1-piperazinylethyl, 4-morpholinylpropyl, 6-piperazinylhexyl, and the like. A heterocyclyl(alkyl) group can be unsubstituted or substituted with one or more of the following groups: halogen, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, hydroxyl, $C_1$-$C_6$alkoxy-, $C_1$-$C_6$alkyl-, $HO_2C$—, ($C_1$-$C_6$alkoxy)carbonyl-, ($C_1$-$C_6$alkyl)C(O)—, 4- to 7-membered monocyclic heterocycle, $C_6$-$C_{14}$aryl-, $C_1$-$C_9$heteroaryl-, or $C_3$-$C_8$cycloalkyl-.

The term "monocyclic heterocycle" refers to a monocyclic non-aromatic cyclic hydrocarbon, in which 1-4 of the ring carbon atoms have been independently replaced with an N, O or S atom. The monocyclic heterocyclic ring can be attached via a nitrogen, sulfur, or carbon atom. In some embodiments, the monocyclic heterocycle can have 3-7 ring atoms (i.e., a 3- to 7-membered monocyclic heterocycle), or 4-7 ring atoms (i.e., a 4- to 7-membered monocyclic heterocycle). Representative examples of 3- to 7-membered monocyclic heterocycle groups include, but are not limited to, aziridine, oxirane, oxirene, thiirane, piperidinyl, piperazinyl, morpholinyl, oxazinyl, and pyrrolidinyl. Representative examples of 4- to 7-membered monocyclic heterocycle groups include, but are not limited to, pyrroline, dihydrofuran, tetrahydrofuran, dihydrothiophene, tetrahydrothiophene, dithiolane, 1,2,3,6-tetrahydropyridine-1-yl, tetrahydropyran, pyran, thiane, thiine, piperazine, oxazine, 5,6-dihydro-4H-1,3-oxazin-2-yl, piperidinyl, piperazinyl, morpholinyl, oxazinyl, and pyrrolidinyl.

A "nitrogen containing 3- to 7-membered monocyclic heterocycle" refers to a 3- to 7-membered monocyclic heterocycle as described above, that contains at least one ring nitrogen atom. Representative examples of nitrogen-containing-3- to 7-membered monocyclic heterocyclic rings include, but are not limited to, pyrroline, piperidinyl, piperazinyl, oxazinyl, 1,2,3,6-tetrahydropyridine-1-yl, 5,6-dihydro-4H-1,3-oxazin-2-yl, pyrrolidinyl, and morpholinyl.

The term "monocyclic heterocycle" refers to a monocyclic non-aromatic cyclic hydrocarbon, in which 1-4 of the ring carbon atoms have been independently replaced with an N, O or S atom. The monocyclic heterocyclic ring can be attached via a nitrogen, sulfur, or carbon atom. In some embodiments, the monocyclic heterocycle can have 3-7 ring atoms (i.e., a 3- to 7-membered monocyclic heterocycle), or 4-7 ring atoms (i.e., a 4- to 7-membered monocyclic heterocycle).

The term "bicyclic heterocycle" refers to a fused or bridged bicyclic non-aromatic hydrocarbon, in which 1-4 of the ring carbon atoms have been independently replaced with an N, O or S atom. In some embodiments, the bicyclic heterocycle can have 6-10 ring atoms (i.e., a 6- to 10-membered bicyclic heterocycle) or from 7-10 ring atoms (i.e., a 7- to 10-membered bicyclic heterocycle). Representative examples of a 6- to 10-membered bicyclic heterocycle group include, but are not limited to, 3-azabicyclo[3.1.0]hexane, 5-azabicyclo[2.1.1]hexane, 6-oxa-3-azabicyclo[3.1.0]hexane, indoline, and 2,3-dihydro-1H-indazole. Representative examples of a 7- to 10-membered bicyclic heterocycle radicals include, but are not limited to, 7-azabicyclo[2.2.1]heptane, 7-oxabicyclo[2.2.1]heptane, 6-azabicyclo[3.1.1]heptane, 3,6-diazabicyclo[3.1.1]heptane, 3-azabicyclo[3.1.1]heptane, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, tetrahydroquinolinyl, and perhydroisoquinolinyl.

A "nitrogen-containing 7- to 10-membered bicyclic heterocycle" refers to a 7- to 10-membered bicyclic heterocycle, defined above, which contains at least one ring nitrogen atom. Representative nitrogen-containing 7- to 10-membered 7-azabicyclo[2.2.1]heptane, 6-azabicyclo[3.1.1]heptane, 3,6-diazabicyclo[3.1.1]heptane, 3-azabicyclo[3.1.1]heptane, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, tetrahydroquinolinyl, perhydroisoquinolinyl, and the like.

"Perfluoroalkyl-" refers to alkyl group, defined above, having two or more fluorine atoms. Examples of a $C_1$-$C_6$ perfluoroalkyl-group include $CF_3$, $CH_2CF_3$, $CF_2CF_3$ and $CH(CF_3)_2$.

The term "—$S(O)_2$-heterocyclylalkyl" as used herein means that a heterocyclyl(alkyl)-group, as defined above, wherein one or more of the alkyl group's hydrogen atoms has been replaced with a —S(O$_2$)$_2$— diradical and linked to the core structure through the sulfur atom. Examples of —S(O)$_2$-heterocyclylalkyl moieties include piperidin-1-yl-methylsulfonyl, 2-(4-methylpiperazin-1-yl)ethylsulfonyl, 3-morpholinopropylsulfonyl, 6-(piperazin-1-yl)hexylsulfonyl, and the like.

The term "optionally substituted", unless otherwise specified, as used herein means that at least one hydrogen atom of the optionally substituted group has been substituted with the indicated substituents. Where no such substituents are named, the substituents are intended to include halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, C$_1$-C$_8$acyl, C$_6$-C$_{14}$aryl, heteroaryl, and C$_3$-C$_8$carbocycle.

The pyrazolopyrimidine and thienopyrimidine compounds of the present invention exhibit an mTOR inhibitory activity and therefore, can be utilized in order to inhibit abnormal cell growth in which mTOR plays a role. Thus, the pyrazolopyrimidine and thienopyrimidine compounds are effective in the treatment of disorders with which abnormal cell growth actions of mTOR are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the pyrazolopyrimidine and thienopyrimidine compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, etc.

As some compounds of the present invention possess an asymmetric carbon atom, the present invention includes the racemate as well as the individual enantiomeric forms of the compounds as described herein and in the claims. Mixtures of isomers of the compounds of the examples or chiral precursors thereof can be separated into individual isomers according to methods, which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high-pressure liquid chromatography columns, according to procedures described herein. Where multiple chiral centers or multiple geometric isomers or multiple tautomers or combinations of two or more such features exist in compounds of the present invention, the invention includes each combination as well as mixtures thereof. All chiral, diastereomeric, racemic forms and all geometric isomeric forms of a structure are intended, unless the specific stereochemistry or isomeric form is specifically indicated.

Certain of the compounds of the present invention can exist in unsolvated forms as well as solvated forms including hydrated forms such as monohydrate, dihydrate, trihydrate, hemihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

Therapeutic Administration

When administered to an animal, the pyrazolopyrimidine and thienopyrimidine compounds or pharmaceutically acceptable salts of the pyrazolopyrimidine and thienopyrimidine compounds can be administered neat or as a component of a composition that comprises a physiologically acceptable carrier or vehicle. A composition of the invention can be prepared using a method comprising admixing the pyrazolopyrimidine and thienopyrimidine compound or a pharmaceutically acceptable salt of the pyrazolopyrimidine and thienopyrimidine compound and a physiologically acceptable carrier, excipient, or diluent. Admixing can be accomplished using methods well known for admixing an pyrazolopyrimidine and thienopyrimidine compound or a pharmaceutically acceptable salt of the pyrazolopyrimidine and thienopyrimidine compound and a physiologically acceptable carrier, excipient, or diluent.

The present compositions, comprising pyrazolopyrimidine and thienopyrimidine compounds or pharmaceutically acceptable salts of the pyrazolopyrimidine and thienopyrimidine compounds of the invention can be administered orally. The pyrazolopyrimidine and thienopyrimidine compounds or pharmaceutically acceptable salts of pyrazolopyrimidine and thienopyrimidine compounds of the invention can also be administered by any other convenient route, for example, by infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the pyrazolopyrimidine and thienopyrimidine compound or a pharmaceutically acceptable salt of the pyrazolopyrimidine and thienopyrimidine compound into the bloodstream. The mode of administration is left to the discretion of the practitioner.

In one embodiment, the pyrazolopyrimidine and thienopyrimidine compound or a pharmaceutically acceptable salt of the pyrazolopyrimidine and thienopyrimidine compound is administered orally.

In another embodiment, the pyrazolopyrimidine and thienopyrimidine compound or a pharmaceutically acceptable salt of the pyrazolopyrimidine and thienopyrimidine compound is administered intravenously.

In another embodiment, it may be desirable to administer the pyrazolopyrimidine and thienopyrimidine compound or a pharmaceutically acceptable salt of the pyrazolopyrimidine and thienopyrimidine compound locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce the pyrazolopyrimidine and thienopyrimidine compound or a pharmaceutically acceptable salt of the pyrazolopyrimidine and thienopyrimidine compound into the central nervous system, circulatory system or gastrointestinal tract by any suitable route, including intraventricular, intrathecal injection, paraspinal injection, epidural injection, enema, and by injection adjacent to the peripheral nerve. An intraventricular catheter, for example, can facilitate intraventricular injection attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the pyrazolopyrimidine and thienopyrimidine compound or a pharmaceutically acceptable salt of the pyrazolopyrimidine and thienopyrimidine compound can be formulated as a suppository, with traditional binders and excipients such as triglycerides.

In another embodiment, the pyrazolopyrimidine and thienopyrimidine compound or a pharmaceutically acceptable salt of the pyrazolopyrimidine and thienopyrimidine compound can be delivered in a vesicle, in particular a liposome (see Langer, *Science* 249:1527-1533 (1990) and Treat et al., *Liposomes in the Therapy of Infectious Disease and Cancer* pp. 317-327 and pp. 353-365 (1989)).

In yet another embodiment, the pyrazolopyrimidine and thienopyrimidine compound or a pharmaceutically acceptable salt of the pyrazolopyrimidine and thienopyrimidine compound can be delivered in a controlled-release system or sustained-release system (see, e.g., Goodson, in *Medical Applications of Controlled Release*, vol. 2, pp. 115-138 (1984)). Other controlled or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment, a controlled- or sustained-release system can be placed in proximity of a target of the pyrazolopyrimidine and thienopyrimidine compound or a pharmaceutically acceptable salt of the pyrazolopyrimidine and thienopyrimidine compound, e.g., the reproductive organs, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment, the physiologically acceptable excipients are sterile when administered to an animal. The physiologically acceptable excipient should be stable under the conditions of manufacture and storage and should be preserved against the contaminating action of microorganisms. Water is a particularly useful excipient when the pyrazolopyrimidine and thienopyrimidine compound or a pharmaceutically acceptable salt of the pyrazolopyrimidine and thienopyrimidine compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Liquid carriers may be used in preparing solutions, suspensions, emulsions, syrups, and elixirs. The pyrazolopyrimidine and thienopyrimidine compound or pharmaceutically acceptable salt of the pyrazolopyrimidine and thienopyrimidine compound of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable physiologically acceptable excipients are described in Remington's Pharmaceutical Sciences pp. 1447-1676 (Alfonso R. Gennaro, ed., 19th ed. 1995).

In one embodiment, the pyrazolopyrimidine and thienopyrimidine compound or a pharmaceutically acceptable salt of the pyrazolopyrimidine and thienopyrimidine compound is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided pyrazolopyrimidine and thienopyrimidine compound or pharmaceutically acceptable salt of the pyrazolopyrimidine and thienopyrimidine compound. In tablets, the pyrazolopyrimidine and thienopyrimidine compound or pharmaceutically acceptable salt of the pyrazolopyrimidine and thienopyrimidine compound is mixed with a carrier having the necessary compression properties in suitable proportions and compacted in the shape and size desired. The powders and tablets can contain up to about 99% of the pyrazolopyrimidine and thienopyrimidine compound or pharmaceutically acceptable salt of the pyrazolopyrimidine and thienopyrimidine compound.

Capsules may contain mixtures of the pyrazolopyrimidine and thienopyrimidine compounds or pharmaceutically acceptable salts of the pyrazolopyrimidine and thienopyrimidine compounds with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrroldine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, the compositions can be coated to delay disintegration and absorption in the gastrointestinal tract, thereby providing a sustained action over an extended period of time. Selectively permeable membranes surrounding an osmotically active driving compound or a pharmaceutically acceptable salt of the compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the pyrazolopyrimidine and thienopyrimidine compound or a pharmaceutically acceptable salt of the pyrazolopyrimidine and thienopyrimidine compound can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the pyrazolopyrimidine and thienopyrimidine compound or a pharmaceutically acceptable salt of the pyrazolopyrimidine and thienopyrimidine compound is to be administered by infusion, it can be dispensed, for example, with an infusion bottle containing sterile pharmaceutical grade water or saline. Where the pyrazolopyrimidine and thienopyrimidine compound or a pharmaceutically acceptable salt of the pyrazolopyrimidine and thienopyrimidine compound is administered by injection, an ampoule of sterile water for injection or saline can be provided so that the ingredients can be mixed prior to administration.

In another embodiment, the pyrazolopyrimidine and thienopyrimidine compound or pharmaceutically acceptable salt of the pyrazolopyrimidine and thienopyrimidine compound can be administered transdermally through the use of a transdermal patch. Transdermal administrations include administrations across the surface of the body and the inner linings of the bodily passages including epithelial and mucosal tissues. Such administrations can be carried out using the present pyrazolopyrimidine and thienopyrimidine compounds or pharmaceutically acceptable salts of the pyrazolopyrimidine and thienopyrimidine compound s, in lotions, creams, foams, patches, suspensions, solutions, and suppositories (e.g., rectal or vaginal).

Transdermal administration can be accomplished through the use of a transdermal patch containing the pyrazolopyrimidine and thienopyrimidine compound or pharmaceutically acceptable salt of the pyrazolopyrimidine and thienopyrimidine compound and a carrier that is inert to the pyrazolopyrimidine and thienopyrimidine compound or pharmaceutically acceptable salt of the pyrazolopyrimidine and thienopyrimidine compound is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the pyrazolopyrimidine and thienopyrimidine compound or pharmaceutically acceptable salt of the pyrazolopyrimidine and thienopyrimidine compound into the blood stream, such as a semi-permeable membrane covering a reservoir containing the pyrazolopyrimidine and thienopyrimidine compound or pharmaceutically acceptable salt of the pyrazolopyrimidine and thienopyrimidine compound with or without a carrier, or a matrix containing the active ingredient.

The pyrazolopyrimidine and thienopyrimidine compounds or pharmaceutically acceptable salts of the pyrazolopyrimidine and thienopyrimidine compounds of the invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

The pyrazolopyrimidine and thienopyrimidine compound or a pharmaceutically acceptable salt of the pyrazolopyrimidine and thienopyrimidine compound can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the pyrazolopyrimidine and thienopyrimidine compound or a pharmaceutically acceptable salt of the pyrazolopyrimidine and thienopyrimidine compound, and can thus reduce the occurrence of adverse side effects.

Controlled- or sustained-release compositions can initially release an amount of the pyrazolopyrimidine and thienopyrimidine compound or a pharmaceutically acceptable salt of the pyrazolopyrimidine and thienopyrimidine compound that promptly produces the desired therapeutic or prophylactic effect, and gradually and continually release other amounts of the pyrazolopyrimidine and thienopyrimidine compound or a pharmaceutically acceptable salt of the pyrazolopyrimidine and thienopyrimidine compound to maintain this level of therapeutic or prophylactic effect over an extended period of time. To maintain a constant level of the pyrazolopyrimidine and thienopyrimidine compound or a pharmaceutically acceptable salt of the pyrazolopyrimidine and thienopyrimidine compound in the body, the pyrazolopyrimidine and thienopyrimidine compound or a pharmaceutically acceptable salt of the pyrazolopyrimidine and thienopyrimidine compound can be released from the dosage form at a rate that will replace the amount of the pyrazolopyrimidine and thienopyrimidine compound or a pharmaceutically acceptable salt of the pyrazolopyrimidine and thienopyrimidine compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or pyrazolopyrimidine and thienopyrimidine compounds.

In certain embodiments, the present invention is directed to prodrugs of the pyrazolopyrimidine and thienopyrimidine compounds or pharmaceutically acceptable salts of pyrazolopyrimidine and thienopyrimidine compounds of the present invention. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); "*Design and Application of Prodrugs*", *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

The amount of the pyrazolopyrimidine and thienopyrimidine compound or a pharmaceutically acceptable salt of the pyrazolopyrimidine and thienopyrimidine compound that is effective for treating or preventing a mTOR-related disorder. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one pyrazolopyrimidine and thienopyrimidine compound or a pharmaceutically acceptable salt of the pyrazolopyrimidine and thienopyrimidine compound is administered, the effective dosage amounts correspond to the total amount administered.

The amount of the pyrazolopyrimidine and thienopyrimidine compound or a pharmaceutically acceptable salt of the pyrazolopyrimidine and thienopyrimidine compound that is effective for treating or preventing an mTOR-related disorder will typically range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 1 mg/kg to about 20 mg/kg of body weight per day.

In one embodiment, the pharmaceutical composition is in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may be given in a single dose or in two or more divided doses.

The pyrazolopyrimidine and thienopyrimidine compound or a pharmaceutically acceptable salt of the pyrazolopyrimidine and thienopyrimidine compound can be assayed in vitro or in vivo for the desired therapeutic or prophylactic activity prior to use in humans. Animal model systems can be used to demonstrate safety and efficacy.

The present methods for treating or preventing an mTOR-related disorder, can further comprise administering another therapeutic agent to the animal being administered the pyrazolopyrimidine and thienopyrimidine compound or a pharmaceutically acceptable salt of the pyrazolopyrimidine and thienopyrimidine compound. In one embodiment, the other therapeutic agent is administered in an effective amount.

Effective amounts of the other therapeutic agents are well known to those skilled in the art. However, it is well within the skilled artisan's purview to determine the other therapeutic agent's optimal effective amount range. The pyrazolopyrimidine and thienopyrimidine compound or a pharmaceutically acceptable salt of the pyrazolopyrimidine and thienopyrimidine compound and the other therapeutic agent can act additively or, in one embodiment, synergistically. In one embodiment, of the invention, where another therapeutic agent is administered to an animal, the effective amount of the pyrazolopyrimidine and thienopyrimidine compound or a pharmaceutically acceptable salt of the pyrazolopyrimidine and thienopyrimidine compound is less than its effective amount would be where the other therapeutic agent is not administered. In this case, without being bound by theory, it is believed that the pyrazolopyrimidine and thienopyrimidine compound or a pharmaceutically acceptable salt of the pyrazolopyrimidine and thienopyrimidine compound and the other therapeutic agent act synergistically.

Figure 2:
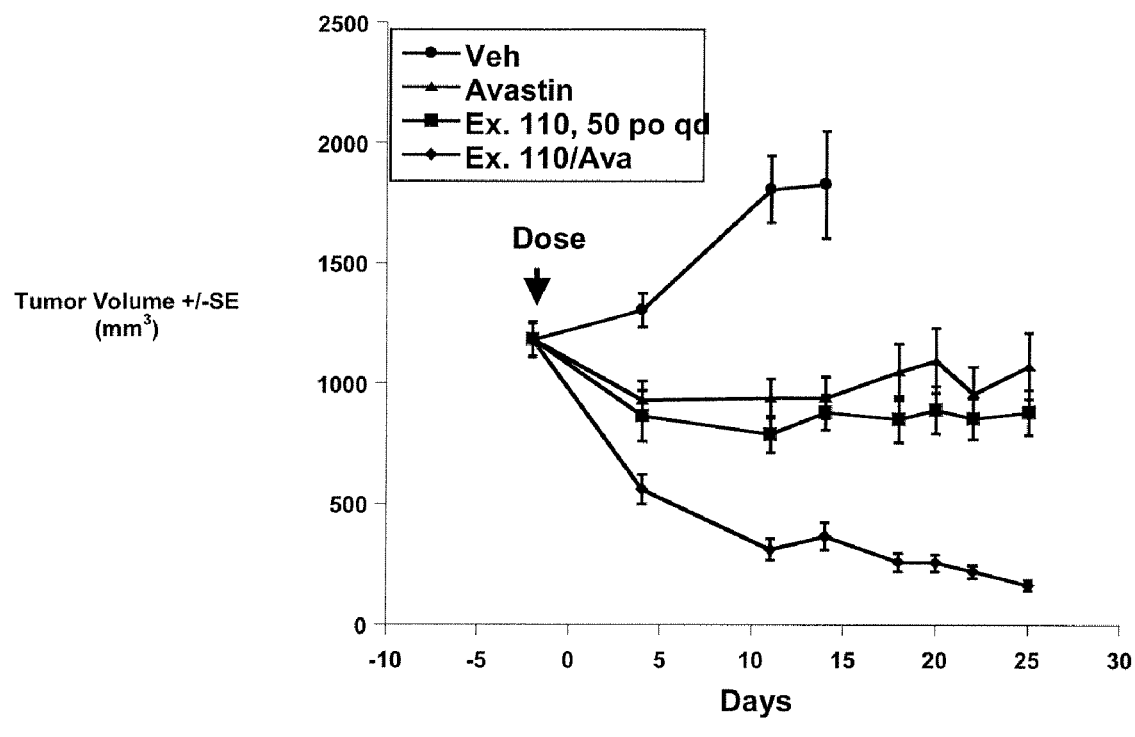
FIG. 2 shows the effect of Avastin (bevacizumab) individually, the Example 110 compound individually, and a combination of Avastin (bevacizumab) and the Example 110 compound, with specified dosing regimens, on tumor size in the A498 renal cell carcinoma model.

Suitable other therapeutic agents useful in the methods and compositions of the present invention include, but are not limited to temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, Avastin (bevacizumab), hexamethylmelamine, topotecan, tyrosine kinase inhibitors, tyrphostins, herbimycin A, genistein, erbstatin, lavendustin A, hydroxyzine, glatiramer acetate, interferon beta-1a, interferon beta-1b, and natalizumab. It has been found, surprisingly, that the compounds of the invention are combinable with Avastin (bevacizumab) and that this combination can result in synergistic reduction in tumor size. For example, FIG. 1 shows the effect of Avastin (bevacizumab) individually, the Example 105 compound individually, and a combination of Avastin (bevacizumab) and the Example 105 compound, with specified dosing regimens, on tumor size in the A498 renal cell carcinoma model. FIG. 2 shows the effect of Avastin (bevacizumab) individually, the Example 110 compound individually, and a combination of Avastin (bevacizumab) and the Example 110 compound, with specified dosing regimens, on tumor size in the A498 renal cell carcinoma model.

Other therapeutic agents useful in the methods and compositions of the present invention include, but are not limited to hydroxyzine, glatiramer acetate, interferon beta-1a, interferon beta-1b, mitoxantrone, and natalizumab.

In one embodiment, the pyrazolopyrimidine and thienopyrimidine compound or a pharmaceutically acceptable salt of the pyrazolopyrimidine and thienopyrimidine compound is administered concurrently with another therapeutic agent.

In one embodiment, a composition comprising an effective amount of the pyrazolopyrimidine and thienopyrimidine compound or a pharmaceutically acceptable salt of the pyrazolopyrimidine and thienopyrimidine compound and an effective amount of another therapeutic agent within the same composition can be administered.

In another embodiment, a composition comprising an effective amount of the pyrazolopyrimidine and thienopyrimidine compound or a pharmaceutically acceptable salt of the pyrazolopyrimidine and thienopyrimidine compound and a separate composition comprising an effective amount of another therapeutic agent can be concurrently administered. In another embodiment, an effective amount of the pyrazolopyrimidine and thienopyrimidine compound or a pharmaceutically acceptable salt of the pyrazolopyrimidine and thienopyrimidine compounds administered prior to or subsequent to administration of an effective amount of another therapeutic agent. In this embodiment, the pyrazolopyrimidine and thienopyrimidine compound or a pharmaceutically acceptable salt of the pyrazolopyrimidine and thienopyrimidine compounds administered while the other therapeutic agent exerts its therapeutic effect, or the other therapeutic agent is administered while the pyrazolopyrimidine and thienopyrimidine compound or a pharmaceutically acceptable salt of the pyrazolopyrimidine and thienopyrimidine compound exerts its preventative or therapeutic effect for treating or preventing an mTOR-related disorder.

In another embodiment, the pharmaceutically acceptable carrier is suitable for oral administration and the composition comprises an oral dosage form.

Methodologies for making the pyrazolopyrimidine and thienopyrimidine compounds of the invention are set forth in the Examples below, and generalized in Schemes 1-47 below. It should be noted that while the Schemes show exemplary substituent variables for the compounds of the invention (for example, hydrogen for each $R^{20}$ and $R^{21}$), the syntheses described in the Schemes are fully applicable to the preparation of compounds having any of the substituent variables as described herein.

Scheme 1:

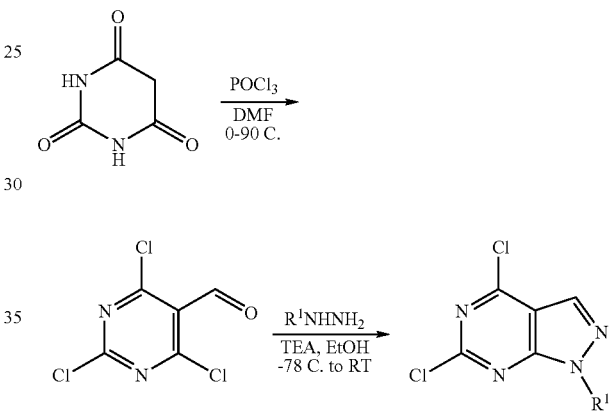

Scheme 2:

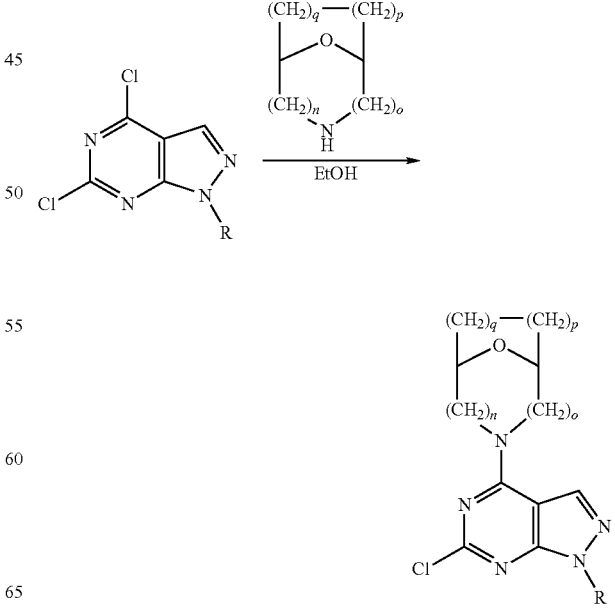

Scheme 3:
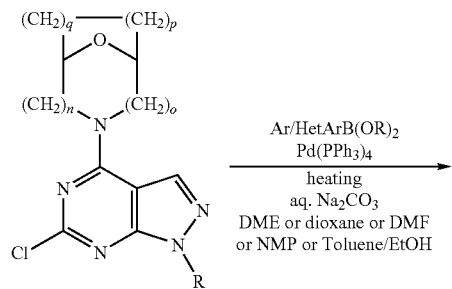
Scheme 4:
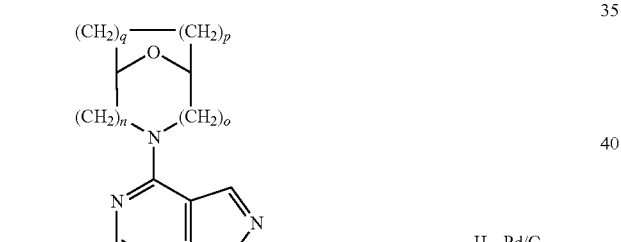
Scheme 5:
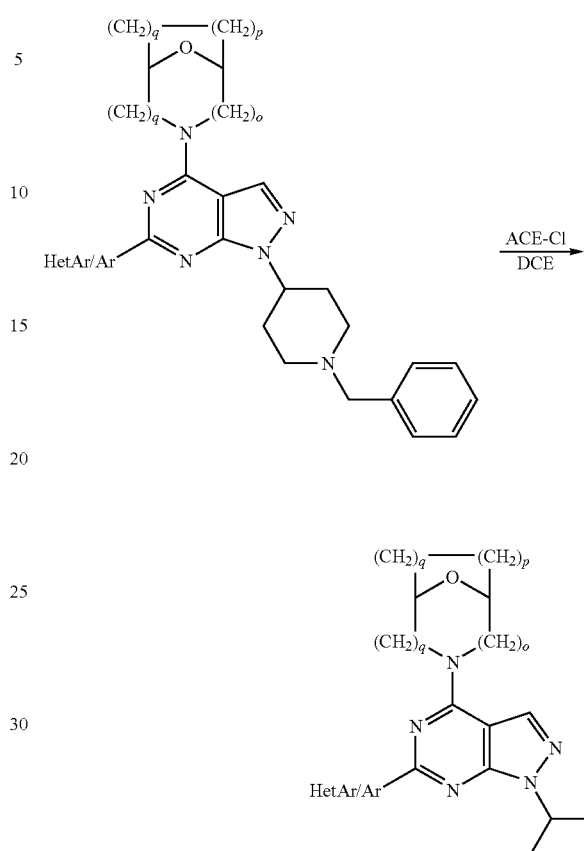
Scheme 6:
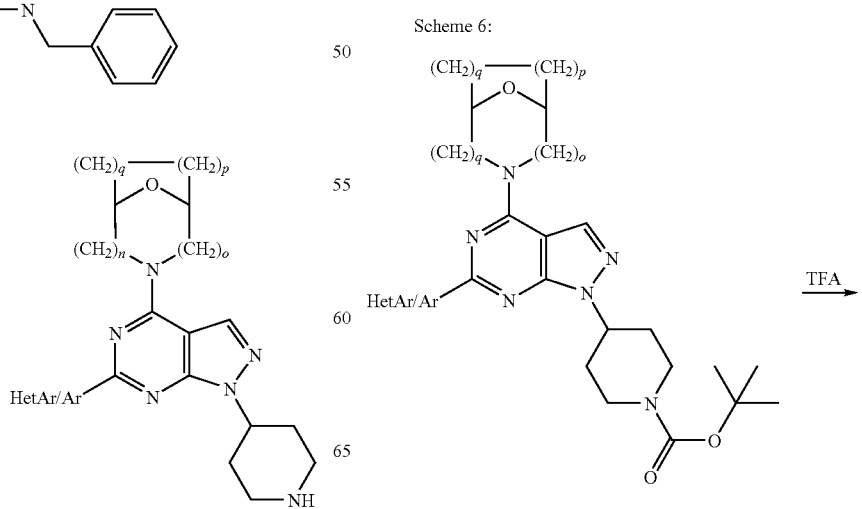

71
-continued
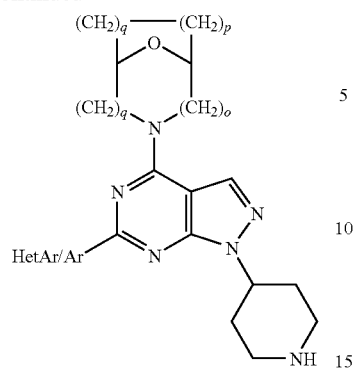
72
-continued
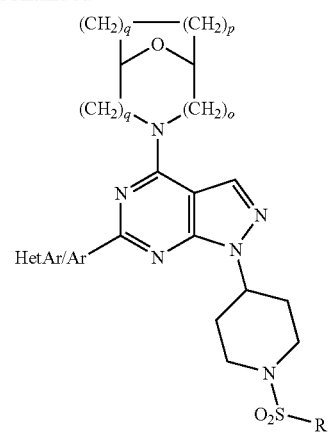
Scheme 7:
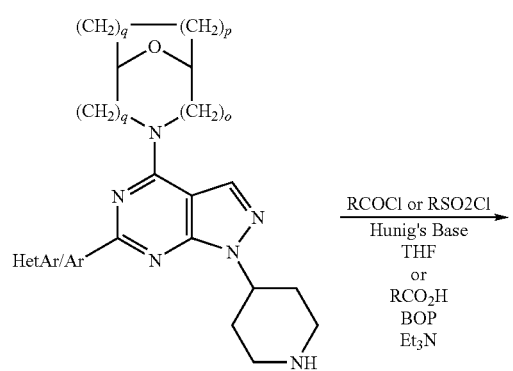
$\xrightarrow{\text{RCOCl or RSO2Cl}}$
Hunig's Base
THF
or
RCO$_2$H
BOP
Et$_3$N
Scheme 8:
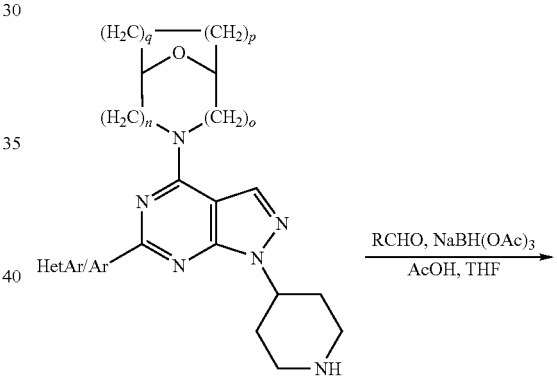
$\xrightarrow{\text{RCHO, NaBH(OAc)}_3}$
AcOH, THF
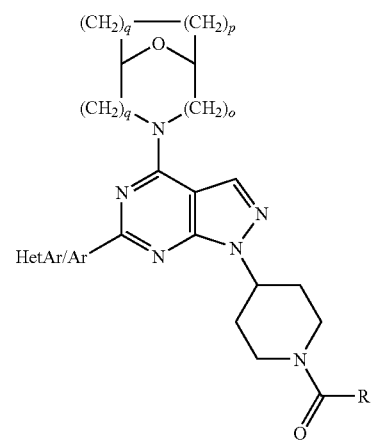
or
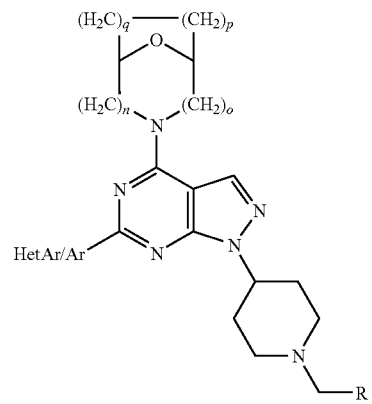

Scheme 9:
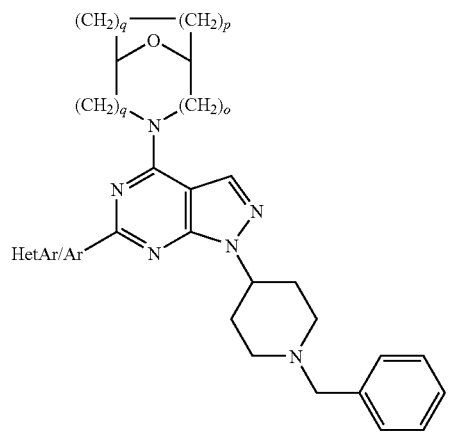
Scheme 10:
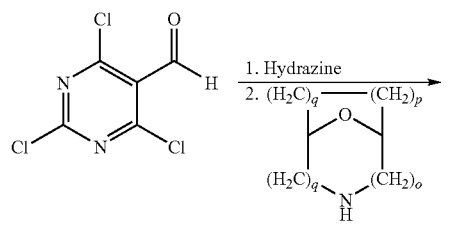
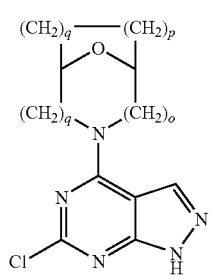 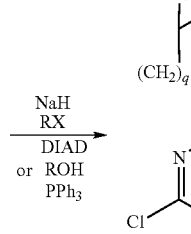
Scheme 11:
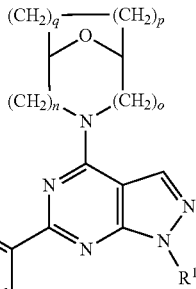
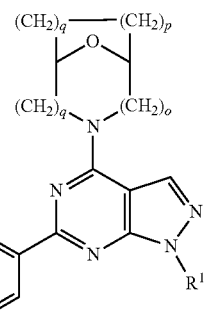
Scheme 12:
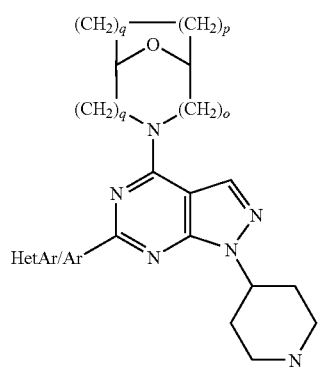
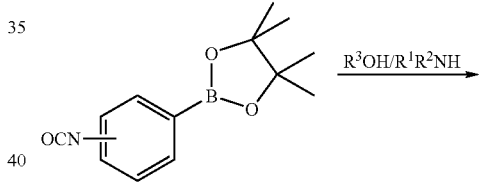
Scheme 13:
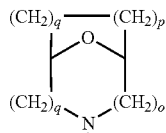
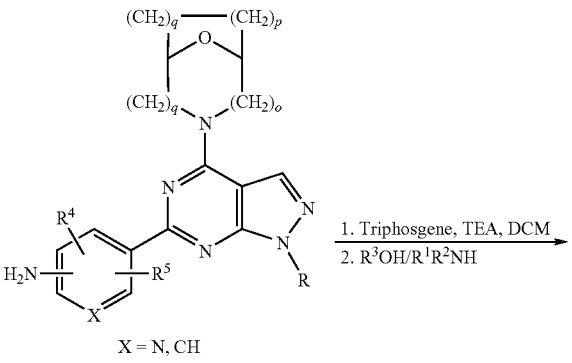

75
-continued
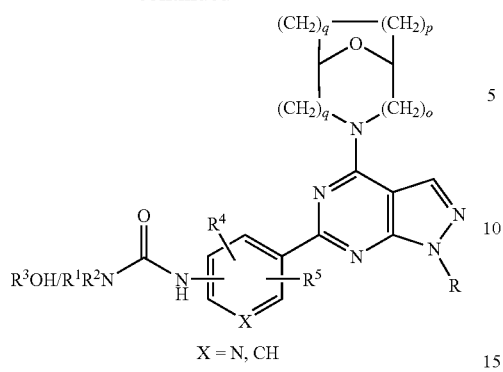
76
-continued
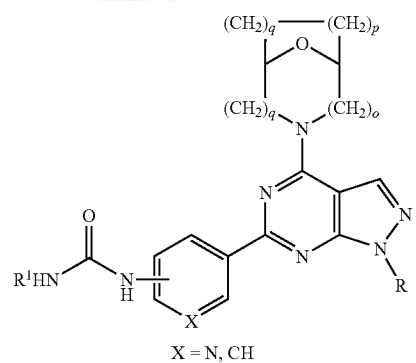
Scheme 15:
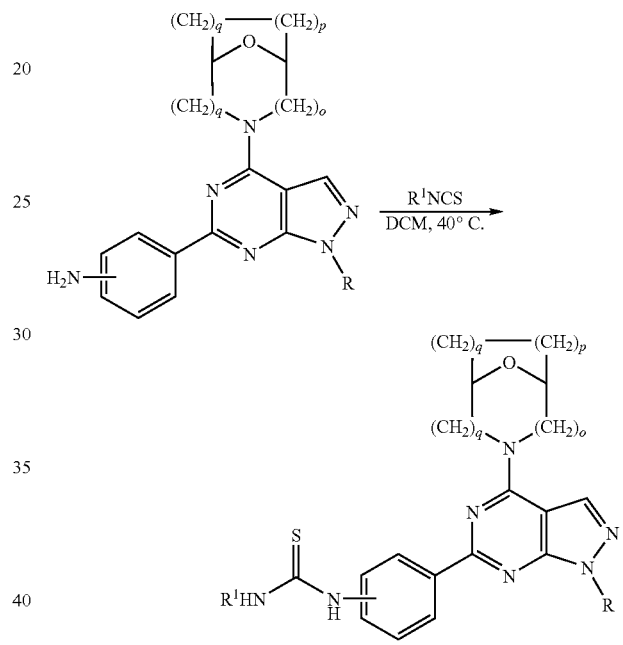
Scheme 14:
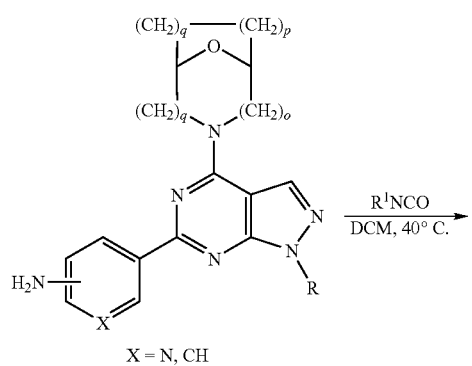
Scheme 16:
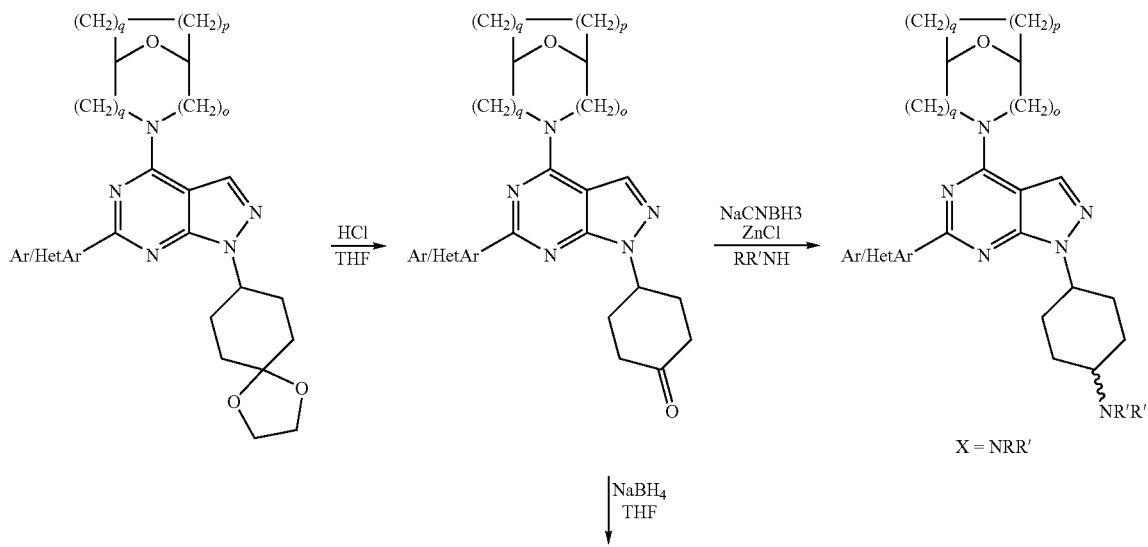

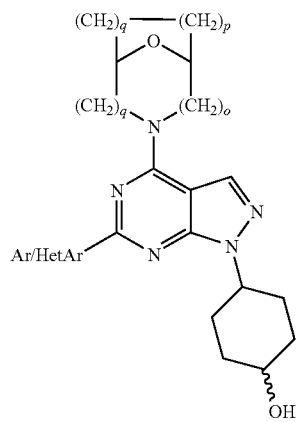
According to Scheme 16, the acetal was treated with HCl in THF to give the corresponding ketone. The ketone was treated with an amine and NaCNBH$_3$ and ZnCl$_2$ to give the desired amine. The alcohol reduction product could also be obtained.
Scheme 17:
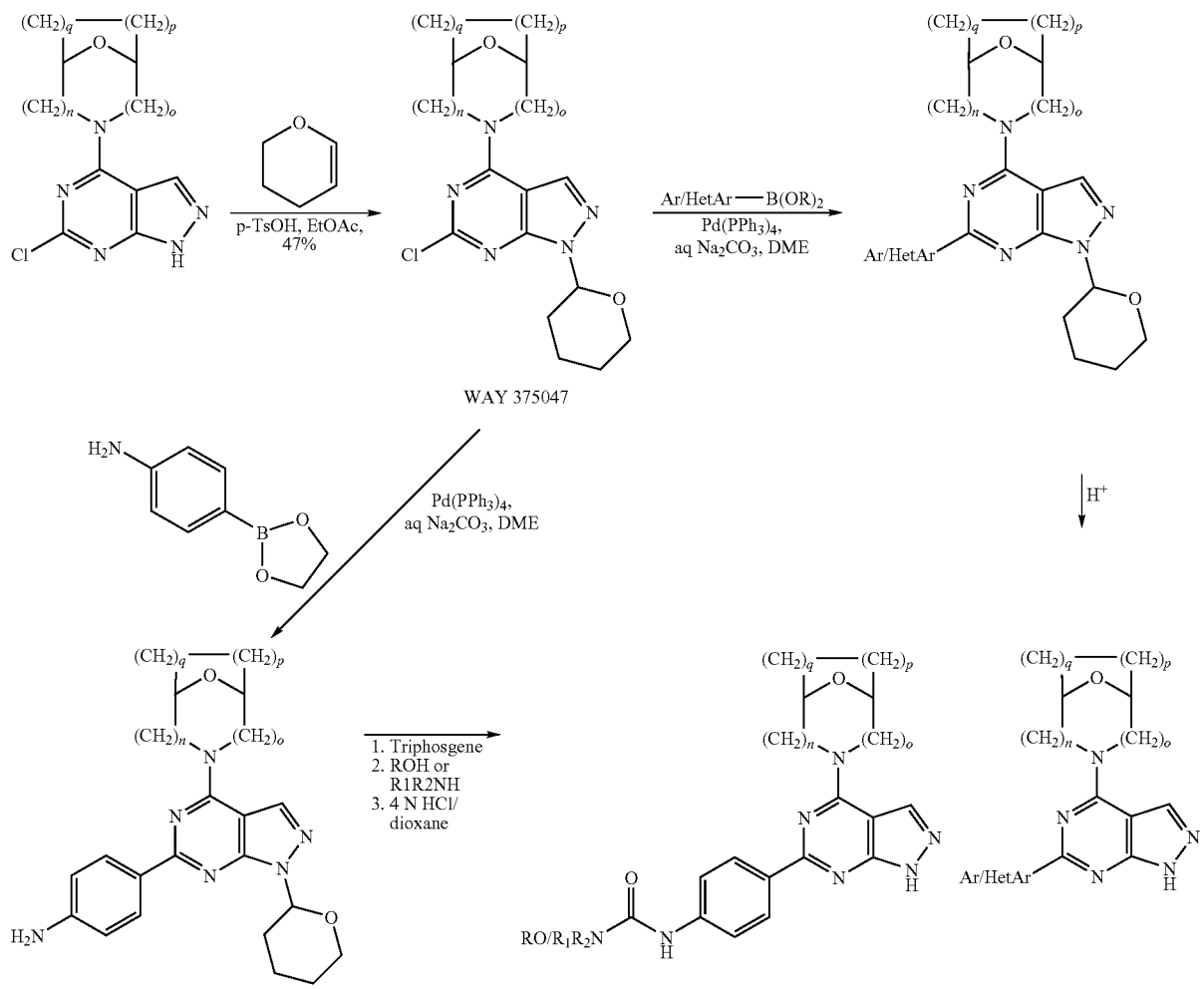

According to Scheme 17, the pyrazole nitrogen was substituted with a tetrahydropyran ring by treatment with dihydropyran in the presence of para-toluenesulfonic acid. Suzuki coupling with an arylboronic acid (Scheme 29), followed by removal of the tetrahydropyran by treatment with HCl in dioxane gave the unsubstituted pyrazole analog. Suzuki reaction with aniline boronate followed by triphosgene, alcohol or amine gave the carbamate or urea, respectively. Removal of the tetrahydropyran with acid gave the unsubstituted pyrazole.

Scheme 18:

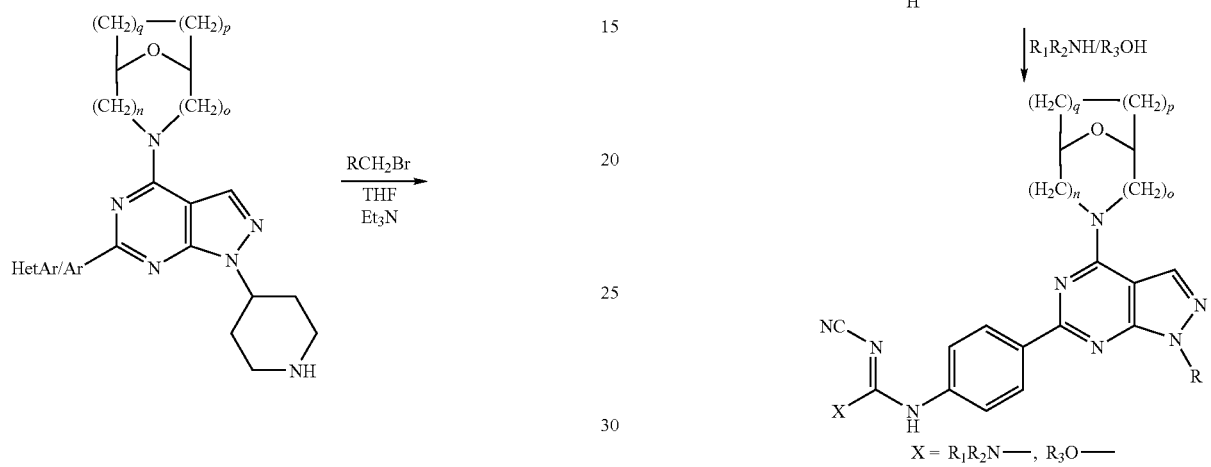

Scheme 19:

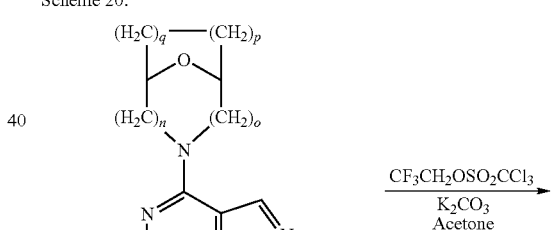

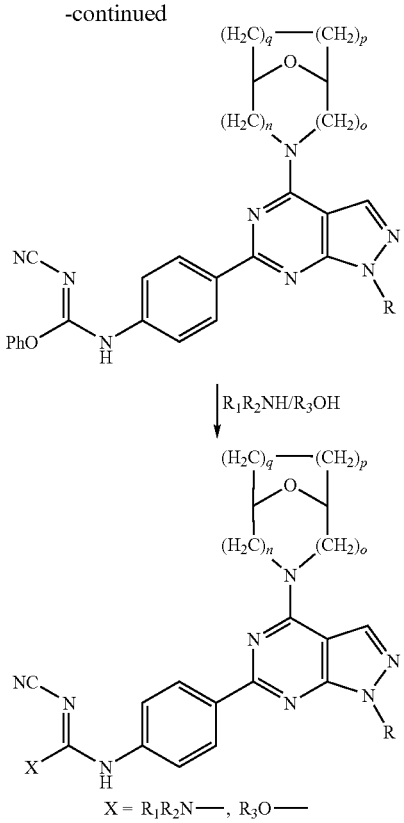

Scheme 20:

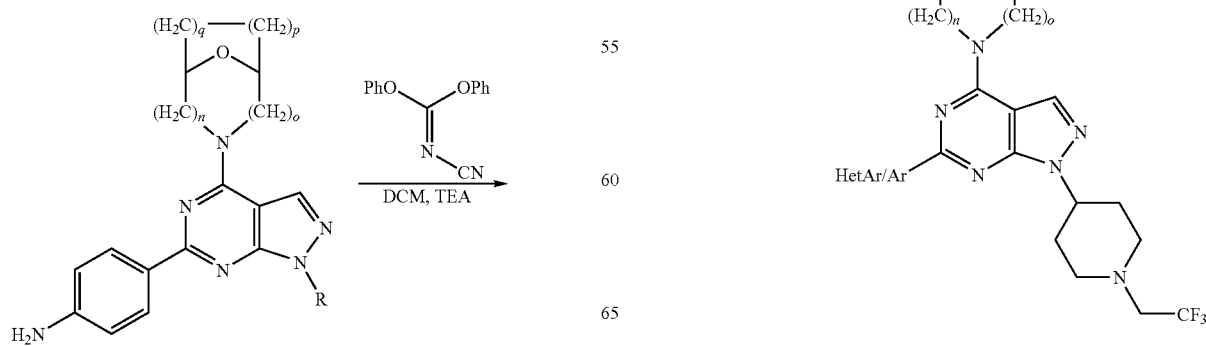

Scheme 21:
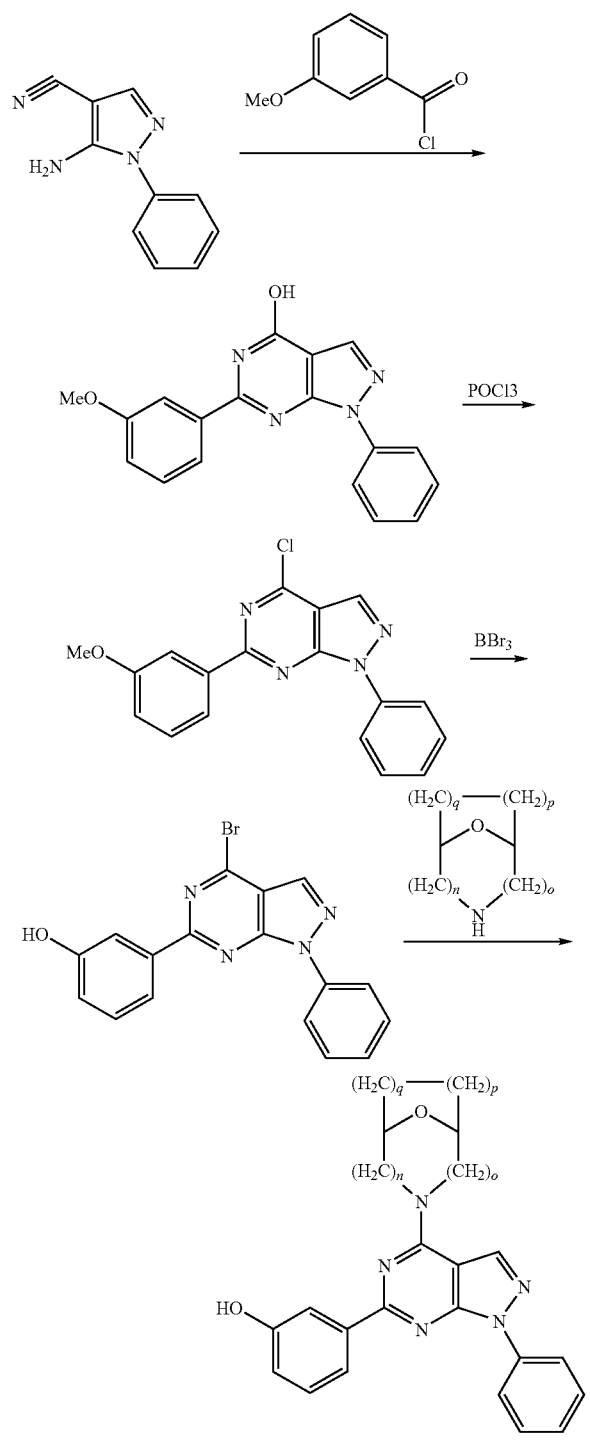
Scheme 22:
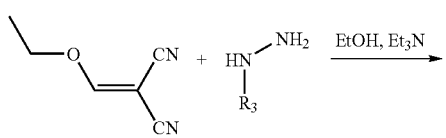
-continued
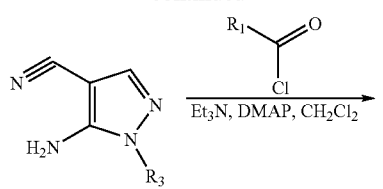
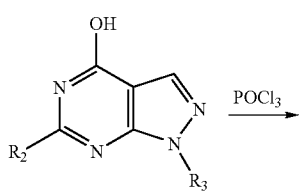
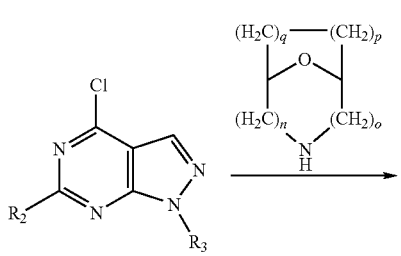
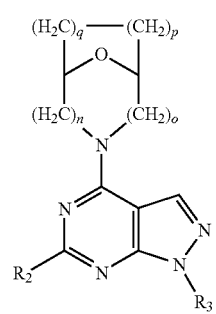
Scheme 23:
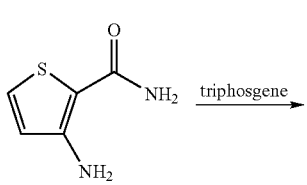
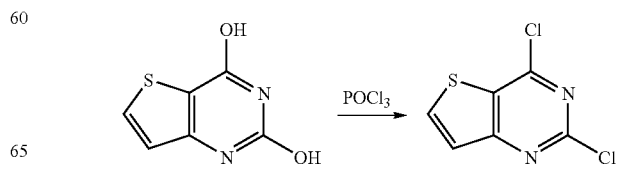

Scheme 24:
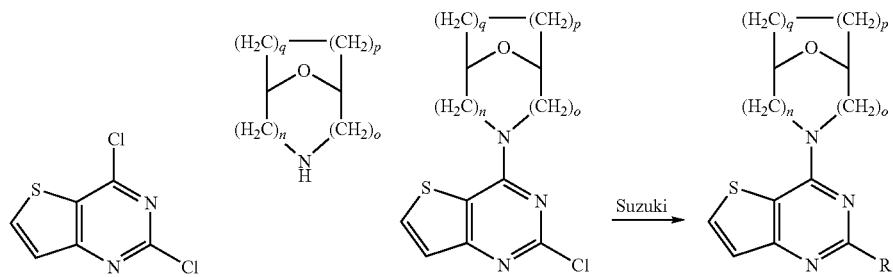
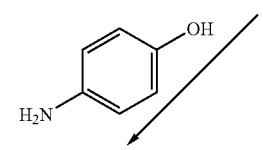
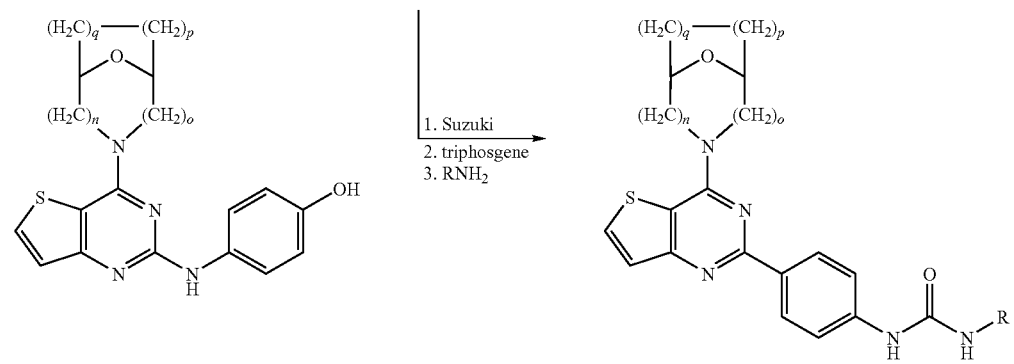
Scheme 25:
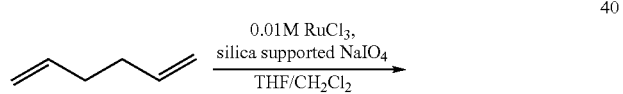
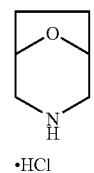
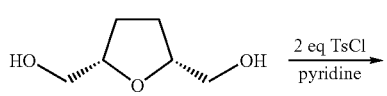
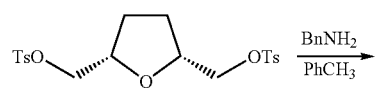
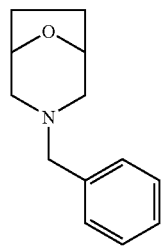
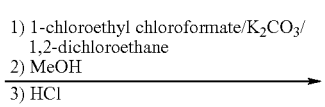
-continued
Scheme 26:
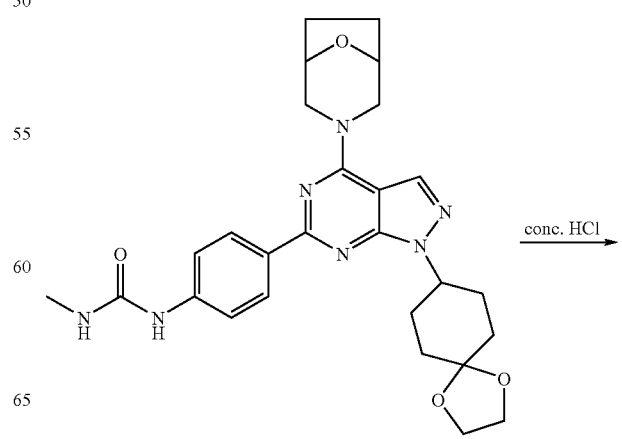

85
-continued
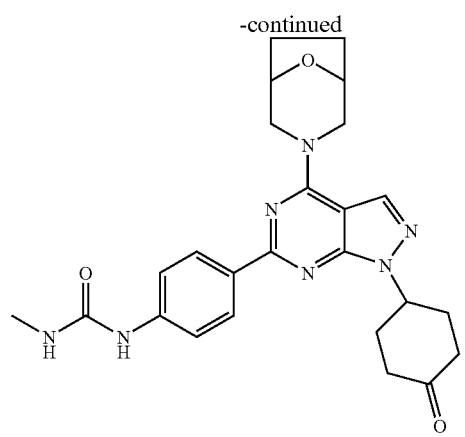
NaBH₄
THF
→
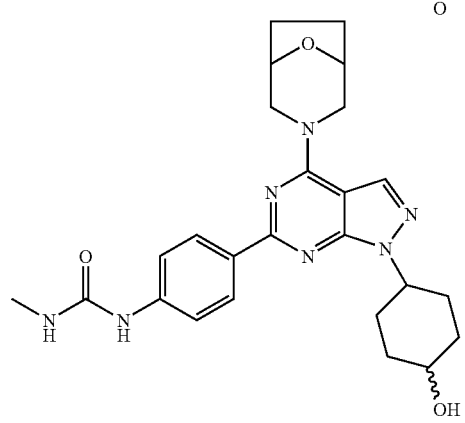
silica gel
→
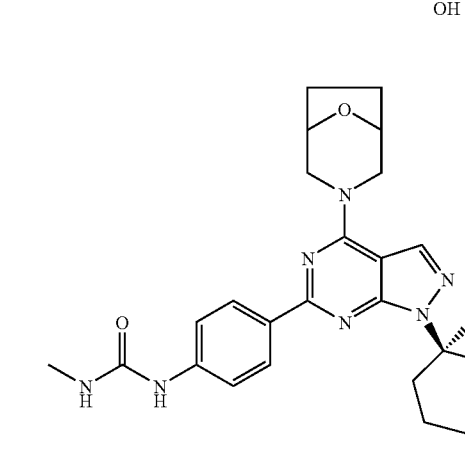
+
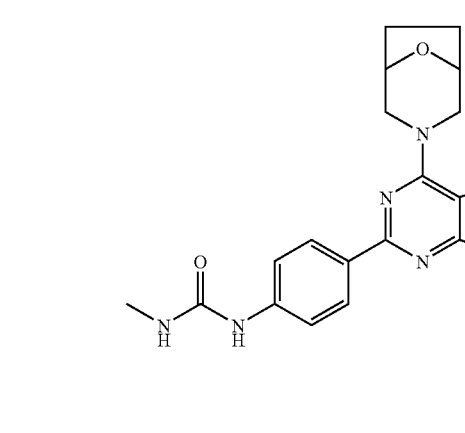
86
Scheme 27:
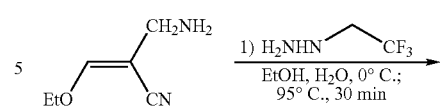
1) H₂NHN⌒CF₃
EtOH, H₂O, 0° C.;
95° C., 30 min
→
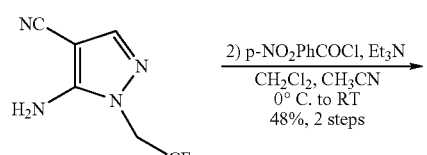
2) p-NO₂PhCOCl, Et₃N
CH₂Cl₂, CH₃CN
0° C. to RT
48%, 2 steps
→
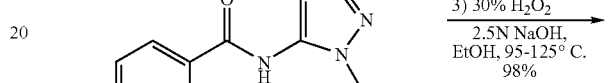
3) 30% H₂O₂
2.5N NaOH,
EtOH, 95-125° C.
98%
→
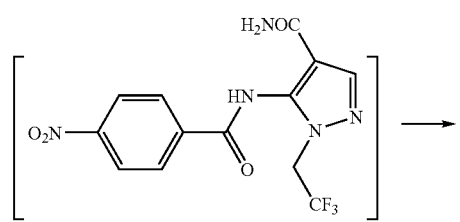
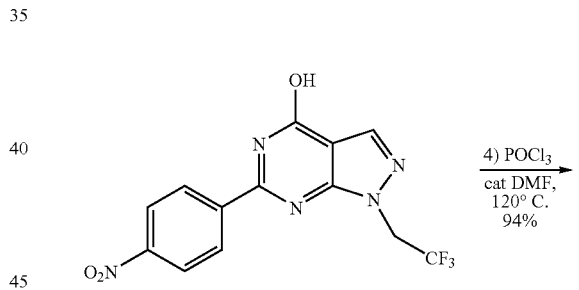
4) POCl₃
cat DMF,
120° C.
94%
5) [morpholine-like amine]·HCl
Et₃N, EtOH
95° C., 30 min
87%
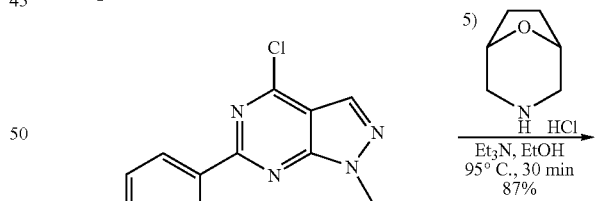
6) 10 Pd/C, H₂
1:1 THF:EtAc
1 atm, RT
90%
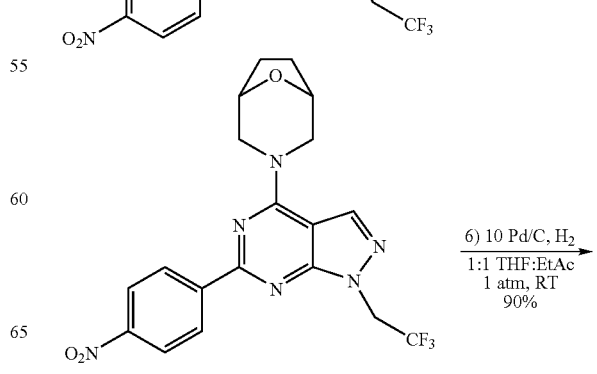

87 -continued
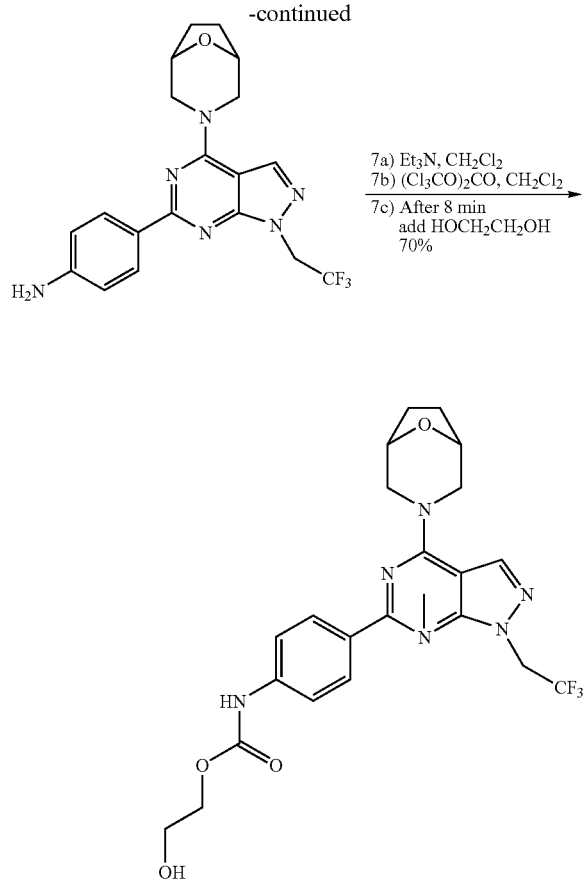
88
Scheme 28
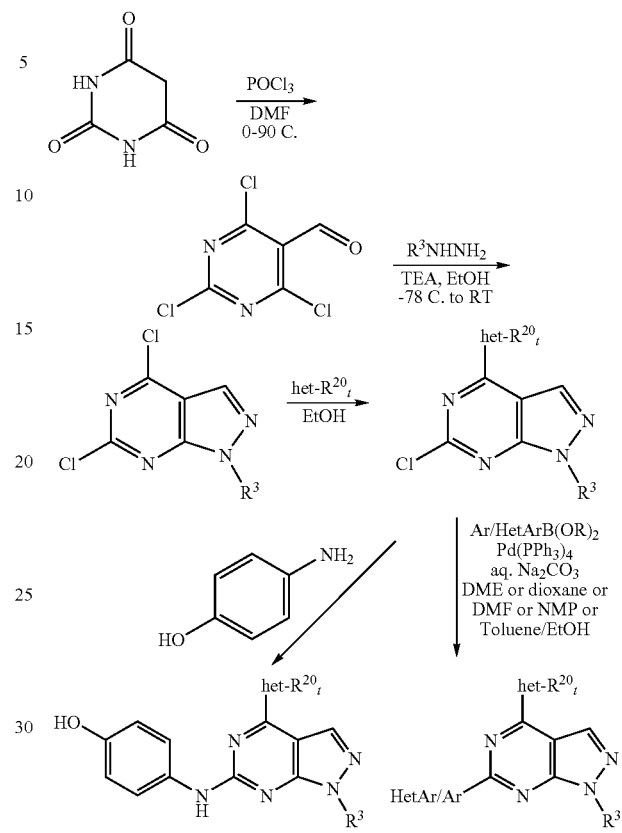
Scheme 29:
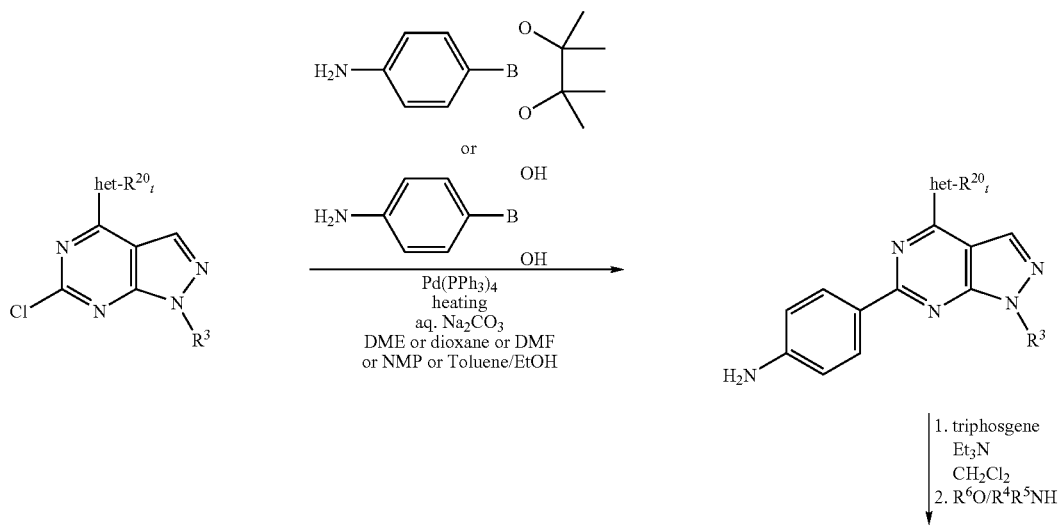

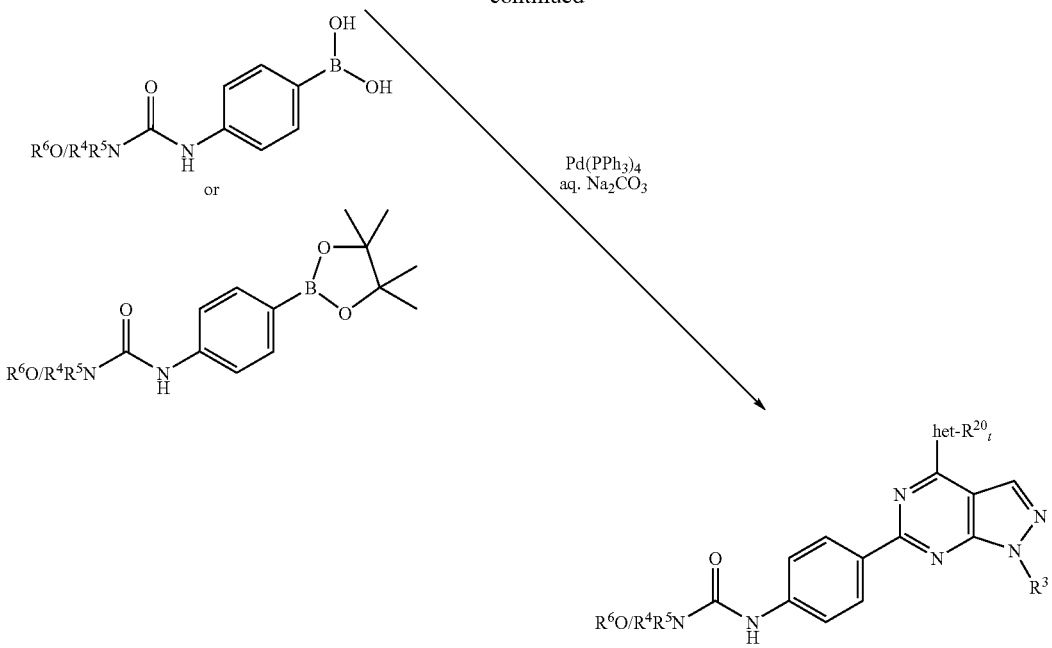
Scheme 30:
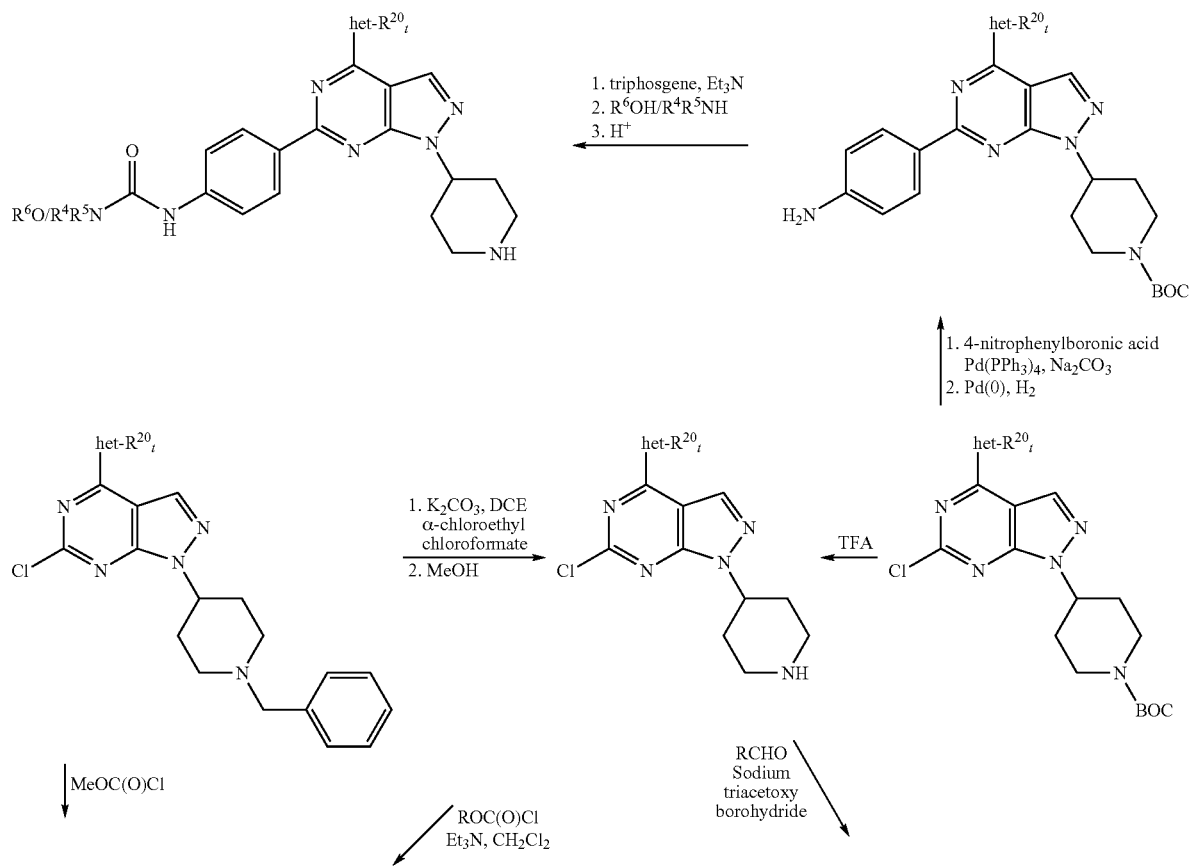

-continued
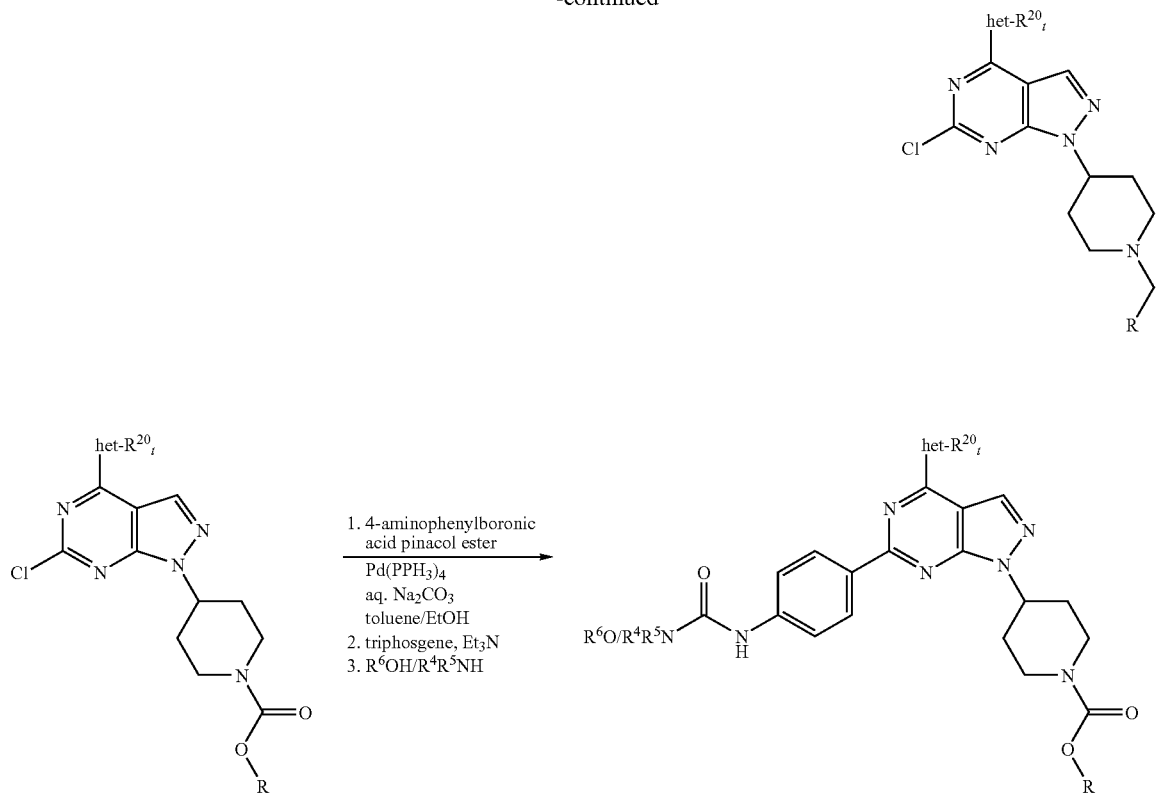
Scheme 31:
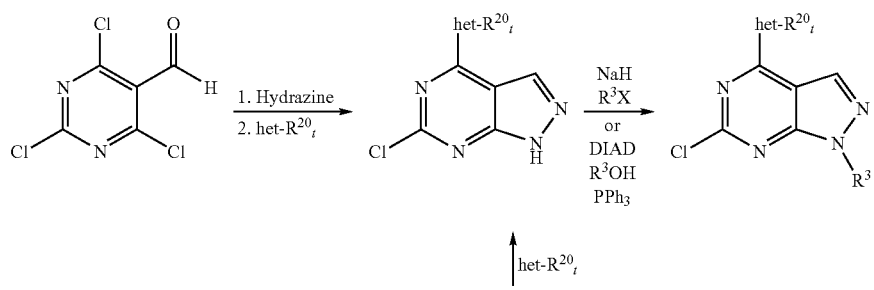
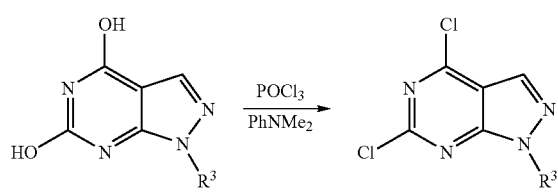

Scheme 32:
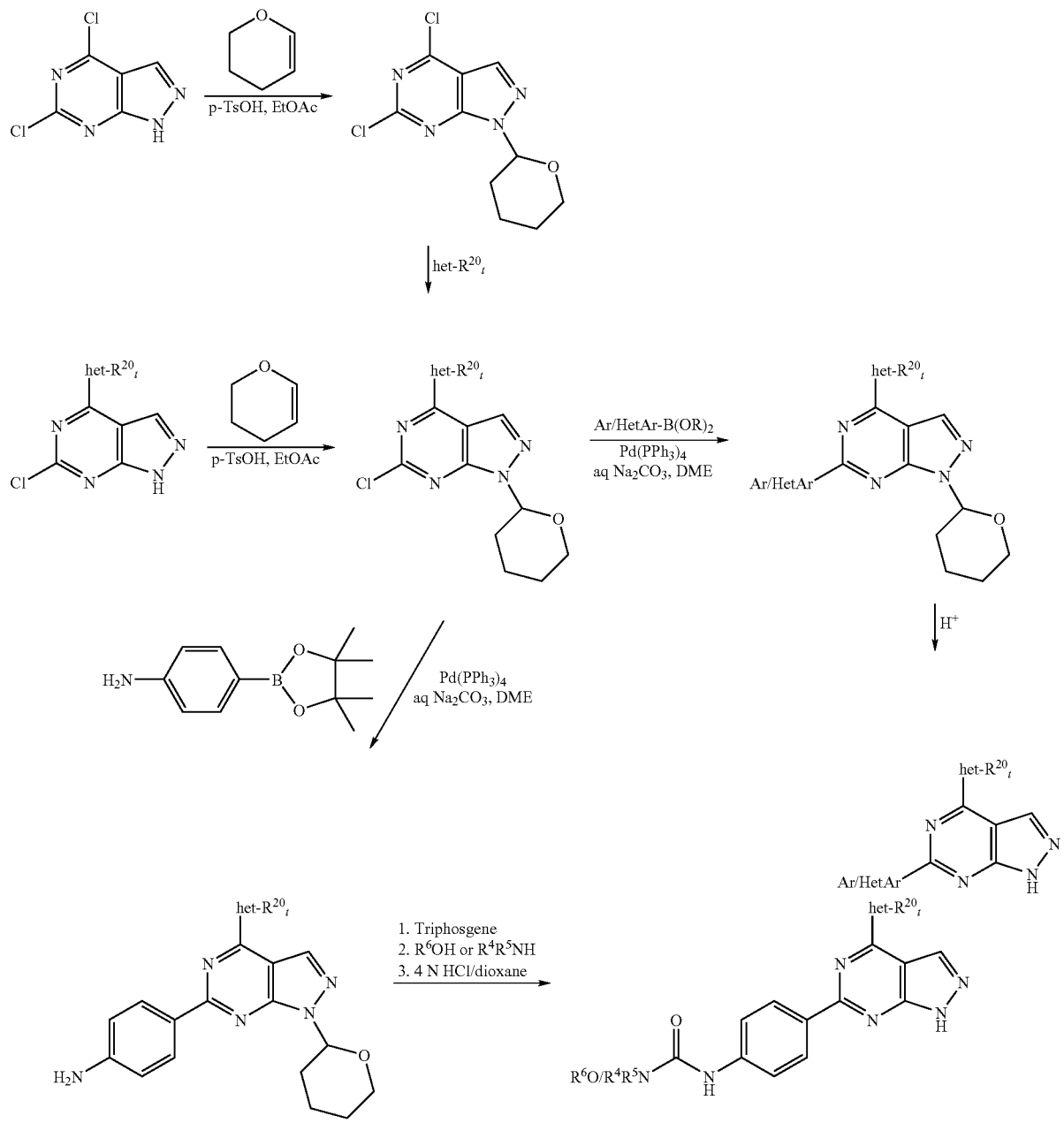
Scheme 33:
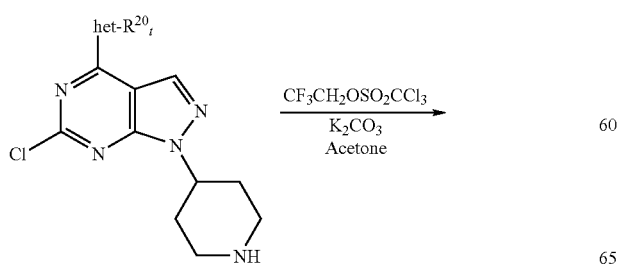
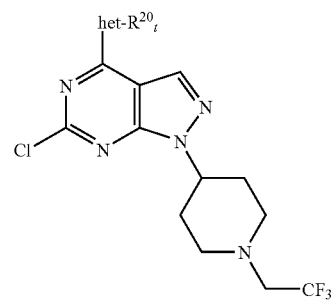
-continued

Scheme 34:
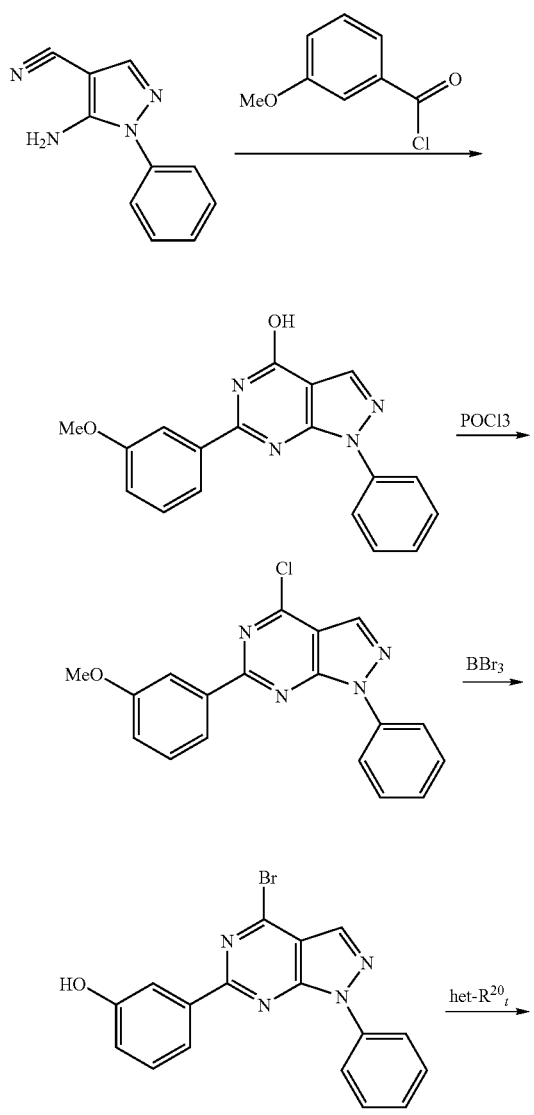
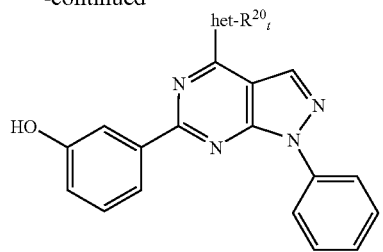
Scheme 35:
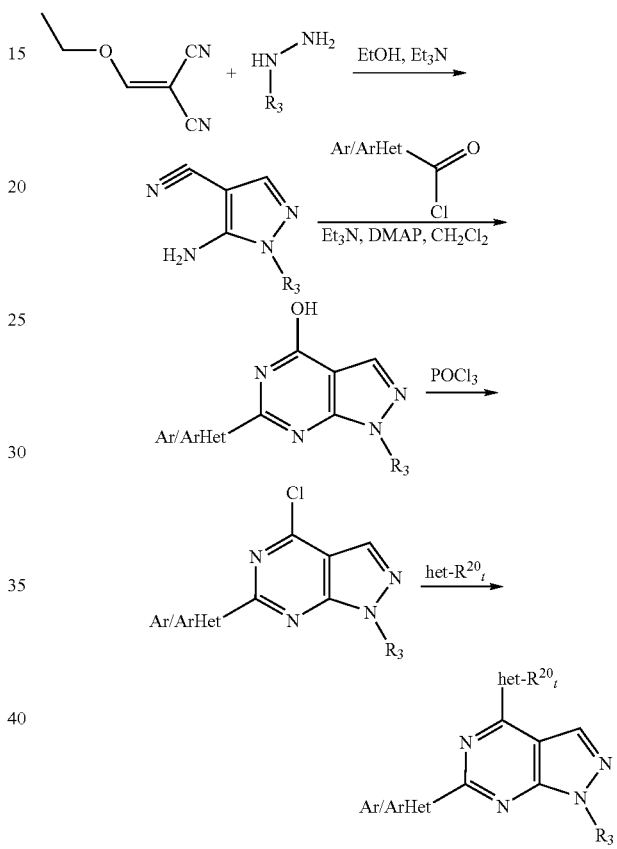
Scheme 36:
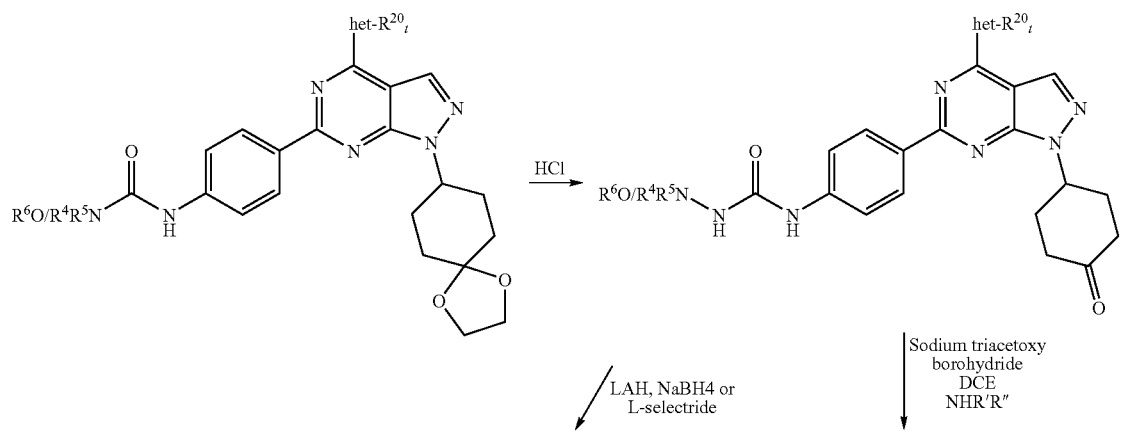

-continued
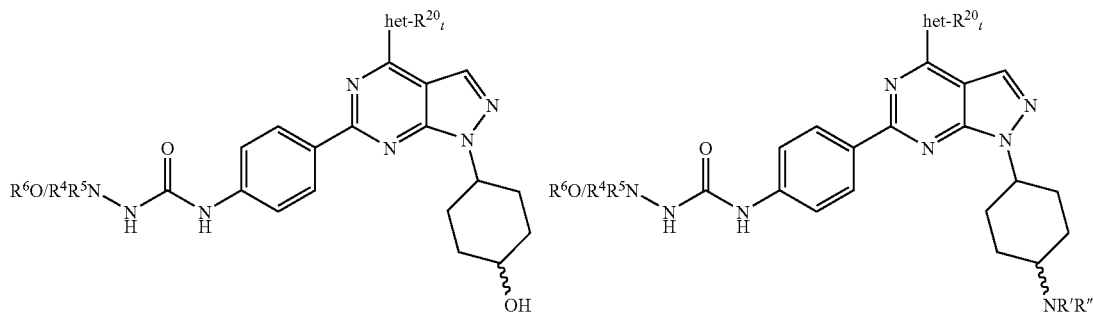
Scheme 37:
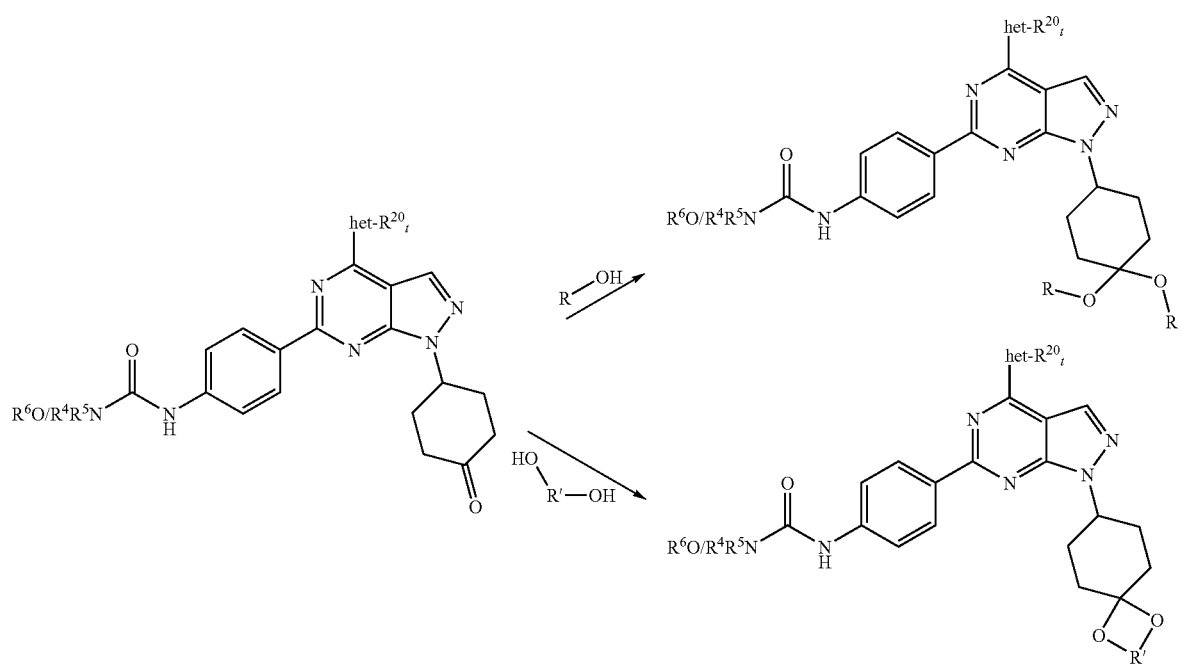
Scheme 38:
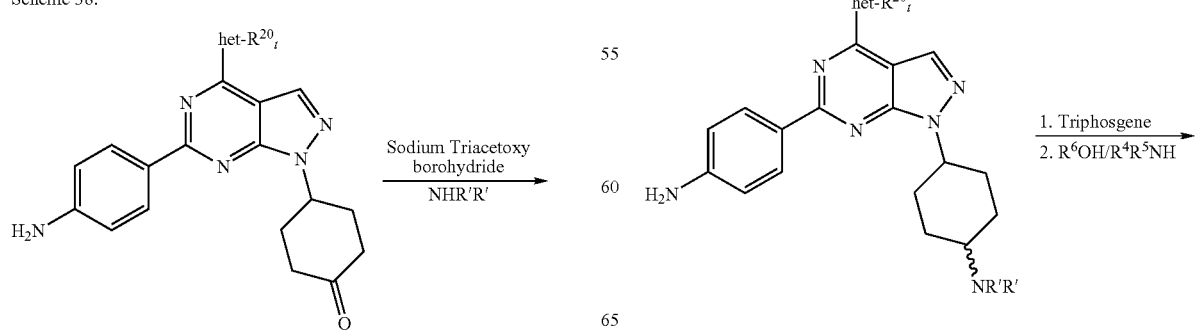

99
-continued
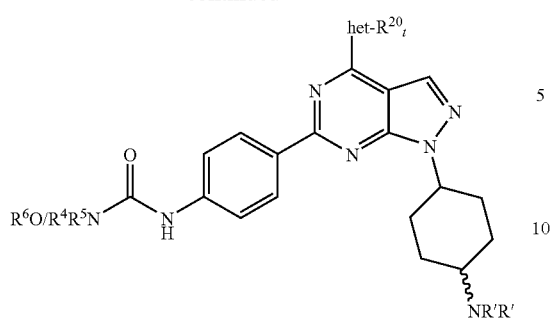
Scheme 39:
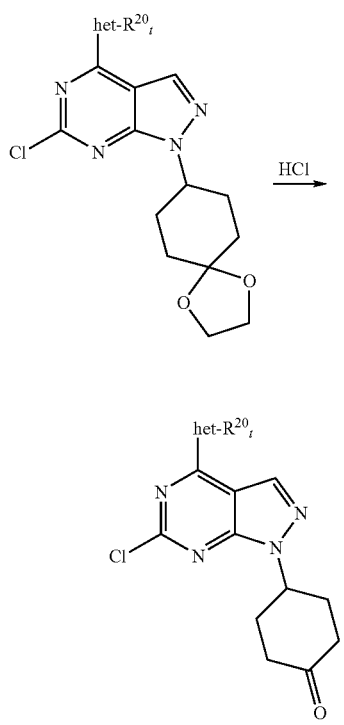
100
-continued
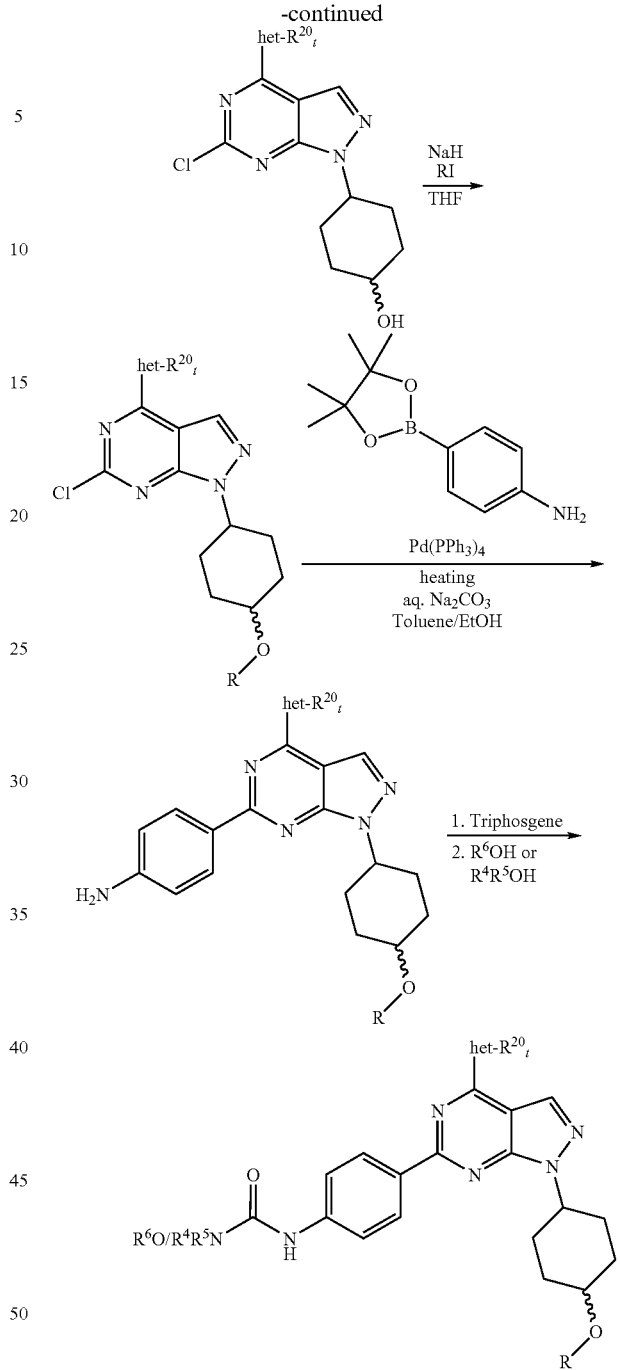
Scheme 40:
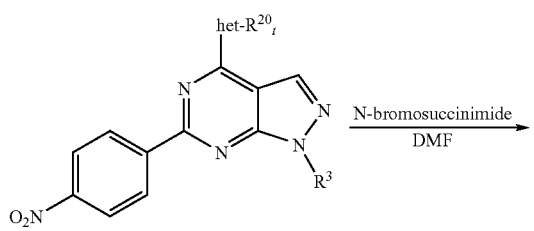

-continued
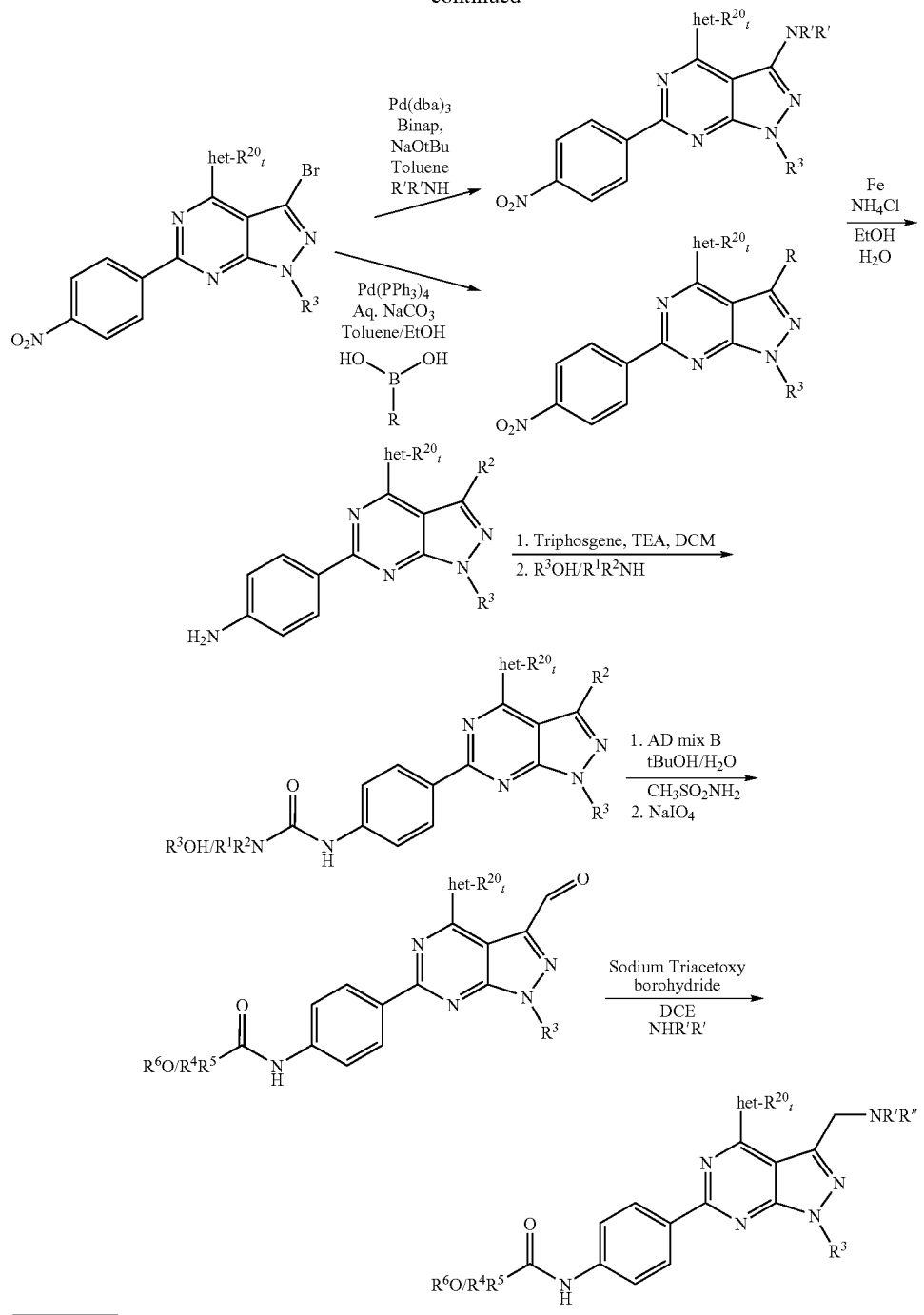
$R^2 = \equiv$
Scheme 41:
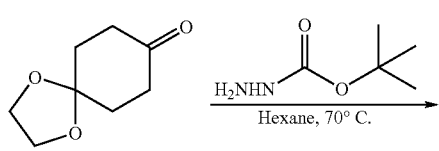
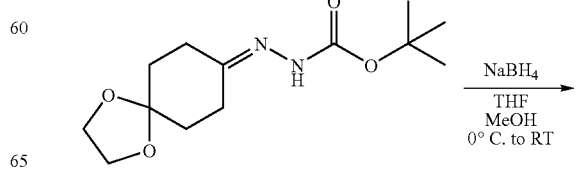

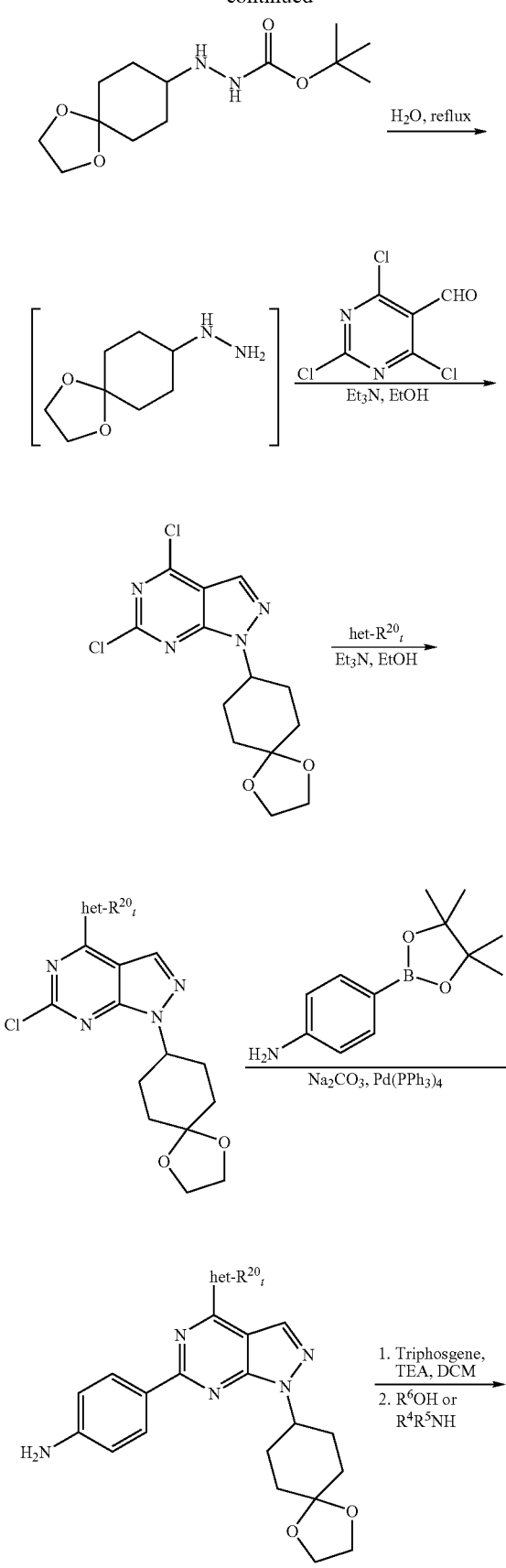
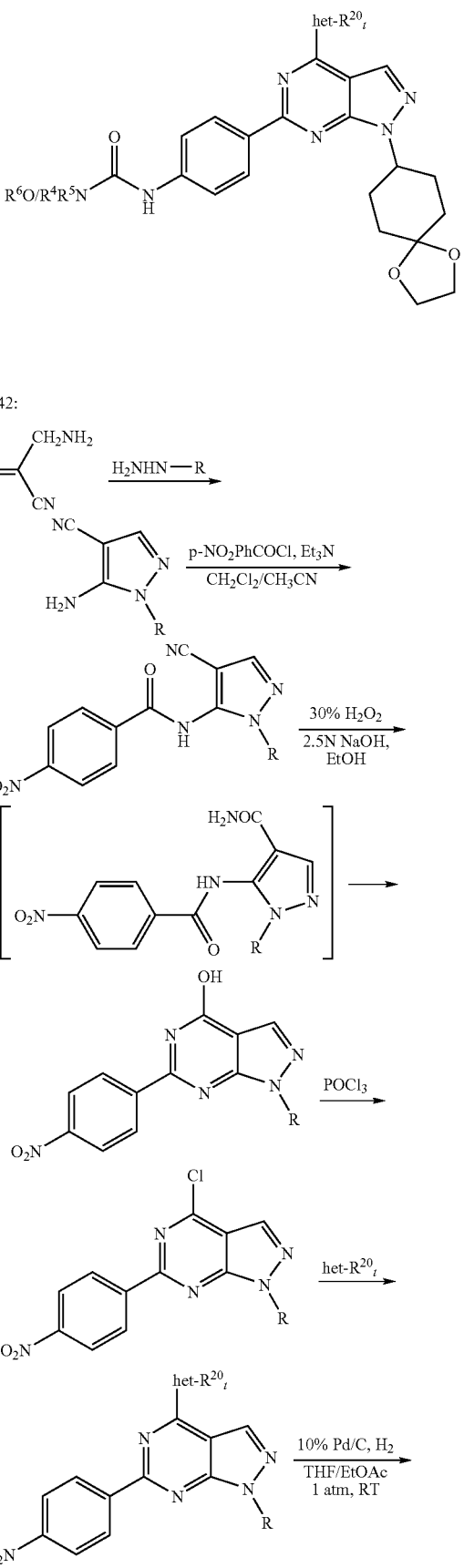
Scheme 42:

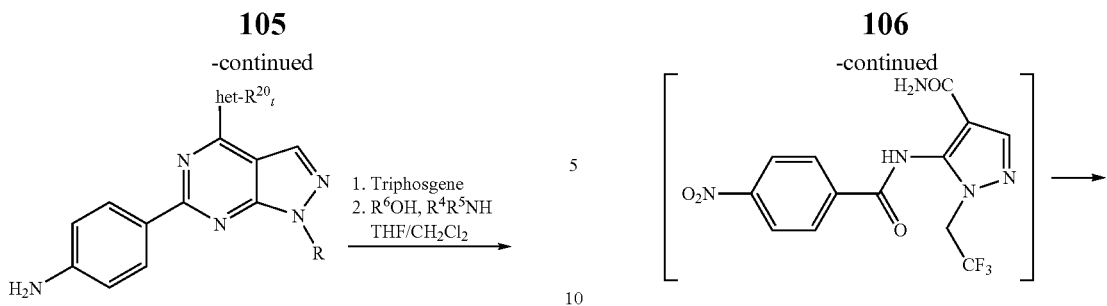
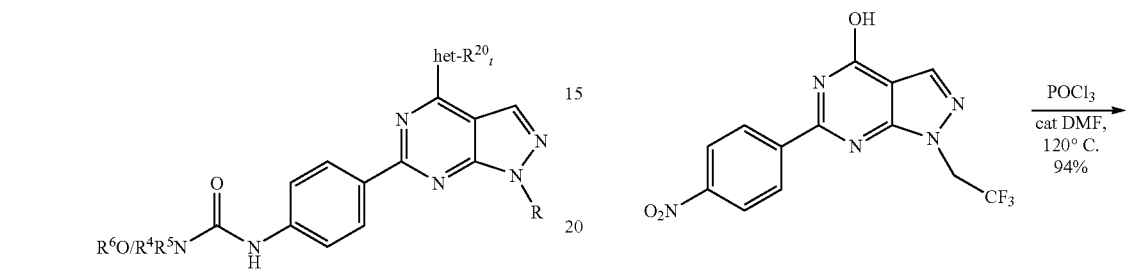
Scheme 43:
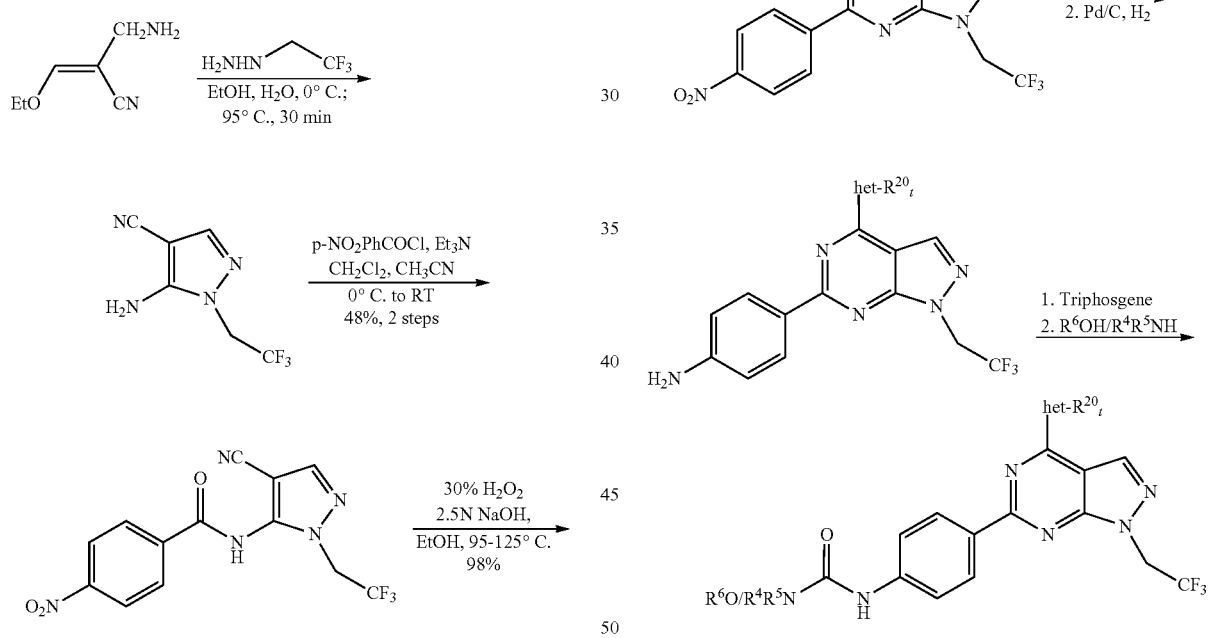
Scheme 44:
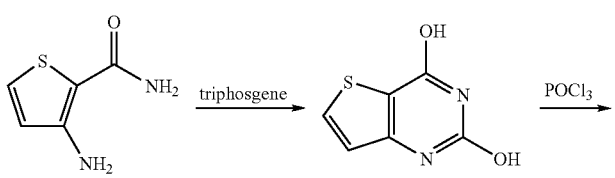

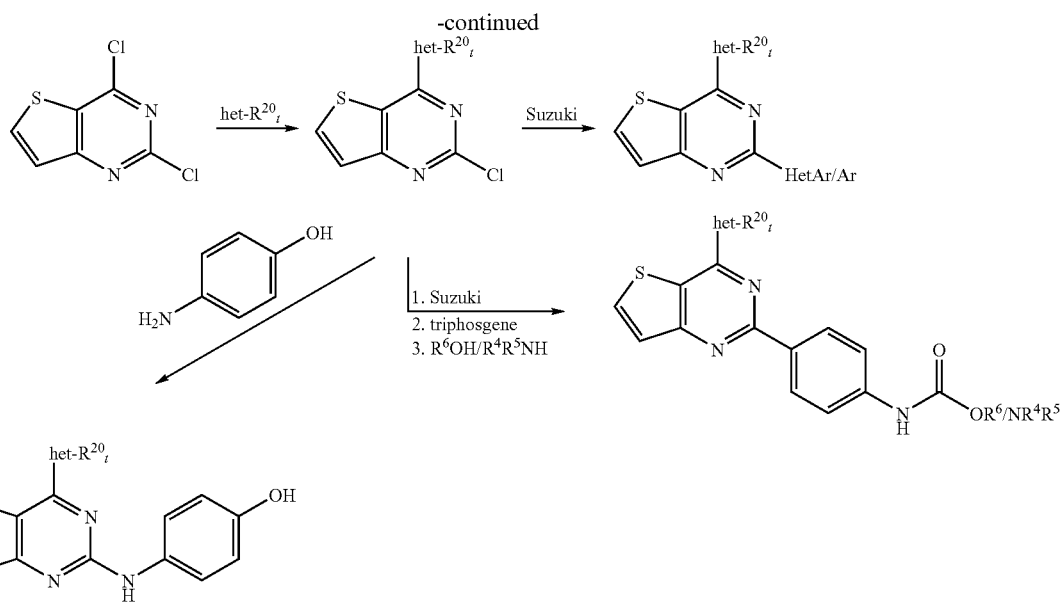
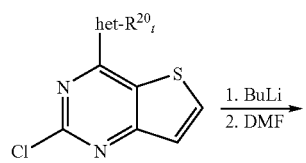
Scheme 45:
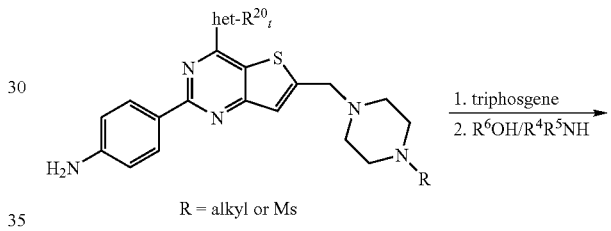
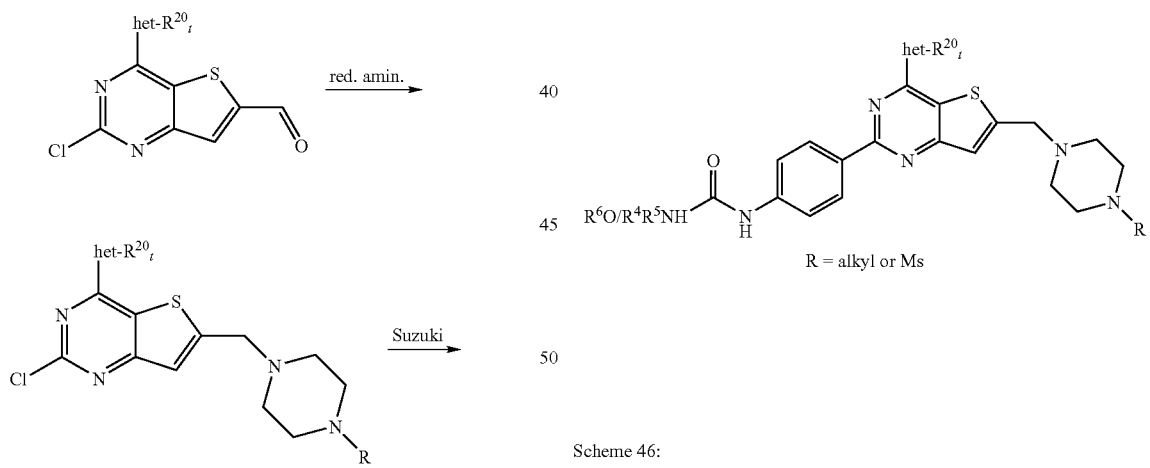
Scheme 46:
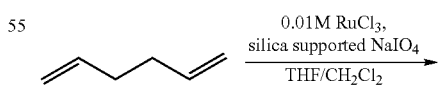
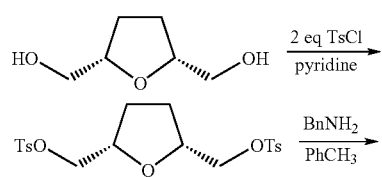

109
-continued

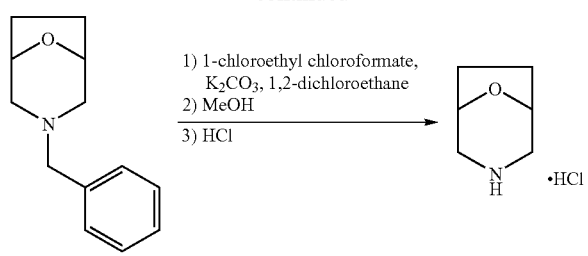

Scheme 47:

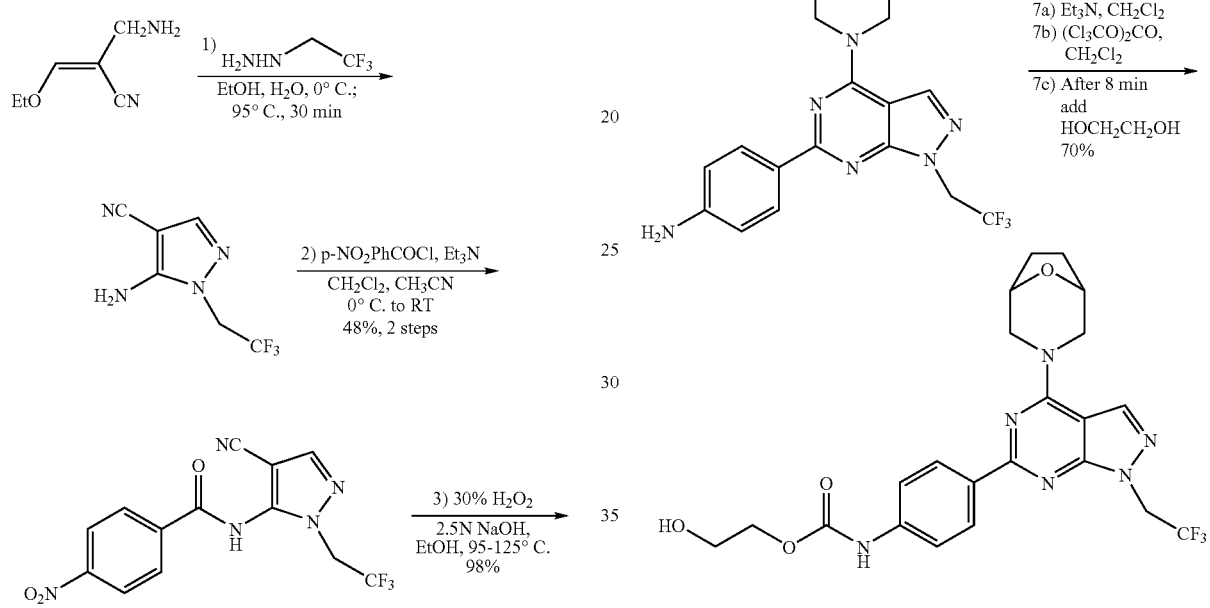

110
-continued

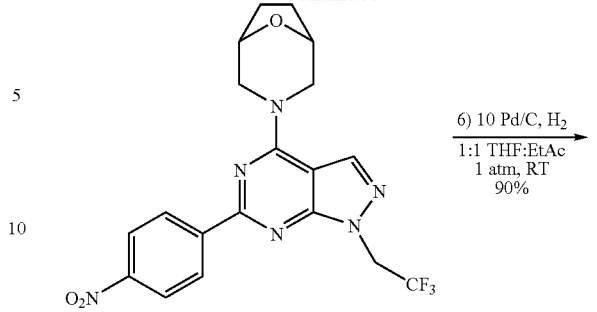

One of skill in the art will recognize that Schemes 1-47 can be adapted to produce the other pyrazolopyrimidine and thienopyrimidine compounds and pharmaceutically acceptable salts of pyrazolopyrimidine and thienopyrimidine compounds according to the present invention.

EXAMPLES

General Methods

The following general methods outline the synthesis the pyrazolopyrimidine and thienopyrimidine compounds of the Examples.

Preparation of
2,4,6-Trichloro-pyrimidine-5-carbaldehyde (Scheme 1)

To a solution of $POCl_3$ (200 mL) in DMF (42 mL) cooled to 0° C. was slowly added barbituric acid (30 g) over 1.5 hrs. The mixture was then heated to reflux for 16 hrs and then evaporated (the distillate was carefully decomposed by SLOWLY pouring into stirred ice methanol slush). The reminder was cooled to 0° C. and it was added very slowly to a solution of ice water upon which a beige solid formed. The solid was filtered, dissolved in DCM, washed with water, washed with a sat $NaHCO_3$ solution, dried ($MgSO_4$), and concentrated in vacuo to afford white crystals (24 g).

Preparation of 4,6-Dichloro-1-methyl-1H-pyrazolo[3,4-d]pyrimidine (Scheme 1)

To a solution of 2,4,6-trichloro-pyrimidine-5-carbaldehyde (3.7 g, 17.5 mmol) in EtOH (50 mL) cooled to −78° C. was added methyl hydrazine (0.93 mL, 17.5 mmol) and TEA (8 mL). The mixture was stirred for 30 minutes at −78 C then 2 hr at 0 C. The solution was concentrated in vacuo without heating. To the reduced volume solution was added EtOAc and the solution washed with a sat NaHCO₃ solution and concentrated in vacuo without heating. Filtration over a small silica gel plug (2:1 EtOAc:Hex) and concentration afforded the desired product as a yellow solid. It should be noted that the reaction with aromatic hydrazine compounds can be conducted at 0° C.

Preparation of 4,6-Dichloro-1-(1-benzyl-piperidin-4-yl)-1H-pyrazolo[3,4-d]pyrimidine (Scheme 1)

To a solution of 2,4,6-trichloro-pyrimidine-5-carbaldehyde (2.5 g, 11.6 mmol) in EtOH (40 mL) cooled to −78 C was added N-benzyl-4-piperidinzyl-hydrazine dihydrochloride (3.3 g, 11.6 mmol) and TEA (5 mL). The mixture was stirred for 30 min at −78 C then 2 hr at 0 C. The solution was concentrated in vacuo without heating. To the reduced volume solution EtOAc and a sat NaHCO₃ solution was added and the solution filtered over Celite™ and separated. The organic layer was dried (MgSO₄) and concentrated in vacuo without heating. Filtration over a small silica gel plug (EtOAc) and concentration afforded the desired product as a yellow solid (3 g).

1-(1-Benzyl-piperidin-4-yl)-6-chloro-4-(8-oxa-3-aza-bicyclo[3.2.1]oct-3-yl)-1H-pyrazolo[3,4-d]pyrimidine (Scheme 28)

To a solution of 1 mmol 1-(1-benzyl-piperidin-4-yl)-4,6-dichloro-1H-pyrazolo[3,4-d]pyrimidine dissolved in EtOH (10 mL) was added 1 mmol 8-oxa-3-aza-bicyclo[3.2.1]octane, (Newth, F. H. and Wiggins, L. F. Journal of the Chemical Society. 1948, pages 155-158) prepared from 1,5-hexadiene by the four-step process of RuCl₃-catalyzed NaIO₄ oxidation, conversion to the bis tosylate, cyclization with benzyl amine, and deprotection with 1-chloroethyl chloroformate followed by methanol (Scheme 46). The reaction was stirred for 18 h. The solvents were evaporated and the reminder was triturated with diethyl ether/hexane. The solid was filtered off and washed with hexane. Drying on the fritted funnel provided a solid.

Synthesis of (1-Benzyl-piperidin-4-yl)-hydrazine dihydrochloride

Benzoic hydrazide (27 g) was dissolved in methanol (150 mL). 1-Benzyl-piperidin-4-one (37.8 g) was added and the solution was heated at 30 C for 1 h and 60 C for 2 h. The solution was cooled to 0 C and sodium borohydride (6.8 g) was added in portions. After 2 h the solution was concentrated in vacuo and the residue was partitioned between dichloromethane and water. The organic phase was dried with anhydrous magnesium sulfate and concentrated leaving an oil (102 g). The oil was dissolved in water (80 mL) containing concentrated hydrochloric acid (140 mL) (extra solvent released at this stage was separated). The aqueous solution was refluxed for 18 h. It was cooled to 0 C. The precipitate of benzoic acid was filtered off. Water was evaporated in vacuo. Anhydrous ethanol was added and the precipitate was filtered off and dried under high vacuum to give the title compound as a white solid (32.4 g).

Preparation of 4-[4-(8-Oxa-3-aza-bicyclo[3.2.1]oct-3-yl)-1-phenyl-1H-pyrazolo[3,4-d]pyrimidin-6-yl]-phenylamine (Scheme 28)

6-Chloro-4-(8-oxa-3-aza-bicyclo[3.2.1]oct-3-yl)-1-phenyl-1H-pyrazolo[3,4-d]pyrimidine (2.5 mmol) and 4-(4,4,5,5-tetramethyl-1,3,2-dioxaborolan-2-yl)aniline (3.0 mmol) are dissolved in a microwave vial in DME (18 mL). Na₂CO₃ (2.5 mL, 2M in water) is added along with a catalytic amount of tetrakis triphenylphosphine palladium. The mixture is heated in a sealed tube under microwave irradiation at 185 C for 40 min. The mixture is diluted with 50 mL EtOAc and washed with a saturated solution of NaHCO₃ (2×50 mL). The aqueous layers are extracted with EtOAc (50 mL) and the combined organic layers are dried over MgSO₄, filtered and concentrated in vacuo. Purification gives the title compound.

6-Chloro-4-(8-oxa-3-aza-bicyclo[3.2.1]oct-3-yl)-1-piperidin-4-yl-1H-pyrazolo[3,4-d]pyrimidine (Scheme 30)

To 1-(1-benzyl-piperidin-4-yl)-6-chloro-4-(8-oxa-3-aza-bicyclo[3.2.1]oct-3-yl)-1H-pyrazolo[3,4-d]pyrimidine (0.24 mmol) in 1,2-dichloroethane (2 mL) is added 1.9 mmol alpha-chloroethyl chloroformate (ACE-Cl) along with a small amount of K₂CO₃. The mixture is stirred for 5.5 h at RT. The reaction is quenched by addition of MeOH and the mixture is filtered and concentrated to dryness. The mixture is dissolved in MeOH and briefly heated to reflux. The title compound is obtained in quantitative yield by evaporation of MeOH. This material is used without further purification in the next step (reductive amination or acylation following the procedures disclosed previously, Scheme 30).

6-Chloro-1-ethyl-4-(8-oxa-3-aza-bicyclo[3.2.1]oct-3-yl)-1H-pyrazolo[3,4-d]pyrimidine (Scheme 31)

To 6-chloro-4-(8-oxa-3-aza-bicyclo[3.2.1]oct-3-yl)-1H-pyrazolo[3,4-d]pyrimidine (0.418 mmol), NaH (60% in oil, 2.1 mmol) and ethyl iodide (2.1 mmol) is added N-methylpyrrolidinone (1 mL). After 5 min the reaction mixture is heated in the microwave at 175 C for 10 min. Reverse phase HPLC gave the product.

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-methylurea (Schemes 4 and 3)

To 6-chloro-4-(8-oxa-3-aza-bicyclo[3.2.1]oct-3-yl)-1H-pyrazolo[3,4-d]pyrimidine (0.9 g, 3.42 mmol), 2-fluoroethanol (0.3 mL, 5.13 mmol) triphenylphosphine (1.35 g, 5.13 mmol) in THF (22.5 mL) at 0 C is added DIAD (1.0 mL, 5.13 mmol) in drops over 5 min. After 20 min the reaction mixture is allowed to warm to 25 C. After 18 h the mixture is concentrated in vacuo, absorbed onto silica gel using ether and chromatographed on silica gel eluting with hexane/ethyl acetate. 3-(6-Chloro-1-(2-fluoroethyl)-1H-pyrazolo[3,4-d]pyrimidin-4-yl)-8-oxa-3-azabicyclo[3.2.1]octane was obtained as a yellow solid (560 mg). MS m/z=312 (M+H). This material (550 mg) was treated with 4-(4,4,5,5-tetramethyl-1,3,2-dioxaborolan-2-yl)aniline (583 mg), aq. Na₂CO₃ (1.3 mL, 2M), and tetrakis triphenylphosphine palladium (50-100 mg) in 1:1 toluene:ethanol (11 mL). The reaction mixture was heated in a microwave at 12° C. for 20 min. It was then dissolved in CH2Cl2 and chromatographed on silica gel using hexane/ethyl acetate as the eluant to give 4-(4-(8-oxa-3-azabicyclo[3.2.1]octan-3-yl)-1-(2-fluoroethyl)-1H-pyrazolo[3,4-d]pyrimidin-6-yl)aniline as a white foam (0.51 g). MS m/z=369 (M+H). A solution of this material (500 mg, 1.36 mmol) and triethylamine (0.95 mL) in dichloromethane was treated with triphosgene (202 mg, 0.68 mmol). After 30 min one tenth of the solution was treated with excess methylamine (2N in THF). Reverse phase HPLC gave the title compound (29 mg) MS m/s=426.2 (M+H).

Using the above procedure and substituting for methylamine with other amines or alcohols in the last step gives the following compounds:

1-ethyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea Using ethylamine in the above procedure gives the title compound (29 mg). MS m/s=440.2 (M+H).

1-cyclopropyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea Using cyclopropylamine in the above procedure gives the title compound (25 mg). MS m/s=452.2 (M+H).

2-hydroxyethyl{4-[1-(2-fluoroethyl)-4-(8-oxa-3-azabicyclo[3.2.1]oct-3-yl)-1H-pyrazolo[3,4-d]pyrimidin-6-yl]phenyl}carbamate Using ethylene glycol in the above procedure gives the title compound (35 mg). MS m/s=457.2 (M+H).

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-pyridin-4-ylurea Using 4-aminopyridine in the above procedure gives the title compound (25 mg). MS m/s=489.2 (M+H).

1-[4-(dimethylamino)phenyl]-3-{4-[1-(2-fluoroethyl)-4-(8-oxa-3-azabicyclo[3.2.1]oct-3-yl)-1H-pyrazolo[3,4-d]pyrimidin-6-yl]phenyl}urea Using N,N-dimethylbenzene-1,4-diamine in the above procedure gives the title compound (48 mg). MS m/s=531.3 (M+H).

1-[4-[2-(dimethylamino)ethoxy]phenyl]-3-{4-[1-(2-fluoroethyl)-4-(8-oxa-3-azabicyclo[3.2.1]oct-3-yl)-1H-pyrazolo[3,4-d]pyrimidin-6-yl]phenyl}urea Using 4-(2-(dimethylamino)ethoxy)-N,N-dimethylaniline in the above procedure gives the title compound (47 mg). MS m/s=575.3 (M+H).

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea Using 4-morpholinoaniline in the above procedure gives the title compound (37 mg). MS m/s=573.3 (M+H).

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea Using (4-aminophenyl)methanol in the above procedure gives the title compound (25 mg). MS m/s=518.2 (M+H).

1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea Using 4-(4-methylpiperazin-1-yl)aniline in the above procedure gives the title compound (9 mg). MS m/s=586.3 (M+H).

2-hydroxyethyl(4-{4-[(6R)-6-hydroxy-8-oxa-3-azabicyclo[3.2.1]oct-3-yl]-1-(2,2,2-trifluoroethyl)-1H-pyrazolo[3,4-d]pyrimidin-6-yl}phenyl)carbamate and 1-{4-[4-(6-hydroxy-3-oxa-8-azabicyclo[3.2.1]oct-8-yl)-1-(2,2,2-trifluoroethyl)-1H-pyrazolo[3,4-d]pyrimidin-6-yl]phenyl}-3-methylurea Materials:

Pooled nude mouse liver microsomes were purchased from XenoTech (Lenexa, Kans.). NADPH was purchased from BD Gentest (Franklin Lakes, N.J.). HPLC grade water, acetonitrile, ethyl acetate, sodium phosphate dibasic, and potassium phosphate monobasic were obtained from EM Science (Gibbstown, N.J.). Ammonium acetate was purchased from Sigma (St. Louis, Mo., USA).

Microsomal Incubation:

2-hydroxyethyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate and 1-methyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea (50 µM each) were incubated separately with nude mouse liver microsomes (1 mg micromal protein/mL of incubation) and NADPH (1 mM) in potassium phosphate buffer (100 mM, pH 7.4) at 37° C. for 90 min. The total incubation volume for each compound was 50 mL. The incubation reaction was initiated by addition of NADPH after 5 min pre-incubation and was stopped by liquid-liquid extraction using ethyl acetate (incubation solution: ethyl acetate=1:4, v/v). The ethyl acetate layer was separated and evaporated to dryness using a rotary evaporator (Buchi, Postfach, Switzerland). The residue was reconstituted with 1 ml of a water-acetonitrile mixture (10:90, v/v) for HPLC isolation.

Metabolite Isolation:

A Waters 2790 HPLC system (Waters, Beverly, Mass., USA) was used for the isolation of these metabolites. The system consisted of two quaternary pumps, a vacuum degasser, a temperature controlled autosampler, a thermostated column compartment, a fraction collector and a PDA detector. The chromatographic separation was carried out using a Luna C18 column (150×4.6 mm i.d., 5 µM particle size) (Phenomenex, Torrance, Calif.) at an oven temperature of 40° C. The mobile phase consisted of solvent A: 10 mM ammonium acetate in water-acetonitrile ($H_2O$:ACN=95:5, v/v) and B: 10 mM ammonium acetate in acetonitrile-water (ACN:$H_2O$=95:5, v/v). The mobile phase gradient started with 20% B, and then increased linearly from 20% to 80% B in 20 min. The flow rate was 1 ml/min. The HPLC elution fractions were collected using a Waters fraction collector. The injection volume was 50 µL and 20 injections were performed in total. The fractions of the isolated metabolite from 20 injections were combined, and were dried down using a Savant (Thermo Quest, Holbrook, N.Y.). The purity and identity of metabolites were checked using LC/UV/MS and LC/MS/MS. The structures of these metabolites were determined using NMR. MS m/z=509.2 (H+H) and MS m/z=478 (M+H), respectively.

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-methylurea (Scheme s 4 and 2)

To 6-chloro-4-(8-oxa-3-aza-bicyclo[3.2.1]oct-3-yl)-1H-pyrazolo[3,4-d]pyrimidine (1 g, 3.8 mmol), 2-(dimethylamino)ethanol (0.57 mL, 5.7 mmol) triphenylphosphine (1.5 g, 5.7 mmol) in THF (25 mL) is added DIAD (1.1 mL, 5.7 mmol) in drops over 5 min. After 2 h the mixture is concentrated in vacuo, diluted with ether and extracted with 1N aq HCl (2×). The aqueous layers are neutralized with NaOH and extracted with CH2Cl2. The organic layers are treated with 4N HCl in dioxane and concentrated in vacuo. The resulting solid was triturated with ether. Material from a reaction conducted with 0.37 g of pyrazolopyrimidine was combined with this material to give 1.29 g of 2-(4-(8-oxa-3-azabicyclo[3.2.1]octan-3-yl)-6-chloro-1H-pyrazolo[3,4-d]pyrimidin-1-yl)-N,N-dimethylethanamine as a solid. This material (0.5 g, 1.34 mmol) was treated with 4-(4,4,5,5-tetramethyl-1,3,2-dioxaborolan-2-yl)aniline (0.44 g, 2.0 mmol), aq. $Na_2CO_3$ (1.84 mL, 2M), and tetrakis triphenylphosphine palladium (50 mg) in 1:1 toluene:ethanol (10 mL). The reaction mixture was heated in a microwave at 12° C. for 60 min. The reaction was repeated. The combined reaction mixtures were diluted with EtOAc and filtered to give a solid (0.51 g). The aq. Phase was washed with EtOAc and the combined organic layers concentrated in vacuo. Trituration of the residue gave a solid (0.28 g). The precipitates were combined to give 4-(4-(8-oxa-3-azabicyclo[3.2.1]octan-3-yl)-1-(2-(dimethylamino)ethyl)-1H-pyrazolo[3,4-d]pyrimidin-6-yl)aniline as a solid (0.79 g). A solution of this material (550 mg, 1.4 mmol) and triethylamine (1.05 mL) in dichloromethane was treated with triphosgene (208 mg, 0.7 mmol). After 30 min one eleventh of the solution was treated with excess methylamine (2N in THF). Reverse phase HPLC gave the title compound (39 mg) MS m/s=451.2 (M+H).

Using the above procedure and substituting for methylamine with other amines or alcohols in the last step gives the following compounds:

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-ethylurea Using ethylamine in the above procedure gives the title compound (67 mg). MS m/s=465.3 (M+H).

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-pyridin-3-ylurea Using 3-aminopyridine in the above procedure gives the title compound (46 mg). MS m/s=514.3 (M+H).

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-phenylurea Using aniline in the above procedure gives the title compound (50 mg). MS m/s=513.3 (M+H).

1-cyclopropyl-3-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)urea Using cyclohexylamine in the above procedure gives the title compound (52.7 mg). MS m/s=477.3 (M+H).

Methyl(4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate Using methanol in the above procedure gives the title compound (59 mg). MS m/s=452.2 (M+H).

2-hydroxyethyl(4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate Using ethylene glycol in the above procedure gives the title compound (57 mg). MS m/s=482.2 (M+H).

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea Using 4-(4-methylpiperazin-1-yl)aniline in the above procedure gives the title compound (35 mg). MS m/s=611.3 (M+H).

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(hydroxymethyl)phenyl]urea Using (4-aminophenyl)methanol in the above procedure gives the title compound (38 mg). MS m/s=543.3 (M+H).

1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(2-hydroxyethyl)phenyl]urea Using (4-aminophenyl)ethanol in the above procedure gives the title compound (27 mg). MS m/s=557.3 (M+H).

1-{4-[4-(8-oxa-3-azabicyclo[3.2.1]oct-3-yl)-1H-pyrazolo[3,4-d]pyrimidin-6-yl]phenyl}-3-pyridin-3-ylurea (Scheme 32)

4,6-Dichloro-1H-pyrazolo[3,4-d]pyrimidine (750 mg, 4.0 mmol), dihydropyran (1 mL), tosic acid monohydrate (25 mg) in EtOAc (10 mL) is heated at 50 C. The reaction mixture is allowed to cool and washed with water. Drying over MgSO4 and concentration in vacuo gave an orange oily solid. Dissolution in CH2Cl2 and chromatography on silica gel eluting with hexane/EtOAc gave 4,6-dichloro-1-(tetrahydro-2H-pyran-2-yl)-1H-pyrazolo[3,4-d]pyrimidine as a white, oily solid (780 mg). This material in ethanol (30 mL) is treated with a solution of 8-oxa-3-azabicyclo[3.2.1]octane hydrochloride (428 mg, 2.86 mmol) and Et3N (0.82 mL, 5.7 mmol) in ethanol (20 mL). Concentration in vacuo, followed by dilution with EtOAc and washing with water, gives 6-chloro-4-(8-oxa-3-azabicyclo[3.2.1]oct-3-yl)-1-(tetrahydro-2H-pyran-2-yl)-1H-pyrazolo[3,4-d]pyrimidine, after drying with MgSO4, as a white foam (1.03 g). MS m/z=350.3 (M+H). This material (0.5 g, 1.43 mmol) was treated with 4-(4,4,5,5-tetramethyl-1,3,2-dioxaborolan-2-yl)aniline (0.34 g, 1.57 mmol), aq. $Na_2CO_3$ (1.08 mL, 2M), and tetrakis triphenylphosphine palladium (25 mg) in DME (7 mL). The reaction mixture was heated in a microwave at 175 C for 15 min. Aq. workup and silica gel chromatography (hexane/EtOAc) gives 4-[4-(8-oxa-3-azabicyclo[3.2.1]oct-3-yl)-1-(tetrahydro-2H-pyran-2-yl)-1H-pyrazolo[3,4-d]pyrimidin-6-yl]aniline as a foam (330 mg). MS m/s=407.4 (M+H) To this material (300 mg, 0.74 mmol) in CH2Cl2 (10 mL) is added Et3N (0.518 mL) and a solution of triphosgene (329 mg, 1.11 mmol) in CH2Cl2 (5 mL). After 30 min 3-aminopyridine (696 mg, 7.4 mmol), as a solution in CH2Cl2 (5 mL) is added. Aq. workup and silica gel chromatography (hexane/EtOAc) gives 1-(4-(4-(8-oxa-3-azabicyclo[3.2.1]octan-3-yl)-1-(tetrahydro-2H-pyran-2-yl)-1H-pyrazolo[3,4-d]pyrimidin-6-yl)phenyl)-3-(pyridin-3-yl)urea as a colorless solid (227 mg). This material (200 mg) in dioxane (5 mL) and water (1.5 mL) was treated with 4 drops of 12N HCl. After heating at 60 C for 4 h and stirring at 25 C for 18 h the reaction mixture was filtered. The yellow solid collected was triturated with Et2O to give the HCl salt of the title compound as an off white solid (200 mg).

1-{4-[4-(6,8-dioxa-3-azabicyclo[3.2.1]oct-3-yl)-1-methyl-1H-pyrazolo[3,4-d]pyrimidin-6-yl]phenyl}-3-pyridin-3-ylurea (Scheme s 1 and 2)

4,6-Dichloro-1-methyl-1H-pyrazolo[3,4-d]pyrimidine (0.5 g, 2.46 mmol), Et3N (1.05 mL, 7.5 mmol) and 6,8-dioxa-3-azabicyclo[3.2.1]octane hydrochloride (373 mg) in CH2Cl2 (5 mL) is stirred for 18 h. Concentration in vacuo followed by silica gel chromatography (hexane/ethyl acetate) gives 3-(6-chloro-1-methyl-1H-pyrazolo[3,4-d]pyrimidin-4-yl)-6,8-dioxa-3-azabicyclo[3.2.1]octane as a white powder (320 mg). This material (0.16 g, 0.57 mmol) was treated with 4-(4,4,5,5-tetramethyl-1,3,2-dioxaborolan-2-yl)aniline (0.186 g, 0.85 mmol), aq. Na2CO3 (0.425 mL, 2M), and tetrakis triphenylphosphine palladium (20 mg) in 1:1 toluene: ethanol. The reaction mixture was heated in a microwave at 120 C for 20 min to give 4-(4-(6,8-dioxa-3-azabicyclo[3.2.1] octan-3-yl)-1-methyl-1H-pyrazolo[3,4-d]pyrimidin-6-yl) aniline. To this material (190 mg, 0.56 mmol) in CH2Cl2 is added Et3N (0.42 mL) and a solution of triphosgene (83 mg, 0.28 mmol) in CH2Cl2. After 30 min half of the solution is added to 3-aminopyridine (105 mg, 1.12 mmol). After 2 h aq. workup and silica gel chromatography (EtOAc/MeOH) gives the title compound as an off-white solid (104 mg). HRMS m/z=459.1894 (M+H).

1-{4-[4-(6,8-dioxa-3-azabicyclo[3.2.1]oct-3-yl)-1-methyl-1H-pyrazolo[3,4-d]pyrimidin-6-yl]phenyl}-3-methylurea Using methylamine in the above procedure gives the title compound as an off-white solid (102 mg).

1-(1,4-dioxaspiro[4.5]dec-8-yl)-6-(1H-indol-5-yl)-4-(8-oxa-3-azabicyclo[3.2.1]oct-3-yl)-1H-pyrazolo[3,4-d]pyrimidine (Scheme 28)

6-Chloro-1-(1,4-dioxaspiro[4.5]dec-8-yl)-4-(8-oxa-3-azabicyclo[3.2.1]oct-3-yl)-1H-pyrazolo[3,4-d]pyrimidine (0.20 g, 0.493 mmol) is treated with 5-(4,4,5,5-tetramethyl-1,3,2-dioxaborolan-2-yl)-1H-indole (0.119 g, 0.74 mmol), aq. Na2CO3 (0.52 mL, 2M), and tetrakis triphenylphosphine palladium (20 mg) in 1:1 toluene:ethanol. The reaction mixture is heated in a microwave at 120 C for 60 min. Aq. workup followed by RP HPLC (H2O, CH3CN, TFA) gives the title compound as a white solid (60 mg). MS m/s=487.2 (M+H)

Preparation of N-{4-[4-(8-Oxa-3-aza-bicyclo[3.2.1] oct-3-yl)-1H-pyrazolo[3,4-d]pyrimidin-6-yl]-phenyl}-acetamide (Scheme 32)

6-Chloro-4-(8-oxa-3-aza-bicyclo[3.2.1]oct-3-yl)-1H-pyrazolo[3,4-d]pyrimidine (21 mmol) is taken up as a suspension in dry ethyl acetate (50 mL). Following the addition of 4-toluenesulfonic acid monohydrate (25 mg), the mixture is heated to 60° C. and 3,4-dihydro-2H-pyran (2.5 mL) is added in drops. The reaction mixture is maintained at 60° C. for 18 hours and is then concentrated under reduced pressure. The residue is purified by flash silica gel chromatography. Following concentration of fractions, 6-chloro-4-(8-oxa-3-aza-bicyclo[3.2.1]oct-3-yl)-1-(tetrahydro-pyran-2-yl)-1H-pyrazolo[3,4-d]pyrimidine is obtained. 6-Chloro-4-(8-oxa-3-aza-bicyclo[3.2.1]oct-3-yl)-1-(tetrahydro-pyran-2-yl)-1H-pyrazolo[3,4-d]pyrimidine (3.1 mmol) is coupled to 4-acetamidophenylboronic acid (0.83 g, 4.6 mmol) with tetrakis(triphenylphosphine) palladium (0) (2.5 mol %), 2 M aqueous sodium carbonate solution, and ethylene glycol dimethyl ether (DME) and under microwave irradiation (175 C, 10 min). Following an aqueous workup and flash chromatography, N-{4-[4-(8-Oxa-3-aza-bicyclo[3.2.1]oct-3-yl)-1-(tetrahydro-pyran-2-yl)-1H-pyrazolo[3,4-d]pyrimidin-6-yl]-phenyl}-acetamide is obtained. N-{4-[4-(8-Oxa-3-aza-bicyclo[3.2.1]oct-3-yl)-1-(tetrahydro-pyran-2-yl)-1H-pyrazolo[3,4-d]pyrimidin-6-yl]-phenyl}-acetamide (1.2 mmol) is taken up in dioxane (5 mL), treated with 4 M hydrogen chloride in dioxane (5 mL), and allowed to stir at room temperature for 3 days. The slurry is concentrated and purified by reverse phase preparative high performance liquid chromatography, employing a Phenomenex Prodigy 250 mm×21.2 mm 5 µm column and a 5% acetonitrile/95% water/0.1% trifluoroacetic acid to 100% acetonitrile gradient over 40 minutes. After concentration, N-{4-[4-(8-Oxa-3-aza-bicyclo[3.2.1]oct-3-yl)-1H-pyrazolo[3,4-d]pyrimidin-6-yl]-phenyl}-acetamide is provided.

4-{[1-(1-benzylpiperidin-4-yl)-4-(8-oxa-3-azabicyclo[3.2.1]oct-3-yl)-1H-pyrazolo[3,4-d]pyrimidin-6-yl]amino}phenol (Scheme 28)

50 mg (0.11 mmol) of 1-(1-benzylpiperidin-4-yl)-6-chloro-4-(8-oxa-3-azabicyclo[3.2.1]oct-3-yl)-1H-pyrazolo [3,4-d]pyrimidine was dissolved in 1 mL ethylene glycol. 0.24 mmol (26.2 mg) 4-aminophenol was added and the mixture was heated under microwave irradiation to 220 C (15 min). The mixture was diluted with 1 mL DMSO and purified by HPLC (TFA buffers) to give 16 mg of the title compound.

8-Oxa-3-aza-bicyclo[3.2.1]octane (Scheme 46)

To a mechanically stirred suspension of silica-supported NaIO4 (240 g) in THF (1260 mL) and CH2Cl2 (138 mL) at 0° C. was added 1,5-hexadiene (8.5 mL) followed by addition in drops of a 0.01 M aqueous solution of RuCl3 (14.4 mL). After 1.5 h, iPrOH (300 mL) was added. Stir 10 min, then filter, wash silica with EtOAc and concentrate filtrate. Pass oil through silica gel eluting with Et2O, EtOAc and 5% MeOH/CHCl3. Yields a clear oil (9.5 g). This material was dissolved in pyridine (90 mL) at 0° C. A solution of TsCl (31 g) in pyridine (36 mL) was added in drops. Allow to warm to RT. After 18 h H2O (300 mL) was added. The white solid was collected by filtration and dried (12 g). This material in toluene (60 mL) was treated with benzylamine (10 mL). Heat at reflux for 18 h. Filter and concentrate in vacuo. Purify by vacuum distillation (5.7 g). This compound (7.3 g) in 1,2-dichloroethane (150 mL) was treated with 1-chloroethyl chloroformate (12 mL) and $K_2CO_3$ (15 g) and heated at reflux overnight. Filter using $CH_2Cl_2$. Concentrate, take up in EtOH and add 12 N HCl (5 mL). Concentrate. Add acetone and filter (4.5 g).

1-(4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea Step 1

1,4-Dioxaspiro[4.5]decan-8-one (34.6 g), tert-butyl hydrazinecarboxylate (30 g), and hexane (461 mL) were mixed in a 3 L 3-necked round-bottomed flask equipped with thermometer, mechanical stirrer, and condenser with a nitrogen inlet. The mixture was heated with a heating mantle to an internal temperature of 75° C. After 25 min the temperature was decreased to 70 deg because of bumping. The product is an insoluble solid and one of starting materials was not totally soluble. After 90 min a Dean-Stark trap was added to collect water. The reaction mixture was heated until all the lumps turned into a fine white solid (~6 h). At this time, 3 mL (75%) of water was in the Dean-Stark trap. The reaction mixture was cooled to an internal temperature of 57° C. and filtered. Rinsing three times with hexane (150 mL) and air-drying over house vacuum 18 h gave a white solid (58.7 g, 98%). A second run of 1,4-dioxaspiro[4.5]decan-8-one (38.7 g) gave tert-Butyl 2-(1,4-dioxaspiro[4.5]decan-8-ylidene)hydrazinecarboxylate (65.6 g, 98%).

Step 2 tert-Butyl 2-(1,4-dioxaspiro[4.5]decan-8-ylidene)hydrazinecarboxylate (58.7 g) was dissolved in THF (462 mL) and MeOH (57.6 mL) in a 3 L 3-necked round-bottomed flask equipped with thermometer, mechanical stirrer, and nitrogen inlet. The flask was cooled and when the internal temperature reached 2° C., sodium borohydride (8.2 g) was added in portions over 5 min. After stirring an additional 15 min at 0° C., the cooling bath was removed and stirring continued as the reaction warmed to RT. After 95 min an aliquot was removed, evaporated, and 1H NMR showed ~14% product, 86% SM. Additional sodium borohydride (8.2 g) was then added in portions over 5 min.

After stirring another 14 h at RT an aliquot was removed, evaporated, and $^1$H NMR showed ~93% product, 7% SM. Water (100 mL) was added in drops to form a gum. When addition was complete (~40 min) more water (100 mL) was added along with and ethyl acetate (500 mL). The resulting mixture was stirred at RT for 3 h, pour into a separatory funnel, and shaken well. The layers were separated, the aqueous layer saturated with solid NaCl, and extract once more ethyl acetate (200 mL). The combined ethyl acetate layers were dried ($Na_2SO_4$), concentrated under reduced pressure to give a gum. The gum was triturated with hexane and filtered. This gave 52.3 g (89%) of N'-(1,4-Dioxa-spiro[4.5]dec-8-yl)-hydrazinecarboxylic acid tert-butyl ester. A second run of tert-butyl 2-(1,4-dioxaspiro[4.5]decan-8-ylidene)hydrazinecarboxylate (65.6 g) gave N'-(1,4-Dioxa-spiro[4.5]dec-8-yl)-hydrazinecarboxylic acid tert-butyl ester (63.3 g, 96%).

Step 3

N'-(1,4-Dioxa-spiro[4.5]dec-8-yl)-hydrazinecarboxylic acid tert-butyl ester (52.3 g) was suspended in water (418 mL) in a 3 L 3-necked round bottomed flask equipped with thermometer, mechanical stirrer, and condenser with nitrogen inlet. The reaction was heated using internal temperature control with a heating mantle set at 100° C. The reaction was followed by LCMS (ES-API, Pos scan):

| 3 h | 32% product | 68% SM |
|---|---|---|
| 4.5 h | 50% product | 50% SM |
| 6 h | 60% product | 40% SM |
| 12 h | 98.7% product | 1.3% SM |

After 12 hr the reaction mixture was a clear, yellow solution.

(1,4-Dioxa-spiro[4.5]dec-8-yl)-hydrazine (46 g, 368 mL of above solution) was cooled in an ice bath, then triethylamine (47 mL) and ethanol (368 mL) were added. When the internal temperature reached 7.6° C., 2,4,6-trichloro-pyrimidine-5-carbaldehyde (32 g, synthesized by method of WO 02/066482) was added as a solid over 1.5 min. The internal temperature jumped to 12.6° C., and continued to rise to 17° C. during 4 min. After stirring a total of 28 min, water (367 mL) was added and the slurry was filtered. The cake was washed well twice with water (300 mL), then hexane (300 mL) and air dried over house vacuum overnight. This gave a damp cake that was washed twice with hexane (400 mL). Air-drying over house vacuum over weekend gave 35.29 g (70.8%) of 4,6-dichloro-1-(1,4-dioxa-spiro[4.5]dec-8-yl)-1H-pyrazolo[3,4-d]pyrimidine, containing ~6.5% of 2,4,6-Trichloro-pyrimidine-5-carbaldehyde. It was important to have a minimal amount of 2,4,6-trichloro-pyrimidine-5-carbaldehyde, which consumes 2 equivalents of 8-oxa-3-azabicyclo[3.2.1]octane in the next step.

Step 4

8-Oxa-3-aza-bicyclo[3.2.1]octane hydrochloride salt (9.5 g), triethylamine (25 mL), and absolute ethanol (199 mL) were mixed in a 3 L 3-necked flask equipped with three stoppers and a large magnetic stir bar to produce a clear, colorless solution. The mixture was stirred vigorously and 4,6-dichloro-1-(1,4-dioxa-spiro[4.5]dec-8-yl)-1H-pyrazolo[3,4-d]pyrimidine (19.7 g) was added as a solid over 1.5 min. An immediate aliquot was removed and HPLC showed two major peaks at 1.960 min (16%, identified by LCMS as 2-chloro-4,6-bis-(8-oxa-3-aza-bicyclo[3.2.1]oct-3-yl)-pyrimidine-5-carbaldehyde) and at 2.104 min (72%, product). After a total of 28 min the yellow slurry was filtered and the flask rinsed twice with ethanol (40 mL). The cake was washed well with ethanol (80 mL) and hexane (80 mL), then dried under the house vacuum for 1.5 h. This gave 21.35 g (86%) of 6-chloro-1-(1,4-dioxa-spiro[4.5]dec-8-yl)-4-(8-oxa-3-azabicyclo[3.2.1]oct-3-yl)-1H-pyrazolo[3,4-d]pyrimidine containing 16 mol % ethanol.

Additional runs of 4,6-dichloro-1-(1,4-dioxa-spiro[4.5]dec-8-yl)-1H-pyrazolo[3,4-d]pyrimidine (5 g and 10 g) gave 6-chloro-1-(1,4-dioxa-spiro[4.5]dec-8-yl)-4-(8-oxa-3-azabicyclo[3.2.1]oct-3-yl)-1H-pyrazolo[3,4-d]pyrimidine (5.43 g and 10.8 g).

A total of 37.58 g of 6-chloro-1-(1,4-dioxa-spiro[4.5]dec-8-yl)-4-(8-oxa-3-aza-bicyclo[3.2.1]oct-3-yl)-1H-pyrazolo[3,4-d]pyrimidine was obtained from 16.7 g of 8-oxa-3-azabicyclo[3.2.1]octane hydrochloride salt consumed.

Step 5

6-Chloro-1-(1,4-dioxa-spiro[4.5]dec-8-yl)-4-(8-oxa-3-aza-bicyclo[3.2.1]oct-3-yl)-1H-pyrazolo[3,4-d]pyrimidine (6.5 g, 16.05 mmol) was dissolved in 1:1 toluene:ethanol (130 mL) and 10 mL of a 2M sodium carbonate solution and stirred at room temperature and degassed with nitrogen for 5 min. Then added 4-aminophenylboronic acid pinacol ester (4.2 g, 19.2 mmol) and tetrakis(triphenylphosphine) palladium (0.92 g, 0.05 mol %) and refluxed overnight under nitrogen.

Quenched with water and extract with ethyl acetate, separate organics and dried over magnesium sulfate. Filter off through Magnesol-XL™ (synthetic magnesium silicate) and conc. under reduced pressure to give and oil. Triturate with ether to precipitate a white solid, filter and wash with ether to give 4.1 g of 1-(4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea. (56%) (M+H=463).

Step 6

1-(4-(4-(8-Oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea (750 mg, 1.6 mmol) was dissolved/suspended in dichloromethane (3.0 mL) along with excess triethylamine (0.2 mL). This mixture is added by drops to a solution of triphosgene (240 mg, 0.8 mmol) in dichloromethane (3.0 mL). The mixture was stirred at room temperature for 10 min. Then added excess methylamine in THF (2.0M. solution) (3.0 mL) and stirred at room temperature for 30 min. Quenched with 0.1N. sodium hydroxide and extract with ethyl acetate, separated organics and dried over magnesium sulfate. Filter off through Magnesol™ and conc. under reduced pressure to give an oil. Triturate with ether to precipitate a white solid, filter and wash with ether to give 750 mg of crude product. Recrystallization from a minimum amount of ethanol to give 480 mg of 1-(4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea. (58%) (M+H=520).

2-Hydroxyethyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate (Scheme 47)

Step 1

To a solution of $CF_3CH_2NHNH_2$ (10 g, 70% aqueous solution in water) and ethanol (40 mL) at 0° C. under nitrogen, was added ethoxymethylenemalononitrile (7.4 g) at once as a solid. The ice bath was removed, and reaction mixture was immediately heated with heating mantle set at 95° C. (external temp) for 30 min. Analysis by HPLC after 20 min showed only the product with a retention time of 0.961 min. Evaporation of the reaction mixture while still warm removed the ethanol and water. A portion of dichloromethane was added and the mixture evaporated at 48° C. The red residue was used without further purification in next step.

Step 2

The red residue was diluted with dichloromethane (80 mL) and $CH_3CN$ (40 mL), then placed under nitrogen. A 24 mL portion of $Et_3N$ was added and the solution cooled to 0° C. Addition of p-nitrobenzoyl chloride (17.2 g) as solid in one portion was followed by removal of the cooling bath and stirring at room temperature. The reaction became warm. (Note that reaction does not go at 0° C.). After 1.5 h the reaction mixture was combined with a previous run of $CF_3CH_2NHNH_2$ (5 g), diluted with EtOAc (400 mL) and washed with saturated $NaHCO_3$ solution (3×200 mL). Evaporation gave a red gum, which was triturated with dichloromethane (<100 mL) and filtered. The collected solid was washed sparingly with dichloromethane to give 9.16 g (29.7%) of product. The filtrate was passed through a silica plug 3"H×4" eluting with 5% methanol in dichloromethane (fractions 1-2, 500 ml fractions), then 10% methanol in dichloromethane (fractions 3-4, 500 ml fractions). The precipitate in fraction 2 was filtered to give additional 5.5 g (18%). The total product was 14.66 g (47.6% for the two steps).

Step 3

A mixture of N-[4-cyano-2-(2,2,2-trifluoro-ethyl)-2H-pyrazol-3-yl]-4-nitro-benzamide (5 g) and 2.5 N NaOH (80 mL) in ethanol (40 mL) was cooled to 0° C. under a nitrogen atmosphere. Addition of a few drops of 30% $H_2O_2$ in less than 1 min caused the reaction mixture to solidify. Removal of the ice bath allowed magnetic stirring to resume and the remaining 30% $H_2O_2$ was added. The total addition time was 3.5 min and a total amount of $H_2O_2$ was 16.7 mL. The reaction mixture was a yellow slurry, slightly thickened. A heating mantle was placed on the flask and warmed to 95° C. (external temp) for 1 hr. Analysis by HPLC indicated no starting material. The peak with 1.870 min retention time had converted to an intermediate peak with 1.507 min retention time and small product peak with 1.906 min retention time. The temperature of the heating mantle was raised to 115° C. (external temp) and the progress of the reaction followed by HPLC:

| 2 h 45 min | 12% amide | 81% product |
| 4 h 45 min | 3.7% amide | 89% product |
| 6 h 45 min | 0.8% amide | 89% product. |

The heating mantle was removed and the volatiles evaporated while still hot. The mushy yellow solid (still wet) was acidified with 2 N HCl (100 mL) to a pH less than 1. The yellow solid turned white. The mixture was filtered, the collected solid washed with water, and placed in drying oven at 40° C. The filtrate was extracted with EtOAc (200 mL), the EtOAc layer, which is a white slurry, was transferred to a round bottom flask and evaporated at 29° C. to give a pale yellow solid. This solid was diluted with hexane (100 mL), crushed, scraped, and then filtered. The solid was washed with hexanes (2×50 mL) and air dry on Buchner funnel covered with a crystallizing dish under house vacuum for at least 5 h to give 4.92 g (98.4%) of product.

Step 4

6-(4-Nitro-phenyl)-1-(2,2,2-trifluoro-ethyl)-1H-pyrazolo[3,4-d]pyrimidin-4-ol (4.73 g) and $POCl_3$ (46 mL) was heated with heating mantle at 120° C. (external temp). Five drops of DMF were added. After 1.5 h, the off-white slurry became an amber, clear solution. Analysis by HPLC indicates reaction done—product peak at 2.781 min. The volatiles were removed at reduced pressure and the reaction mixture diluted with $CHCl_3$ and evaporated again. Combined with another run of 6-(4-nitro-phenyl)-1-(2,2,2-trifluoro-ethyl)-1H-pyrazolo[3,4-d]pyrimidin-4-ol (3.9 g). The combined tan solid was taken up in water (200 mL), the solid was crushed, and the mixture filtered. The collected sold was washed with water (4×50 mL), then washed with hexanes (4×100 mL). Air-drying on a fritted funnel covered with a crystallizing dish under house vacuum for at least 3 h gave 8.55 g (94%) of crude product.

Step 5

To 4-chloro-6-(4-nitro-phenyl)-1-(2,2,2-trifluoro-ethyl)-1H-pyrazolo[3,4-d]pyrimidine (3.79 g) in ethanol (106 mL) was added as a solid at once 8-oxa-3-aza-bicyclo[3.2.1]octane hydrochloride (1.68 g). The bridgehead amine was followed with $Et_3N$ (4.4 mL). The resulting pale yellow slurry was heated with a heating mantle at 90° C. (external temp). After 15 min the solution became very thick. Analysis by HPLC shows mostly product (59%) with a retention time at 2.716 min and a small amount of starting material with a 2.769 min. retention time. The heating was discontinued after total of 30 min. After standing at room temperature for 14 h, the mixture was combined with another run of 4-chloro-6-(4- nitro-phenyl)-1-(2,2,2-trifluoro-ethyl)-1H-pyrazolo[3,4-d] pyrimidine (3.38 g). The combined reaction mixtures were filtered, rinsed sparingly with ethanol, dried, and triturated with hexane. Air-drying on a fritted filter covered with a crystallizing dish under house vacuum gave 8.4 g (87%) of product.

Step 6

6-(4-nitro-phenyl)-4-(8-oxa-3-aza-bicyclo[3.2.1]oct-3-yl)-1-(2,2,2-trifluoro-ethyl)-1H-pyrazolo[3,4-d]pyrimidine (4.18 g) was placed in THF (96 mL) and ethyl acetate (96 mL). The slurry was evacuated and flushed with argon five times. A small amount of crushed Dry Ice was added to make a $CO_2$ blanket. The 10% Pd/C (0.29 g) catalyst was added, and the reaction was again evacuated and flushed with argon three times. Using a balloon and a three-way stopcock, the reaction was evacuated and flushed with hydrogen three times. The resulting white slurry was stirred under a hydrogen atmosphere using two balloons attached via three-way stopcock. After 12 h the slurry dissolved, however LCMS indicates the presence of hydroxylamine (M−1 at m/e 419). (Note that ES-API negative shows hydroxylamine (M−1 with m/e 419) and ES-API positive shows amine (M+1 with m/e 405); HPLC analysis (10-100% acetonitrile in water with 0.1% TFA) shows no separation between hydroxylamine and amine. The hydrogen filled balloons were replaced with new ones, and stirring was continued at room temperature. After an additional 24 h, LCMS indicated no hydroxylamine, only the desired product. The reaction mixture was filtered through a Celite™ pad, and rinsed well with ethyl acetate (2×100 mL). The filtrated were combined with those from another 4 g run of 6-(4-nitro-phenyl)-4-(8-oxa-3-aza-bicyclo[3.2.1] oct-3-yl)-1-(2,2,2-trifluoro-ethyl)-1H-pyrazolo[3,4-d]pyrimidine. Concentration under reduced pressure gave 7.64 g (90.5%) of desired amine.

Step 7

4-[4-(8-Oxa-3-aza-bicyclo[3.2.1]oct-3-yl)-1-(2,2,2-trifluoro-ethyl)-1H-pyrazolo[3,4-d]pyrimidin-6-yl]-phenylamine (7.96 g) from the previous step was reacted in 0.5 g portions. Into a 50 mL round-bottomed flask with stopper and magnetic stir bar was added amine (0.5 g) and methylene chloride (7.5 mL). With good stirring $Et_3N$ (0.5 mL) was added, followed by a clear, colorless solution of triphosgene (0.22 g) in methylene chloride (2.5 mL). After 1 min at room temperature, an aliquot of the reaction mixture was diluted in MeOH to form the methyl carbamate. Analysis by HPLC indicated methyl carbamate peak with a retention time of 2.315 min (91%) and an amine starting material peak with a retention time of 1.650 (1.9%). After 8 min total reaction time ethylene glycol (1.38 mL) was added at once. The cloudy solution turned into a clear, yellow solution. Stirring at room temperature continued for 75 min, at which time HPLC analysis indicates a new peak with a retention time of 2.032 min (88%). The 32 0.5 g runs were combined and the combined product was divided into two portions. Each portion was diluted with methylene chloride (400 mL), and washed with water (4×100 mL), dried with brine (100 mL), and then dried over $Na_2SO_4$. Concentration under reduced pressure and combination of the two portions gave 8.77 g of 83.3% pure material. This was triturated with methylene chloride to give 1.2 g of {4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenyl}-carbamic acid 2-hydroxy-ethyl ester. Repeated chromatography of mother liquors with gradient of 0-5% MeOH in methylene chloride gave an additional 5.6 g of desired product, for a total of 6.8 g (70%).

2-hydroxyethyl{4-[1-(1-benzylpiperidin-4-yl)-4-(8-oxa-3-azabicyclo[3.2.1]oct-3-yl)-1H-pyrazolo[3,4-d] pyrimidin-6-yl]phenyl}carbamate (Scheme 29)

A mixture of 4-aminophenylboronic acid pinacol ester (67 mg, 0.31 mmol) in tetrahydrofuran (3 mL) and triethylamine (0.16 mL) was treated with triphosgene (47 mg, 0.16 mmol). After three minutes, the resultant slurry with treated with ethylene glycol (0.2 mL). The mixture was concentrated under reduced pressure and was then taken up as a solution in toluene/ethanol (1:1, 7 mL) and added to a 10-20 mL Smith process vial containing 1-(1-benzyl-piperidin-4-yl)-6-chloro-4-(8-oxa-3-aza-bicyclo[3.2.1]oct-3-yl)-1H-pyrazolo [3,4-d]pyrimidine (90 mg, 0.21 mmol) and tetrakis(triphenylphosphine)palladium(0) (35 mg, 10 mol %). To the suspension was added 2 M aqueous sodium carbonate solution (3 mL). The triphasic mixture was heated in the microwave for 20 minutes at 120° C. After cooling, the mixture was diluted with water and extracted with ethyl acetate. The organic extracts were washed with saturated aqueous sodium chloride solution, dried over anhydrous magnesium sulfate, filtered, and concentrated to dryness under reduced pressure. The crude solid residue was purified by reverse-phase high performance liquid chromatography using a Phenomenex Prodigy 21 mm×250 mm column, running a gradient elution of 12% acetonitrile/88% of 0.1% aqueous trifluoroacetic acid to 100% acetonitrile over 35 minutes. After the concentration of fractions under reduced pressure, 2-hydroxyethyl{4-[1-(1-benzylpiperidin-4-yl)-4-(8-oxa-3-azabicyclo[3.2.1]oct-3-yl)-1H-pyrazolo[3,4-d]pyrimidin-6-yl]phenyl}carbamate trifluoroacetic acid salt was obtained as a clear maroon amorphous solid (124 mg, 84%) MS (ES$^+$): 584.2, 585.2 (M+H)$^+$ Methyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate.TFA (Scheme 30)

A suspension of 1-(1-benzyl-piperidin-4-yl)-6-chloro-4-(8-oxa-3-aza-bicyclo[3.2.1]oct-3-yl)-1H-pyrazolo[3,4-d]pyrimidine (1.0 g, 2.3 mmol) and potassium carbonate (0.94 g, 6.8 mmol) in 1,2-dichloroethane (15 mL) was treated with methyl chloroformate (0.53 mL, 6.8 mmol) and then heated for two hours in a 55-60° C. oil bath. The mixture was filtered through a pad of diatomaceous earth, eluting with dichloromethane. The filtrate was concentrated to dryness under reduced pressure to furnish methyl 4-(4-(8-oxa-3-azabicyclo [3.2.1]octan-3-yl)-6-chloro-1H-pyrazolo[3,4-d]pyrimidin-1-yl)piperidine-1-carboxylate. MS (ES$^+$): 407.5, 409.6 (M+H)$^+$ A suspension of methyl 4-(4-(8-oxa-3-azabicyclo[3.2.1] octan-3-yl)-6-chloro-1H-pyrazolo[3,4-d]pyrimidin-1-yl)piperidine-1-carboxylate (2.3 mmol), 4-aminophenylboronic acid pinacol ester (0.76 g, 3.5 mmol), and tetrakis(triphenylphosphine)palladium(0) (0.27 g, 10 mol %) in toluene/ethanol (1:1, 12 mL) and 2 M aqueous sodium carbonate solution (2.5 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude residue was purified via reverse-phase high performance liquid chromatography using a Phenomenex Gemini column, running a gradient elution of 20% acetonitrile/80% of 0.07% aqueous ammonium hydroxide to 95% acetonitrile over 10 minutes. After the concentration of fractions under reduced pressure, methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate was obtained. MS (ES+): 464.6 (M+H)+

A solution of methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (30 mg, 0.06 mmol) in dichloromethane (2 mL) was treated with triphosgene (10 mg, 0.03 mmol) as a solution in dichloromethane (1 mL). After the passage of five minutes, one mmol of the appropriate nucleophile—in this case, 3-aminopyridine—was added to the resulting isocyanate mixture. After 10 minutes of stirring at room temperature, the mixture was concentrated to dryness under reduced pressure. The residue was purified via reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile. After the concentration of fractions under reduced pressure, methyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate.TFA was obtained. MS (ES+): 584.3 (M+H)+

The following ureas and carbamates were made via the addition of the appropriate nucleophile (1 mmol) to the isocyanate (0.06 mmol) derived from methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate, in accordance with the general procedure described for the preparation of methyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate.TFA.

Methyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate Nucleophile added to isocyanate: aniline. MS (ES+): 583.4 (M+H)+

Methyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate.TFA Nucleophile added to isocyanate: 4-aminopyridine MS (ES+): 584.3 (M+H)+

Methyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Nucleophile added to isocyanate: 2.0 M ethylamine solution in tetrahydrofuran MS (ES+): 535.4 (M+H)+

Methyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Nucleophile added to isocyanate: cyclopropylamine MS (ES+): 547.4 (M+H)+

Methyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate 2-fluoroethylamine hydrochloride (1 mmol) was dissolved in 1 M aqueous sodium hydroxide solution (1 mL). The solution of isocyanate (0.07 mmol) was added to the aqueous amine solution. The biphasic mixture was agitated on a vortex and then the aqueous phase was decanted. The organic layer was concentrated under reduced pressure and purified as usual by reverse-phase high performance liquid chromatography. MS (ES+): 553.4 (M+H)+

Methyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Nucleophile added to isocyanate (0.37 mmol): 2.0 M methylamine solution in tetrahydrofuran (2 mL) MS (ES+): 521.4 (M+H)+

2-hydroxyethyl(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)carbamate (Scheme s 4 and 2)

A nearly homogeneous suspension of 2,4,6-trichloro-pyrimidine-5-carbaldehyde (example 1, Scheme 28, 2.1 g, 10 mmol) in dichloromethane/ethanol (8:2, 100 mL) was cooled to −78° C. in a dry-ice/acetone bath. Anhydrous hydrazine (0.31 mL, 10 mmol) was added in drops via syringe, followed by triethylamine (4 mL), also via dropwise addition. The cooling bath was removed and after one hour, the opaque maroon mixture was treated with 8-oxa-3-aza-bicyclo[3.2.1] octane hydrochloride (1.4 g, 9.4 mmol), followed by triethylamine (2 mL). The mixture was allowed to stir overnight. The maroon solid was collected by Buchner filtration, washed with ethanol, and then dried under house vacuum to give 3-(6-chloro-1H-pyrazolo[3,4-d]pyrimidin-4-yl)-8-oxa-3-azabicyclo[3.2.1]octane (0.82 g, 31%). MS (ES+): 266.2, 268.2 (M+H)+

Diisopropyl azodicarboxylate (0.71 mL, 3.6 mmol) was added in drops to a suspension of 3-(6-chloro-1H-pyrazolo[3,4-d]pyrimidin-4-yl)-8-oxa-3-azabicyclo[3.2.1]octane (0.53 g, 2.0 mmol), tert-butyl 4-hydroxy-1-piperidinecarboxylate (0.48 g, 2.4 mmol), and triphenylphosphine (0.79 g, 3.0 mmol) in tetrahydrofuran (20 mL). After stirring at room temperature for 16 hours, the mixture was adsorbed onto flash silica gel and purified by automated flash chromatography (hexanes/ethyl acetate) to provide tert-butyl 4-(4-(8-oxa-3-azabicyclo[3.2.1]octan-3-yl)-6-chloro-1H-pyrazolo[3,4-d]pyrimidin-1-yl)piperidine-1-carboxylate as a white solid contaminated with a light yellow material (0.81 g, 90%). MS (ES+): 448.9, 450.2 (M+H)+

Tert-butyl 4-(4-(8-oxa-3-azabicyclo[3.2.1]octan-3-yl)-6-chloro-1H-pyrazolo[3,4-d]pyrimidin-1-yl)piperidine-1-carboxylate (0.60 g, 1.3 mmol) was dissolved in dichloromethane (10 mL) and treated with trifluoroacetic acid (5 mL). When LC/MS analysis revealed the deprotection of the Boc group, the mixture was concentrated to dryness under reduced pressure. Diethyl ether was evaporated three times from the crude material in order to afford a solid residue. The trifluoroacetate salt was dissolved in approximately 15 mL of warm acetone and added to a 10-20 mL Smith process vial charged with 2,2,2-trifluoroethyl trichloromethanesulfonate (0.56 g, 2.0 mmol). Potassium carbonate (0.90 g, 6.5 mmol) was added and the suspension was heated in the microwave for one hour at 100° C. After cooling to room temperature, the mixture was concentrated to dryness under reduced pressure. The residue was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. 3-(6-Chloro-1-(1-(2,2,2-trifluoroethyl)piperidin-4-yl)-1H-pyrazolo[3,4-d]pyrimidin-4-yl)-8-oxa-3-azabicyclo[3.2.1]octane was thus obtained as a yellow foam (0.55 g, 100%). MS (ES$^+$): 430.9, 432.9 (M+H)$^+$ A mixture of 3-(6-chloro-1-(1-(2,2,2-trifluoroethyl)piperidin-4-yl)-1H-pyrazolo[3,4-d]pyrimidin-4-yl)-8-oxa-3-azabicyclo[3.2.1]octane (0.55 g, 1.3 mmol), 4-aminophenylboronic acid pinacol ester (0.42 g, 1.9 mmol), and tetrakis(triphenylphosphine)palladium(0) (0.15 g, 10 mol %) in toluene/ethanol (1:1, 10 mL) and 2 M aqueous sodium carbonate solution (2 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude residue was purified via reverse-phase high performance liquid chromatography using a Phenomenex Prodigy 21 mm×250 mm column, running a gradient elution of 10% acetonitrile/90% of 0.1% aqueous trifluoroacetic acid to 95% acetonitrile over 30 minutes. After the concentration of fractions under reduced pressure, 4-(4-(8-oxa-3-azabicyclo[3.2.1]octan-3-yl)-1-(1-(2,2,2-trifluoroethyl)piperidin-4-yl)-1H-pyrazolo[3,4-d]pyrimidin-6-yl)aniline was obtained as a maroon oil that solidified upon standing. MS (ES$^+$): 488.4 (M+H)$^+$ A solution of 4-(4-(8-oxa-3-azabicyclo[3.2.1]octan-3-yl)-1-(1-(2,2,2-trifluoroethyl)piperidin-4-yl)-1H-pyrazolo[3,4-d]pyrimidin-6-yl)aniline (85 mg, 0.17 mmol) in tetrahydrofuran (6 mL) was treated with triphosgene (26 mg, 0.09 mmol), followed by triethylamine (0.11 mL). After the passage of five minutes, ethylene glycol (0.14 mL) was added. The mixture was concentrated to dryness under reduced pressure. The resultant residue was purified via reverse-phase high performance liquid chromatography using a Phenomenex Gemini 21 mm×100 mm column, running a gradient elution of 10% acetonitrile/90% of 0.1% aqueous trifluoroacetic acid to 70% acetonitrile over 20 minutes. After the concentration of fractions under reduced pressure, 2-hydroxyethyl(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)carbamate (55 mg, 56%) was obtained as clear blond semi-solid. MS (ES$^+$): 576.1, 577.1 (M+H)$^+$ 1-cyclopropyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea A solution of 4-(4-(8-oxa-3-azabicyclo[3.2.1]octan-3-yl)-1-(1-(2,2,2-trifluoroethyl)piperidin-4-yl)-1H-pyrazolo[3,4-d]pyrimidin-6-yl)aniline (47 mg, 0.097 mmol) in dichloromethane (3 mL) was treated with triethylamine (0.13 mL), followed by triphosgene (14 mg, 0.048 mmol). After the passage of five minutes, cyclopropylamine (0.14 mL) was added. The mixture was concentrated to dryness under reduced pressure. The resultant residue was purified via reverse-phase high performance liquid chromatography using a Phenomenex Gemini 21 mm×100 mm column, running a gradient elution of 10% acetonitrile/90% of 0.1% aqueous trifluoroacetic acid to 75% acetonitrile over 30 minutes. After the concentration of fractions under reduced pressure, 1-cyclopropyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea (67 mg) was obtained. MS (ES$^+$): 571.5, 572.5 (M+H)$^+$ 1-methyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea A solution of 4-(4-(8-oxa-3-azabicyclo[3.2.1]octan-3-yl)-1-(1-(2,2,2-trifluoroethyl)piperidin-4-yl)-1H-pyrazolo[3,4-d]pyrimidin-6-yl)aniline (110 mg, 0.22 mmol) in a mixture of dichloromethane (10 mL) and tetrahydrofuran (10 mL) was treated with triethylamine (0.10 mL), followed by triphosgene (100 mg, 0.34 mmol). After the passage of five minutes, 2.0 M methylamine solution in tetrahydrofuran (10 mL) was added. The mixture was concentrated to dryness under reduced pressure. The resultant residue was purified via reverse-phase high performance liquid chromatography using a Phenomenex Prodigy 21 mm×250 mm column, running a gradient elution of 10% acetonitrile/90% of 0.1% aqueous trifluoroacetic acid to 95% acetonitrile. After the concentration of fractions under reduced pressure, 1-methyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea was obtained. MS (ES$^+$): 545.2 (M+H)$^+$ 2-hydroxyethyl(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)carbamate
(Scheme 30)

Tert-butyl 4-(4-(8-oxa-3-azabicyclo[3.2.1]octan-3-yl)-6-chloro-1H-pyrazolo[3,4-d]pyrimidin-1-yl)piperidine-1-carboxylate (0.20 g, 0.45 mmol) was dissolved in dichloromethane (10 mL) and treated with trifluoroacetic acid (2 mL). When LC/MS analysis revealed the deprotection of the Boc group, the mixture was concentrated to dryness under reduced pressure. Diethyl ether was evaporated three times from the crude material in order to afford a solid residue. The trifluoroacetate salt was dissolved in dichloromethane (10 mL) and then treated with triethylamine (0.18 mL). The mixture was concentrated to dryness under reduced pressure. The residue was taken up in dichloromethane (10 mL) and treated with 3-pyridinecarboxaldehyde (0.064 mL). The mixture was allowed to stir for 10 minutes before the addition of sodium triacetoxyborohydride (0.15 g, 0.68 mmol). After stirring overnight, the mixture was diluted with dichloromethane and washed with 1 M aqueous sodium hydroxide solution. The aqueous phase was back extracted once with dichloromethane and then the combined organics were dried over anhydrous magnesium sulfate, filtered, and concentrated to dryness under reduced pressure. 3-(6-Chloro-1-(1-(pyridin-3-ylmethyl)piperidin-4-yl)-1H-pyrazolo[3,4-d]pyrimidin-4-yl)-8-oxa-3-azabicyclo[3.2.1]octane (0.20 g, 100%) was thus obtained as a yellow crystalline solid. MS (ES$^+$): 440.0, 441.2 (M+H)$^+$ A mixture of 3-(6-chloro-1-(1-(pyridin-3-ylmethyl)piperidin-4-yl)-1H-pyrazolo[3,4-d]pyrimidin-4-yl)-8-oxa-3-azabicyclo[3.2.1]octane (0.20 g, 0.46 mmol), 4-aminophenylboronic acid pinacol ester (0.15 g, 0.68 mmol), and tetrakis(triphenylphosphine)palladium(0) (0.053 g, 10 mol %) in toluene/ethanol (1:1, 8 mL) and 2 M aqueous sodium carbonate solution (2 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude 4-(4-(8-oxa-3-azabicyclo[3.2.1]octan-3-yl)-1-(1-(pyridin-3-ylmethyl)piperidin-4-yl)-1H-pyrazolo[3,4-d]pyrimidin-6-yl)aniline was carried on to the next step without further purification. MS (ES$^+$): 497.2, 498.2 (M+H)$^+$ A solution of crude 4-(4-(8-oxa-3-azabicyclo[3.2.1]octan-3-yl)-1-(1-(pyridin-3-ylmethyl)piperidin-4-yl)-1H-pyrazolo[3,4-d]pyrimidin-6-yl)aniline (83 mg, 0.17 mmol maximum) in tetrahydrofuran (5 mL) was treated with triphosgene (25 mg, 0.08 mmol), followed by triethylamine (0.11 mL). After the passage of five minutes, ethylene glycol (0.14 mL) was added. The mixture was concentrated to dryness under reduced pressure. The resultant residue was purified via reverse-phase high performance liquid chromatography using a Phenomenex Gemini 21 mm×100 mm column, running a gradient elution of 10% acetonitrile/90% of 0.1% aqueous trifluoroacetic acid to 60% acetonitrile over 20 minutes. After the concentration of fractions under reduced pressure, 2-hydroxyethyl(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)carbamate.2TFA (47 mg, 34%) was obtained as clear brown semi-solid. MS (ES$^+$): 585.1, 586.1 (M+H)$^+$ The following ureas and carbamates were made via the addition of the appropriate nucleophile to the isocyanate (0.06 mmol) derived from 4-(4-(8-oxa-3-azabicyclo[3.2.1]octan-3-yl)-1-(1-(pyridin-3-ylmethyl)piperidin-4-yl)-1H-pyrazolo[3,4-d]pyrimidin-6-yl)aniline, in accordance with the general procedure described for the preparation of 2-hydroxyethyl(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)carbamate.2TFA.

1-(2-fluoroethyl)-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea.2TFA 2-fluoroethylamine hydrochloride (100 mg) was dissolved in 1 M aqueous sodium hydroxide solution (1 mL). The solution of isocyanate (0.06 mmol) was added to the aqueous amine solution. The biphasic mixture was agitated on a vortex and then was concentrated under reduced pressure and purified as usual by reverse-phase high performance liquid chromatography. Yield: 47 mg, 90% MS (ES$^+$): 586.2 (M+H)$^+$ 1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-phenylurea.2TFA Nucleophile added to isocyanate: Aniline (91 µL) Yield: 50 mg, 85% MS (ES$^+$): 616.6 (M+H)$^+$ 1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-3-ylurea.3TFA Nucleophile added to isocyanate: 3-aminopyridine (94 mg) MS (ES$^+$): 617.6 (M+H)$^+$ 1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-4-ylurea.3TFA Nucleophile added to isocyanate: 4-aminopyridine (94 mg) MS (ES$^+$): 617.2 (M+H)$^+$ 1-ethyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea.2TFA Nucleophile added to isocyanate: 2 M ethylamine in tetrahydrofuran (1 mL) MS (ES$^+$): 568.6 (M+H)$^+$ 1-methyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea.2TFA Nucleophile added to isocyanate (0.23 mmol): 2 M methylamine in tetrahydrofuran (10 mL) MS (ES$^+$): 545.4 (M+H)$^+$ tert-butyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate
(Scheme 30)

A mixture of tert-butyl 4-(4-(8-oxa-3-azabicyclo[3.2.1]octan-3-yl)-6-chloro-1H-pyrazolo[3,4-d]pyrimidin-1-yl)piperidine-1-carboxylate (2.9 mmol), 4-nitrophenylboronic acid (0.73 g, 4.4 mmol), and tetrakis(triphenylphosphine)palladium(0) (0.34 g, 10 mol %) in toluene/ethanol (1:1, 12 mL) and 2 M aqueous sodium carbonate solution (3 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed twice with 1 M aqueous sodium hydroxide solution, once with saturated aqueous sodium chloride solution, dried over anhydrous magnesium sulfate, filtered, and concentrated to dryness under reduced pressure. The crude residue was further purified by automated flash chromatography (methanol/dichloromethane) to provide tert-butyl 4-(4-(8-oxa-3-azabicyclo[3.2.1]octan-3-yl)-6-(4-nitrophenyl)-1H-pyrazolo[3,4-d]pyrimidin-1-yl)piperidine-1-carboxylate. MS (ES$^+$): 536.3 (M+H)$^+$ A solution of tert-butyl 4-(4-(8-oxa-3-azabicyclo[3.2.1]octan-3-yl)-6-(4-nitrophenyl)-1H-pyrazolo[3,4-d]pyrimidin-1-yl)piperidine-1-carboxylate (0.13 g, 0.24 mmol) in tetrahydrofuran (5 mL) was degassed by the addition of crushed solid carbon dioxide. Palladium-on-carbon (5%, 20 mg) was then added. The mixture was stirred magnetically overnight under a balloon of hydrogen gas. The mixture was filtered through a pad of diatomaceous earth, eluting with ethyl acetate. The filtrate was concentrated under reduced pressure to provide tert-butyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate as a pale yellow foam. MS (ES$^+$): 506.4 (M+H)$^+$ A solution of tert-butyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (130 mg, 0.26 mmol) in dichloromethane (5 mL) was treated with triphosgene (37 mg, 0.12 mmol) as a solution in dichloromethane (2 mL). After the passage of five minutes, the appropriate nucleophile—in this case, 2.0 M methylamine solution in tetrahydrofuran (2 mL)—was added to the resulting isocyanate mixture. After 30 minutes of stirring at room temperature, the mixture was concentrated to dryness under reduced pressure. The residue was purified via reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile. After the concentration of fractions under reduced pressure, tert-butyl 4-[6-{4-[(methylcarbamoyl)

amino]phenyl}-4-(8-oxa-3-azabicyclo[3.2.1]oct-3-yl)-1H-pyrazolo[3,4-d]pyrimidin-1-yl]piperidine-1-carboxylate was obtained. MS (ES$^+$): 563.4 (M+H)$^+$ The following ureas and carbamates were made via the addition of the appropriate nucleophile to the isocyanate (0.07 mmol) derived from tert-butyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate, in accordance with the general procedure described for the preparation of tert-butyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate. (Scheme 30)

tert-butyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate 2-fluoroethylamine hydrochloride (0.10 g, 1 mmol) was dissolved in 1 M aqueous sodium hydroxide solution (1 mL). The solution of isocyanate was added to the aqueous amine. The biphasic mixture was agitated on a vortex and then the aqueous phase was decanted. The organic layer was concentrated under reduced pressure and purified as usual by reverse-phase high performance liquid chromatography. MS (ES$^+$): 595.2 (M+H)$^+$ tert-butyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Nucleophile added to isocyanate: 2 M ethylamine in tetrahydrofuran (0.5 mL, 1 mmol) MS (ES$^+$): 577.2 (M+H)$^+$ tert-butyl 4-[4-(8-oxa-3-azabicyclo[3.2.1]oct-3-yl)-6-{4-[(pyridin-3-ylcarbamoyl)amino]phenyl}-1H-pyrazolo[3,4-azabicyclo[3.2.1]oct-3-yl)-1H-pyrazolo[3,4-d]pyrimidin-1-yl]piperidine-1-carboxylate Nucleophile added to isocyanate: 3-aminopyridine (94 mg) MS (ES$^+$): 626.2 (M+H)$^+$ tert-butyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate.TFA Nucleophile added to isocyanate: 4-aminopyridine (94 mg) MS (ES$^+$): 626.2 (M+H)$^+$ tert-butyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Nucleophile added to isocyanate: Cyclopropylamine (69 µL) MS (ES$^+$): 589.2 (M+H)$^+$ tert-butyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate Nucleophile added to isocyanate: Aniline (182 µL) MS (ES$^+$): 625.2 (M+H)$^+$ Methyl{4-[1-isopropyl-4-(8-oxa-3-azabicyclo[3.2.1]oct-3-yl)-1H-pyrazolo[3,4-d]pyrimidin-6-yl]phenyl}carbamate (Scheme 42)

A mixture of ethoxymethylenemalonitrile (0.55 g, 4.5 mmol) and iso-propylhydrazine (0.50 g, 4.5 mmol) in ethanol (10 mL) in a 10-20 mL Smith process vial was treated with triethylamine (0.88 mL). The vial was capped and heated in the microwave reactor for one hour at 150° C. Following cooling of the vial, the mixture was concentrated to dryness under reduced pressure. The residue was partitioned between ethyl acetate and water. The aqueous phase was extracted with ethyl acetate. The combined organic extracts were washed with saturated aqueous sodium chloride solution, dried over anhydrous magnesium sulfate, filtered, and concentrated to dryness under reduced pressure to provide 5-amino-1-isopropyl-1H-pyrazole-4-carbonitrile as a slowly solidifying syrup (0.72 g, >100%). MS (ES$^+$): 151.2 (M+H)$^+$ A mixture of crude 5-amino-1-isopropyl-1H-pyrazole-4-carbonitrile (0.72 g, 4.5 mmol maximum) and 4-nitrobenzoylchloride (1.3 g, 6.8 mmol) in dichloromethane (20 mL) was treated successively with triethylamine (1.8 mL, 14 mmol) and 4-N,N-dimethylaminoaniline (DMAP, 55 mg, 10 mol %). The mixture was heated to reflux (oil bath) for one hour and then allowed to cool to room temperature. The mixture was then concentrated to dryness under reduced pressure. The residue was dissolved in pyridine (20 mL). Water was added, followed by concentrated aqueous ammonium hydroxide (5 mL). The reaction vessel was swirled manually and then left overnight at room temperature. The mixture was concentrated to dryness under reduced pressure. The residue was partitioned between ethyl acetate and water. The aqueous phase was extracted three times with ethyl acetate. The combined extracts were washed twice with saturated aqueous sodium hydrogen carbonate solution and once each with 0.25 M aqueous hydrochloric acid and saturated aqueous sodium chloride solution. Drying over anhydrous magnesium sulfate was followed by filtration and then concentration under reduced pressure to provide N-(4-cyano-1-isopropyl-1H-pyrazol-5-yl)-4-nitrobenzamide as a dark yellow solid (1.3 g, 100%). MS (ES$^+$): 299.6, 299.9 (M+H)$^+$ A suspension of N-(4-cyano-1-isopropyl-1H-pyrazol-5-yl)-4-nitrobenzamide (1.3 g, 4.3 mmol) in 1 M aqueous sodium hydroxide solution (9 mL) was made into a homogeneous mixture by the addition of approximately 40 mL of ethanol. Aqueous hydrogen peroxide solution (30%, 5 mL) was added and the mixture was slowly heated to reflux, at which state it remained overnight. After the mixture was allowed to cool to room temperature, it was treated with concentrated hydrochloric acid (5 mL), precipitating a light yellow solid. The solid was collected via Buchner filtration, washed with water, and dried under house vacuum to provide 1-isopropyl-6-(4-nitrophenyl)-1H-pyrazolo[3,4-d]pyrimidin-4-ol as a pale yellow solid (0.76 g, 58%). MS (ES$^+$): 299.8 (M+H)$^+$ A suspension of 1-isopropyl-6-(4-nitrophenyl)-1H-pyrazolo[3,4-d]pyrimidin-4-ol (0.76 g, 2.5 mmol) in phosphorus oxychloride (20 mL) was heated a sealed tube with a heat gun until all of the starting material was dissolved. After allowing the mixture to cool to room temperature it was concentrated to dryness under reduced pressure, leaving a pale yellow solid which was then triturated with water and collected by Buchner filtration. The solid was further washed with water and dried under house vacuum to provide 4-chloro-1-isopropyl-6-(4-nitrophenyl)-1H-pyrazolo[3,4-d]pyrimidine (0.90 g, >100%) as a pale yellow solid. MS (ES$^+$): 317.7, 319.8 (M+H)$^+$ A suspension of crude 4-chloro-1-isopropyl-6-(4-nitrophenyl)-1H-pyrazolo[3,4-d]pyrimidine (2.5 mmol maximum) and 8-oxa-3-aza-bicyclo[3.2.1]octane hydrochloride (0.47 g, 3.1 mmol) in ethanol (12 mL) was treated with triethylamine (1.1 mL) and then heated for 20 minutes in the microwave reactor at 140° C. At the completion of the reaction, the mixture was refrigerated overnight before collection of the precipitate via Buchner filtration. The solid was washed with methanol and dried under house vacuum to provide 3-(1-isopropyl-6-(4-nitrophenyl)-1H-pyrazolo[3,4-d]pyrimidin-4-yl)-8-oxa-3-azabicyclo[3.2.1]octane as a yellow powder (0.96 g, 97% over 2 steps). MS (ES$^+$): 394.9, 396.0 (M+H)$^+$ 3-(1-Isopropyl-6-(4-nitrophenyl)-1H-pyrazolo[3,4-d]pyrimidin-4-yl)-8-oxa-3-azabicyclo[3.2.1]octane (0.96 g, 2.4 mmol) was taken up as a suspension in tetrahydrofuran (20 mL) and ethyl acetate (10 mL) in a Parr bottle. After degassing the mixture, 10% palladium on carbon (approximately 50 mg) was added, followed by concentrated hydrochloric acid (approximately 0.1 mL). The mixture was shaken under 50 psi of hydrogen until no more hydrogen was consumed. The completed reaction mixture was filtered through a pad of diatomaceous earth, eluting with 20% methanol/dichloromethane. The filtrate was concentrated to dryness under reduced pressure to provide crude 4-(4-(8-oxa-3-azabicyclo[3.2.1]octan-3-yl)-1-isopropyl-1H-pyrazolo[3,4-d]pyrimidin-6-yl)aniline hydrochloride (1.3 g, >100%), which was purified by reverse-phase high performance liquid chromatography using a Phenomenex Prodigy 21 mm×250 mm column, running a gradient elution of 17% acetonitrile/90% of 0.1% aqueous trifluoroacetic acid to 100% acetonitrile over 30 minutes. The desired fractions were concentrated to almost to dryness when the suspension was treated with saturated aqueous sodium hydrogen carbonate solution. The material was collected by Buchner filtration and dried under house vacuum to provide the free base 4-(4-(8-oxa-3-azabicyclo[3.2.1]octan-3-yl)-1-isopropyl-1H-pyrazolo[3,4-d]pyrimidin-6-yl)aniline as a tan solid (0.32 g, 37%). MS (ES$^+$): 364.9, 365.8 (M+H)$^+$ A solution of 4-(4-(8-oxa-3-azabicyclo[3.2.1]octan-3-yl)-1-isopropyl-1H-pyrazolo[3,4-d]pyrimidin-6-yl)aniline (0.027 g, 0.07 mmol) in dichloromethane (2 mL) was treated with triethylamine (0.028 mL), followed by a solution of triphosgene (0.011 g, 0.04 mmol) in dichloromethane (1 mL). After the passage of 10 minutes, the appropriate nucleophile—in the case, methanol (excess)—was added to the 3-(6-(4-isocyanatophenyl)-1-isopropyl-1H-pyrazolo[3,4-d]pyrimidin-4-yl)-8-oxa-3-azabicyclo[3.2.1]octane ("isocyanate") mixture. After 10 minutes, the reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile over 35 minutes to provide methyl{4-[1-isopropyl-4-(8-oxa-3-azabicyclo[3.2.1]oct-3-yl)-1H-pyrazolo[3,4-d]pyrimidin-6-yl]phenyl}carbamate (15 mg, 48%). MS (ES$^+$): 423.2 (M+H)$^+$ The following ureas and carbamates were made via the addition of the appropriate nucleophile to the isocyanate (0.07 mmol) derived from 4-(4-(8-oxa-3-azabicyclo[3.2.1]octan-3-yl)-1-isopropyl-1H-pyrazolo[3,4-d]pyrimidin-6-yl)aniline, in accordance with the general procedure described for methyl{4-[1-isopropyl-4-(8-oxa-3-azabicyclo[3.2.1]oct-3-yl)-1H-pyrazolo[3,4-d]pyrimidin-6-yl]phenyl}carbamate.

2,3-dihydroxypropyl{4-[1-isopropyl-4-(8-oxa-3-azabicyclo[3.2.1]oct-3-yl)-1H-pyrazolo[3,4-d]pyrimidin-6-yl]phenyl}carbamate Nucleophile added to isocyanate: (±)-2,2-Dimethyl-1,3-dioxolane-4-methanol (0.19 mL, 1.5 mmol). After concentration, the residue was dissolved in aqueous dioxane (1:1, 2 mL) and treated with 12N HCl (2 drops). The mixture was stirred in a 60° C. oil bath for 20 minutes, concentrated under reduced pressure, and then purified as usual via reverse-phase HPLC to provide 2,3-dihydroxypropyl{4-[1-isopropyl-4-(8-oxa-3-azabicyclo[3.2.1]oct-3-yl)-1H-pyrazolo[3,4-d]pyrimidin-6-yl]phenyl}carbamate (23 mg, 65%). MS (ES$^+$): 483.2 (M+H)$^+$ 1-(2-hydroxyethyl)-3-{4-[1-isopropyl-4-(8-oxa-3-azabicyclo[3.2.1]oct-3-yl)-1H-pyrazolo[3,4-d]pyrimidin-6-yl]phenyl}urea Nucleophile added to isocyanate: Ethanolamine (0.091 mL) Yield: 21 mg, 62%. MS (ES$^+$): 452.2 (M+H)$^+$ 1-{4-[1-isopropyl-4-(8-oxa-3-azabicyclo[3.2.1]oct-3-yl)-1H-pyrazolo[3,4-d]pyrimidin-6-yl]phenyl}-3-pyridin-4-ylurea.TFA Nucleophile added to isocyanate: 4-aminopyridine (141 mg) Yield: 24 mg, 55% MS (ES$^+$): 485.2 (M+H)$^+$ 1-{4-[1-isopropyl-4-(8-oxa-3-azabicyclo[3.2.1]oct-3-yl)-1H-pyrazolo[3,4-d]pyrimidin-6-yl]phenyl}-3-methylurea Nucleophile added to isocyanate: 2 M methylamine in tetrahydrofuran (0.75 mL, 1.5 mmol) Yield: 19 mg, 63% MS (ES$^+$): 422.2 (M+H)$^+$ 1-cyclopropyl-3-{4-[1-isopropyl-4-(8-oxa-3-azabicyclo[3.2.1]oct-3-yl)-1H-pyrazolo[3,4-d]pyrimidin-6-yl]phenyl}urea Nucleophile added to isocyanate: Cyclopropylamine (0.10 mL) Yield: 17 mg, 51% MS (ES$^+$): 448.2 (M+H)$^+$ 3-hydroxypropyl{4-[1-isopropyl-4-(8-oxa-3-azabicyclo[3.2.1]oct-3-yl)-1H-pyrazolo[3,4-d]pyrimidin-6-yl]phenyl}carbamate Nucleophile added to isocyanate: 1,3-propanediol (0.11 mL) Yield: 16 mg, 47% MS (ES$^+$): 467.2 (M+H)$^+$ 1-ethyl-3-{4-[1-isopropyl-4-(8-oxa-3-azabicyclo[3.2.1]oct-3-yl)-1H-pyrazolo[3,4-d]pyrimidin-6-yl]phenyl}urea Nucleophile added to isocyanate: 2 M ethylamine in tetrahydrofuran (0.75 mL, 1.5 mmol) Yield: 20 mg, 61% MS (ES$^+$): 436.2 (M+H)$^+$ 1-(2-fluoroethyl)-3-{4-[1-isopropyl-4-(8-oxa-3-azabicyclo[3.2.1]oct-3-yl)-1H-pyrazolo[3,4-d]pyrimidin-6-yl]phenyl}urea 2-fluoroethylamine hydrochloride (0.15 g, 1.5 mmol) was dissolved in 1 M aqueous sodium hydroxide solution (1.5 mL). The solution of isocyanate (0.07 mmol) was added to the aqueous amine. The biphasic mixture was agitated on a vortex and then the aqueous phase was decanted. The organic layer was concentrated under reduced pressure and purified as usual by reverse-phase high performance liquid chromatography. Yield: 20 mg, 44% MS (ES⁺): 454.2 (M+H)⁺

1-{4-[1-isopropyl-4-(8-oxa-3-azabicyclo[3.2.1]oct-3-yl)-1H-pyrazolo[3,4-d]pyrimidin-6-yl]phenyl}-3-phenylurea Nucleophile added to isocyanate: Aniline (0.14 mL) Yield: 24 mg, 67% MS (ES⁺): 484.2 (M+H)⁺

2-hydroxyethyl{4-[1-isopropyl-4-(8-oxa-3-azabicyclo[3.2.1]oct-3-yl)-1H-pyrazolo[3,4-d]pyrimidin-6-yl]phenyl}carbamate Nucleophile added to isocyanate: Ethylene glycol (0.084 mL) Yield: 22 mg, 66% MS (ES⁺): 453.2 (M+H)⁺

1-{4-[1-isopropyl-4-(8-oxa-3-azabicyclo[3.2.1]oct-3-yl)-1H-pyrazolo[3,4-d]pyrimidin-6-yl]phenyl}-3-pyridin-3-ylurea.TFA Nucleophile added to isocyanate: 3-aminopyridine (0.14 g) Yield: 28 mg, 64% MS (ES⁺): 485.2 (M+H)⁺

1-(6-morpholin-4-ylpyridin-3-yl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea.TFA (Scheme 42)

A solution of 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine (50 mg, 0.12 mmol) in dichloromethane (4 mL) was treated with triethylamine (0.16 mL), followed by a solution of triphosgene (19 mg, 0.064 mmol) in dichloromethane (1 mL). After the passage of 5 minutes, the appropriate nucleophile—in the case, 6-morpholinopyridin-3-amine (86 mg, 0.48 mmol)—was added to the 3-(6-(4-isocyanatophenyl)-1-(2,2,2-trifluoroethyl)-1H-pyrazolo[3,4-d]pyrimidin-4-yl)-8-oxa-3-azabicyclo[3.2.1]octane ("isocyanate") mixture. After being left overnight at room temperature, the reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile over 30 minutes to provide 1-(6-morpholin-4-ylpyridin-3-yl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea.TFA (18 mg, 21%). MS (ES⁺): 610.2 (M+H)⁺

The following ureas and carbamates were made via the addition of the appropriate nucleophile to the isocyanate (0.12 mmol, unless stated otherwise) derived from 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine, in accordance with the general procedure described for 1-(6-morpholin-4-ylpyridin-3-yl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea.TFA. (Scheme 42)

3-aminobenzyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate Nucleophile added to isocyanate: (3-aminophenyl)methanol (59 mg, 0.48 mmol) Yield: 13 mg, 20% MS (ES⁺): 554.2 (M+H)⁺

1-[4-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate: (4-aminophenyl)methanol (59 mg, 0.48 mmol) Yield: 15 mg, 22% MS (ES⁺): 554.2 (M+H)⁺

1-[3-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate: (3-aminophenyl)methanol (59 mg, 0.48 mmol) Yield: 22 mg, 33% MS (ES⁺): 554.2 (M+H)⁺

1-(4-morpholin-4-ylphenyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate: 4-morpholinoaniline (86 mg, 0.48 mmol) Yield: 5 mg, 7% MS (ES⁺): 609.2 (M+H)⁺

1-[3-(dimethylamino)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate: N',N'-dimethylbenzene-1,3-diamine dihydrochloride (100 mg, 0.48 mmol) Yield: 4 mg, 6% MS (ES⁺): 567.2 (M+H)⁺ 1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-(4-piperazin-1-ylphenyl)urea.HCl Nucleophile added to isocyanate (0.45 mmol): tert-butyl 4-(4-aminophenyl)piperazine-1-carboxylate (620 mg, 2.2 mmol).

The reverse-phase HPLC purified product, tert-butyl 4-(4-(3-(4-(4-(8-oxa-3-azabicyclo[3.2.1]octan-3-yl)-1-(2,2,2-trifluoroethyl)-1H-pyrazolo[3,4-d]pyrimidin-6-yl)phenyl)ureido)phenyl)piperazine-1-carboxylate was taken up in dichloromethane (10 mL) and then treated with trifluoroacetic acid (1 mL). When the Boc group was deemed to have been removed (LC/MS analysis), the mixture was concentrated under reduced pressure and purified as usual by reverse-phase HPLC using HCl modifier instead of trifluoroacetic acid. Yield: 50 mg, 17% MS (ES⁺): 608.3 (M+H)⁺

1-cyclopropyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate (0.49 mmol): Cyclopropylamine (340 mg, 4.9 mmol) Yield: 240 mg, 100% MS (ES⁺): 488.2 (M+H)⁺

1-(2-fluoroethyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea 2-fluoroethylamine hydrochloride (60 mg, 0.60 mmol) was dissolved in 1 M aqueous sodium hydroxide solution (600 µL). The solution of isocyanate (0.1 mmol) was added to the aqueous amine. The biphasic mixture was agitated on a vortex and then the aqueous phase was decanted. The organic layer was concentrated under reduced pressure and purified as usual by reverse-phase high performance liquid chromatography. Yield: 38 mg, 79% MS (ES+): 494.1 (M+H)+

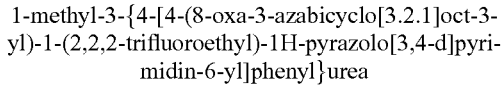

1-methyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate (0.1 mmol): 2 M methylamine in tetrahydrofuran (excess) Yield: 37 mg, 80% MS (ES+): 462.6 (M+H)+

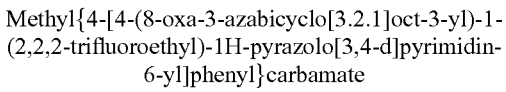

Methyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate Nucleophile added to isocyanate (0.1 mmol): methanol (excess) Yield: 37 mg, 80% MS (ES+): 463.1 (M+H)+

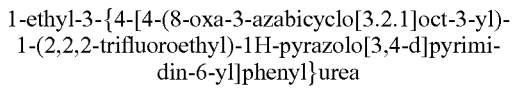

1-ethyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea Nucleophile added to isocyanate (0.1 mmol): 2 M ethylamine in tetrahydrofuran (excess) Yield: 34 mg, 72% MS (ES+): 476.7 (M+H)+

1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-3-ylurea.TFA Nucleophile added to isocyanate (0.1 mmol): 3-aminopyridine (1 mmol) Yield: 57 mg, 1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea.TFA Nucleophile added to isocyanate (0.1 mmol): 4-aminopyridine (1 mmol) Yield: 37 mg, 58% MS (ES+): 525.7 (M+H)+

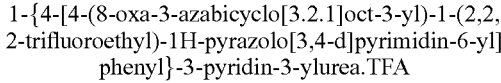

3-(dimethylamino)phenyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate Nucleophile added to isocyanate: 3-(dimethylamino)phenol (66 mg, 0.48 mmol) Yield: 21 mg, 30% MS (ES+): 568.2 (M+H)+

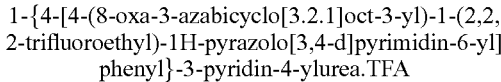

1-cyclopropyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea (Scheme 43)

To a 150-mL sealed tube containing a suspension of 4-chloro-6-(4-nitro-phenyl)-1-(2,2,2-trifluoro-ethyl)-1H-pyrazolo[3,4-d]pyrimidine (0.72 g, 2.0 mmol) and 3-oxa-8-azabicyclo[3.2.1]octane hydrochloride (0.33 g, 2.2 mmol) in ethanol (20 mL) was added triethylamine (1.0 mL, 2.2 mmol). The mixture was heated with a heat gun until all solid material was dissolved, then mixture was allowed to cool, at which time a precipitate was formed. The solid was collected by Buchner filtration, washed with methanol, and dried under house vacuum to provide 8-(6-(4-nitrophenyl)-1-(2,2,2-trifluoroethyl)-1H-pyrazolo[3,4-d]pyrimidin-4-yl)-3-oxa-8-azabicyclo[3.2.1]octane as a pale yellow solid (0.59 g, 68%). MS (ES+): 435.0 (M+H)+

A suspension of 8-(6-(4-nitrophenyl)-1-(2,2,2-trifluoroethyl)-1H-pyrazolo[3,4-d]pyrimidin-4-yl)-3-oxa-8-azabicyclo[3.2.1]octane (0.59 g, 1.4 mmol) in tetrahydrofuran (40 mL) and ethyl acetate (10 mL) was degassed by the addition of crushed dry ice and then treated with 10% palladium on carbon (100 mg). The resulting suspension was evacuated under weak vacuum and then filled with hydrogen gas (balloon). This evacuation/fill cycle was performed three more times and on the final iteration, the mixture was left to stir overnight under a hydrogen-filled balloon. The mixture was filtered through a pad of diatomaceous earth, eluting with methanol. The filtrate was concentrated under reduced pressure to afford 4-(4-(3-oxa-8-azabicyclo[3.2.1]octan-8-yl)-1-(2,2,2-trifluoroethyl)-1H-pyrazolo[3,4-d]pyrimidin-6-yl)aniline as a white solid (0.51 g, 89%). MS (ES+): 405.0 (M+H)+

A solution of 4-(4-(3-oxa-8-azabicyclo[3.2.1]octan-8-yl)-1-(2,2,2-trifluoroethyl)-1H-pyrazolo[3,4-d]pyrimidin-6-yl)aniline (30 mg, 0.074 mmol) in dichloromethane (1 mL) was treated with triethylamine (0.05 mL), followed by a solution of triphosgene (11 mg, 0.037 mmol) in dichloromethane (1 mL). After the passage of 5 minutes, the appropriate nucleophile—in the case, cyclopropylamine (17 mg, 0.30 mmol)—was added to the 8-(6-(4-isocyanatophenyl)-1-(2,2,2-trifluoroethyl)-1H-pyrazolo[3,4-d]pyrimidin-4-yl)-3-oxa-8-azabicyclo[3.2.1]octane ("isocyanate") mixture. After being left overnight at room temperature, the reaction mixture was concentrated to dryness under reduced pressure. The residue was purified by reverse-phase high performance liquid chromatography using a Phenomenex Gemini 21 mm×100 mm column, running a gradient elution of 5% acetonitrile/95% of 0.1% aqueous trifluoroacetic acid to 60% or 75% acetonitrile over 30 minutes to provide 1-cyclopropyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea (15 mg, 41%). MS (ES+): 488.2 (M+H)+

The following ureas and carbamates were made via the addition of the appropriate nucleophile to the isocyanate (0.074 mmol, unless stated otherwise) derived from 4-(4-(3-oxa-8-azabicyclo[3.2.1]octan-8-yl)-1-(2,2,2-trifluoroethyl)-1H-pyrazolo[3,4-d]pyrimidin-6-yl)aniline, in accordance with the general procedure described for 1-cyclopropyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea. (Scheme 43)

1-(4-morpholin-4-ylphenyl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea Nucleophile added to isocyanate: 4-morpholinoaniline (53 mg, 0.30 mmol) Yield: 22 mg, 48% MS (ES+): 609.2 (M+H)+

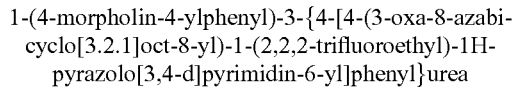

1-[4-(2-hydroxyethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea Nucleophile added to isocyanate: 2-(4-aminophenyl)ethanol (41 mg, 0.30 mmol) Yield: 13 mg, 31% MS (ES+): 568.2 (M+H)+

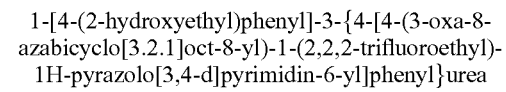

2-hydroxyethyl{4-[4-(3-oxa-8-azabicyclo[3.2.1]oct-8-yl)-1-(2,2,2-trifluoroethyl)-1H-pyrazolo[3,4-d]pyrimidin-6-yl]phenyl}carbamate Nucleophile added to isocyanate: ethylene glycol (excess) Yield: 36 mg, 99% MS (ES+): 493.2 (M+H)+

1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-pyridin-3-ylurea.TFA Nucleophile added to isocyanate: 3-aminopyridine (28 mg, 0.30 mmol) Yield: 35 mg, 74% MS (ES+): 525.2 (M+H)+

1-[4-(hydroxymethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea Nucleophile added to isocyanate: (4-aminophenyl)methanol (37 mg, 0.30 mmol) Yield: 11 mg, 27% MS (ES+): 554.2 (M+H)+

1-methyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea Nucleophile added to isocyanate: 2 M methylamine solution in tetrahydrofuran (excess) Yield: 29 mg, 85% MS (ES+): 462.2 (M+H)+

1-[4-(4-methylpiperazin-1-yl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea.TFA Nucleophile added to isocyanate: 4-(4-methylpiperazin-1-yl)aniline (57 mg, 0.30 mmol) Yield: 34 mg, 62% MS (ES+): 622.3 (M+H)+

1-{4-[2-(dimethylamino)ethoxy]phenyl}-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea.TFA Nucleophile added to isocyanate: 4-(2-(dimethylamino)ethoxy)aniline (54 mg, 0.30 mmol) Yield: 40 mg, 75% MS (ES+): 611.3 (M+H)+

1-(6-morpholin-4-ylpyridin-3-yl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea.TFA Nucleophile added to isocyanate: 6-morpholinopyridin-3-amine (54 mg, 0.30 mmol) Yield: 26 mg, 49% MS (ES+): 610.2 (M+H)+

1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-(4-piperazin-1-ylphenyl)urea.HCl Nucleophile added to isocyanate (0.49 mmol): tert-butyl 4-(4-aminophenyl)piperazine-1-carboxylate (430 mg, 1.55 mmol).
The reverse-phase HPLC purified product, tert-butyl 4-(4-(3-(4-(4-(3-oxa-8-azabicyclo[3.2.1]octan-8-yl)-1-(2,2,2-trifluoroethyl)-1H-pyrazolo[3,4-d]pyrimidin-6-yl)phenyl)ureido)phenyl)piperazine-1-carboxylate was taken up in dichloromethane (5 mL) and then treated with trifluoroacetic acid (2 mL). When the Boc group was deemed to have been removed (LC/MS analysis), the mixture was concentrated under reduced pressure and purified as usual by reverse-phase HPLC using HCl modifier instead of trifluoroacetic acid. Yield: 141 mg, 45% MS (ES+): 608.3 (M+H)+

3-[4-(3-oxa-8-azabicyclo[3.2.1]oct-8-yl)-1-phenyl-1H-pyrazolo[3,4-d]pyrimidin-6-yl]phenol (Scheme 34)

A Smith process vial was charged with a suspension of 3-(4-bromo-1-phenyl-1H-pyrazolo[3,4-d]pyrimidin-6-yl)phenol (0.18 g, 0.49 mmol) and 3-oxa-8-azabicyclo[3.2.1]octane hydrochloride (approximately 100 mg, 0.67 mmol) in ethanol (4 mL). The suspension was treated with triethylamine (750 µL, 5.7 mmol) and was then heated in the microwave reactor for 10 minutes at 130° C. The reaction mixture was concentrated to dryness under reduced pressure, and the residue was purified by reverse-phase high performance liquid chromatography using a Phenomenex Prodigy 21 mm×250 mm column, running a gradient elution of 20% acetonitrile/80% of 0.1% aqueous trifluoroacetic acid to 100% acetonitrile to provide 3-(4-(3-oxa-8-azabicyclo[3.2.1]octan-8-yl)-1-phenyl-1H-pyrazolo[3,4-d]pyrimidin-6-yl)phenol. MS (ES+): 400.3 (M+H)+

3-[4-(8-oxa-3-azabicyclo[3.2.1]oct-3-yl)-1-phenyl-1H-pyrazolo[3,4-d]pyrimidin-6-yl]phenol (Scheme 34)

A Smith process vial was charged with a suspension of 3-(4-bromo-1-phenyl-1H-pyrazolo[3,4-d]pyrimidin-6-yl)phenol (0.15 g, 0.41 mmol) and 8-oxa-3-azabicyclo[3.2.1]octane hydrochloride (approximately 1 mmol) in ethanol (5 mL). The suspension was treated with triethylamine (500 µL, 3.8 mmol) and was then heated in the microwave reactor for 10 minutes at 180° C. The reaction mixture was concentrated to dryness under reduced pressure, and the residue was purified by reverse-phase high performance liquid chromatography using a Phenomenex Prodigy 21 mm×250 mm column, running a gradient elution of 15% acetonitrile/88% of 0.1% aqueous trifluoroacetic acid to 100% acetonitrile to provide 3-[4-(8-oxa-3-azabicyclo[3.2.1]oct-3-yl)-1-phenyl-1H-pyrazolo[3,4-d]pyrimidin-6-yl]phenol. MS (ES+): 400.1 (M+H)+

2-hydroxyethyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate (Scheme s 4 and 2)

Diisopropyl azodicarboxylate (1.1 mL, 5.4 mmol) was added in drops to a suspension of 3-(6-chloro-1H-pyrazolo[3,4-d]pyrimidin-4-yl)-8-oxa-3-azabicyclo[3.2.1]octane (1.1 g, 4.1 mmol), 1,3-dimethoxypropan-2-ol (0.65 g, 5.4 mmol), and triphenylphosphine (1.4 g, 5.4 mmol) in tetrahydrofuran (33 mL). When this Mitsunobu reaction was deemed to be complete by LC/MS analysis, the mixture was adsorbed onto flash silica gel and purified by automated flash chromatography (methanol/chloroform) to provide 3-(6-chloro-1-(1,3-dimethoxypropan-2-yl)-1H-pyrazolo[3,4-d]pyrimidin-4-yl)-8-oxa-3-azabicyclo[3.2.1]octane as an amber glass (1.9 g, >100%) contaminated with triphenylphosphine oxide. MS (ES+): 368.2, 370.2 (M+H)+

The following reaction was conducted twice on the same scale and under the same conditions. The two reaction mixtures were combined for the aqueous work-up and flash chromatography.

A mixture of triphenylphosphine-contaminated 3-(6-chloro-1-(1,3-dimethoxypropan-2-yl)-1H-pyrazolo[3,4-d]pyrimidin-4-yl)-8-oxa-3-azabicyclo[3.2.1]octane (0.95 g), 4-aminophenylboronic acid pinacol ester (0.60 g, 2.7 mmol), and tetrakis(triphenylphosphine)palladium(0) (0.24 g) in toluene/ethanol (1:1, 10 mL) and 2 M aqueous sodium carbonate solution (2 mL) was heated in a 10-20 mL Smith process vial in the microwave reactor for one hour at 120° C. The pooled mixtures were partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude residue was purified via automated flash chromatography (methanol/chloroform) to provide 4-(4-(8-oxa-3-azabicyclo[3.2.1]octan-3-yl)-1-(1,3-dimethoxypropan-2-yl)-1H-pyrazolo[3,4-d]pyrimidin-6-yl)aniline as tan foam (1.3 g, 76% over 2 steps). MS (ES$^+$): 425.2 (M+H)$^+$ A solution of 4-(4-(8-oxa-3-azabicyclo[3.2.1]octan-3-yl)-1-(1,3-dimethoxypropan-2-yl)-1H-pyrazolo[3,4-d]pyrimidin-6-yl)aniline (65 mg, 0.15 mmol) in dichloromethane (1.5 mL) was treated with triethylamine (0.2 mL), followed by a solution of triphosgene (23 mg, 0.08 mmol) in dichloromethane (1 mL). After the passage of 10 minutes, the appropriate nucleophile—in the case, ethylene glycol (84 µL, 1.5 mmol)—was added to the 3-(1-(1,3-dimethoxypropan-2-yl)-6-(4-isocyanatophenyl)-1H-pyrazolo[3,4-d]pyrimidin-4-yl)-8-oxa-3-azabicyclo[3.2.1]octane ("isocyanate") mixture. After 3 hours, the reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile to provide 2-hydroxyethyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate (41 mg, 53%). MS (ES$^+$): 513.2 (M+H)$^+$ The following ureas and carbamates were made via the addition of the appropriate nucleophile to the isocyanate (0.15 mmol, unless stated otherwise) derived from 4-(4-(8-oxa-3-azabicyclo[3.2.1]octan-3-yl)-1-(1,3-dimethoxypropan-2-yl)-1H-pyrazolo[3,4-d]pyrimidin-6-yl)aniline, in accordance with the general procedure described for 2-hydroxyethyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate.

1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-phenylurea Nucleophile added to isocyanate: aniline (137 µL, 1.5 mmol) Yield: 44 mg, 54% MS (ES$^+$): 544.3 (M+H)$^+$ 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea.TFA Nucleophile added to isocyanate: 4-(4-methylpiperazin-1-yl)aniline (115 mg, 0.60 mmol) Yield: 62 mg, 55% MS (ES$^+$): 642.3 (M+H)$^+$ 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-methylurea Nucleophile added to isocyanate: 2 M methylamine solution in tetrahydrofuran (excess) Yield: 43 mg, 58% MS (ES$^+$): 482.3 (M+H)$^+$ 1-(2-hydroxyethyl)-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea Nucleophile added to isocyanate: ethanolamine (91 µL, 1.5 mmol) Yield: 37 mg, 48% MS (ES$^+$): 512.3 (M+H)$^+$ Methyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate Nucleophile added to isocyanate: methanol (excess) Yield: 25 mg, 35% MS (ES$^+$): 483.2 (M+H)$^+$ 1-cyclopropyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea Nucleophile added to isocyanate: cyclopropylamine (104 µL, 1.5 mmol) Yield: 43 mg, 56% MS (ES$^+$): 508.3 (M+H)$^+$ 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-4-ylurea.TFA Nucleophile added to isocyanate: 4-aminopyridine (141 mg, 1.5 mmol) Yield: 48 mg, 48% MS (ES$^+$): 545.3 (M+H)$^+$ 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-3-ylurea.TFA Nucleophile added to isocyanate: 3-aminopyridine (141 mg, 1.5 mmol) Yield: 49 mg, 50% MS (ES$^+$): 545.3 (M+H)$^+$ 1-ethyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea Nucleophile added to isocyanate: 2 M ethylamine solution in tetrahydrofuran (excess) Yield: 40 mg, 54% MS (ES$^+$): 496.3 (M+H)$^+$ 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-(4-piperazin-1-ylphenyl)urea.TFA Nucleophile added to isocyanate: tert-butyl 4-(4-aminophenyl)piperazine-1-carboxylate (100 mg, 0.38 mmol).

The reverse-phase HPLC purified product, tert-butyl 4-(4-(3-(4-(4-(8-oxa-3-azabicyclo[3.2.1]octan-3-yl)-1-(1,3-dimethoxypropan-2-yl)-1H-pyrazolo[3,4-d]pyrimidin-6-yl)phenyl)ureido)phenyl)piperazine-1-carboxylate was taken up in dichloromethane (5 mL) and then treated with trifluoroacetic acid (1 mL). When the Boc group was deemed to have been removed (LC/MS analysis), the mixture was concentrated under reduced pressure and purified as usual by reverse-phase HPLC to provide 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-(4-piperazin-1-ylphenyl)urea.TFA. Yield: 39 mg, 35% MS (ES$^+$): 628.3 (M+H)$^+$

1-{4-[(2,2-dimethylhydrazino)carbonyl]phenyl}-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea A solution of 4-(4-(8-oxa-3-azabicyclo[3.2.1]octan-3-yl)-1-(1,3-dimethoxypropan-2-yl)-1H-pyrazolo[3,4-d]pyrimidin-6-yl)aniline (580 mg, 1.4 mmol) in dichloromethane (10 mL) was treated with triethylamine (0.91 mL), followed by a solution of isocyanatomethyl benzoate (0.29 g, 1.6 mmol). The mixture was quenched with methanol, concentrated under reduced pressure, and the residue was purified by reverse phase high performance liquid chromatography to provide methyl 4-(3-(4-(4-(8-oxa-3-azabicyclo[3.2.1]octan-3-yl)-1-(1,3-dimethoxypropan-2-yl)-1H-pyrazolo[3,4-d]pyrimidin-6-yl)phenyl)ureido)benzoate. MS (ES$^+$): 602.3 (M+H)$^+$ A suspension of methyl 4-(3-(4-(4-(8-oxa-3-azabicyclo[3.2.1]octan-3-yl)-1-(1,3-dimethoxypropan-2-yl)-1H-pyrazolo[3,4-d]pyrimidin-6-yl)phenyl)ureido)benzoate (25 mg) in tetrahydrofuran/methanol/water (2:2:1, 20 mL) was treated with two pellets of sodium hydroxide. The mixture was heated overnight at 60° C. and then acidified with concentrated hydrochloric acid to precipitate a fine solid, which, after collection via Buchner filtration, washing with water, and drying under house vacuum, provided 4-(3-(4-(4-(8-oxa-3-azabicyclo[3.2.1]octan-3-yl)-1-(1,3-dimethoxypropan-2-yl)-1H-pyrazolo[3,4-d]pyrimidin-6-yl)phenyl)ureido)benzoic acid. MS (ES$^+$): 588.3 (M+H)$^+$ A mixture of 4-(3-(4-(4-(8-oxa-3-azabicyclo[3.2.1]octan-3-yl)-1-(1,3-dimethoxypropan-2-yl)-1H-pyrazolo[3,4-d]pyrimidin-6-yl)phenyl)ureido)benzoic acid (0.11 g, 0.19 mmol), 1-hydroxybenzotriazole hydrate (HOBT, 51 mg, 0.37 mmol), N-methylmorpholine (63 µL, 0.57 mmol), and N,N-dimethylhydrazine (63 µL, 0.57 mmol) in dimethylformamide (3 mL) was treated with N-(3-dimethylaminopropyl)-N'-ethylcarbodiimide hydrochloride (EDC, 72 mg, 0.37 mmol). After approximately 20 minutes, additional quantities of N,N-dimethylhydrazine (100 µL) and EDC (100 mg) were added. The mixture was stirred overnight at room temperature and then purified by reverse-phase high performance liquid chromatography using a Phenomenex Prodigy 21 mm×250 mm column, running a gradient elution of 5% acetonitrile/95% of 0.1% aqueous trifluoroacetic acid to 75% acetonitrile to provide 1-{4-[(2,2-dimethylhydrazino)carbonyl]phenyl}-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea (114 mg, 95%). MS (ES$^+$): 630.3 (M+H)$^+$ tert-butyl 7-[6-{4-[(pyridin-4-ylcarbamoyl)amino]phenyl}-1-(2,2,2-trifluoroethyl)-1H-pyrazolo[3,4-d]pyrimidin-4-yl]-9-oxa-3,7-diazabicyclo[3.3.1]nonane-3-carboxylate.HCl (Scheme 43)

To a Smith process vial containing a suspension of 4-chloro-6-(4-nitro-phenyl)-1-(2,2,2-trifluoro-ethyl)-1H-pyrazolo[3,4-d]pyrimidine (0.50 g, 1.4 mmol) and tert-butyl 9-oxa-3,7-diazabicyclo[3.3.1]nonane-3-carboxylate (0.34 g, 1.5 mmol) in ethanol (10 mL) was added triethylamine (0.55 mL, 4.2 mmol). The mixture was heated in the microwave reactor for 12 minutes at 150° C. The precipitate was collected by Buchner filtration, washed with methanol, and dried under house vacuum to provide tert-butyl 7-(6-(4-nitrophenyl)-1-(2,2,2-trifluoroethyl)-1H-pyrazolo[3,4-d]pyrimidin-4-yl)-9-oxa-3,7-diazabicyclo[3.3.1]nonane-3-carboxylate as a pale yellow solid (0.54 g, 70%). MS (ES$^+$): 550.2 (M+H)$^+$ A suspension of tert-butyl 7-(6-(4-nitrophenyl)-1-(2,2,2-trifluoroethyl)-1H-pyrazolo[3,4-d]pyrimidin-4-yl)-9-oxa-3,7-diazabicyclo[3.3.1]nonane-3-carboxylate (0.54 g, 0.98 mmol) in tetrahydrofuran (10 mL) and ethanol (10 mL) was degassed by the addition of crushed dry ice and then treated with 10% palladium on carbon (30 mg). The resulting suspension was evacuated under weak vacuum and then filled with hydrogen gas (balloon). This evacuation/fill cycle was performed three more times and on the final iteration, the mixture was left to stir overnight under a hydrogen-filled balloon. The mixture was filtered through a pad of diatomaceous earth, eluting with ethanol. The filtrate was concentrated under reduced pressure to afford tert-butyl 7-(6-(4-aminophenyl)-1-(2,2,2-trifluoroethyl)-1H-pyrazolo[3,4-d]pyrimidin-4-yl)-9-oxa-3,7-diazabicyclo[3.3.1]nonane-3-carboxylate as a white solid (0.48 g, 94%). MS (ES$^+$): 520.2 (M+H)$^+$ A solution of tert-butyl 7-(6-(4-aminophenyl)-1-(2,2,2-trifluoroethyl)-1H-pyrazolo[3,4-d]pyrimidin-4-yl)-9-oxa-3,7-diazabicyclo[3.3.1]nonane-3-carboxylate (0.48 g, 0.92 mmol) in dichloromethane (15 mL) was treated with triethylamine (1.2 mL), followed by a solution of triphosgene (0.14 g, 0.46 mmol). After the passage of 5 minutes, a solution of 4-aminopyridine (0.26 g, 2.8 mmol) in warm tetrahydrofuran was added to the tert-butyl 7-(6-(4-isocyanatophenyl)-1-(2,2,2-trifluoroethyl)-1H-pyrazolo[3,4-d]pyrimidin-4-yl)-9-oxa-3,7-diazabicyclo[3.3.1]nonane-3-carboxylate ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 65% acetonitrile to provide tert-butyl 7-(6-(4-(3-pyridin-4-ylureido)phenyl)-1-(2,2,2-trifluoroethyl)-1H-pyrazolo[3,4-d]pyrimidin-4-yl)-9-oxa-3,7-diazabicyclo[3.3.1]nonane-3-carboxylate.hydrochloride as pale golden flakes. (282 mg, 45%). MS (ES$^+$): 640.3 (M+H)$^+$

1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea.2TFA Tert-butyl 7-(6-(4-(3-pyridin-4-ylureido)phenyl)-1-(2,2,2-trifluoroethyl)-1H-pyrazolo[3,4-d]pyrimidin-4-yl)-9-oxa-3,7-diazabicyclo[3.3.1]nonane-3-carboxylate.hydrochloride (256 mg, 0.38 mmol) was dissolved in dichloromethane (20 mL) with the aid of a minimum volume of methanol. The solution was treated with 4 N hydrogen chloride in dioxane (2 mL), which caused the precipitation of a white solid within 10 minutes. The solid was collected by Buchner filtration, washed with methanol, and dried under house vacuum. A portion of the crude solid (assumed dihydrochloride) was purified by reverse-phase high performance liquid chromatography using a Phenomenex Prodigy 21 mm×250 mm column, running a gradient elution of 5% acetonitrile/95% of 0.1% aqueous trifluoroacetic acid to 65% acetonitrile to provide 1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea.2TFA (22 mg). MS (ES$^+$): 540.2 (M+H)$^+$

1-{4-[4-(7-formyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea.TFA 1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea.2HCl (51 mg, 0.08 mmol) was taken up in dichloromethane (2 mL) and treated with formic acid (98-100%, 10 µL). The mixture was cooled in an ice-water bath. N,N'-dicyclohexylcarbodiimide (DCC, 50 mg) was added, followed by 4-(dimethylamino)pyridine (DMAP, 10 mg). Triethylamine was added in drops (approximately 10 drops), followed by additional formic acid (approximately 50 µL). The mixture was warmed gently with a heat gun and then concentrated under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 75% acetonitrile to provide 1-{4-[4-(7-formyl-9-oxa-3,7-diazabicyclo[3.3.1]non-3-yl)-1-(2,2,2-trifluoroethyl)-1H-pyrazolo[3,4-d]pyrimidin-6-yl] phenyl}-3-pyridin-4-ylurea.TFA (28 mg, 51%). MS (ES$^+$): 568.2 (M+H)$^+$ 1-{4-[4-(7-acetyl-9-oxa-3,7-diazabicyclo[3.3.1]non-3-yl)-1-(2,2,2-trifluoroethyl)-1H-pyrazolo[3,4-d] pyrimidin-6-yl]phenyl}-3-pyridin-4-ylurea.TFA 1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea.2HCl (61 mg, 0.1 mmol) was taken up in dichloromethane (2 mL) and treated with triethylamine (100 µL). The suspension was cooled in an ice-water bath and treated with acetyl chloride in drops. The suspension was allowed to warm to room temperature and then concentrated under reduced pressure. The residue was dissolved in methanol (3 mL) and treated with 5 M sodium hydroxide aqueous solution (10 drops). The mixture was stirred overnight, acidified with concentrated hydrochloric acid, and concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 75% acetonitrile to provide 1-{4-[4-(7-acetyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea.TFA (20 mg, 29%). MS (ES$^+$): 582.2 (M+H)$^+$ 2-hydroxyethyl(4-{4-[(1S,4S)-2-oxa-5-azabicyclo [2.2.1]hept-5-yl]-1-(2,2,2-trifluoroethyl)-1H-pyrazolo[3,4-d]pyrimidin-6-yl}phenyl)carbamate (Scheme 43)

To a Smith process vial containing a suspension of 4-chloro-6-(4-nitro-phenyl)-1-(2,2,2-trifluoro-ethyl)-1H-pyrazolo[3,4-d]pyrimidine (0.30 g, 0.84 mmol) and (1S,4S)-2-oxa-5-azabicyclo[2.2.1]heptane hydrochloride (0.12 g, 0.88 mmol) in ethanol (4 mL) was added triethylamine (0.33 mL, 2.5 mmol). The mixture was heated in the microwave reactor for 15 minutes at 120° C. The precipitate was collected by Buchner filtration, washed with methanol, and dried under house vacuum to provide (1S,4S)-5-(6-(4-nitrophenyl)-1-(2,2,2-trifluoroethyl)-1H-pyrazolo[3,4-d]pyrimidin-4-yl)-2-oxa-5-azabicyclo[2.2.1]heptane as a bright yellow powder (0.42 g, >100%). MS (ES$^+$): 421.1 (M+H)+

A suspension of (1S,4S)-5-(6-(4-nitrophenyl)-1-(2,2,2-trifluoroethyl)-1H-pyrazolo[3,4-d]pyrimidin-4-yl)-2-oxa-5-azabicyclo[2.2.1]heptane (0.84 mmol maximum) in tetrahydrofuran (15 mL) and ethyl acetate (15 mL) was degassed by the addition of crushed dry ice and then treated with 10% palladium on carbon (50 mg). The resulting suspension was evacuated under weak vacuum and then filled with hydrogen gas (balloon). This evacuation/fill cycle was performed three more times and on the final iteration, the mixture was left to stir overnight under a hydrogen filled balloon. The mixture was filtered through a pad of diatomaceous earth, eluting with methanol. The filtrate was concentrated under reduced pressure to afford 4-(4-((1S,4S)-2-oxa-5-azabicyclo[2.2.1]heptan-5-yl)-1-(2,2,2-trifluoroethyl)-1H-pyrazolo[3,4-d]pyrimidin-6-yl)aniline as a white foam (0.26 g, 78% over 2 steps). MS (ES$^+$): 391.1 (M+H)$^+$ A solution of 4-(4-((1S,4S)-2-oxa-5-azabicyclo[2.2.1] heptan-5-yl)-1-(2,2,2-trifluoroethyl)-1H-pyrazolo[3,4-d]pyrimidin-6-yl)aniline (26 mg, 0.07 mmol) in dichloromethane (2 mL) was treated with triethylamine (86 µL), followed by a solution of triphosgene (10 mg, 0.03 mmol) in dichloromethane (1 mL). After the passage of 20 minutes, the appropriate nucleophile—in the case, ethylene glycol (excess)—was added to the (1S,4S)-5-(6-(4-isocyanatophenyl)-1-(2,2,2-trifluoroethyl)-1H-pyrazolo[3,4-d]pyrimidin-4-yl)-2-oxa-5-azabicyclo[2.2.1]heptane ("isocyanate") mixture. After standing overnight at room temperature, the reaction mixture was concentrated to dryness under reduced pressure. The residue was purified by reverse-phase high performance liquid chromatography using a Phenomenex Prodigy 21 mm×250 mm column, running a gradient elution of 15% acetonitrile/85% of 0.1% aqueous trifluoroacetic acid to 88% acetonitrile to provide 2-hydroxyethyl(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)carbamate. MS (ES$^+$): 479.2 (M+H)$^+$ The following ureas and carbamates were made via the addition of the appropriate nucleophile to the isocyanate (0.07 mmol, unless stated otherwise) derived from 4-(4-((1S,4S)-2-oxa-5-azabicyclo[2.2.1]heptan-5-yl)-1-(2,2,2-trifluoroethyl)-1H-pyrazolo[3,4-d]pyrimidin-6-yl)aniline, in accordance with the general procedure described for 2-hydroxyethyl(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)carbamate. (Scheme 43)

1-[4-(2-hydroxyethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl) urea Nucleophile added to isocyanate: 2-(4-aminophenyl)ethanol (36 mg, 0.26 mmol) MS (ES$^+$): 554.2 (M+H)$^+$ 1-[4-(hydroxymethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl) urea Nucleophile added to isocyanate: (4-aminophenyl)methanol (32 mg, 0.26 mmol) MS (ES$^+$): 540.2 (M+H)$^+$ 1-(6-morpholin-4-ylpyridin-3-yl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl) urea Nucleophile added to isocyanate: 6-morpholinopyridin-3-amine (47 mg, 0.26 mmol) MS (ES$^+$): 596.2 (M+H)$^+$ 1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea.TFA Nucleophile added to isocyanate: 3-aminopyridine (25 mg, 0.26 mmol) MS (ES$^+$): 511.2 (M+H)$^+$ 1-(4-morpholin-4-ylphenyl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea Nucleophile added to isocyanate: 4-morpholinoaniline (46 mg, 0.26 mmol) MS (ES$^+$): 595.2 (M+H)$^+$ 1-{4-[2-(dimethylamino)ethoxy]phenyl}-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea.TFA Nucleophile added to isocyanate: 4-(2-(dimethylamino)ethoxy)aniline dihydrochloride (47 mg, 0.19 mmol) MS (ES$^+$): 597.2 (M+H)$^+$ 1-[4-(4-methylpiperazin-1-yl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea.TFA Nucleophile added to isocyanate: 4-(4-methylpiperazin-1-yl)aniline (50 mg, 0.60 mmol) MS (ES$^+$): 608.3 (M+H)$^+$ 1-cyclopropyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea Nucleophile added to isocyanate (0.49 mmol): Cyclopropylamine (15 mg, 0.26 mmol) MS (ES$^+$): 474.2 (M+H)$^+$ 1-methyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea Nucleophile added to isocyanate: 2 M methylamine solution in tetrahydrofuran (excess) MS (ES$^+$): 448.2 (M+H)$^+$ 1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-(4-piperazin-1-ylphenyl)urea.HCl Nucleophile added to isocyanate (0.4 mmol): tert-butyl 4-(4-aminophenyl)piperazine-1-carboxylate (166 mg, 0.6 mmol).
The reverse-phase HPLC purified product, tert-butyl 4-(4-(3-(4-(4-((1S,4S)-2-oxa-5-azabicyclo[2.2.1]heptan-5-yl)-1-(2,2,2-trifluoroethyl)-1H-pyrazolo[3,4-d]pyrimidin-6-yl)phenyl)ureido)phenyl)piperazine-1-carboxylate was taken up in dichloromethane (5 mL) and then treated with trifluoroacetic acid (1 mL). When the Boc group was deemed to have been removed (LC/MS analysis), the mixture was concentrated under reduced pressure and purified as usual by reverse-phase HPLC (using hydrochloric acid modifier instead of trifluoroacetic acid) to provide 1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-(4-piperazin-1-ylphenyl)urea.HCl. MS (ES$^+$): 594.4 (M+H)$^+$ 3-{4-[(1S,4S)-2-oxa-5-azabicyclo[2.2.1]hept-5-yl]-1-phenyl-1H-pyrazolo[3,4-d]pyrimidin-6-yl}phenol
(Scheme 34

A Smith process vial was charged with a suspension of 3-(4-bromo-1-phenyl-1H-pyrazolo[3,4-d]pyrimidin-6-yl)phenol (56 mg, 0.15 mmol) and (1S,4S)-2-oxa-5-azabicyclo[2.2.1]heptane hydrochloride (22 mg, 0.16 mmol) in ethanol (4 mL). The suspension was treated with triethylamine (59 µL, 0.45 mmol) and was then heated in the microwave reactor for 15 minutes at 150° C. The reaction mixture was concentrated to dryness under reduced pressure, and the residue was purified by reverse-phase high performance liquid chromatography using a Phenomenex Prodigy 21 mm×250 mm column, running a gradient elution of 10% acetonitrile/90% of 0.1% aqueous trifluoroacetic acid to 75% acetonitrile to provide 3-{4-[(1S,4S)-2-oxa-5-azabicyclo[2.2.1]hept-5-yl]-1-phenyl-1H-pyrazolo[3,4-d]pyrimidin-6-yl}phenol. MS (ES$^+$): 386.3 (M+H)$^+$ 2-hydroxyethyl(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)carbamate
(Scheme 43)

To a Smith process vial containing a suspension of 4-chloro-6-(4-nitro-phenyl)-1-(2,2,2-trifluoro-ethyl)-1H-pyrazolo[3,4-d]pyrimidine (0.68 g, 1.9 mmol) and (1R,4R)-2-oxa-5-azabicyclo[2.2.1]heptane trifluoroacetate (prepared starting from cis-1-Boc-4-hydroxy-D-prolinate, 3.1 mmol) in ethanol (14 mL) was added triethylamine (4 mL, 31 mmol). The mixture was heated in the microwave reactor for 10 minutes at 140° C. The precipitate was collected by Buchner filtration and washed successively with methanol, water, methanol, and diethyl ether. Solid was dried under house vacuum to provide (1R,4R)-5-(6-(4-nitrophenyl)-1-(2,2,2-trifluoroethyl)-1H-pyrazolo[3,4-d]pyrimidin-4-yl)-2-oxa-5-azabicyclo[2.2.1]heptane as a pale yellow solid (0.56 g, 70%). MS (ES$^+$): 421.1 (M+H)$^+$ A suspension of (1R,4R)-5-(6-(4-nitrophenyl)-1-(2,2,2-trifluoroethyl)-1H-pyrazolo[3,4-d]pyrimidin-4-yl)-2-oxa-5-azabicyclo[2.2.1]heptane (0.50 g, 1.2 mmol) in tetrahydrofuran (20 mL) and water (5 mL) was degassed by the addition of crushed dry ice and then treated with 10% palladium on carbon (50 mg). The resulting suspension was evacuated under weak vacuum and then filled with hydrogen gas (balloon). This evacuation/fill cycle was performed three more times and on the final iteration, the mixture was left to stir overnight under a hydrogen filled balloon. The mixture was filtered through a pad of diatomaceous earth, eluting with methanol. The filtrate was concentrated under reduced pressure to afford 4-(4-((1R,4R)-2-oxa-5-azabicyclo[2.2.1]heptan-5-yl)-1-(2,2,2-trifluoroethyl)-1H-pyrazolo[3,4-d]pyrimidin-6-yl)aniline as a gray foam (0.44 g, 93%). MS (ES$^+$): 391.2 (M+H)$^+$ A solution of 4-(4-((1R,4R)-2-oxa-5-azabicyclo[2.2.1]heptan-5-yl)-1-(2,2,2-trifluoroethyl)-1H-pyrazolo[3,4-d]pyrimidin-6-yl)aniline (62 mg, 0.16 mmol) in dichloromethane (2 mL) was treated with triethylamine (130 µL), followed by a solution of triphosgene (24 mg, 0.08 mmol) in dichloromethane (1 mL). After the passage of 5 minutes, the appropriate nucleophile—in the case, ethylene glycol (56 µL)—was added to the (1R,4R)-5-(6-(4-isocyanatophenyl)-1-(2,2,2-trifluoroethyl)-1H-pyrazolo[3,4-d]pyrimidin-4-yl)-2-oxa-5-azabicyclo[2.2.1]heptane ("isocyanate") mixture. After standing overnight at room temperature, the reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 95% acetonitrile to provide 2-hydroxyethyl(4-{4-[(1R,4R)-2-oxa- 5-azabicyclo[2.2.1]hept-5-yl]-1-(2,2,2-trifluoroethyl)-1H-pyrazolo[3,4-d]pyrimidin-6-yl}phenyl)carbamate. MS (ES+): 479.2 (M+H)+

The following ureas and carbamates were made via the addition of the appropriate nucleophile to the isocyanate (0.16 mmol, unless stated otherwise) derived from 4-(4-((1R,4R)-2-oxa-5-azabicyclo[2.2.1]heptan-5-yl)-1-(2,2,2-trifluoroethyl)-1H-pyrazolo[3,4-d]pyrimidin-6-yl)aniline, in accordance with the general procedure described for 2-hydroxyethyl(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)carbamate. (Scheme 43)

1-cyclopropyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea Nucleophile added to isocyanate: Cyclopropylamine (69 μL) MS (ES+): 474.2 (M+H)+

1-[4-(4-methylpiperazin-1-yl)phenyl]-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea.TFA Nucleophile added to isocyanate: 4-(4-methylpiperazin-1-yl)aniline (38 mg) MS (ES+): 608.3 (M+H)+

1-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea.TFA Nucleophile added to isocyanate: 3-aminopyridine (47 mg) MS (ES+): 511.2 (M+H)+

1-methyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea Nucleophile added to isocyanate: 2 M methylamine solution in tetrahydrofuran (excess) MS (ES+): 448.2 (M+H)+

1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea (Stereochemistry assigned arbitrarily) (Scheme s 4 and 2)

Diisopropyl azodicarboxylate (2.6 mL, 13 mmol) was added in drops to a mixture of 3-(6-chloro-1H-pyrazolo[3,4-d]pyrimidin-4-yl)-8-oxa-3-azabicyclo[3.2.1]octane (2.6 g, 10 mmol), 1-oxaspiro[4.5]decan-8-ol (U.S. Pat. No. 4,438,130, Mar. 20, 1984, 1.6 g, 11 mmol), and triphenylphosphine (2.9 g, 11 mmol) in tetrahydrofuran (80 mL). After stirring at room temperature, the mixture was purified by reverse phase high performance liquid chromatography on a Phenomenex Prodigy 21 mm×250 mm column, running a gradient elution of 15% acetonitrile/85% of 0.1% aqueous trifluoroacetic acid to 100% acetonitrile to provide two separable diastereomers of 3-(6-chloro-1-(1-oxaspiro[4.5]decan-8-yl)-1H-pyrazolo[3,4-d]pyrimidin-4-yl)-8-oxa-3-azabicyclo[3.2.1]octane. MS (ES+): 404.2 (M+H)+

A mixture of 3-(6-chloro-1-(1-oxaspiro[4.5]decan-8-yl)-1H-pyrazolo[3,4-d]pyrimidin-4-yl)-8-oxa-3-azabicyclo[3.2.1]octane (assigned as trans diastereomer, 0.61 g, 1.5 mmol), 4-aminophenylboronic acid pinacol ester (0.50 g, 2.3 mmol), and tetrakis(triphenylphosphine)palladium(0) (0.17 g, 10 mol %) in toluene/ethanol (1:1, 10 mL) and 2 M aqueous sodium carbonate solution (2 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude residue was purified via reverse-phase high performance liquid chromatography using a Phenomenex Prodigy 21 mm×250 mm column, running a gradient elution of 5% acetonitrile/95% of 0.1% aqueous hydrochloric acid to 100% acetonitrile. After the concentration of fractions under reduced pressure, 4-(4-(8-oxa-3-azabicyclo[3.2.1]octan-3-yl)-1-((5r,8r)-1-oxaspiro[4.5]decan-8-yl)-1H-pyrazolo[3,4-d]pyrimidin-6-yl)aniline was obtained. MS (ES+): 461.2 (M+H)+

A solution of 4-(4-(8-oxa-3-azabicyclo[3.2.1]octan-3-yl)-1-((5r,8r)-1-oxaspiro[4.5]decan-8-yl)-1H-pyrazolo[3,4-d]pyrimidin-6-yl)aniline (33 mg, 0.07 mmol) in dichloromethane (5 mL) was treated with triethylamine (60 μL), followed by triphosgene (11 mg, 0.04 mmol). After the passage of 5 minutes, the appropriate nucleophile—in the case, 2 M methylamine solution in tetrahydrofuran (excess)—was added to the 3-(6-(4-isocyanatophenyl)-1-((5r,8r)-1-oxaspiro[4.5]decan-8-yl)-1H-pyrazolo[3,4-d]pyrimidin-4-yl)-8-oxa-3-azabicyclo[3.2.1]octane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 90% acetonitrile to provide crude 1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea.

The impure material was purified using a Phenomenex Gemini 21 mm×100 mm column, running a gradient elution of 5% acetonitrile/95% of 0.1% aqueous trifluoroacetic acid to 65% acetonitrile to provide pure 1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea. MS (ES+): 518.3 (M+H)+

The following ureas and carbamates were made via the addition of the appropriate nucleophile to the isocyanate derived from 4-(4-(8-oxa-3-azabicyclo[3.2.1]octan-3-yl)-1-((5r,8r)-1-oxaspiro[4.5]decan-8-yl)-1H-pyrazolo[3,4-d]pyrimidin-6-yl)aniline, in accordance with the general procedure described for 1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea. (Stereochemistry assigned arbitrarily) (Scheme s 4 and 2)

1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-pyridin-4-ylurea.TFA Nucleophile added to isocyanate (0.10 mmol): 4-aminopyridine (50 mg) as a solution in warm tetrahydrofuran. MS (ES+): 581.3 (M+H)+

1-cyclopropyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea Nucleophile added to isocyanate (0.08 mmol): cyclopropylamine (55 μL) MS (ES+): 544.3 (M+H)+

2-hydroxyethyl(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)carbamate Nucleophile added to isocyanate (0.10 mmol) in tetrahydrofuran solvent, instead of dichloromethane: ethylene glycol (excess) MS (ES$^+$): 549.3 (M+H)$^+$

1-[4-(4-methylpiperazin-1-yl)phenyl]-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea.TFA Nucleophile added to isocyanate (0.09 mmol): 4-(4-methylpiperazin-1-yl)aniline (86 mg, 0.45 mmol) MS (ES$^+$): 678.4 (M+H)$^+$

1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-(4-piperazin-1-ylphenyl)urea.TFA Nucleophile added to isocyanate (0.10 mmol): tert-butyl 4-(4-aminophenyl)piperazine-1-carboxylate (110 mg, 0.4 mmol).

The concentrated reaction mixture was taken up in dichloromethane (5 mL) and then treated with trifluoroacetic acid (1 mL). When the Boc group was deemed to have been removed (LC/MS analysis), the mixture was concentrated under reduced pressure and purified as usual by reverse-phase HPLC to provide 1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-(4-piperazin-1-ylphenyl)urea.TFA. MS (ES$^+$): 664.4 (M+H)$^+$

Methyl{4-[1-ethyl-4-(8-oxa-3-azabicyclo[3.2.1]oct-3-yl)-1H-pyrazolo[3,4-d]pyrimidin-6-yl]phenyl}carbamate (Schemes 1 and 2)

To a cloudy solution of 2,4,6-trichloro-pyrimidine-5-carbaldehyde (1.1 g, 5.2 mmol) in chloroform (50 mL) cooled to −78° C. was added ethylhydrazine oxalate (0.78 g, 5.2 mmol) in two portions, followed by triethylamine (2.7 mL). The cooling bath was then removed and ethanol (10 mL) was added to the reaction mixture, which was allowed to warm to room temperature. 8-Oxa-3-azabicyclo[3.2.1]octane hydrochloride (0.69 g, 4.6 mmol) was added to the mixture. The mixture was concentrated under reduced pressure and the residue was partitioned between ethyl acetate and water. The aqueous phase was extracted three times with ethyl acetate. The combined organics were washed successively with 5% aqueous potassium hydrogen sulfate solution, water, saturated aqueous sodium hydrogen carbonate solution, and saturated aqueous sodium chloride solution. Organics were dried over anhydrous magnesium sulfate, filtered, and concentrated under reduced pressure to provide 3-(6-chloro-1-ethyl-1H-pyrazolo[3,4-d]pyrimidin-4-yl)-8-oxa-3-azabicyclo[3.2.1]octane. MS (ES$^+$): 293.9, 295.9 (M+H)$^+$ A mixture of 3-(6-chloro-1-ethyl-1H-pyrazolo[3,4-d]pyrimidin-4-yl)-8-oxa-3-azabicyclo[3.2.1]octane (0.55 g, 1.9 mmol), 4-aminophenylboronic acid pinacol ester (0.62 g, 2.8 mmol), and tetrakis(triphenylphosphine)palladium(0) (0.22 g, 10 mol %) in toluene/ethanol (1:1, 12 mL) and 2 M aqueous sodium carbonate solution (2 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude residue was purified via automated flash chromatography (methanol/chloroform) to provide 4-(4-(8-oxa-3-azabicyclo[3.2.1]octan-3-yl)-1-ethyl-1H-pyrazolo[3,4-d]pyrimidin-6-yl)aniline. MS (ES$^+$): 351.0 (M+H)$^+$ A solution of 4-(4-(8-oxa-3-azabicyclo[3.2.1]octan-3-yl)-1-ethyl-1H-pyrazolo[3,4-d]pyrimidin-6-yl)aniline (150 mg, 0.43 mmol) in dichloromethane (5 mL) was treated with triphosgene (64 mg, 0.21 mmol). After the passage of 5 minutes, an excess of methanol was added to the mixture. The reaction mixture was concentrated to dryness under reduced pressure. The residue was purified by reverse-phase high performance liquid chromatography using a Phenomenex Prodigy 21 mm×250 mm column, running a gradient elution of 10% acetonitrile/90% of 0.1% aqueous trifluoroacetic acid to 100% acetonitrile to provide methyl{4-[1-ethyl-4-(8-oxa-3-azabicyclo[3.2.1]oct-3-yl)-1H-pyrazolo[3,4-d]pyrimidin-6-yl]phenyl}carbamate. MS (ES$^+$): 409.0 (M+H)$^+$ The following ureas and carbamates were made via the addition of the appropriate nucleophile to the isocyanate (0.11 mmol) derived from 4-(4-(8-oxa-3-azabicyclo[3.2.1]octan-3-yl)-1-ethyl-1H-pyrazolo[3,4-d]pyrimidin-6-yl)aniline, in accordance with the general procedure described for the preparation of methyl{4-[1-ethyl-4-(8-oxa-3-azabicyclo[3.2.1]oct-3-yl)-1H-pyrazolo[3,4-d]pyrimidin-6-yl]phenyl}carbamate.

1-{4-[1-ethyl-4-(8-oxa-3-azabicyclo[3.2.1]oct-3-yl)-1H-pyrazolo[3,4-d]pyrimidin-6-yl]phenyl}-3-pyridin-4-ylurea.TFA Nucleophile added to isocyanate: 4-aminopyridine (104 mg) MS (ES$^+$): 471.1 (M+H)$^+$

2-hydroxyethyl{4-[1-ethyl-4-(8-oxa-3-azabicyclo[3.2.1]oct-3-yl)-1H-pyrazolo[3,4-d]pyrimidin-6-yl]phenyl}carbamate Nucleophile added to isocyanate: ethylene glycol (61 µL) MS (ES$^+$): 439.2 (M+H)$^+$

1-{4-[1-ethyl-4-(8-oxa-3-azabicyclo[3.2.1]oct-3-yl)-1H-pyrazolo[3,4-d]pyrimidin-6-yl]phenyl}-3-phenylurea Nucleophile added to isocyanate: aniline (100 µL) MS (ES$^+$): 470.1 (M+H)$^+$

1-{4-[1-ethyl-4-(8-oxa-3-azabicyclo[3.2.1]oct-3-yl)-1H-pyrazolo[3,4-d]pyrimidin-6-yl]phenyl}-3-(2-fluoroethyl)urea 2-fluoroethylamine hydrochloride (0.11 g, 1.1 mmol) was dissolved in 1 M aqueous sodium hydroxide solution (1.1 mL). The solution of isocyanate was added to the aqueous amine. The biphasic mixture was agitated on a vortex and then the aqueous phase was decanted. The organic layer was concentrated under reduced pressure and purified as usual by reverse-phase high performance liquid chromatography. MS (ES$^+$): 440.2 (M+H)$^+$

1-{4-[1-ethyl-4-(8-oxa-3-azabicyclo[3.2.1]oct-3-yl)-1H-pyrazolo[3,4-d]pyrimidin-6-yl]phenyl}-3-[3-(methylamino)propyl]urea.TFA Nucleophile added to isocyanate: tert-butyl 3-aminopropyl (methyl)carbamate (0.21 g). The HPLC-purified, BOC-protected intermediate, tert-butyl 3-(3-(4-(4-(8-oxa-3-azabicyclo[3.2.1]octan-3-yl)-1-ethyl-1H-pyrazolo[3,4-d]pyrimidin-6-yl)phenyl)ureido)propyl(methyl)carbamate, was dissolved in dichloromethane (5 mL) and treated with trifluoroacetic acid (1 mL). The mixture was concentrated under reduced pressure and then purified by HPLC to give the title compound. MS (ES+): 465.2 (M+H)+

1-{4-[1-ethyl-4-(8-oxa-3-azabicyclo[3.2.1]oct-3-yl)-1H-pyrazolo[3,4-d]pyrimidin-6-yl]phenyl}-3-methylurea

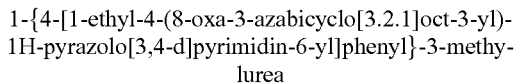

Nucleophile added to isocyanate: 2 M methylamine solution in tetrahydrofuran (550 µL) MS (ES+): 408.2 (M+H)+

1-ethyl-3-{4-[1-ethyl-4-(8-oxa-3-azabicyclo[3.2.1]oct-3-yl)-1H-pyrazolo[3,4-d]pyrimidin-6-yl]phenyl}urea

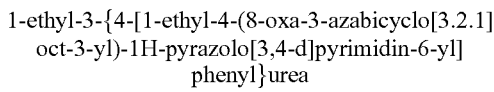

Nucleophile added to isocyanate: 2 M ethylamine solution in tetrahydrofuran (550 µL) MS (ES+): 422.2 (M+H)+

1-{4-[1-ethyl-4-(8-oxa-3-azabicyclo[3.2.1]oct-3-yl)-1H-pyrazolo[3,4-d]pyrimidin-6-yl]phenyl}-3-pyridin-3-ylurea.TFA

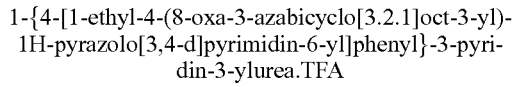

Nucleophile added to isocyanate: 3-aminopyridine (104 mg) MS (ES+): 471.1 (M+H)+

1-cyclopropyl-3-{4-[1-ethyl-4-(8-oxa-3-azabicyclo[3.2.1]oct-3-yl)-1H-pyrazolo[3,4-d]pyrimidin-6-yl]phenyl}urea

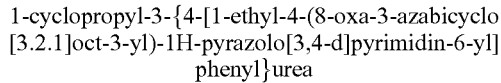

Nucleophile added to isocyanate: cyclopropylamine (76 µL) MS (ES+): 434.2 (M+H)+

1-{4-[1-ethyl-4-(8-oxa-3-azabicyclo[3.2.1]oct-3-yl)-1H-pyrazolo[3,4-d]pyrimidin-6-yl]phenyl}-3-(2-hydroxyethyl)urea

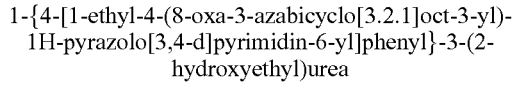

Nucleophile added to isocyanate: ethanolamine (66 µL) MS (ES+): 438.2 (M+H)+

3-[1-ethyl-4-(8-oxa-3-azabicyclo[3.2.1]oct-3-yl)-1H-pyrazolo[3,4-d]pyrimidin-6-yl]phenol (Scheme 28)

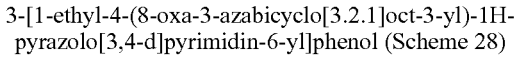

A mixture of 3-(6-chloro-1-ethyl-1H-pyrazolo[3,4-d]pyrimidin-4-yl)-8-oxa-3-azabicyclo[3.2.1]octane (80 mg, 0.27 mmol), 3-hydroxyphenylboronic acid (56 mg, 0.41 mmol), and tetrakis(triphenylphosphine)palladium(0) (35 mg, 10 mol %) in toluene/ethanol (1:1, 3 mL) and 2 M aqueous sodium carbonate solution (1 mL) was heated in a Smith process vial in the microwave reactor for one hour at 120° C. The cooled mixture was acidified with concentrated hydrochloric acid and then concentrated to dryness under reduced pressure. The crude residue was purified via reverse-phase high performance liquid chromatography using a Phenomenex Prodigy 21 mm×250 mm column to provide 3-[1-ethyl-4-(8-oxa-3-azabicyclo[3.2.1]oct-3-yl)-1H-pyrazolo[3,4-d]pyrimidin-6-yl]phenol MS (ES+): 352.2 (M+H)+

1-ethyl-6-(1H-indol-5-yl)-4-(8-oxa-3-azabicyclo[3.2.1]oct-3-yl)-1H-pyrazolo[3,4-d]pyrimidine (Scheme 28)

A mixture of 3-(6-chloro-1-ethyl-1H-pyrazolo[3,4-d]pyrimidin-4-yl)-8-oxa-3-azabicyclo[3.2.1]octane (80 mg, 0.27 mmol), 5-indoylboronic acid (66 mg, 0.41 mmol), and tetrakis(triphenylphosphine)palladium(0) (35 mg, 10 mol %) in toluene/ethanol (1:1, 3 mL) and 2 M aqueous sodium carbonate solution (1 mL) was heated in a Smith process vial in the microwave reactor for one hour at 120° C. The cooled mixture was acidified with concentrated hydrochloric acid and then concentrated to dryness under reduced pressure. The crude residue was purified via reverse-phase high performance liquid chromatography using a Phenomenex Prodigy 21 mm×250 mm column to provide 1-ethyl-6-(1H-indol-5-yl)-4-(8-oxa-3-azabicyclo[3.2.1]oct-3-yl)-1H-pyrazolo[3,4-d]pyrimidine. MS (ES+): 375.2 (M+H)+

1-cyclopropyl-3-{4-[1-methyl-4-(8-oxa-3-azabicyclo[3.2.1]oct-3-yl)-1H-pyrazolo[3,4-d]pyrimidin-6-yl]phenyl}urea (Scheme s 1 and 2)

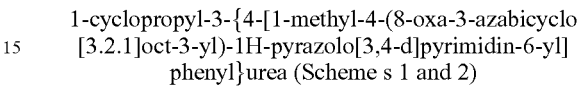

To a cloudy solution of 2,4,6-trichloro-pyrimidine-5-carbaldehyde (1.1 g, 5.2 mmol) in chloroform (50 mL) cooled to −78° C. was added in drops methylhydrazine (0.24 g, 5.2 mmol), followed by triethylamine (1.4 mL). The cooling bath was then removed, allowing the mixture to warm to room temperature. The mixture was concentrated to dryness under reduced pressure, and the residue was dissolved in ethanol (50 mL). Triethylamine (1 mL) was added to the mixture, followed by 8-oxa-3-azabicyclo[3.2.1]octane hydrochloride (0.51 g, 3.4 mmol). The mixture was concentrated under reduced pressure and the residue was purified by automated flash chromatography (methanol/chloroform) to provide 3-(6-chloro-1-methyl-1H-pyrazolo[3,4-d]pyrimidin-4-yl)-8-oxa-3-azabicyclo[3.2.1]octane. MS (ES+): 280.0, 281.9 (M+H)+

A mixture of 3-(6-chloro-1-methyl-1H-pyrazolo[3,4-d]pyrimidin-4-yl)-8-oxa-3-azabicyclo[3.2.1]octane (0.40 g, 1.4 mmol), 4-aminophenylboronic acid pinacol ester (0.47 g, 2.1 mmol), and tetrakis(triphenylphosphine)palladium(0) (0.16 g, 10 mol %) in toluene/ethanol (1:1, 7 mL) and 2 M aqueous sodium carbonate solution (2 mL) was heated in a 10-20 mL Smith process vial in the microwave reactor for one hour at 120° C. The cooled mixture was partitioned between ethyl acetate and water. The aqueous phase was extracted three times with ethyl acetate. The combined extracts were washed with saturated aqueous sodium chloride solution, dried over anhydrous magnesium sulfate, filtered, and concentrated to dryness under reduced pressure. The crude residue was triturated with dichloromethane and the light brown solid was collected by Buchner filtration to furnish 4-(4-(8-oxa-3-azabicyclo[3.2.1]octan-3-yl)-1-methyl-1H-pyrazolo[3,4-d]pyrimidin-6-yl)aniline. MS (ES+): 337.0 (M+H)+

A solution of 4-(4-(8-oxa-3-azabicyclo[3.2.1]octan-3-yl)-1-methyl-1H-pyrazolo[3,4-d]pyrimidin-6-yl)aniline (51 mg, 0.15 mmol) in dichloromethane (4 mL) was treated with triphosgene (23 mg, 0.08 mmol) as a solution in dichloromethane (1 mL). After the passage of 5 minutes, the appropriate nucleophile—in the case, cyclopropylamine (104 µL, 10 equivalents, 1.5 mmol)—was added to the 3-(6-(4-isocyanatophenyl)-1-methyl-1H-pyrazolo[3,4-d]pyrimidin-4-yl)-8-oxa-3-azabicyclo[3.2.1]octane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 10% acetonitrile/90% of 0.1% aqueous trifluoroacetic acid to 90% acetonitrile to provide 1-cyclopropyl-3-{4-[1-methyl-4-(8-oxa-3-azabicyclo[3.2.1]oct-3-yl)-1H-pyrazolo[3,4-d]pyrimidin-6-yl]phenyl}urea. MS (ES+): 420.2 (M+H)+

The following ureas and carbamates were made via the addition of the appropriate nucleophile to the isocyanate (0.15 mmol) derived from 4-(4-(8-oxa-3-azabicyclo[3.2.1]octan-3-yl)-1-methyl-1H-pyrazolo[3,4-d]pyrimidin-6-yl)aniline, in accordance with the general procedure described for the preparation of 1-cyclopropyl-3-{4-[1-methyl-4-(8-oxa-3-azabicyclo[3.2.1]oct-3-yl)-1H-pyrazolo[3,4-d]pyrimidin-6-yl]phenyl}urea. (Scheme s 1 and 2)

1-[3-(dimethylamino)propyl]-3-{4-[1-methyl-4-(8-oxa-3-azabicyclo[3.2.1]oct-3-yl)-1H-pyrazolo[3,4-d]pyrimidin-6-yl]phenyl}urea.TFA Nucleophile added to isocyanate: N,N-dimethylpropane-1,3-diamine (190 µL) MS (ES$^+$): 465.2 (M+H)$^+$ 1-{4-[1-methyl-4-(8-oxa-3-azabicyclo[3.2.1]oct-3-yl)-1H-pyrazolo[3,4-d]pyrimidin-6-yl]phenyl}-3-phenylurea Nucleophile added to isocyanate: aniline (137 µL) MS (ES$^+$): 456.1 (M+H)$^+$ 1-{4-[1-methyl-4-(8-oxa-3-azabicyclo[3.2.1]oct-3-yl)-1H-pyrazolo[3,4-d]pyrimidin-6-yl]phenyl}-3-pyridin-4-ylurea.TFA Nucleophile added to isocyanate: 4-aminopyridine (141 mg) MS (ES$^+$): 457.0 (M+H)$^+$ 1-(2-fluoroethyl)-3-{4-[1-methyl-4-(8-oxa-3-azabicyclo[3.2.1]oct-3-yl)-1H-pyrazolo[3,4-d]pyrimidin-6-yl]phenyl}urea 2-fluoroethylamine hydrochloride (0.15 g, 1.5 mmol) was dissolved in 1 M aqueous sodium hydroxide solution (1.5 mL). The solution of isocyanate was added to the aqueous amine. The biphasic mixture was agitated on a vortex and then the aqueous phase was decanted. The organic layer was concentrated under reduced pressure and purified as usual by reverse-phase high performance liquid chromatography. MS (ES$^+$): 426.1 (M+H)$^+$ 1-(2-hydroxyethyl)-3-{4-[1-methyl-4-(8-oxa-3-azabicyclo[3.2.1]oct-3-yl)-1H-pyrazolo[3,4-d]pyrimidin-6-yl]phenyl}urea Nucleophile added to isocyanate: ethanolamine (91 µL) MS (ES$^+$): 424.2 (M+H)$^+$ 1-[2-(dimethylamino)ethyl]-3-{4-[1-methyl-4-(8-oxa-3-azabicyclo[3.2.1]oct-3-yl)-1H-pyrazolo[3,4-d]pyrimidin-6-yl]phenyl}urea.TFA Nucleophile added to isocyanate: N,N-dimethylethane-1,2-diamine (165 µL) MS (ES$^+$): 451.2 (M+H)$^+$ 1-{4-[1-methyl-4-(8-oxa-3-azabicyclo[3.2.1]oct-3-yl)-1H-pyrazolo[3,4-d]pyrimidin-6-yl]phenyl}-3-pyridin-3-ylurea.TFA Nucleophile added to isocyanate: 3-aminopyridine (141 mg) MS (ES$^+$): 457.1 (M+H)$^+$ 1-methyl-3-{4-[1-methyl-4-(8-oxa-3-azabicyclo[3.2.1]oct-3-yl)-1H-pyrazolo[3,4-d]pyrimidin-6-yl]phenyl}urea Nucleophile added to isocyanate: 2 M methylamine solution in tetrahydrofuran (750 µL) MS (ES$^+$): 394.2 (M+H)$^+$ 1-ethyl-3-{4-[1-methyl-4-(8-oxa-3-azabicyclo[3.2.1]oct-3-yl)-1H-pyrazolo[3,4-d]pyrimidin-6-yl]phenyl}urea Nucleophile added to isocyanate: 2 M ethylamine solution in tetrahydrofuran (750 µL) MS (ES$^+$): 408.2 (M+H)$^+$ Methyl{4-[1-methyl-4-(8-oxa-3-azabicyclo[3.2.1]oct-3-yl)-1H-pyrazolo[3,4-d]pyrimidin-6-yl]phenyl}carbamate Nucleophile added to isocyanate: methanol (excess) MS (ES$^+$): 395.2 (M+H)$^+$ 3-[1-methyl-4-(8-oxa-3-azabicyclo[3.2.1]oct-3-yl)-1H-pyrazolo[3,4-d]pyrimidin-6-yl]phenol (Scheme 28)

A mixture of 3-(6-chloro-1-methyl-1H-pyrazolo[3,4-d]pyrimidin-4-yl)-8-oxa-3-azabicyclo[3.2.1]octane (95 mg, 0.34 mmol), 3-hydroxyphenylboronic acid (70 mg, 0.51 mmol), and tetrakis(triphenylphosphine)palladium(0) (39 mg, 10 mol %) in toluene/ethanol (1:1, 3 mL) and 2 M aqueous sodium carbonate solution (2 mL) was heated in a Smith process vial in the microwave reactor for one hour at 120° C. The cooled mixture was partitioned between ethyl acetate and water. The aqueous phase was acidified with 1 M aqueous hydrochloric acid and then extracted three times with ethyl acetate. The combined extracts were washed successively with water, saturated aqueous sodium hydrogen carbonate solution and saturated aqueous sodium chloride solution. The extracts were then dried over anhydrous magnesium sulfate, filtered, and concentrated to dryness under reduced pressure. The crude residue was purified via reverse-phase high performance liquid chromatography using a Phenomenex Prodigy 21 mm×250 mm column, running a gradient elution of 5% acetonitrile/95% of 0.1% aqueous trifluoroacetic acid to 90% acetonitrile to provide, after concentration, 3-[1-methyl-4-(8-oxa-3-azabicyclo[3.2.1]oct-3-yl)-1H-pyrazolo[3,4-d]pyrimidin-6-yl]phenol. MS (ES$^+$): 338.0 (M+H)$^+$ 1-ethyl-3-{4-[4-(8-oxa-3-azabicyclo[3.2.1]oct-3-yl)-1-piperidin-4-yl-1H-pyrazolo[3,4-d]pyrimidin-6-yl]phenyl}urea.TFA (Scheme 30)

A solution of tert-butyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate (31 mg, 0.05 mmol) in dichloromethane (3 mL) was treated with trifluoroacetic acid (0.3 mL). Evaporation of the volatiles under reduced pressure gave the title compound. MS (ES$^+$): 477.2 (M+H)$^+$ 1-{4-[4-(8-oxa-3-azabicyclo[3.2.1]oct-3-yl)-1-piperidin-4-yl-1H-pyrazolo[3,4-d]pyrimidin-6-yl]phenyl}-3-phenylurea.TFA (Scheme 30)

A solution of tert-butyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate (33 mg, 0.05 mmol) in dichloromethane (3 mL) was treated with trifluoroacetic acid (0.3 mL). Evaporation of the volatiles under reduced pressure gave the title compound. MS (ES$^+$): 525.2 (M+H)$^+$ 1-{4-[1-benzyl-4-(8-oxa-3-azabicyclo[3.2.1]oct-3-yl)-1H-pyrazolo[3,4-d]pyrimidin-6-yl]phenyl}-3-methylurea (Scheme 42)

4-(1-benzyl-4-(8-oxa-3-azabicyclo[3.2.1]octan-3-yl)-1H-pyrazolo[3,4-d]pyrimidin-6-yl)aniline was prepared from 3-(1-benzyl-6-(4-nitrophenyl)-1H-pyrazolo[3,4-d]pyrimidin-4-yl)-8-oxa-3-azabicyclo[3.2.1]octane, which was prepared utilizing the same sequence of steps that provided 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine. In the first step, however, 2,2,2-trifluoroethylhydrazine was replaced by benzylhydrazine dihydrochloride. This substitution necessitated the addition of two equivalents of triethylamine to the reaction mixture.

A solution of 4-(1-benzyl-4-(8-oxa-3-azabicyclo[3.2.1]octan-3-yl)-1H-pyrazolo[3,4-d]pyrimidin-6-yl)aniline (22 mg, 0.05 mmol) in a mixture of dichloromethane (3 mL) and tetrahydrofuran (2 mL) was treated with triphosgene (8 mg, 0.03 mmol) as a solution in dichloromethane (1 mL). After the passage of 5 minutes, the appropriate nucleophile—in the case, 2.0 M methylamine solution in tetrahydrofuran (1 mL)—was added to the 3-(1-benzyl-6-(4-isocyanatophenyl)-1H-pyrazolo[3,4-d]pyrimidin-4-yl)-8-oxa-3-azabicyclo[3.2.1]octane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile to provide 1-{4-[1-benzyl-4-(8-oxa-3-azabicyclo[3.2.1]oct-3-yl)-1H-pyrazolo[3,4-d]pyrimidin-6-yl]phenyl}-3-methylurea. MS (ES$^+$): 470.0 (M+H)$^+$ The following ureas and carbamates were made via the addition of the appropriate nucleophile to the isocyanate (0.05 mmol) derived from 4-(1-benzyl-4-(8-oxa-3-azabicyclo[3.2.1]octan-3-yl)-1H-pyrazolo[3,4-d]pyrimidin-6-yl)aniline, in accordance with the general procedure described for the preparation of 1-{4-[1-benzyl-4-(8-oxa-3-azabicyclo[3.2.1]oct-3-yl)-1H-pyrazolo[3,4-d]pyrimidin-6-yl]phenyl}-3-methylurea.

1-{4-[1-benzyl-4-(8-oxa-3-azabicyclo[3.2.1]oct-3-yl)-1H-pyrazolo[3,4-d]pyrimidin-6-yl]phenyl}-3-ethylurea Nucleophile added to isocyanate: 2 M ethylamine solution in tetrahydrofuran (1 mL) MS (ES$^+$): 484.5 (M+H)$^+$ 1-{4-[1-benzyl-4-(8-oxa-3-azabicyclo[3.2.1]oct-3-yl)-1H-pyrazolo[3,4-d]pyrimidin-6-yl]phenyl}-3-pyridin-4-ylurea.TFA Nucleophile added to isocyanate: 4-aminopyridine (100 mg) as a solution in warm tetrahydrofuran (4 mL) MS (ES$^+$): 533.1 (M+H)$^+$ Methyl{4-[1-tert-butyl-4-(8-oxa-3-azabicyclo[3.2.1]oct-3-yl)-1H-pyrazolo[3,4-d]pyrimidin-6-yl]phenyl}carbamate 4-(4-(8-oxa-3-azabicyclo[3.2.1]octan-3-yl)-1-tert-butyl-1H-pyrazolo[3,4-d]pyrimidin-6-yl)aniline was prepared from 3-(1-tert-butyl-6-(4-nitrophenyl)-1H-pyrazolo[3,4-d]pyrimidin-4-yl)-8-oxa-3-azabicyclo[3.2.1]octane, which was prepared utilizing the same sequence of steps that provided 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine. In the first step, however, 2,2,2-trifluoroethylhydrazine was replaced by tert-butylhydrazine hydrochloride. This substitution necessitated the addition of one equivalent of triethylamine to the reaction mixture.

A solution of 4-(4-(8-oxa-3-azabicyclo[3.2.1]octan-3-yl)-1-tert-butyl-1H-pyrazolo[3,4-d]pyrimidin-6-yl)aniline (65 mg, 0.17 mmol) in a mixture of dichloromethane (2 mL) and tetrahydrofuran (2 mL) was treated with triphosgene (26 mg, 0.09 mmol) as a solution in dichloromethane (1 mL). After the passage of 10 minutes, the appropriate nucleophile—in the case, methanol (excess)—was added to the 3-(1-tert-butyl-6-(4-isocyanatophenyl)-1H-pyrazolo[3,4-d]pyrimidin-4-yl)-8-oxa-3-azabicyclo[3.2.1]octane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 5% acetonitrile/95% of 0.1% aqueous trifluoroacetic acid to 100% acetonitrile to provide methyl{4-[1-tert-butyl-4-(8-oxa-3-azabicyclo[3.2.1]oct-3-yl)-1H-pyrazolo[3,4-d]pyrimidin-6-yl]phenyl}carbamate. MS (ES$^+$): 437.2 (M+H)$^+$ The following ureas and carbamates were made via the addition of the appropriate nucleophile to the isocyanate (0.17 mmol) derived from 4-(4-(8-oxa-3-azabicyclo[3.2.1]octan-3-yl)-1-tert-butyl-1H-pyrazolo[3,4-d]pyrimidin-6-yl)aniline, in accordance with the general procedure described for the preparation of methyl{4-[1-tert-butyl-4-(8-oxa-3-azabicyclo[3.2.1]oct-3-yl)-1H-pyrazolo[3,4-d]pyrimidin-6-yl]phenyl}carbamate.

1-{4-[1-tert-butyl-4-(8-oxa-3-azabicyclo[3.2.1]oct-3-yl)-1H-pyrazolo[3,4-d]pyrimidin-6-yl]phenyl}-3-methylurea Nucleophile added to isocyanate: 2 M methylamine solution in tetrahydrofuran (1.7 mL) MS (ES$^+$): 436.2 (M+H)$^+$ 2-hydroxyethyl{4-[1-tert-butyl-4-(8-oxa-3-azabicyclo[3.2.1]oct-3-yl)-1H-pyrazolo[3,4-d]pyrimidin-6-yl]phenyl}carbamate Nucleophile added to isocyanate: ethylene glycol (190 µL) MS (ES$^+$): 467.2 (M+H)$^+$ 1-{4-[1-tert-butyl-4-(8-oxa-3-azabicyclo[3.2.1]oct-3-yl)-1H-pyrazolo[3,4-d]pyrimidin-6-yl]phenyl}-3-phenylurea Nucleophile added to isocyanate: aniline (310 µL) MS (ES$^+$): 498.3 (M+H)$^+$ 1-{4-[1-tert-butyl-4-(8-oxa-3-azabicyclo[3.2.1]oct-3-yl)-1H-pyrazolo[3,4-d]pyrimidin-6-yl]phenyl}-3-pyridin-3-ylurea.TFA Nucleophile added to isocyanate: 3-aminopyridine (320 mg) MS (ES$^+$): 499.2 (M+H)$^+$ 1-{4-[1-tert-butyl-4-(8-oxa-3-azabicyclo[3.2.1]oct-3-yl)-1H-pyrazolo[3,4-d]pyrimidin-6-yl]phenyl}-3-pyridin-4-ylurea.TFA Nucleophile added to isocyanate: 4-aminopyridine (320 mg) MS (ES$^+$): 499.2 (M+H)$^+$

1-{4-[1-tert-butyl-4-(8-oxa-3-azabicyclo[3.2.1]oct-3-yl)-1H-pyrazolo[3,4-d]pyrimidin-6-yl]phenyl}-3-(2-fluoroethyl)urea 2-fluoroethylamine hydrochloride (340 mg) was dissolved in 1 M aqueous sodium hydroxide solution (3.4 mL). The solution of isocyanate was added to the aqueous amine solution. The biphasic mixture was agitated on a vortex and then was concentrated under reduced pressure and purified as usual by reverse-phase high performance liquid chromatography. MS (ES$^+$): 468.2 (M+H)$^+$

1-{4-[1-tert-butyl-4-(8-oxa-3-azabicyclo[3.2.1]oct-3-yl)-1H-pyrazolo[3,4-d]pyrimidin-6-yl]phenyl}-3-cyclopropylurea Nucleophile added to isocyanate: cyclopropylamine (236 µL) MS (ES$^+$): 462.3 (M+H)$^+$

1-{4-[1-tert-butyl-4-(8-oxa-3-azabicyclo[3.2.1]oct-3-yl)-1H-pyrazolo[3,4-d]pyrimidin-6-yl]phenyl}-3-ethylurea Nucleophile added to isocyanate: 2 M ethylamine solution in tetrahydrofuran (1.7 mL) MS (ES$^+$): 450.3 (M+H)$^+$

1-{4-[1-tert-butyl-4-(8-oxa-3-azabicyclo[3.2.1]oct-3-yl)-1H-pyrazolo[3,4-d]pyrimidin-6-yl]phenyl}-3-(2-hydroxyethyl)urea Nucleophile added to isocyanate: ethanolamine (205 µL) MS (ES$^+$): 466.2 (M+H)$^+$

1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-methylurea (Scheme 43)

4-(4-(3,7-Dioxa-9-azabicyclo[3.3.1]nonan-9-yl)-1-(2,2,2-trifluoroethyl)-1H-pyrazolo[3,4-d]pyrimidin-6-yl)aniline was prepared from 9-(6-(4-nitrophenyl)-1-(2,2,2-trifluoroethyl)-1H-pyrazolo[3,4-d]pyrimidin-4-yl)-3,7-dioxa-9-azabicyclo[3.3.1]nonane according to the method used for 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine, except in step 5, 3,7-dioxa-9-azabicyclo[3.3.1]nonane formate replaced 8-oxa-3-aza-bicyclo[3.2.1]octane hydrochloride.

A solution of 4-(4-(3,7-dioxa-9-azabicyclo[3.3.1]nonan-9-yl)-1-(2,2,2-trifluoroethyl)-1H-pyrazolo[3,4-d]pyrimidin-6-yl)aniline (47 mg, 0.11 mmol) in dichloromethane (2 mL) was treated triethylamine (140 µL), followed by triphosgene (25 mg, 0.08 mmol) as a solution in dichloromethane (1 mL). After the passage of 5 minutes, the appropriate nucleophile—in the case, 2.0 M methylamine solution in tetrahydrofuran (1.1 mL)—was added to the 9-(6-(4-isocyanatophenyl)-1-(2,2,2-trifluoroethyl)-1H-pyrazolo[3,4-d]pyrimidin-4-yl)-3,7-dioxa-9-azabicyclo[3.3.1]nonane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 10% acetonitrile/90% of 0.1% aqueous trifluoroacetic acid to 100% acetonitrile to provide 1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-methylurea. MS (ES$^+$): 478.3 (M+H)$^+$ The following urea and carbamate were made via the addition of the appropriate nucleophile to the isocyanate (0.11 mmol) derived from 4-(4-(3,7-dioxa-9-azabicyclo[3.3.1]nonan-9-yl)-1-(2,2,2-trifluoroethyl)-1H-pyrazolo[3,4-d]pyrimidin-6-yl)aniline, in accordance with the general procedure described for the preparation of 1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-methylurea.

2-hydroxyethyl 4-(4-(3,7-dioxa-9-azabicyclo[3.3.1]nonan-9-yl)-1-(2,2,2-trifluoroethyl)-1H-pyrazolo[3,4-d]pyrimidin-6-yl)phenylcarbamate Nucleophile added to isocyanate: ethylene glycol (120 µL) MS (ES$^+$): 509.3 (M+H)$^+$

1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea.TFA Nucleophile added to isocyanate: 4-(2-(dimethylamino)ethoxy)aniline (40 mg) as a solution in dichloromethane (1 mL) MS (ES$^+$): 627.5 (M+H)$^+$

1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-methylurea 4-(4-(3-oxa-9-azabicyclo[3.3.1]nonan-9-yl)-1-(2,2,2-trifluoroethyl)-1H-pyrazolo[3,4-d]pyrimidin-6-yl)aniline was prepared from 9-(6-(4-nitrophenyl)-1-(2,2,2-trifluoroethyl)-1H-pyrazolo[3,4-d]pyrimidin-4-yl)-3-oxa-9-azabicyclo[3.3.1]nonane according to the method used for 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine, except in step 5, 3-oxa-9-azabicyclo[3.3.1]nonane hydrochloride replaced 8-oxa-3-aza-bicyclo[3.2.1]octane hydrochloride.

A solution of 4-(4-(3-oxa-9-azabicyclo[3.3.1]nonan-9-yl)-1-(2,2,2-trifluoroethyl)-1H-pyrazolo[3,4-d]pyrimidin-6-yl)aniline (50 mg, 0.12 mmol) in dichloromethane (3 mL) was treated triethylamine (160 µL), followed by triphosgene (27 mg, 0.09 mmol) as a solution in dichloromethane (1 mL). After the passage of 5 minutes, the appropriate nucleophile—in the case, 2.0 M methylamine solution in tetrahydrofuran (1.2 mL)—was added to the 9-(6-(4-isocyanatophenyl)-1-(2,2,2-trifluoroethyl)-1H-pyrazolo[3,4-d]pyrimidin-4-yl)-3-oxa-9-azabicyclo[3.3.1]nonane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 10% acetonitrile/90% of 0.1% aqueous trifluoroacetic acid to 100% acetonitrile to provide 1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-methylurea. MS (ES$^+$): 476.3 (M+H)$^+$ The following urea and carbamate were made via the addition of the appropriate nucleophile to the isocyanate (0.12 mmol) derived from 4-(4-(3-oxa-9-azabicyclo[3.3.1]nonan-9-yl)-1-(2,2,2-trifluoroethyl)-1H-pyrazolo[3,4-d]pyrimidin-6-yl)aniline, in accordance with the general procedure described for the preparation of 1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-methylurea.

2-hydroxyethyl 4-(4-(3-oxa-9-azabicyclo[3.3.1]nonan-9-yl)-1-(2,2,2-trifluoroethyl)-1H-pyrazolo[3,4-d]pyrimidin-6-yl)phenylcarbamate Nucleophile added to isocyanate: ethylene glycol (140 µL) MS (ES+): 507.3 (M+H)+

1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea.TFA Nucleophile added to isocyanate: 4-(2-(dimethylamino)ethoxy)aniline (43 mg) as a solution in dichloromethane (1 mL) MS (ES+): 625.4 (M+H)+

1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-methylurea 4-(4-(2-oxa-5-azabicyclo[2.2.2]octan-5-yl)-1-(2,2,2-trifluoroethyl)-1H-pyrazolo[3,4-d]pyrimidin-6-yl)aniline was prepared from 5-(6-(4-nitrophenyl)-1-(2,2,2-trifluoroethyl)-1H-pyrazolo[3,4-d]pyrimidin-4-yl)-2-oxa-5-azabicyclo[2.2.2]octane according to the method used for 4-[4-(8-oxa-3-aza-bicyclo[3.2.1]oct-3-yl)-1-(2,2,2-trifluoro-ethyl)-1H-pyrazolo[3,4-d]pyrimidin-6-yl]-phenylamine, except in step 5, 2-oxa-5-azabicyclo[2.2.2]octane hydrochloride replaced 8-oxa-3-aza-bicyclo[3.2.1]octane hydrochloride.

A solution of 4-(4-(2-oxa-5-azabicyclo[2.2.2]octan-5-yl)-1-(2,2,2-trifluoroethyl)-1H-pyrazolo[3,4-d]pyrimidin-6-yl)aniline (50 mg, 0.12 mmol) in dichloromethane (2.5 mL) was treated triethylamine (160 µL), followed by triphosgene (27 mg, 0.09 mmol) as a solution in dichloromethane (1 mL). After the passage of 5 minutes, the appropriate nucleophile—in the case, 2.0 M methylamine solution in tetrahydrofuran (1.2 mL)—was added to the 5-(6-(4-isocyanatophenyl)-1-(2,2,2-trifluoroethyl)-1H-pyrazolo[3,4-d]pyrimidin-4-yl)-2-oxa-5-azabicyclo[2.2.2]octane ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 10% acetonitrile/90% of 0.1% aqueous trifluoroacetic acid to 100% acetonitrile to provide 1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-methylurea. MS (ES+): 462.3 (M+H)+

The following urea and carbamate were made via the addition of the appropriate nucleophile to the isocyanate (0.12 mmol) derived from 4-(4-(2-oxa-5-azabicyclo[2.2.2]octan-5-yl)-1-(2,2,2-trifluoroethyl)-1H-pyrazolo[3,4-d]pyrimidin-6-yl)aniline, in accordance with the general procedure described for the preparation of 1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-methylurea.

2-hydroxyethyl 4-(4-(2-oxa-5-azabicyclo[2.2.2]octan-5-yl)-1-(2,2,2-trifluoroethyl)-1H-pyrazolo[3,4-d]pyrimidin-6-yl)phenylcarbamate Nucleophile added to isocyanate: ethylene glycol (140 µL) MS (ES+): 493.3 (M+H)+

1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(4-(2-(dimethylamino)ethoxy)phenyl)urea.TFA Nucleophile added to isocyanate: 4-(2-(dimethylamino)ethoxy)aniline (43 mg) as a solution in dichloromethane (1 mL) MS (ES+): 611.3 (M+H)+tert-butyl

9-(6-(4-(3-methylureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate tert-butyl 9-(6-(4-aminophenyl)-1-(2,2,2-trifluoroethyl)-1H-pyrazolo[3,4-d]pyrimidin-4-yl)-3-oxa-7,9-diazabicyclo[3.3.1]nonane-7-carboxylate was prepared from tert-butyl 9-(6-(4-nitrophenyl)-1-(2,2,2-trifluoroethyl)-1H-pyrazolo[3,4-d]pyrimidin-4-yl)-3-oxa-7,9-diazabicyclo[3.3.1]nonane-7-carboxylate according to the method used for 4-[4-(8-oxa-3-aza-bicyclo[3.2.1]oct-3-yl)-1-(2,2,2-trifluoroethyl)-1H-pyrazolo[3,4-d]pyrimidin-6-yl]-phenylamine, except in step 5, tert-butyl 3-oxa-7,9-diazabicyclo[3.3.1]nonane-7-carboxylate replaced 8-oxa-3-aza-bicyclo[3.2.1]octane hydrochloride.

A solution of tert-butyl 9-(6-(4-aminophenyl)-1-(2,2,2-trifluoroethyl)-1H-pyrazolo[3,4-d]pyrimidin-4-yl)-3-oxa-7,9-diazabicyclo[3.3.1]nonane-7-carboxylate (230 mg, 0.45 mmol) in dichloromethane (6 mL) was treated triethylamine (520 µL), followed by triphosgene (90 mg, 0.30 mmol) as a solution in dichloromethane (2 mL). After the passage of 5 minutes, the appropriate nucleophile—in the case, 2.0 M methylamine solution in tetrahydrofuran (4 mL)—was added to tert-butyl 9-(6-(4-isocyanatophenyl)-1-(2,2,2-trifluoroethyl)-1H-pyrazolo[3,4-d]pyrimidin-4-yl)-3-oxa-7,9-diazabicyclo[3.3.1]nonane-7-carboxylate ("isocyanate") mixture. The reaction mixture was concentrated to dryness under reduced pressure. The residue was purified by reverse-phase high performance liquid chromatography using a Phenomenex Prodigy 21 mm×250 mm column, running a gradient elution of 10% acetonitrile/90% of 0.1% aqueous trifluoroacetic acid to 100% acetonitrile to provide tert-butyl 9-(6-(4-(3-methylureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate. MS (ES+): 577.2 (M+H)+

The following urea and carbamate were made via the addition of the appropriate nucleophile to the isocyanate (0.45 mmol) derived from tert-butyl 9-(6-(4-aminophenyl)-1-(2,2,2-trifluoroethyl)-1H-pyrazolo[3,4-d]pyrimidin-4-yl)-3-oxa-7,9-diazabicyclo[3.3.1]nonane-7-carboxylate, in accordance with the general procedure described for the preparation of tert-butyl 9-(6-(4-(3-methylureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate.

tert-butyl 9-(6-(4-((2-hydroxyethoxy)carbonylamino)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate Nucleophile added to isocyanate: ethylene glycol (450 µL) MS (ES+): 608.2 (M+H)+ tert-butyl 9-(6-(4-(3-(4-(2-(dimethylamino)ethoxy)phenyl)ureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate.TFA Nucleophile added to isocyanate: 4-(2-(dimethylamino)ethoxy)aniline (140 mg) as a solution in dichloromethane (1.5 mL) MS (ES+): 726.3 (M+H)+

1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea.2TFA (Scheme 43)

A solution of tert-butyl 9-(6-(4-(3-(4-(2-(dimethylamino)ethoxy)phenyl)ureido)phenyl)-1-(2,2,2-trifluoroethyl)-1H- pyrazolo[3,4-d]pyrimidin-4-yl)-3-oxa-7,9-diazabicyclo [3.3.1]nonane-7-carboxylate.TFA (174 mg) in dichloromethane (5 mL) was treated with trifluoroacetic acid (1 mL). After concentration, the residue was purified by reverse-phase high performance liquid chromatography to provide, after concentration, the title compound. MS (ES$^+$): 626.3 (M+H)$^+$ 1-(4-(4-(3-oxa-7,9-diazabicyclo[3.3.1]nonan-9-yl)-1- (2,2,2-trifluoroethyl)-1H-pyrazolo[3,4-d]pyrimidin- 6-yl)phenyl)-3-methylurea.TFA A solution of tert-butyl 9-(6-(4-(3-methylureido)phenyl)- 1-(2,2,2-trifluoroethyl)-1H-pyrazolo[3,4-d]pyrimidin-4-yl)- 3-oxa-7,9-diazabicyclo[3.3.1]nonane-7-carboxylate (65 mg) in dichloromethane (5 mL) was treated with trifluoroacetic acid (1 mL). After concentration, the residue was purified by reverse-phase high performance liquid chromatography to provide, after concentration, the title compound. MS (ES$^+$): 477.4 (M+H)$^+$ 2-hydroxyethyl 4-(4-(3-oxa-7,9-diazabicyclo[3.3.1] nonan-9-yl)-1-(2,2,2-trifluoroethyl)-1H-pyrazolo[3, 4-d]pyrimidin-6-yl)phenylcarbamate.TFA A solution of tert-butyl 9-(6-(4-((2-hydroxyethoxy)carbonylamino)phenyl)-1-(2,2,2-trifluoroethyl)-1H-pyrazolo[3,4- d]pyrimidin-4-yl)-3-oxa-7,9-diazabicyclo[3.3.1]nonane-7- carboxylate (68 mg) in dichloromethane (5 mL) was treated with trifluoroacetic acid (1 mL). After concentration, the residue was purified by reverse-phase high performance liquid chromatography to provide, after concentration, the title compound. MS (ES$^+$): 508.1 (M+H)$^+$ Preparation of methyl{4-[4-(8-oxa-3-azabicyclo [3.2.1]oct-3-yl)-1-(4-oxocyclohexyl)-1H-pyrazolo[3, 4-d]pyrimidin-6-yl]phenyl}carbamate (Scheme 36)

Methyl{4-[1-(1,4-dioxaspiro[4.5]dec-8-yl)-4-(8-oxa-3- azabicyclo[3.2.1]oct-3-yl)-1H-pyrazolo[3,4-d]pyrimidin-6- yl]phenyl}carbamate (0.2 g, 0.38 mmol) was dissolved in conc. HCl (2.0 mL) and stirred at room temperature for 1 hr. The reaction was cooled in an ice bath and basified with 10N sodium hydroxide to precipitate a white solid. The solid was filtered and washed with water and purified by Gilson HPLC to give the desired product (93 mg) MS m/z=477 (M+H).

Preparation of methyl{4-[1-(4-hydroxycyclohexyl)- 4-(8-oxa-3-azabicyclo[3.2.1]oct-3-yl)-1H-pyrazolo [3,4-d]pyrimidin-6-yl]phenyl}carbamate (Scheme 36)

To a solution of methyl{4-[4-(8-oxa-3-azabicyclo[3.2.1] oct-3-yl)-1-(4-oxocyclohexyl)-1H-pyrazolo[3,4-d]pyrimidin-6-yl]phenyl}carbamate (63 mg) (0.13 mmol) in THF (2.0 mL) was added an excess of sodium borohydride. The mixture was stirred for 1 hr. at 50 C. The reaction was then cooled and quenched with water and extracted three times with EtOAc. Organics were dried (MgSO4) and concentrated in vacuo. The resulting oil was triturated with diethyl ether to give a white solid. The solid was filtered and washed the diethyl ether to give (44 mg) MS m/z=479.2 (M+H).

The following compounds were synthesized using the above procedures (Scheme 36)

2-hydroxyethyl{4-[4-(8-oxa-3-azabicyclo[3.2.1]oct- 3-yl)-1-(4-oxocyclohexyl)-1H-pyrazolo[3,4-d]pyrimidin-6-yl]phenyl}carbamate MS m/z=507.2 (M+H)

2-hydroxyethyl{4-[1-(4-hydroxycyclohexyl)-4-(8- oxa-3-azabicyclo[3.2.1]oct-3-yl)-1H-pyrazolo[3,4-d] pyrimidin-6-yl]phenyl}carbamate MS m/z=509.2 (M+H)

1-[4-(4-methylpiperazin-1-yl)phenyl]-3-{4-[4-(8- oxa-3-azabicyclo[3.2.1]oct-3-yl)-1-(4-oxocyclohexyl)-1H-pyrazolo[3,4-d]pyrimidin-6-yl] phenyl}urea MS m/z=636 (M+H)

1-{4-[1-(trans-4-hydroxycyclohexyl)-4-(8-oxa-3- azabicyclo[3.2.1]oct-3-yl)-1H-pyrazolo[3,4-d]pyrimidin-6-yl]phenyl}-3-[4-(4-methylpiperazin-1-yl) phenyl]urea Used lithium aluminum hydride in place of sodium borohydride. MS m/z=638 (M+H)

1-{4-[1-(cis-4-hydroxycyclohexyl)-4-(8-oxa-3-azabicyclo[3.2.1]oct-3-yl)-1H-pyrazolo[3,4-d]pyrimidin- 6-yl]phenyl}-3-[4-(4-methylpiperazin-1-yl)phenyl] urea Used L-selectride hydride in place of sodium borohydride. MS m/z=638 (M+H)

1-cyclopropyl-3-{4-[4-(8-oxa-3-azabicyclo[3.2.1] oct-3-yl)-1-(4-oxocyclohexyl)-1H-pyrazolo[3,4-d] pyrimidin-6-yl]phenyl}urea MS m/z=502 (M+H)

1-cyclopropyl-3-{4-[1-(trans-4-hydroxycyclohexyl)- 4-(8-oxa-3-azabicyclo[3.2.1]oct-3-yl)-1H-pyrazolo [3,4-d]pyrimidin-6-yl]phenyl}urea Used lithium aluminum hydride in place of sodium borohydride MS m/z=504 (M+H)

1-cyclopropyl-3-{4-[1-(cis-4-hydroxycyclohexyl)-4- (8-oxa-3-azabicyclo[3.2.1]oct-3-yl)-1H-pyrazolo[3, 4-d]pyrimidin-6-yl]phenyl}urea Used L-selectride hydride in place of sodium borohydride. MS m/z=504 (M+H)
1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-methylurea Used L-selectride hydride in place of sodium borohydride. MS m/z=478 (M+H)
1-{4-[1-(trans-4-hydroxycyclohexyl)-4-(8-oxa-3-azabicyclo[3.2.1]oct-3-yl)-1H-pyrazolo[3,4-d]pyrimidin-6-yl] phenyl}-3-methylurea Used lithium aluminum hydride in place of sodium borohydride (MS m/z=478 (M+H)

Preparation of 1-{4-[1-(4,4-dimethoxycyclohexyl)-4- (8-oxa-3-azabicyclo[3.2.1]oct-3-yl)-1H-pyrazolo[3, 4-d]pyrimidin-6-yl]phenyl}-3-methylurea (Scheme 36)

To a solution of 1-methyl-3-{4-[4-(8-oxa-3-azabicyclo [3.2.1]oct-3-yl)-1-(4-oxocyclohexyl)-1H-pyrazolo[3,4-d]

pyrimidin-6-yl]phenyl}urea (80 mg) (0.17 mmol) in DCM (2.0 mL) was added trimethylorthoformate and methanol in excess and a catalytic amount of p-toluene sulfonic acid along with molecular sieves and stirred at room temperature overnight. The added water and extracted 3 times with EtOAc. The organics were dried (MgSO4) and filtered off through a pad of Magnesol and concentrated in vacuo. to afford a solid. The solid was triturated with diethyl ether to give a white solid that was filtered and washed with diethyl ether to give (54 mg) MS m/z=476.2 (M+H).

The following compounds were synthesized using the above procedures (Scheme 36)

1-{4-[1-(1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea The following reagents were used: tripropyl orthoformate and 1,3-propanediol. MS m/z=534 (M+H)

1-{4-[1-(3,3-dimethyl-1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea The following reagents were used: 2,2-dimethyl, 1,3-propanediol in refluxing toluene MS m/z=531.3 (M+H)

Preparation of 1-methyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea (Scheme 36)

To a solution of 1-methyl-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea (65 mg) in DCE (2.0 mL) was added excess N-methylpiperizine, acetic acid (0.012 mL) and excess sodium triacetoxyborohydride. The mixture was stirred at room temperature overnight. The reaction was quenched with water and the organics were separated and concentrated under nitrogen and purified by Gilson HPLC to give the desired product (56 mg) MS m/z=560.3 (M+H).

The following compounds were synthesized using the above procedures (Scheme 36)

1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-pyridin-3-ylurea MS m/z=623.3 (M+H)

1-methyl-3-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}urea Used excess pyrrolidine MS m/z=531.3 (M+H)

1-(4-{1-[4-(2,2-dimethylhydrazino)cyclohexyl]-4-(8-oxa-3-azabicyclo[3.2.1]oct-3-yl)-1H-pyrazolo[3,4-d]pyrimidin-6-yl}phenyl)-3-methylurea Used excess N,N-dimethylhydrazine MS m/z=520.3 (M+H)

1-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}-3-pyridin-3-ylurea Used excess pyrrolidine MS m/z=594.3 (M+H)

1-{4-[1-{4-[(2-hydroxyethyl)amino]cyclohexyl}-4-(8-oxa-3-azabicyclo[3.2.1]oct-3-yl)-1H-pyrazolo[3,4-d]pyrimidin-6-yl]phenyl}-3-methylurea Used excess ethanolamine MS m/z=521.3 (M+H)

The following compounds were synthesized using the above procedures (Scheme 38)

1-cyclopropyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea MS m/z=586.4 (M+H)

1-(2-fluoroethyl)-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea MS m/z=592.3 (M+H)

2-hydroxyethyl(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)carbamate MS m/z=591.3 (M+H)

1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-phenylurea MS m/z=622.4 (M+H)

1-ethyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea MS m/z=574.4 (M+H)

Preparation of 6-chloro-1-(4-methoxycyclohexyl)-4-(8-oxa-3-azabicyclo[3.2.1]oct-3-yl)-1H-pyrazolo[3,4-d]pyrimidine (Scheme 39)

To a solution of 4-[6-chloro-4-(8-oxa-3-azabicyclo[3.2.1]oct-3-yl)-1H-pyrazolo[3,4-d]pyrimidin-1-yl]cyclohexanol (2.5 g) in THF (21 mL) was added excess of sodium hydride and excess of iodomethane and heated the mixture at 40 C for 4 hr. The reaction was cooled and quenched with water and then extracted three times with EtOAc. Organics were dried (MgSO$_4$) and filtered off through a pad of Magnesol and concentrated in vacuo. to afford a solid that was triturated with diethyl ether. The solid was filtered and washed the diethyl ether to give (1.8 g) MS m/z=378 (M+H).

The Following Compounds were Synthesized Using the Above Procedures (Scheme 39)

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea MS m/z=652.4 (M+H)

2-hydroxyethyl{4-[1-(4-methoxycyclohexyl)-4-(8-oxa-3-azabicyclo[3.2.1]oct-3-yl)-1H-pyrazolo[3,4-d]pyrimidin-6-yl]phenyl}carbamate MS m/z=523.3 (M+H)

1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-methylurea MS m/z=492.2 (M+H)

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea MS m/z=653.4 (M+H)

4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-yl-benzamide MS m/z=666.3 (M+H)

1-[4-(hydroxymethyl)phenyl]-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea MS m/z=584.3 (M+H)

1-cyclopropyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea MS m/z=518.3 (M+H)

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-methylurea MS m/z=492 (M+H)

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-4-ylurea MS m/z=555.3 (M+H)

1-cyclopropyl-3-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}urea MS m/z=518 (M+H)

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-(4-piperazin-1-ylphenyl)urea MS m/z=638.3 (M+H)

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-3-ylurea MS m/z=555 (M+H)

1-{4-[2-(dimethylamino)ethoxy]phenyl}-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea MS m/z=641 (M+H)

1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-methylurea MS m/z=492 (M+H)

1-ethyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea MS m/z=506.3 (M+H)

4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]benzamide MS m/z=597.3 (M+H)

1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea MS m/z=652.3 (M+H)

1-cyclopropyl-3-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}urea MS m/z=518.3 (M+H)

1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea

MS M/Z=652 (M+H)

1-cyclopropyl-3-{4-[1-(4-ethoxycyclohexyl)-4-(8-oxa-3-azabicyclo[3.2.1]oct-3-yl)-1H-pyrazolo[3,4-d]pyrimidin-6-yl]phenyl}urea MS m/z=532 (M+H)

1-cyclopropyl-3-{4-[4-(8-oxa-3-azabicyclo[3.2.1]oct-3-yl)-1-(4-propoxycyclohexyl)-1H-pyrazolo[3,4-d]pyrimidin-6-yl]phenyl}urea MS m/z=546 (M+H)

1-{4-[1-(4-ethoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea MS m/z=666 (M+H)

1-[4-(4-methylpiperazin-1-yl)phenyl]-3-{4-[4-(8-oxa-3-azabicyclo[3.2.1]oct-3-yl)-1-(4-propoxycyclohexyl)-1H-pyrazolo[3,4-d]pyrimidin-6-yl]phenyl}urea MS m/z=680 (M+H)

Preparation of 3-bromo-1-ethyl-6-(4-nitrophenyl)-4-(8-oxa-3-azabicyclo[3.2.1]oct-3-yl)-1H-pyrazolo[3,4-d]pyrimidine (Scheme 40)

To a solution of 1-ethyl-6-(4-nitrophenyl)-4-(8-oxa-3-azabicyclo[3.2.1]oct-3-yl)-1H-pyrazolo[3,4-d]pyrimidine (7.9 g)(20.8 mmol) in DMF (140 mL) was added N-bromosuccinimide (18.5 g) and heated to 85 C for 24 hr. The reaction was cooled and poured into water (1.0 L) to precipitate tan solids. The solids were filtered off and washed with water. The crude solid was purified by silica gel chromatography (EtOAc/Hexanes) to give 2.8 g of a yellow solid. MS m/z=459.2 (M+H)

Preparation of 1-ethyl-6-(4-nitrophenyl)-4-(8-oxa-3-azabicyclo[3.2.1]oct-3-yl)-3-pyrrolidin-1-yl-1H-pyrazolo[3,4-d]pyrimidine (Scheme 40)

To a solution of 3-bromo-1-ethyl-6-(4-nitrophenyl)-4-(8-oxa-3-azabicyclo[3.2.1]oct-3-yl)-1H-pyrazolo[3,4-d]pyrimidine (100 mg)(0.21 mmol) in toluene (2.0 mL) was added Pd(dba)$_3$ (20 mg)(10 mol %), Binap (80 mg) (30 mol %), sodium tert butoxide (82 mg) and excess pyrrolidine. The mixture was purged under nitrogen for 5 minutes and then heated to 65 C overnight. Concentrated in vacuo to give an oil that was purified by silica gel chromatography (EtOAc/Hexanes) to afford 35 mg of the desired product as a yellow oil. MS m/z=450 (M+H)

Preparation of 1-ethyl-6-(4-nitrophenyl)-4-(8-oxa-3-azabicyclo[3.2.1]oct-3-yl)-3-pyridin-3-yl-1H-pyrazolo[3,4-d]pyrimidine (Scheme 40)

To a solution of 3-bromo-1-ethyl-6-(4-nitrophenyl)-4-(8-oxa-3-azabicyclo[3.2.1]oct-3-yl)-1H-pyrazolo[3,4-d]pyrimidine (100 mg)(0.21 mmol) in toluene/EtOH (1:1) (2.0 mL) was added Pd(PPh$_3$)$_4$ (12 mg) (10 mol %), aqueous sodium bicarbonate solution (2.0 M) (0.135 mL) and 3-pyridine boronic acid (32 mg) (0.26 mmol). The reaction was heated in the microwave for 20 minutes at 140 C. The reaction was cooled and added water and then extracted three times with EtOAc. Organics were dried (MgSO$_4$) and filtered off through a pad of Magnesol and concentrated in vacuo. to give a yellow oil 100 mg. MS m/z=458 (M+H)

Preparation of 4-[1-ethyl-4-(8-oxa-3-azabicyclo[3.2.1]oct-3-yl)-3-pyridin-3-yl-1H-pyrazolo[3,4-d]pyrimidin-6-yl]aniline (Scheme 40)

To a solution of 1-ethyl-6-(4-nitrophenyl)-4-(8-oxa-3-azabicyclo[3.2.1]oct-3-yl)-3-pyridin-3-yl-1H-pyrazolo[3,4-d]pyrimidine (100 mg) (0.22 mmol) in EtOH (1.2 mL), water (0.6 mL) was added iron powder (36 mg) and ammonium chloride (100 mg). The mixture was heated to reflux for 2 h. Then the reaction was filtered through Celite while still warm, then extracted three times with EtOAc. The organics were dried (MgSO$_4$) and filtered off through a pad of Magnesol and concentrated in vacuo. to give a yellow solid that was collected with diethyl ether to give 88 mg. MS m/z=428 (M+H)

The Following Compounds were Synthesized Using the Above Procedures (Scheme 40)

1-{4-[1-ethyl-3-(4-methylpiperazin-1-yl)-4-(8-oxa-3-azabicyclo[3.2.1]oct-3-yl)-1H-pyrazolo[3,4-d]pyrimidin-6-yl]phenyl}-3-methylurea MS m/z=506.3 (M+H)

1-{4-[1-ethyl-4-(8-oxa-3-azabicyclo[3.2.1]oct-3-yl)-3-pyridin-3-yl-1H-pyrazolo[3,4-d]pyrimidin-6-yl]phenyl}-3-methylurea MS m/z=485.2 (M+H)

1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-pyridin-3-ylurea MS m/z=540 (M+H)

1-{4-[3-bromo-1-ethyl-4-(8-oxa-3-azabicyclo[3.2.1]oct-3-yl)-1H-pyrazolo[3,4-d]pyrimidin-6-yl]phenyl}-3-methylurea MS m/z=487 (M+H)

1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-methylurea MS m/z=477.3 (M+H)

1-{4-[1-ethyl-4-(8-oxa-3-azabicyclo[3.2.1]oct-3-yl)-3-vinyl-1H-pyrazolo[3,4-d]pyrimidin-6-yl]phenyl}-3-methylurea MS m/z=477.3 (M+H)

Preparation of 1-{4-[3-(1,2-dihydroxyethyl)-1-ethyl-4-(8-oxa-3-azabicyclo[3.2.1]oct-3-yl)-1H-pyrazolo[3,4-d]pyrimidin-6-yl]phenyl}-3-methylurea (Scheme 40)

To a solution of 1-{4-[1-ethyl-4-(8-oxa-3-azabicyclo[3.2.1]oct-3-yl)-3-vinyl-1H-pyrazolo[3,4-d]pyrimidin-6-yl]phenyl}-3-methylurea (200 mg) (0.46 mmol) in tert-butanol:water (1:1) (8.0 mL) was added AD mix 0 (2.0 g) and methanesulfonamide (400 mg). The mixture was stirred overnight. To the reaction was added 10% Na$_2$SO$_3$ solution and extracted three times with EtOAc. Organics were dried (MgSO$_4$) and filtered off and then concentrated in vacuo. to give a white solid 178 mg. MS m/z=468.2 (M+H)

Preparation of 1-{4-[1-ethyl-3-formyl-4-(8-oxa-3-azabicyclo[3.2.1]oct-3-yl)-1H-pyrazolo[3,4-d]pyrimidin-6-yl]phenyl}-3-methylurea (Scheme 40)

To a solution of 1-{4-[3-(1,2-dihydroxyethyl)-1-ethyl-4-(8-oxa-3-azabicyclo[3.2.1]oct-3-yl)-1H-pyrazolo[3,4-d]pyrimidin-6-yl]phenyl}-3-methylurea (158 mg) (0.34 mmol) in DCM:THF (2:1) (6.0 mL) was added excess sodium NaIO$_4$ on silica gel and the mixture was stirred for 1 hr. at room temperature. The insoluble material was filtered off and the organics were dried (Na$_2$SO$_4$) and filtered off through Magnesol and then concentrated in vacuo. to give a white solid that was collected with diethyl ether to give 110 mg. MS m/z=436.2.2 (M+H).

Preparation of 1-(4-{1-ethyl-3-[(4-methylpiperazin-1-yl)methyl]-4-(8-oxa-3-azabicyclo[3.2.1]oct-3-yl)-1H-pyrazolo[3,4-d]pyrimidin-6-yl}phenyl)-3-Methylurea (Scheme 40)

To a solution of 1-{4-[1-ethyl-3-formyl-4-(8-oxa-3-azabicyclo[3.2.1]oct-3-yl)-1H-pyrazolo[3,4-d]pyrimidin-6-yl]phenyl}-3-methylurea (50 mg) (0.115 mmol) in DCE (2.0 mL) and excess N-methyl piperidine was added sodium triacetoxyborohydride (36 mg) (0.17 mmol) and stirred for 2 hr. at room temperature. The reaction was treated with aqueous sodium bicarbonate, the organics were separated and concentrated under nitrogen and then purified by Gilson HPLC to give 47 mg of desired product. MS m/z=520.3 (M+H)

The Following Compounds were Synthesized Using the Above Procedures (Scheme 40)

1-{4-[1-ethyl-4-(8-oxa-3-azabicyclo[3.2.1]oct-3-yl)-3-(pyrrolidin-1-ylmethyl)-1H-pyrazolo[3,4-d]pyrimidin-6-yl]phenyl}-3-methylurea MS m/z=491.3 (M+H)

The following compounds were synthesized using the above procedures (Scheme 40)

1-ethyl-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea MS m/z=547.3 (M+H)

1-(2-hydroxyethyl)-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea MS m/z=563.3 (M+H)

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-methylurea MS m/z=533.3 (M+H)

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-3-ylurea MS m/z=596.3 (M+H)

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-phenylurea MS m/z=595.3 (M+H)

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-4-ylurea MS m/z=596.3 (M+H)

1-cyclopropyl-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea MS m/z=559.3 (M+H)

4-[1-(1-isobutyrylpiperidin-4-yl)-4-(8-oxa-3-azabicyclo[3.2.1]oct-3-yl)-1H-pyrazolo[3,4-d]pyrimidin-6-yl]aniline MS m/z=476.3 (M+H)

1-(2-fluoroethyl)-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea MS m/z=565.3 (M+H)

The Following Compounds were Synthesized Using the Above Procedures (Scheme 41)

methyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate methanol was used in place of methylamine. MS m/z=521 (M+H).

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-3-ylurea 3-aminopyridine was used in place of methylamine. MS m/z=583 (M+H).

The Following Compound was Prepared Using the Above Procedures (Scheme s 1)

6-(1H-indol-5-yl)-4-(8-oxa-3-azabicyclo[3.2.1]oct-3-yl)-1-[1-(pyridin-3-ylmethyl)piperidin-4-yl]-1H-pyrazolo[3,4-d]pyrimidine MS m/z=521 (M+H).

The Following Compound was Prepared Using the Above Procedures (Scheme 31)

1-{4-[1-(1,3-dioxan-5-yl)-4-(8-oxa-3-azabicyclo[3.2.1]oct-3-yl)-1H-pyrazolo[3,4-d]pyrimidin-6-yl]phenyl}-3-methylurea MS m/z=466 (M+H).

Preparation of 3-(1-(1-benzylpiperidin-4-yl)-6-chloro-1H-pyrazolo[3,4-d]pyrimidin-4-yl)-8-oxa-3-azabicyclo[3.2.1]octane (Scheme 28)

A solution of 2,4,6-trichloropyrimidine-5-carbaldehyde (26.82 mmol) in CH$_2$Cl$_2$ (225 mL) is cooled to −78° C. To this is added a suspension of 1-benzyl-4-hydrazinylpiperidine hydrochloride (26.82 mmol) in Et$_3$N (160.9 mmol), CH$_2$Cl$_2$ (25 mL), and ethanol (15 mL). The solution is allowed to stir at this temperature for 5 minutes, then warmed to room temperature and stirred for an additional 30 minutes, then concentrated in vacuo at 30° C. This dichloride intermediate is dissolved in ethanol (225 mL) and a solution of 8-oxa-3-azabicyclo[3.2.1]octane hydrochloride (24.14 mmol) in Et$_3$N (160.9 mmol) and ethanol (20 mL) is added. The mixture is stirred at room temperature for 1 hour, concentrated, and purified by column chromatography (0-4% methanol in CH$_2$Cl$_2$) provides 3-(1-(1-benzylpiperidin-4-yl)-6-chloro-1H-pyrazolo[3,4-d]pyrimidin-4-yl)-8-oxa-3-azabicyclo[3.2.1]octane. (66%, MS=439.3 (M+H))

Preparation of ethyl 4-(4-(8-oxa-3-azabicyclo[3.2.1]octan-3-yl)-6-chloro-1H-pyrazolo[3,4-d]pyrimidin-1-yl)piperidine-1-carboxylate (Scheme 30)

A solution of 3-(1-(1-benzylpiperidin-4-yl)-6-chloro-1H-pyrazolo[3,4-d]pyrimidin-4-yl)-8-oxa-3-azabicyclo[3.2.1]octane (5.70 mmol) in dichloroethane (50 mL) is prepared and α-chloroethylchloroformate (17.09 mmol) and K$_2$CO$_3$ (17.09 mmol) is added. The mixture is heated to 95° C. for 14 hours, filtered, and the filtrate is concentrated. Methanol (50 mL) is added and the solution is heated to 75° C. for 1.5 hours, then concentrated. The crude amine hydrochloride (1.43 mmol) is dissolved in CH$_2$Cl$_2$ (15 mL) and Et$_3$N (5.72 mmol). Ethyl chloroformate (1.86 mmol) is added and the reaction is stirred at room temperature for 2 hours, diluted with CH$_2$Cl$_2$, washed with saturated aqueous sodium bicarbonate, brine, dried over sodium sulfate, and concentrated in vacuo. Purification by column chromatography (20-100% ethyl acetate in hexanes) provides ethyl 4-(4-(8-oxa-3-azabicyclo[3.2.1]octan-3-yl)-6-chloro-1H-pyrazolo[3,4-d]pyrimidin-1-yl)piperidine-1-carboxylate (61% for second step). (HRMS=421.1749 (M+H, obs.), 421.1749 (M+H, calc.))

Preparation of ethyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (Scheme 30)

A solution of ethyl 4-(4-(8-oxa-3-azabicyclo[3.2.1]octan-3-yl)-6-chloro-1H-pyrazolo[3,4-d]pyrimidin-1-yl)piperidine-1-carboxylate (0.785 mmol) in toluene (4 mL) and ethanol (4 mL) is prepared in a microwave vial and purged with nitrogen for 5 minutes. 4-aminophenyl boronic acid pinacol ester (1.02 mmol) and tetrakistriphenylphosphine palladium (0) (0.079 mmol) is added. The vial is sealed and heated to 120° C. via microwave irradiation for 1 hour. The mixture is cooled, diluted with CH$_2$Cl$_2$, washed with brine, dried, and concentrated in vacuo. Purification by column chromatography (0-3.5% methanol in CH$_2$Cl$_2$) provides ethyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (70%). (HRMS=478.2561 (M+H, obs.), 478.2561 (M+H, calc.))

Preparation of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate (Scheme 30)

A solution of triphosgene (0.534 mmol) in CH$_2$Cl$_2$ (13 mL) is prepared. To this is added a solution of ethyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (1.07 mmol) in CH$_2$Cl$_2$ (13 mL) and Et$_3$N (3.21 mmol) and the reaction is stirred at room temperature for 30 minutes. A portion of the resulting solution (1.5 mL) is then transferred to a vial containing ethylamine (2N in THF, 10.7 mmol) and CH$_2$Cl$_2$ (0.5 mL). The mixture is allowed to stir at room temperature for 14 hours, then concentrated. Purification by HPLC (5-100% acetonitrile in water) provides ethyl 4-(4-(8-oxa-3-azabicyclo[3.2.1]octan-3-yl)-6-(4-(3-ethylureido) phenyl)-1H-pyrazolo[3,4-d]pyrimidin-1-yl)piperidine-1-carboxylate (57%). (MS=549.3 (M+H)

Preparation of ethyl 4-(4-(8-oxa-3-azabicyclo[3.2.1] octan-3-yl)-6-(4-(3-(2-fluoroethyl)ureido)phenyl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting fluoroethylamine hydrochloride (10.7 mmol in 0.820 mL 1N NaOH) for ethylamine. (41%, MS=567.3 (M+H))

Preparation of ethyl 4-(4-(8-oxa-3-azabicyclo[3.2.1] octan-3-yl)-6-(4-(3-phenylureido)phenyl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting aniline (10.7 mmol) for ethylamine. (64%, MS=597.3 (M+H))

Preparation of ethyl 4-(4-(8-oxa-3-azabicyclo[3.2.1] octan-3-yl)-6-(4-(3-pyridin-3-ylureido)phenyl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting 3-aminopyridine (10.7 mmol) for ethylamine. (57%, MS=598.3 (M+H))

Preparation of ethyl 4-(4-(8-oxa-3-azabicyclo[3.2.1] octan-3-yl)-6-(4-(3-pyridin-4-ylureido)phenyl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting 4-aminopyridine (10.7 mmol) for ethylamine. (60%, MS=598.3 (M+H))

Preparation of ethyl 4-(4-(8-oxa-3-azabicyclo[3.2.1] octan-3-yl)-6-(4-(3-(1-methylpiperidin-4-yl)ureido) phenyl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting 4-amino-1-methylpiperidine (10.7 mmol) for ethylamine. (63%, MS=618.3 (M+H))

Preparation of tert-butyl 4-(3-(4-(4-(8-oxa-3-azabicyclo[3.2.1]octan-3-yl)-1-(1-(ethoxycarbonyl)piperidin-4-yl)-1H-pyrazolo[3,4-d]pyrimidin-6-yl)phenyl) ureido)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting 4-amino-1-Boc-piperidine (10.7 mmol) for ethylamine. (Quantitative yield, MS=704.4 (M+H))

Preparation of ethyl 4-(4-(8-oxa-3-azabicyclo[3.2.1] octan-3-yl)-6-(4-(3-piperidin-4-ylureido)phenyl)-1H-pyrazolo[3,4-d]pyrimidin-1-yl)piperidine-1-carboxylate (Scheme 30)

A solution of tert-butyl 4-(3-(4-(4-(8-oxa-3-azabicyclo [3.2.1]octan-3-yl)-1-(1-(ethoxycarbonyl)piperidin-4-yl)-1H-pyrazolo[3,4-d]pyrimidin-6-yl)phenyl)ureido)piperidine-1-carboxylate (0.054 mmol) in $CH_2Cl_2$ (1 mL) and trifluoroacetic acid (0.2 mL) is stirred at room temperature for 2 hours, diluted with saturated sodium bicarbonate, extracted with $CH_2Cl_2$, washed with brine, dried and concentrated. Purification by HPLC provides ethyl 4-(4-(8-oxa-3-azabicyclo[3.2.1]octan-3-yl)-6-(4-(3-piperidin-4-ylureido)phenyl)-1H-pyrazolo[3,4-d]pyrimidin-1-yl)piperidine-1-carboxylate (88%). (HRMS=604.3356 (M+H, obs.), 604.3354 (M+H, calc.))

Preparation of ethyl 4-(4-(8-oxa-3-azabicyclo[3.2.1] octan-3-yl)-6-(4-(3-(3-(methylamino)propyl)ureido) phenyl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting N-methyl-1,3-propanediamine (10.7 mmol) for ethylamine. (37%, MS=592.3 (M+H))

Preparation of ethyl 4-(6-(4-(3-1H-pyrazol-5-ylureido)phenyl)-4-(8-oxa-3-azabicyclo[3.2.1]octan-3-yl)-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, substituting 3-aminopyrazole (10.7 mmol) for ethylamine. (32%, MS=587.3 (M+H))

Preparation of methyl 4-(4-(8-oxa-3-azabicyclo [3.2.1]octan-3-yl)-6-chloro-1H-pyrazolo[3,4-d]pyrimidin-1-yl)piperidine-1-carboxylate (Scheme 30)

A procedure similar to that used for the synthesis of ethyl 4-(4-(8-oxa-3-azabicyclo[3.2.1]octan-3-yl)-6-chloro-1H-pyrazolo[3,4-d]pyrimidin-1-yl)piperidine-1-carboxylate is used, substituting methyl chloroformate for ethyl chloroformate (Quantitative yield for carbamate formation). (HRMS=407.1595 (M+H, obs.), 407.1593 (M+H, calc.)

Preparation of methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (Scheme 30)

A Suzuki coupling procedure similar to that used for the synthesis of ethyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate is used, using methyl 4-(4-(8-oxa-3-azabicyclo[3.2.1]octan-3-yl)-6-chloro-1H-pyrazolo[3,4-d]

pyrimidin-1-yl)piperidine-1-carboxylate as the chloride component (68%, MS=464.2 (M+H))

Preparation of methyl 4-(4-(8-oxa-3-azabicyclo[3.2.1]octan-3-yl)-6-(4-(3-(4-(hydroxymethyl)phenyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminobenzyl alcohol as the aniline component. (15%, MS=613.3 (M+H))

Preparation of methyl 4-(4-(8-oxa-3-azabicyclo[3.2.1]octan-3-yl)-6-(4-(3-(4-(2-hydroxyethyl)phenyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminophenethyl alcohol as the aniline component. (43%, MS=627.3 (M+H))

Preparation of methyl 4-(4-(8-oxa-3-azabicyclo[3.2.1]octan-3-yl)-6-(4-(3-(4-(4-methylpiperazin-1-yl)phenyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(4-methylpiperazino)aniline as the aniline component. (7%, MS=681.4 (M+H))

Preparation of methyl 4-(4-(8-oxa-3-azabicyclo[3.2.1]octan-3-yl)-6-(4-(3-(6-(4-methylpiperazin-1-yl)pyridin-3-yl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(4-methylpiperazino)-3-pyridinamine as the aniline component. (15%, MS=682.4 (M+H))

Preparation of methyl 4-(6-(4-(3-(2-aminoethyl)ureido)phenyl)-4-(8-oxa-3-azabicyclo[3.2.1]octan-3-yl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing ethylenediamine as the aniline component. (31%, MS=550.3 (M+H))

Preparation of methyl 4-(4-(8-oxa-3-azabicyclo[3.2.1]octan-3-yl)-6-(4-(3-(2-(dimethylamino)ethyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing N,N-dimethylethylenediamine as the aniline component. (23%, MS=578.3 (M+H))

Preparation of methyl 4-(4-(8-oxa-3-azabicyclo[3.2.1]octan-3-yl)-6-(4-(3-(2-(4-methylpiperazin-1-yl)ethyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 2-(4-methylpiperazin-1-yl)-ethanamine as the aniline component. (17%, MS=633.4 (M+H))

Preparation of methyl 4-(4-(8-oxa-3-azabicyclo[3.2.1]octan-3-yl)-6-(4-(3-(3-(hydroxymethyl)phenyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 3-aminobenzylalcohol as the aniline component. (12%, MS=613.3 (M+H))

Preparation of methyl 4-(4-(8-oxa-3-azabicyclo[3.2.1]octan-3-yl)-6-(4-(3-(2-(hydroxymethyl)phenyl)ureido)phenyl)-1H-pyrazolo[3,4-d]pyrimidin-1-yl)piperidine-1-carboxylate (Scheme 30)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 2-aminobenzylalcohol as the aniline component. (12%, MS=613.3 (M+H))

Preparation of 3-(6-chloro-1-ethyl-1H-pyrazolo[3,4-d]pyrimidin-4-yl)-8-oxa-3-azabicyclo[3.2.1]octane (Scheme 2)

Preparation of 4-(4-(8-oxa-3-azabicyclo[3.2.1]octan-3-yl)-1-ethyl-1H-pyrazolo[3,4-d]pyrimidin-6-yl)aniline (Scheme 2)

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-(hydroxymethyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminobenzylalcohol as the aniline component. (84%, MS=500.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-(hydroxymethyl)phenyl)urea (Scheme 2)

A urea formation procedure similar to that used for the synthesis of ethyl 4-(4-(8-oxa-3-azabicyclo[3.2.1]octan-3- yl)-6-(4-(3-ethylureido)phenyl)-1H-pyrazolo[3,4-d]pyrimidin-1-yl)piperidine-1-carboxylate is used, utilizing 4-aminophenethylalcohol as the aniline component. (89%, MS=514.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-morpholinopyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 3-amino-6-morpholinopyridine as the aniline component. (29%, MS=556.3 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-(4-methylpiperazin-1-yl)pyridin-3-yl)urea Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(4-methylpiperazino)-3-pyridinamine as the aniline component. (37%, MS=569.3 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-(2-(dimethylamino)ethoxy)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(2-(dimethylamino)ethoxy)aniline as the aniline component. (23%, MS=557.3 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-methoxyphenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing p-anisidine as the aniline component. (20%, MS=500.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-chlorophenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-chloroaniline as the aniline component. (22%, MS=504.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-p-tolylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing p-toluidine as the aniline component. (18%, MS=484.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-cyanophenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-cyanoaniline as the aniline component. (9%, MS=495.2 (M+H))

Preparation of 2-hydroxypropyl 4-(4-(8-oxa-3-azabicyclo[3.2.1]octan-3-yl)-1-ethyl-1H-pyrazolo[3,4-d]pyrimidin-6-yl)phenylcarbamate (Scheme 2)

A carbamate formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 1,2-propanediol as the alcohol component. (24%, MS=453.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-(pyrrolidin-1-yl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(1-pyrrolidinyl)-aniline as the aniline component. (41%, MS=539.3 (M+H))A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 2-(4-aminophenoxy)ethanol (prepared by the reduction of 2-(4-nitrophenoxy)ethanol in ethyl acetate and methanol with palladium on carbon and hydrogen gas) as the aniline component. (2%, MS=530.4 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-(2-hydroxyethoxy)pyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 2-(5-aminopyridin-2-yloxy)ethanol (prepared by the reduction of 2-(5-nitropyridin-2-yloxy)ethanol in ethyl acetate and methanol with palladium on carbon and hydrogen gas) as the aniline component. (5%, MS=531.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-(2-morpholinoethoxy)pyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(2-morpholinoethoxy)pyridin-3-amine as the aniline component. (37%, MS=600.3 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-(dimethylamino)pyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(2-morpholinoethoxy)pyridin-3-amine N2,N2-dimethylpyridine-2,5-diamine as the aniline component. (5%, MS=514.3 (M+H))

Preparation of 4-(3-(4-(4-(8-oxa-3-azabicyclo[3.2.1]octan-3-yl)-1-ethyl-1H-pyrazolo[3,4-d]pyrimidin-6-yl)phenyl)ureido)benzamide (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing p-amino benzamide as the aniline component. (9%, MS=513.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-(methylamino)pyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing t-butyl 5-aminopyridin-2-yl(methyl)carbamate as the aniline component. Treatment with trifluoroacetic acid and $CH_2Cl_2$ provides the desired compound. (34%, MS=500.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(6-aminopyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing t-butyl 5-aminopyridin-2-ylcarbamate as the aniline component. Treatment with trifluoroacetic acid and $CH_2Cl_2$ provides the desired compound. (19%, MS=486.2 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-(piperazin-1-yl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing t-butyl 4-(4-aminophenyl)piperazine-1-carboxylate as the aniline component. Treatment with trifluoroacetic acid and $CH_2Cl_2$ provides the desired compound. (34%, MS=554.3 (M+H))

Preparation of 1-(4-(4-(8-oxa-3-azabicyclo[3.2.1]octan-3-yl)-1-ethyl-1H-pyrazolo[3,4-d]pyrimidin-6-yl)phenyl)-3-(4-(2,2-dimethylhydrazinecarbonyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-amino-N',N'-dimethylbenzohydrazide as the aniline component. (37%, MS=556.3 (M+H))

Preparation of 4-(3-(4-(4-(8-oxa-3-azabicyclo[3.2.1]octan-3-yl)-1-ethyl-1H-pyrazolo[3,4-d]pyrimidin-6-yl)phenyl)ureido)-N-(pyrrolidin-1-yl)benzamide (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-amino-N-(pyrrolidin-1-yl)benzamide as the aniline component. (8%, MS=582.3 (M+H))

Preparation of 3-(6-chloro-1-ethyl-1H-pyrazolo[3,4-d]pyrimidin-4-yl)-8-oxa-3-azabicyclo[3.2.1]octane (Scheme 2)

Preparation of 4-(4-(8-oxa-3-azabicyclo[3.2.1]octan-3-yl)-1-methyl-1H-pyrazolo[3,4-d]pyrimidin-6-yl)aniline (Scheme 2)

Preparation of 1-(4-(4-(8-oxa-3-azabicyclo[3.2.1]octan-3-yl)-1-methyl-1H-pyrazolo[3,4-d]pyrimidin-6-yl)phenyl)-3-(4-(hydroxymethyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminobenzyl alcohol as the aniline component. (32%, MS=486.2 (M+H))

Preparation of 1-(4-(4-(8-oxa-3-azabicyclo[3.2.1]octan-3-yl)-1-methyl-1H-pyrazolo[3,4-d]pyrimidin-6-yl)phenyl)-3-(4-(2-hydroxyethyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminophenethyl alcohol as the aniline component. (41%, MS=500.2 (M+H))

Preparation of 1-(4-(4-(8-oxa-3-azabicyclo[3.2.1]octan-3-yl)-1-methyl-1H-pyrazolo[3,4-d]pyrimidin-6-yl)phenyl)-3-(4-(dimethylamino)phenyl)urea A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing N,N-dimethyl-1,4-phenylenediamine as the aniline component. (24%, MS=499.2 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(4-aminophenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 1,4-phenylenediamine as the aniline component. (25%, MS=471.2 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(6-(4-methylpiperazin-1-yl)pyridin-3-
yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(4-methylpiperazino)-3-pyridinamine as the aniline component. (16%, MS=555.3 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(4-(4-methylpiperazin-1-yl)phenyl)
urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(4-methylpiperazino)aniline as the aniline component. (13%, MS=554.3 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(6-morpholinopyridin-3-yl)urea
(Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 3-amino-6-morpholinopyridine as the aniline component. (26%, MS=542.3 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(4-morpholinophenyl)urea (Scheme
2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-morpholinoaniline as the aniline component. (13%, MS=541.3 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(4-(methylsulfonyl)phenyl)urea
(Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(methylsulfonyl)aniline as the aniline component. (15%, MS=534.2 (M+H))

Preparation of 1-(4-(4-(8-oxa-3-azabicyclo[3.2.1]
octan-3-yl)-1-methyl-1H-pyrazolo[3,4-d]pyrimidin-
6-yl)phenyl)-3-(4-(2-(piperidin-1-yl)ethylsulfonyl)
phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(2-(piperidin-1-yl)ethylsulfonyl)aniline (which may be prepared via: Tetrahedron Letters, 48 (51), 9040-9043, 2007) as the aniline component. (6%, MS=631.3 (M+H))

Preparation of 4-(4-(8-oxa-3-azabicyclo[3.2.1]octan-
3-yl)-1-(2,2,2-trifluoroethyl)-1H-pyrazolo[3,4-d]
pyrimidin-6-yl)aniline (Scheme 42)

Preparation of 1-(4-(4-(8-oxa-3-azabicyclo[3.2.1]
octan-3-yl)-1-(2,2,2-trifluoroethyl)-1H-pyrazolo[3,4-
d]pyrimidin-6-yl)phenyl)-3-(4-(2-hydroxyethyl)phe-
nyl)urea (Scheme 42)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminophenethyl alcohol as the aniline component. (29%, MS=568.2 (M+H))

Preparation of 1-(4-(4-(8-oxa-3-azabicyclo[3.2.1]
octan-3-yl)-1-(2,2,2-trifluoroethyl)-1H-pyrazolo[3,4-
d]pyrimidin-6-yl)phenyl)-3-(4-(4-methylpiperazin-1-
yl)phenyl)urea (Scheme 42)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(4-methylpiperazino)aniline as the aniline component. (33%, MS=622.3 (M+H))

Preparation of 1-(4-(4-(8-oxa-3-azabicyclo[3.2.1]
octan-3-yl)-1-(2,2,2-trifluoroethyl)-1H-pyrazolo[3,4-
d]pyrimidin-6-yl)phenyl)-3-(6-(4-methylpiperazin-1-
yl)pyridin-3-yl)urea (Scheme 42)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(4-methylpiperazino)-3-pyridinamine as the aniline component. (39%, MS=623.3 (M+H))

Preparation of 1-(4-(4-(8-oxa-3-azabicyclo[3.2.1]
octan-3-yl)-1-(2,2,2-trifluoroethyl)-1H-pyrazolo[3,4-
d]pyrimidin-6-yl)phenyl)-3-(4-(2-hydroxyethoxy)
phenyl)urea (Scheme 42)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 2-(4-aminophenoxy)ethanol (prepared by the reduction of 2-(4- nitrophenoxy)ethanol in ethyl acetate and methanol with palladium on carbon and hydrogen gas) as the aniline component. (7%, MS=584.2 (M+H))

Preparation of 8-(6-chloro-1-ethyl-1H-pyrazolo[3,4-d]pyrimidin-4-yl)-3-oxa-8-azabicyclo[3.2.1]octane (Scheme 2)

A procedure similar to that used for the synthesis of 3-(1-(1-benzylpiperidin-4-yl)-6-chloro-1H-pyrazolo[3,4-d]pyrimidin-4-yl)-8-oxa-3-azabicyclo[3.2.1]octane is used, using ethyl hydrazine as the hydrazine component and substituting 3-oxa-8-azabicyclo[3.2.1]octane for 8-oxa-3-azabicyclo[3.2.1]octane. (65%, MS=294.3 (M+H))

Preparation of 4-(4-(3-oxa-8-azabicyclo[3.2.1]octan-8-yl)-1-ethyl-1H-pyrazolo[3,4-d]pyrimidin-6-yl)aniline (Scheme 2)

A Suzuki coupling procedure similar to that used for the synthesis of ethyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate is used. (63%, MS=351.3 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-((4-methylpiperazin-1-yl)methyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-((4-methylpiperazin-1-yl)methyl)aniline as the aniline component. (30%, MS=582.3 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-(aminomethyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing tert-butyl 4-aminobenzylcarbamate as the aniline component. Treatment with trifluoroacetic acid and $CH_2Cl_2$ provides the desired compound. (60%, MS=499.2 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-(2-(pyrrolidin-1-yl)ethoxy)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(2-(pyrrolidin-1-yl)ethoxy)aniline as the aniline component. (50%, MS=583.5 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-((dimethylamino)methyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-((dimethylamino)methyl)aniline as the aniline component. (23%, MS=527.2 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-(pyrrolidin-1-ylmethyl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(pyrrolidin-1-ylmethyl)aniline as the aniline component. (52%, MS=553.5 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-(2-(dimethylamino)ethylamino)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing tert-butyl 4-aminophenyl(2-(dimethylamino)ethyl)carbamate as the aniline component. Treatment with trifluoroacetic acid and $CH_2Cl_2$ provides the desired compound. (39%, MS=556.3 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-((2-(dimethylamino)ethyl)(methyl)amino)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing N1-(2-(dimethylamino)ethyl)-N1-methylbenzene-1,4-diamine as the aniline component. (40%, MS=570.5 (M+H))

Preparation of 2-hydroxyethyl 4-(4-(3-oxa-8-azabicyclo[3.2.1]octan-8-yl)-1-ethyl-1H-pyrazolo[3,4-d]pyrimidin-6-yl)phenylcarbamate (Scheme 2)

A carbamate formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing ethylene glycol as the alcohol component. (53%, MS=439.3 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-methylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing methylamine (2M in THF) as the aniline component. (51%, MS=408.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-ethylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing ethylamine (2M in THF) as the aniline component. (46%, MS=422.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-cyclopropylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing cyclopropylamine as the aniline component. (47%, MS=434.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-cyclobutylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing cyclobutylamine as the aniline component. (44%, MS=448.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-cyclopentylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing cyclopentylamine as the aniline component. (46%, MS=462.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-phenylurea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing aniline as the aniline component. (51%, MS=470.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(pyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 3-aminopyridine as the aniline component. (49%, MS=471.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(pyridin-4-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-aminopyridine as the aniline component. (15%, MS=471.4 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-(4-methylpiperazin-1-yl)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(4-methylpiperazin-1-yl)aniline as the aniline component. (53%, MS=568.5 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(6-(4-methylpiperazin-1-yl)pyridin-3-yl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 6-(4-methylpiperazin-1-yl)pyridin-3-amine as the aniline component. (56%, MS=569.5 (M+H))

Preparation of 1-(4-(4-(3-oxa-8-azabicyclo[3.2.1]octan-8-yl)-1-ethyl-1H-pyrazolo[3,4-d]pyrimidin-6-yl)phenyl)-3-(4-(2-(dimethylamino)ethoxy)phenyl)urea (Scheme 2)

A urea formation procedure similar to that used for the synthesis of ethyl 4-(4-(8-oxa-3-azabicyclo[3.2.1]octan-3-yl)-6-(4-(3-ethylureido)phenyl)-1H-pyrazolo[3,4-d]pyrimidin-1-yl)piperidine-1-carboxylate is used, utilizing 4-(2-(dimethylamino)ethoxy)aniline as the aniline component. (34%, MS=557.5 (M+H))

Thieno[3,2-d]pyrimidine-2,4-diol (Scheme 44)

50 mg (0.35 mmol) 3-amino-thiophene-2-carboxamide is dissolved in 3 mL dioxane. 52 mg (0.175 mmol, 0.5 eq) triphosgene is added and the mixture is heated at 80 C. After 30 min, TLC and LCMS indicate that the reaction is complete. The mixture is cooled down to RT and the resulting white precipitate is collected and washed with diethyl ether. Yield: 46 mg (0.27 mmol, 78%).

Thieno[3,2-d]pyrimidine-2,4-diol (Scheme 44): (Alternative Synthesis)

50 mg (0.35 mmol) 3-amino-2-aminocarbonyl-thiophene is covered with urea. The urea is heated until molten. After 5 minutes of heating, the molten mixture is poured into 1 N NaOH (2 mL). Acetic acid is added to neutralize the mixture (pH 7) and the resulting white precipitate is collected. Yield: 39 mg (0.23 mmol, 66%).

Thieno[3,2-d]pyrimidine-2,4-diol (Scheme 44): (Large Scale Synthesis)

500 mg (3.5 mmol) 3-amino-thiophene-2-carboxamide is dissolved in 30 mL dioxane. 520 mg (1.75 mmol, 0.5 eq) triphosgene is added and the mixture is heated at 80 C for 1 h.

The mixture is concentrated and triturated from hot methanol. The resulting solids are collected. The filtrate is concentrated and triturated again from hot methanol. The 2 crops of solids are combined to give 432 mg of the title compound (2.57 mmol, 73%).

2,4-Dichlorothieno[3,2-d]pyrimidine (Scheme 44)

85 mg thieno[3,2-d]pyrimidine-2,4-diol (0.5 mmol) is suspended in 1.25 mL POCl3. The mixture is heated at 100 C overnight. POCl3 is removed under reduced pressure. The mixture is dissolved in dichloromethane and quenched with ice. The product is collected by extraction with dichloromethane (2×). The combined organic layers are dried over MGSO4 and concentrated to give 2,4-dichloro-thieno[3,2-d]pyrimidine in quantitative yield, which was used in the next step without further purification.

432 mg thieno[3,2-d]pyrimidine-2,4-diol (2.57 mmol) is suspended in 6.25 mL POCl3. The mixture is heated at 100 C overnight. POCl3 is removed under reduced pressure, toluene added, and the distillation repeated. The mixture is dissolved in dichloromethane and quenched with ice. The product is collected by extraction with dichloromethane (2×). The combined organic layers are dried over MGSO4 and concentrated to give 2,4-dichloro-thieno[3,2-d]pyrimidine in quantitative yield, which was used in the next step without further purification.

2-Chloro-4-(8-oxa-3-aza-bicyclo[3.2.1]oct-3-yl)-thieno[3,2-d]pyrimidine (Scheme 44)

432 mg (2.57 mmol) of thieno[3,2-d]pyrimidine-2,4-diol was chlorinated as above (heat 100° C. overnight in 6.25 mL POCl$_3$) to give 2,4-dichloro-thieno[3,2-d]pyrimidine after the usual workup (removal of toluene, quenching with ice and extraction with dichloromethane followed by drying over MgSO$_4$ and concentration). Thus obtained 2,4-dichloro-thieno[3,2-d]pyrimidine was reacted without any further purification. 2,4-Dichloro-thieno[3,2-d]pyrimidine was dissolved in 25 mL ethanol and 5 mL dichloromethane and 8-oxa-3-aza-bicyclo[3.2.1]octane hydrochloride (384 mg, 2.57 mmol) and 2.1 mL triethylamine (15 mmol, 6 equivalents) were added. After stirring at room temperature for 45 minutes, the mixture was concentrated, dissolved in dichloromethane and washed with sat. NH$_4$Cl, water and sat. NaHCO$_3$. The organic phase was dried over MgSO$_4$ and concentrated to give 626 mg (2.22 mmol, 86% over 2 steps) of the title compound.

General procedure for Suzuki reaction of 2-chloro-4-(8-oxa-3-aza-bicyclo[3.2.1]oct-3-yl)-thieno[3,2-d]pyrimidine (Scheme 44)

30 mg (0.11 mmol) of 2-chloro-4-(8-oxa-3-aza-bicyclo[3.2.1]oct-3-yl)-thieno[3,2-d]pyrimidine and 0.2 mmol of the aryl boronic acid/boronic acid pinacol ester was dissolved in 1 mL toluene and 0.6 mL ethanol. 0.24 mL of a 2M solution of Na$_2$CO$_3$ was added and nitrogen was bubbled through the mixture for 5 min to degas. 14 mg (10 mol %) Pd(PPh$_3$)$_4$ was added and the mixture was heated under microwave irradiation for 60 min at 120 C. The solvents were removed under a stream of nitrogen, the residue was dissolved in 2 mL DMSO, filtered and purified by HPLC (TFA buffers).
The Following Compounds were all Prepared According to the General Procedure for the Suzuki Reaction:
4-[4-(8-oxa-3-azabicyclo[3.2.1]oct-3-yl)thieno[3,2-d]pyrimidin-2-yl]aniline: MS: 339.1 [M+H], RT 1.67

N-{4-[4-(8-oxa-3-azabicyclo[3.2.1]oct-3-yl)thieno[3,2-d]pyrimidin-2-yl]phenyl}acetamide: MS: 381.1 [M+H], RT 1.72
methyl{4-[4-(8-oxa-3-azabicyclo[3.2.1]oct-3-yl)thieno[3,2-d]pyrimidin-2-yl]phenyl}carbamate: MS: 397.1 [M+H], RT 1.80
3-[4-(8-oxa-3-azabicyclo[3.2.1]oct-3-yl)thieno[3,2-d]pyrimidin-2-yl]phenol: MS: 340.1 [M+H], RT 1.69
4-[4-(8-oxa-3-azabicyclo[3.2.1]oct-3-yl)thieno[3,2-d]pyrimidin-2-yl]phenol: MS: 340.1 [M+H], RT 1.65
2-(1H-indol-5-yl)-4-(8-oxa-3-azabicyclo[3.2.1]oct-3-yl)thieno[3,2-d]pyrimidine: MS: 363.1 [M+H], RT 1.81
5-[4-(8-oxa-3-azabicyclo[3.2.1]oct-3-yl)thieno[3,2-d]pyrimidin-2-yl]pyridin-2-amine: MS: 340.1 [M+H], RT 1.63
5-[4-(8-oxa-3-azabicyclo[3.2.1]oct-3-yl)thieno[3,2-d]pyrimidin-2-yl]pyrimidin-2-amine: MS: 341.1 [M+H], RT 1.72

General Procedure for Formation of Urea Compounds from 2-chloro-4-(8-oxa-3-aza-bicyclo[3.2.1] oct-3-yl)-thieno[3,2-d]pyrimidine (Scheme 44)

30 mg (0.11 mmol) of chloride 2-Chloro-4-(8-oxa-3-azabicyclo[3.2.1]oct-3-yl)-thieno[3,2-d]pyrimidine was reacted with 4-aminophenylboronic acid, pinacol ester as above. Upon completion of the Suzuki reaction, the mixture was diluted with EtOAc and filtered over Celite™. The mixture was washed 2× with brine and the organic phase was dried over MgSO$_4$ and concentrated. The resulting product was dissolved in 1 mL dichloromethane and 0.065 mL NEt$_3$ was added. The resulting solution was added in drops to a solution of triphosgene (18 mg, 0.06 mmol, 0.5 eq) in 1 mL dichloromethane. After stirring at room temperature for 20 minutes, the mixture was added to a solution of 1 mmol of amine in dichloromethane (for cyclopropylamine, 2-aminoethanol, aniline, 2-aminopyridine and 3-aminopyridine) or to a solution of 2 mmol of amine in THF (for methyl amine or ethyl amine) or to a solution of 1 mmol of the amine (HCl salt) in 1 mL 1 N NaOH (for 2-fluoroethylamine.HCl). The mixture was stirred overnight at room temperature and concentrated. The residue was dissolved in 2 mL DMSO, filtered and purified by HPLC (TFA buffers).
The Following Compounds were all Prepared According to the General Procedure for the Formation of Urea Compounds:
1-methyl-3-{4-[4-(8-oxa-3-azabicyclo[3.2.1]oct-3-yl)thieno[3,2-d]pyrimidin-2-yl]phenyl}urea: MS: 396.1 [M+H], RT 1.69
1-ethyl-3-{4-[4-(8-oxa-3-azabicyclo[3.2.1]oct-3-yl)thieno[3,2-d]pyrimidin-2-yl]phenyl}urea: MS: 410.2 [M+H], RT 1.75
1-(2-fluoroethyl)-3-{4-[4-(8-oxa-3-azabicyclo[3.2.1]oct-3-yl)thieno[3,2-d]pyrimidin-2-yl]phenyl}urea: MS: 428.1 [M+H], RT 1.73
1-(2-hydroxyethyl)-3-{4-[4-(8-oxa-3-azabicyclo[3.2.1]oct-3-yl)thieno[3,2-d]pyrimidin-2-yl]phenyl}urea: MS: 426.2 [M+H], RT 1.64
1-cyclopropyl-3-{4-[4-(8-oxa-3-azabicyclo[3.2.1]oct-3-yl)thieno[3,2-d]pyrimidin-2-yl]phenyl}urea: MS: 422.2 [M+H], RT 1.76
1-{4-[4-(8-oxa-3-azabicyclo[3.2.1]oct-3-yl)thieno[3,2-d]pyrimidin-2-yl]phenyl}-3-phenylurea: MS: 458.2 [M+H], RT 1.99
1-{4-[4-(8-oxa-3-azabicyclo[3.2.1]oct-3-yl)thieno[3,2-d]pyrimidin-2-yl]phenyl}-3-pyridin-3-ylurea: MS: 459.2 [M+H], RT 1.64

1-{4-[4-(8-oxa-3-azabicyclo[3.2.1]oct-3-yl)thieno[3,2-d]pyrimidin-2-yl]phenyl}-3-pyridin-4-ylurea: MS: 459.2 [M+H], RT 1.61

4-[4-(8-Oxa-3-aza-bicyclo[3.2.1]oct-3-yl)-thieno[3,2-d]pyrimidin-2-ylamino]-phenol (Scheme 44)

30 mg (0.11 mmol) of 2-Chloro-4-(8-oxa-3-aza-bicyclo[3.2.1]oct-3-yl)-thieno[3,2-d]pyrimidine was dissolved in 1 mL ethylene glycol. 0.5 mmol (54 mg) 4-aminophenol was added and the mixture was heated under microwave irradiation to 220 C (2×30 min). The mixture was diluted with 1 mL DMSO and purified by HPLC (TFA buffers) to give 25 mg (0.07 mmol, 66%) of the title compound.

isopropyl 4-(4-(8-oxa-3-azabicyclo[3.2.1]octan-3-yl)-6-chloro-1H-pyrazolo[3,4-d]pyrimidin-1-yl)piperidine-1-carboxylate: (Scheme 30)

650 mg (1.7 mmol) of 3-(6-chloro-1-(piperidin-4-yl)-1H-pyrazolo[3,4-d]pyrimidin-4-yl)-8-oxa-3-azabicyclo[3.2.1]octane was suspended in 15 mL dichloromethane and triethylamine (0.5 mL) was added followed by addition of a 1N solution of isopropyl chloroformate in toluene. The mixture was stirred at room temperature overnight, diluted with dichloromethane and washed with sat. aqueous NaHCO3. The organic phase was dried over MgSO4, filtered and concentrated to give 696 mg (1.6 mmol) of the title compound. MS: 435.3/437.3 [M+H].

Isopropyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (Scheme 30)

isopropyl 4-(4-(8-oxa-3-azabicyclo[3.2.1]octan-3-yl)-6-chloro-1H-pyrazolo[3,4-d]pyrimidin-1-yl)piperidine-1-carboxylate (680 mg, 1.56 mmol) was dissolved in ethanol (8 mL) and toluene (8 mL) and divided over two microwave vials. To each vial was added 1.3 eq of aminophenylboronic acid, pinacol ester (220 mg, 1 mmol to each vial) and a 2M aqueous solution of Na2CO3 (1.57 mL, 3.14 mmol, 4 eq. to each vial). The vials were purged with nitrogen gas and 10 mol % tetrakis(triphenylphosphine)palladium was added (91 mg to each vial). Each vial was heated under microwave irradiation for 60 minutes. The contents of both vials were combined, diluted with dichloromethane and water and filtered over Celite. The organic phase was washed with brine (2×), dried over MgSO4 and concentrated to give the product as an orange foam, which was used without further purification. MS: 492.3 [M+H], RT 2.31

General Procedure for Formation of Urea and Carbamate Compounds from isopropyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (Scheme 30)

1.1 mmol of isopropyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate was suspended in 18 mL dichloromethane containing 0.585 mL triethylamine. The mixture was added in drops to a solution of 320 mg triphosgene (1.1 mmol) in 9 mL dichloromethane and stirred for 30 minutes at room temperature. The mixture was divided over 9 vials, each vial containing excess amine or alcohol as specified below. The mixtures were stirred overnight at room temperature, concentrated and purified by HPLC (Gilson, TFA buffers).

The Following Compounds were all Prepared According to General Procedure for Formation of Urea and Carbamate Compounds:

Isopropyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Using 1 mL of a 2 N solution of methylamine in THF, the title compound was obtained. MS: 549.3 [M+H], RT 2.33

Isopropyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Using 1 mL of a 2 N solution of ethylamine in THF, the title compound was obtained. MS: 563.3 [M+H], RT 2.37

Isopropyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate Using 99 mg 2-fluoroethylamine.HCl in 1 mL 1N NaOH, the title compound was obtained. MS: 581.3 [M+H], RT 2.35

Isopropyl 4-[6-(4-{[(2-hydroxyethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate Using 61 uL of 2-hydroxyethylamine in 1 mL dichloromethane, the title compound was obtained. MS: 579.3 [M+H], RT 2.21

Isopropyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate Using 70 uL of cyclopropylamine in 1 mL dichloromethane, the title compound was obtained. MS: 575.3 [M+H], RT 2.39

Isopropyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate Using 93 uL of aniline in 1 mL dichloromethane, the title compound was obtained. MS: 611.3 [M+H], RT 2.59

Isopropyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate Using 93 mg of 3-aminopyridine in 1 mL dichloromethane, the title compound was obtained. MS: 612.3 [M+H], RT 2.18

Isopropyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate Using 93 mg of 4-aminopyridine in 1 mL dichloromethane, the title compound was obtained. MS: 612.3 [M+H], RT 2.10

Isopropyl 4-[6-{4-[(methoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate Using 1 mL methanol, the title compound was obtained. MS: 550.3 [M+H], RT 2.51

Methyl 4-(4-(8-oxa-3-azabicyclo[3.2.1]octan-3-yl)-6-chloro-1H-pyrazolo[3,4-d]pyrimidin-1-yl)piperidine-1-carboxylate (Scheme 30)

In a 100 mL round-bottomed flask was placed 3-(1-(1-benzylpiperidin-4-yl)-6-chloro-1H-pyrazolo[3,4-d]pyrimidin-4-yl)-8-oxa-3-azabicyclo[3.2.1]octane (1.5 g, 3.42 mmol) in dichloromethane (5 ml) to give an orange suspension. methyl chloroformate (1.323 ml, 17.09 mmol) was added and the mixture was stirred at room temperature, resulting in an orange solution.
LCMS after 15 min showed that the reaction was nearly complete (RT 3.3, M+H=407.3/409.3, M+Na=429.2/431.2) with only a trace of starting material. The mixture was concentrated under reduced pressure and thoroughly dried under vacuum.
The crude product was added to a silica gel column and was eluted with ethyl acetate in hexanes (50-80%). Collected fractions were concentrated to give 1.262 g (3.1 mmol, 91%) of a light yellow solid. HRMS: 407.1595 [M+H]$^+$. For [M+H]+ mass error=0.2 mDa or 0.59 ppm Methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate: (Scheme 30)

methyl 4-(4-(8-oxa-3-azabicyclo[3.2.1]octan-3-yl)-6-chloro-1H-pyrazolo[3,4-d]pyrimidin-1-yl)piperidine-1-carboxylate (1.25 mmol) and 4-aminophenylboronic acid, pinacol ester (1.5 mmol, 1.2 eq, 329 mg) were dissolved in toluene (10.5 mL) and ethanol (6.25 mL). A 2M aq. Solution of Na$_2$CO$_3$ was added (2.5 mL). The mixture was degassed by bubbling a stream of nitrogen gas through the solution. Tetrakis(triphenylphosphine)palladium (10 mol %, 0.125 mmol, 144 mg) was added and the mixture was heated under microwave irradiation for 1 h at 120 C. The mixture was diluted with ethyl acetate, filtered over Celite and washed with brine. The organic phase was dried over MgSO4, concentrated and used in the next step without further purification. MS: 464.2 [M+H], RT 2.18

General procedure for formation of carbamate compounds from methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate: (Scheme 30)

methyl 4-(6-(4-aminophenyl)-4-(8-oxa-3-azabicyclo[3.2.1]octan-3-yl)-1H-pyrazolo[3,4-d]pyrimidin-1-yl)piperidine-1-carboxylate (1.125 mmol) was dissolved in 9 mL dichloromethane and 0.585 mL triethylamine was added. This mixture was added dropwise to a solution of triphosgene (186 mg) in dichloromethane (9 mL). The mixture was stirred for 20 minutes at room temperature and was then divided over 9 vials containing alcohols as specified below. The mixtures were stirred for 2 hours at room temperature. Where appropriate, the Boc protective group was removed by addition of 1 mL trifluoroacetic acid and an additional 30 minutes of stirring at room temperature. The samples were concentrated and purified by HPLC (Gilson, TFA buffers).

The Following Compounds were all Made According to the General Procedure for Formation of Carbamate Compounds:

Methyl 4-[6-[4-[(ethoxycarbonyl)amino]phenyl]-4-(8-oxa-3-azabicyclo[3.2.1]oct-3-yl)-1H-pyrazolo[3,4-d]pyrimidin-1-yl]piperidine-1-carboxylate Using 1 mL ethanol, the title compound was obtained. MS: 536.3 [M+H], RT 2.52

Methyl 4-[6-(4-{[(2-hydroxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate Using 60 uL ethylene glycol in 1 mL dichloromethane, the title compound was obtained. MS: 552.2 [M+H], RT 2.22

Methyl 4-[6-(4-{[(2-methoxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate Using 79 uL 2-methoxy-ethanol in 1 mL dichloromethane, the title compound was obtained. MS: 566.3 [M+H], RT 2.42

Methyl 4-[6-(4-{[(2-aminoethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate Using 155 uL (2-hydroxyethyl)-carbamic acid tert-butyl ester in 1 mL dichloromethane, the title compound was obtained. MS: 551.3 [M+H], RT 1.88

Methyl 4-{6-[4-({[2-(dimethylamino)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate Using 100 uL 2-dimethylaminoethanol in 1 mL dichloromethane, the title compound was obtained. MS: 579.3 [M+H], RT 1.94

Methyl 4-[4-(8-oxa-3-azabicyclo[3.2.1]oct-3-yl)-6-(4-{[(2-pyrrolidin-1-ylethoxy)carbonyl]amino}phenyl)-1H-pyrazolo[3,4-d]pyrimidin-1-yl]piperidine-1-carboxylate Using 118 uL 2-pyrrolidin-1-yl-ethanol in 1 mL dichloromethane, the title compound was obtained. MS: 605.3 [M+H], RT 1.99

Methyl 4-[6-(4-{[(2-morpholin-4-ylethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate Using 123 uL 2-morpholin-4-yl-ethanol in 1 mL dichloromethane, the title compound was obtained. MS: 621.3 [M+H], RT 1.95

Methyl 4-{6-[4-({[2-(4-methylpiperazin-1-yl)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate Using 144 mg 2-(4-methyl-piperazin-1-yl)-ethanol in 1 mL dichloromethane, the title compound was obtained. MS: 634.3 [M+H], RT 1.96

Methyl 4-[6-[4-[(methoxycarbonyl)amino]phenyl]-4-(8-oxa-3-azabicyclo[3.2.1]oct-3-yl)-1H-pyrazolo[3,4-d]pyrimidin-1-yl]piperidine-1-carboxylate Using 1 mL methanol, the title compound was obtained. MS: 522.2 [M+H], RT 2.42

General Procedure for the Preparation of Urea or Carbamate Compounds from 4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)aniline: (Scheme 41)

4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)aniline (1.25 mmol, 578 mg) was suspended in dichloromethane (8 mL) and triethylamine (0.52 mL) was added. The mixture was added dropwise to a solution of triphosgene (186 mg) in dichloromethane (8 mL). After stirring at room temperature for 10 minutes, the mixture was divided over 8 vials containing alcohol or amine as specified below. The mixtures were stirred for 16 h, concentrated and purified by HPLC.

The following compounds were prepared according to the general procedure for formation of urea or carbamate compounds:

2-hydroxyethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate using 60 uL ethylene glycol in 1 mL dichloromethane, the title compound was obtained. MS: 551.3 [M+H], RT 2.21

3-hydroxypropyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate using 72 uL 1,3-propanediol in 1 mL dichloromethane, the title compound was obtained. MS: 565.3 [M+H], RT 2.28

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-ethylurea using 1 mL of a 2N solution of ethylamine in tetrahydrofuran, the title compound was obtained. MS: 534.3 [M+H], RT 2.26.

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-fluoroethyl)urea Using 99 mg 2-fluoroethylamine.HCl in 1 mL 1N NaOH, the title compound was obtained. MS: 552.3 [M+H], RT 2.24

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-hydroxyethyl)urea using 61 uL 2-aminoethanol in 1 mL dichloromethane, the title compound was obtained. MS: 550.3 [M+H], RT 2.09

1-cyclopropyl-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea using 70 uL cyclopropylamine in 1 mL dichloromethane, the title compound was obtained. MS: 546.3 [M+H], RT 2.29

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-phenylurea using 93 uL aniline in 1 mL dichloromethane, the title compound was obtained. MS: 582.3 [M+H], RT 2.49

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-4-ylurea using 94 mg 4-aminopyridine in 1 mL dichloromethane, the title compound was obtained. MS: 583.3 [M+H], RT 1.99

2,2,2-trifluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate using 73 uL 2,2,2-trifluoroethanol and 1 mmol NaH in 1 mL dichloromethane, the title compound was obtained. MS: 589.2 [M+H], RT 2.56

2-fluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate using 500 uL 2-fluoroethanol in 1 mL dichloromethane, the title compound was obtained. MS: 553.2 [M+H], RT 2.42

3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-1,3-oxazolidin-2-one using 59 uL 2-fluoroethanol and 1 mmol NaH in 1 mL dichloromethane, the title compound was obtained as the major product. MS: 533.2 [M+H], RT 2.33

2-({4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}amino)ethanol using 59 uL 2-fluoroethanol and 1 mmol NaH in 1 mL dichloromethane, the title compound was obtained as a minor product. MS: 507.3 [M+H], RT 2.13

1-[2-(dimethylamino)ethyl]-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea:

using 22 uL N,N-dimethylethylenediamine in 0.5 mL dichloromethane, the title compound was obtained. MS: 577.3 [M+H], RT 1.90

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea using 29 mg 2-(4-methylpiperazin-1-yl)ethanamine in 0.5 mL dichloromethane, the title compound was obtained. MS: 632.4 [M+H], RT 1.86

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea using 36 mg 4-(4-methylpiperazino)aniline in 0.5 mL dichloromethane, the title compound was obtained. MS: 680.4 [M+H], RT 2.06

2-fluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate was also prepared by an alternative route: 36 mg 4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)aniline was dissolved in dichloromethane (0.5 mL) containing triethylamine (100 uL). 93 uL 2-fluoroethyl chloroformate was added and the mixture was stirred for 30 minutes. The mixture was concentrated and the title compound was obtained after HPLC purification. MS: 553.2 [M+H], RT 2.42.

3-(6-chloro-1-ethyl-1H-pyrazolo[3,4-d]pyrimidin-4-yl)-8-oxa-3-azabicyclo[3.2.1]octane: (Scheme 28)

2,4,6-trichloropyrimidine-5-carbaldehyde (5 g, 23.6 mmol) in ethanol (75 mL) was cooled to 0C. Ethylhydrazine oxalate (3.54 g, 23.6 mmol) was added followed by addition of triethylamine (10 mL). The mixture was stirred at 0 C for 45 minutes and 8-oxa-3-azabicyclo[3.2.1]octane, HCl (3.53 g, 23.6 mmol) was added. The mixture was allowed to warm to room temperature. The mixture was stirred for 16 h and additional triethylamine (10 mL) was added. The mixture was stirred for an additional 2 h, concentrated, dissolved in ethyl acetate and washed with sat. NaHCO3. The aqueous phase was extracted with ethyl acetate and the combined organic layers were washed with 0.1N HCl, dried over MgSO4 and filtered over magnesol. The mixture was concentrated, dissolved in dichloromethane and filtered over magnesol to give 4.564 g (15.5 mmol, 66%) of the crude product. The crude product was purified by trituration from diethyl ether to give 1.86 g (6.3 mmol, 27%) of the title compound as a light yellow solid. The mother liquor was concentrated, applied to a silica gel column and eluted with ethyl acetate in hexanes (20-55%) to give an additional 1.22 g (4.15 mmol) of product. MS: 294.2/296.2 [M+H].

4-(4-(8-oxa-3-azabicyclo[3.2.1]octan-3-yl)-1-ethyl-1H-pyrazolo[3,4-d]pyrimidin-6-yl)aniline: (Scheme 2)

3-(6-chloro-1-ethyl-1H-pyrazolo[3,4-d]pyrimidin-4-yl)-8-oxa-3-azabicyclo[3.2.1]octane (3.08 g, 10.5 mmol) was dissolved in toluene (95 mL) and ethanol (55 mL). 4-Aminophenylboronic acid, pinacol ester (2.53 g, 11.55 mmol) was added followed by the addition of a 2M aqueous solution of Na2CO3 (21 mL). The mixture was degassed by bubbling a stream of nitrogen through the solution and tetrakis(triphenylphosphine)palladium (606 mg) was added. The mixture was heated under reflux for 16 h, cooled to room temperature and concentrated. The mixture was dissolved in ethyl acetate and washed with brine. The organic phase was dried over MgSO4 and filtered over magnesol. The aqueous phase was extracted with ethyl acetate, which was dried over MgSO4. The combined organic phases were concentrated. The crude product was applied to a silica gel column and eluted with ethyl acetate in hexanes (30-100%) to give 3.6 g of the title compound. HRMS: 351.1925 [M+H]. For [M+H]+ mass error=−0.3 mDa or −0.92 ppm.

General Procedure for the Preparation of Urea or Carbamate Compounds from 4-(4-(8-oxa-3-azabicyclo[3.2.1]octan-3-yl)-1-ethyl-1H-pyrazolo[3,4-d]pyrimidin-6-yl)aniline: (Scheme 2)

4-(4-(8-oxa-3-azabicyclo[3.2.1]octan-3-yl)-1-ethyl-1H-pyrazolo[3,4-d]pyrimidin-6-yl)aniline (473 mg, 1.35 mmol) was dissolved in dichloromethane (13.5 mL) and triethylamine was added (585 uL). The mixture was added dropwise to a solution of triphosgene (200 mg, 0.675 mmol) in dichloromethane (9 mL). The mixture was stirred at room temperature for 20 minutes and was then divided over 9 vials containing amine or alcohol as specified below. The mixtures were stirred for 16 h. Where appropriate, Boc protective groups were removed by addition of trifluoroacetic acid (2 mL) and stirring for 40 min. The mixtures were concentrated and purified by HPLC.

The Following Compounds were Prepared Following the General Procedure for Formation of Urea or Carbamate Compounds

1-(2-aminoethyl)-3-{4-[1-ethyl-4-(8-oxa-3-azabicyclo[3.2.1]oct-3-yl)-1H-pyrazolo[3,4-d]pyrimidin-6-yl]phenyl}urea using 67 uL ethylene diamine in 1 mL dichloromethane, the title compound was obtained. MS: 437.2 [M+H], RT 1.71

1-{4-[1-ethyl-4-(8-oxa-3-azabicyclo[3.2.1]oct-3-yl)-1H-pyrazolo[3,4-d]pyrimidin-6-yl]phenyl}-3-[2-(methylamino)ethyl]urea using 179 uL N-Boc-N-methylethylene diamine in 1 mL dichloromethane, the title compound was obtained after Boc deprotection. MS: 451.2 [M+H], RT 1.74

1-[2-(dimethylamino)ethyl]-3-{4-[1-ethyl-4-(8-oxa-3-azabicyclo[3.2.1]oct-3-yl)-1H-pyrazolo[3,4-d]pyrimidin-6-yl]phenyl}urea using 109 uL N,N-dimethylethylene diamine in 1 mL dichloromethane, the title compound was obtained. MS: 465.3 [M+H], RT 1.77

1-(3-aminopropyl)-3-{4-[1-ethyl-4-(8-oxa-3-azabicyclo[3.2.1]oct-3-yl)-1H-pyrazolo[3,4-d]pyrimidin-6-yl]phenyl}urea using 83 uL 1,3-diaminopropane in 1 mL dichloromethane, the title compound was obtained. MS: 451.2 [M+H], RT 1.73.

1-[3-(dimethylamino)propyl]-3-{4-[1-ethyl-4-(8-oxa-3-azabicyclo[3.2.1]oct-3-yl)-1H-pyrazolo[3,4-d]pyrimidin-6-yl]phenyl}urea using 126 uL 3-(dimethylamino)-1-propylamine in 1 mL dichloromethane, the title compound was obtained. MS: 479.3 [M+H], RT 1.79.

1-{4-[1-ethyl-4-(8-oxa-3-azabicyclo[3.2.1]oct-3-yl)-
1H-pyrazolo[3,4-d]pyrimidin-6-yl]phenyl}-3-[2-(4-
methylpiperazin-1-yl)ethyl]urea using 86 mg of 2-(4-methylpiperazin-1-yl)ethanamine in 1 mL dichloromethane, the title compound was obtained. MS: 520.3 [M+H], RT 1.73.

1-{4-[1-ethyl-4-(8-oxa-3-azabicyclo[3.2.1]oct-3-yl)-
1H-pyrazolo[3,4-d]pyrimidin-6-yl]phenyl}-3-(2-
morpholin-4-ylethyl)urea using 78 uL 4-(2-aminoethyl)morpholine in 1 mL dichloromethane, the title compound was obtained. MS: 507.3 [M+H], RT 1.78.

1-{4-[1-ethyl-4-(8-oxa-3-azabicyclo[3.2.1]oct-3-yl)-
1H-pyrazolo[3,4-d]pyrimidin-6-yl]phenyl}-3-[4-(4-
methylpiperazin-1-yl)phenyl]urea using 115 mg 4-(4-methylpiperazino)aniline in 1 mL dichloromethane, the title compound was obtained. MS: 568.3 [M+H], RT 1.96.

1-{4-[1-ethyl-4-(8-oxa-3-azabicyclo[3.2.1]oct-3-yl)-
1H-pyrazolo[3,4-d]pyrimidin-6-yl]phenyl}-3-(4-
morpholin-4-ylphenyl)urea using 107 mg 4-morpholinoaniline in 1 mL dichloromethane, the title compound was obtained. MS: 555.3 [M+H], RT 2.27.

1-[2-(2-aminoethoxy)ethyl]-3-{4-[1-ethyl-4-(8-oxa-
3-azabicyclo[3.2.1]oct-3-yl)-1H-pyrazolo[3,4-d]
pyrimidin-6-yl]phenyl}urea using 52 mg 2,2'-oxybis(ethylamine) in 1 mL dichloromethane, the title compound was obtained. MS: 481.3 [M+H], RT 1.74.

1-{4-[1-ethyl-4-(8-oxa-3-azabicyclo[3.2.1]oct-3-yl)-
1H-pyrazolo[3,4-d]pyrimidin-6-yl]phenyl}-3-[(1-
methylpiperidin-4-yl)methyl]urea using 64 mg (1-methyl-4-piperidinyl)methanamine in 1 mL dichloromethane, the title compound was obtained. MS: 505.3 [M+H], RT 1.80.

1-cyclohexyl-3-{4-[1-ethyl-4-(8-oxa-3-azabicyclo
[3.2.1]oct-3-yl)-1H-pyrazolo[3,4-d]pyrimidin-6-yl]
phenyl}urea using 58 uL cyclohexylamine in 1 mL dichloromethane, the title compound was obtained. MS: 476.3 [M+H], RT 2.36.

1-{4-[1-ethyl-4-(8-oxa-3-azabicyclo[3.2.1]oct-3-yl)-
1H-pyrazolo[3,4-d]pyrimidin-6-yl]phenyl}-3-(1-
methylpiperidin-4-yl)urea using 57 mg 4-amino-1-methyl-piperidine in 1 mL dichloromethane, the title compound was obtained. MS: 491.3 [M+H], RT 1.78.

1-(cis-4-aminocyclohexyl)-3-{4-[1-ethyl-4-(8-oxa-3-
azabicyclo[3.2.1]oct-3-yl)-1H-pyrazolo[3,4-d]pyri-
midin-6-yl]phenyl}urea using 57 mg cis-1,4-cyclohexanediamine in 1 mL dichloromethane, the title compound was obtained. MS: 491.3 [M+H], RT 1.78.

Methyl{4-[1-ethyl-4-(8-oxa-3-azabicyclo[3.2.1]oct-
3-yl)-1H-pyrazolo[3,4-d]pyrimidin-6-yl]
phenyl}carbamate using methanol, the title compound was obtained. HRMS: 409.19774 [M+H], Exptl−Calc'd=−0.53 mmu.

1-{4-[1-ethyl-4-(8-oxa-3-azabicyclo[3.2.1]oct-3-yl)-
1H-pyrazolo[3,4-d]pyrimidin-6-yl]phenyl}-3-[2-(4-
methylpiperazin-1-yl)-2-oxoethyl]urea using ~1 mmol 2-amino-1-(4-methylpiperazin-1-yl) ethanone.2HCl in 2 mL dichloromethane and 2 mL 1N NaOH, the title compound was obtained. MS: 534.3 [M+H], RT 1.84.

1-{4-[1-ethyl-4-(8-oxa-3-azabicyclo[3.2.1]oct-3-yl)-
1H-pyrazolo[3,4-d]pyrimidin-6-yl]phenyl}-3-[3-(4-
methylpiperazin-1-yl)-3-oxopropyl]urea using ~1 mmol 3-amino-1-(4-methylpiperazin-1-yl)propan-1-one.2HCl in 2 mL dichloromethane and 2 mL 1N NaOH, the title compound was obtained. MS: 548.3 [M+H], RT 1.83.

N-[2-(dimethylamino)ethyl]-N2-({4-[1-ethyl-4-(8-
oxa-3-azabicyclo[3.2.1]oct-3-yl)-1H-pyrazolo[3,4-d]
pyrimidin-6-yl]phenyl}carbamoyl)glycinamide using ~1 mmol 2-amino-N-(2-(dimethylamino)ethyl) acetamide.2HCl in 2 mL dichloromethane and 2 mL 1N NaOH, the title compound was obtained. MS: 522.3 [M+H], RT 1.80.

N-[2-(dimethylamino)ethyl]-N3-({4-[1-ethyl-4-(8-
oxa-3-azabicyclo[3.2.1]oct-3-yl)-1H-pyrazolo[3,4-d]
pyrimidin-6-yl]phenyl}carbamoyl)-beta-alaninamide using ~1 mmol 3-amino-N-(2-(dimethylamino)ethyl) propanamide.2HCl in 2 mL dichloromethane and 2 mL 1N NaOH, the title compound was obtained. MS: 536.3 [M+H], RT 1.88.

The Following Compound was Isolated in the Last 4 Examples:

N-[3-(dimethylamino)propyl]-N-(ethylcarbamoyl)-
N3-({4-[1-ethyl-4-(8-oxa-3-azabicyclo[3.2.1]oct-3-
yl)-1H-pyrazolo[3,4-d]pyrimidin-6-yl]
phenyl}carbamoyl)-beta-alaninamide

MS: 621.4 [M+H], RT 1.91.

1-{4-[1-Ethyl-4-(8-oxa-3-aza-bicyclo[3.2.1]oct-3-
yl)-1H-pyrazolo[3,4-d]pyrimidin-6-yl]-phenyl}-3-[4-
(4-methyl-piperazin-1-ylmethyl)-phenyl]-urea using 74 mg of 4-(4-methylpiperazin-1-ylmethyl)phenylamine in 1 mL dichloromethane, the title compound was obtained. MS: 582.5 [M+H], RT 2.77.

1-(4-Aminomethyl-phenyl)-3-{4-[1-ethyl-4-(8-oxa-3-aza-bicyclo[3.2.1]oct-3-yl)-1H-pyrazolo[3,4-d]pyrimidin-6-yl]-phenyl}-urea using 80 mg of 4-[(N-Boc)aminomethyl]aniline in 1 mL dichloromethane, the title compound was obtained. MS: 499.2 [M+H], RT 2.62.

1-(4-Dimethylaminomethyl-phenyl)-3-{4-[1-ethyl-4-(8-oxa-3-aza-bicyclo[3.2.1]oct-3-yl)-1H-pyrazolo[3,4-d]pyrimidin-6-yl]-phenyl}-urea using 67 mg of 4-dimethylaminomethyl-aniline.HCl in 0.36 mL 1N NaOH, the title compound was obtained. MS: 527.2 [M+H], RT 2.81.

1-{4-[1-Ethyl-4-(8-oxa-3-aza-bicyclo[3.2.1]oct-3-yl)-1H-pyrazolo[3,4-d]pyrimidin-6-yl]-phenyl}-3-(4-pyrrolidin-1-ylmethyl-phenyl)-urea using 63 mg of 4-pyrrolidin-1-ylmethyl-aniline in 1 mL dichloromethane, the title compound was obtained. MS: 553.2 [M+H], RT 2.87.

1-[4-(2-Dimethylamino-ethylamino)-phenyl]-3-{4-[1-ethyl-4-(8-oxa-3-aza-bicyclo[3.2.1]oct-3-yl)-1H-pyrazolo[3,4-d]pyrimidin-6-yl]-phenyl}-urea:

using 101 mg of (4-amino-phenyl)-(2-dimethylamino-ethyl)-carbamic acid tert-butyl ester in 1 mL dichloromethane, the title compound was obtained. MS: 556.2 [M+H], RT 2.74.

1-{4-[(2-Dimethylamino-ethyl)-methyl-amino]-phenyl}-3-{4-[1-ethyl-4-(8-oxa-3-aza-bicyclo[3.2.1]oct-3-yl)-1H-pyrazolo[3,4-d]pyrimidin-6-yl]-phenyl}-urea:

using 70 mg of N-(2-dimethylamino-ethyl)-N-methyl-benzene-1,4-diamine in 1 mL dichloromethane, the title compound was obtained. MS: 570.2 [M+H], RT 2.87.

1-Cyclobutyl-3-{4-[1-ethyl-4-(8-oxa-3-aza-bicyclo[3.2.1]oct-3-yl)-1H-pyrazolo[3,4-d]pyrimidin-6-yl]-phenyl}-urea using 31 uL of cyclobutylamine in 1 mL dichloromethane, the title compound was obtained. MS: 448.4 [M+H], RT 3.58

1-Cyclopentyl-3-{4-[1-ethyl-4-(8-oxa-3-aza-bicyclo[3.2.1]oct-3-yl)-1H-pyrazolo[3,4-d]pyrimidin-6-yl]-phenyl}-urea using 336 uL of cyclopentylamine in 1 mL dichloromethane, the title compound was obtained. MS: 462.4 [M+H], RT 3.71

2-(4-(8-oxa-3-azabicyclo[3.2.1]octan-3-yl)-6-chloro-1H-pyrazolo[3,4-d]pyrimidin-1-yl)ethanol: (Scheme 28)

2,4,6-trichloropyrimidine-5-carbaldehyde (2.12 g, 10 mmol) in ethanol (30 mL) was cooled to 0 C. 2-Hydroxyethylhydrazine (753 uL) was added followed by addition of triethylamine (5.6 mL). The mixture was stirred at 0 C for 30 minutes and 8-oxa-3-azabicyclo[3.2.1]octane, HCl (1.5 g, 10 mmol) was added. The mixture was allowed to warm to room temperature and the crude product was collected by filtration. The crude product was dissolved in dichloromethane and washed with sat. NaHCO3 and 0.2N HCl. The organic phase dried over MgSO4 and concentrated to give the title compound as yellow crystals (1.023 g, 3.3 mmol, 33%). HRMS: 310.1070 [M+H]. For [M+H]+ mass error=0.5 mDa or 1.51 ppm.

General Procedure for Formation of Ureidophenyl or Carbamoylphenyl Compounds from 2-(4-(8-oxa-3-azabicyclo[3.2.1]octan-3-yl)-6-chloro-1H-pyrazolo[3,4-d]pyrimidin-1-yl)ethanol: (Scheme 2)

4-Isocyanatophenylboronic acid, pinacol ester (0.2 mmol, 49 mg) was reacted with amine or alcohol as specified below. To the resulting carbamoylphenylboronic acid, pinacol ester or ureidophenylboronic acid, pinacol ester in toluene (1 mL) was added 2-(4-(8-oxa-3-azabicyclo[3.2.1]octan-3-yl)-6-chloro-1H-pyrazolo[3,4-d]pyrimidin-1-yl)ethanol (50 mg), ethanol (0.6 mL) and a 2M aqueous solution of Na$_2$CO$_3$ (0.25 mL). The mixture was degassed by bubbling a stream of nitrogen and a catalytic amount of tetrakis(triphenylphosphine)palladium was added. The mixture was heated under microwave irradiation for 30 min at 12° C. The mixture was concentrated and purified by HPLC.

The Following Compounds were Prepared According to the General Procedure for Preparation of Ureidophenyl or Carbamoylphenyl Compounds:

Methyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate using 1 mL methanol, the carbamoylphenylboronate was prepared. The solvents were removed, toluene (1 mL) was added and the title compound was obtained after Suzuki coupling according to the general procedure. MS: 425.2 [M+H], RT 2.00.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-methylurea using 1 mL of a 2N solution of methylamine in THF, the ureidophenylboronate was prepared. The solvents were removed, toluene (1 mL) was added and the title compound was obtained after Suzuki coupling according to the general procedure. MS: 424.2 [M+H], RT 1.83.

1-ethyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea using 1 mL of a 2N solution of ethylamine in THF, the ureidophenylboronate was prepared. The solvents were removed, toluene (1 mL) was added and the title compound was obtained after Suzuki coupling according to the general procedure. MS: 438.2 [M+H], RT 1.90.

2-hydroxyethyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate using 112 uL ethylene glycol in 1 mL toluene, the carbamoylphenylboronate was prepared. The title compound was obtained after Suzuki coupling according to the general procedure. MS: 455.2 [M+H], RT 1.85.

1-(2-hydroxyethyl)-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea using 0.2 mmol ethanolamine in 1 mL toluene, the ureidophenylboronate was prepared. The title compound was obtained after Suzuki coupling according to the general procedure. MS: 454.2 [M+H], RT 1.75.

1-cyclopropyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea using 0.2 mmol cyclopropylamine in 1 mL toluene, the ureidophenylboronate was prepared. The title compound was obtained after Suzuki coupling according to the general procedure. MS: 450.2 [M+H], RT 1.92.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-phenylurea using 0.2 mmol aniline in 1 mL toluene, the ureidophenylboronate was prepared. The title compound was obtained after Suzuki coupling according to the general procedure. MS: 486.2 [M+H], RT 2.16.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-3-ylurea using 0.2 mmol 3-aminopyridine in 1 mL toluene, the ureidophenylboronate was prepared. The title compound was obtained after Suzuki coupling according to the general procedure. MS: 487.2 [M+H], RT 1.73.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-4-ylurea using 0.2 mmol 4-aminopyridine in 1 mL toluene, the ureidophenylboronate was prepared. The title compound was obtained after Suzuki coupling according to the general procedure. MS: 487.2 [M+H], RT 1.71.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea using 0.2 mmol 4-aminobenzyl alcohol in 1 mL toluene, the ureidophenylboronate was prepared. The title compound was obtained after Suzuki coupling according to the general procedure. MS: 516.2 [M+H], RT 1.97.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea using 0.2 mmol 4-aminophenethyl alcohol in 1 mL toluene, the ureidophenylboronate was prepared. The title compound was obtained after Suzuki coupling according to the general procedure. MS: 530.2 [M+H], RT 2.01.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea using 0.2 mmol 4-(4-methylpiperazino)aniline in 1 mL toluene, the ureidophenylboronate was prepared. The title compound was obtained after Suzuki coupling according to the general procedure. MS: 584.3 [M+H], RT 1.78.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea using 0.2 mmol 4-morpholinoaniline in 1 mL toluene, the ureidophenylboronate was prepared. The title compound was obtained after Suzuki coupling according to the general procedure. MS: 571.3 [M+H], RT 2.03.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea using 0.2 mmol 6-(4-methylpiperazino)-3-pyridinamine in 1 mL toluene, the ureidophenylboronate was prepared. The title compound was obtained after Suzuki coupling according to the general procedure. MS: 585.3 [M+H], RT 1.72.

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea using 0.2 mmol 3-amino-6-morpholinopyridine in 1 mL toluene, the ureidophenylboronate was prepared. The title compound was obtained after Suzuki coupling according to the general procedure. MS: 572.3 [M+H], RT 1.80.

The Following Compounds were Isolated as Minor By-Products During Preparation of compounds according to the general procedure for preparation of ureidophenyl or carbamoylphenyl compounds:

2-[6-(4-aminophenyl)-4-(8-oxa-3-azabicyclo[3.2.1]oct-3-yl)-1H-pyrazolo[3,4-d]pyrimidin-1-yl]ethanol: MS: 367.2 [M+H], RT 1.70.

Ethyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate

MS: 439.2 [M+H], RT 2.10.

3-(4-(8-oxa-3-azabicyclo[3.2.1]octan-3-yl)-6-chloro-1H-pyrazolo[3,4-d]pyrimidin-1-yl)propanenitrile: (Scheme 28)

2,4,6-trichloropyrimidine-5-carbaldehyde (1.06 g, 5 mmol) in ethanol (15 mL) was cooled to 0 C. 2-cyanoethylhydrazine (404 uL, 5 mmol)) was added followed by addition of triethylamine (2.8 mL). The mixture was stirred at 0 C for 20 minutes and 8-oxa-3-azabicyclo[3.2.1]octane, HCl (0.75 g, 5 mmol) was added. The mixture was allowed to warm to room temperature, stirred for 16 and the crude product was collected by filtration to give the title compound as a tan solid (1.86 mmol, 37%).

3-(6-(4-aminophenyl)-4-(8-oxa-3-azabicyclo[3.2.1]octan-3-yl)-1H-pyrazolo[3,4-d]pyrimidin-1-yl)propanenitrile: (Scheme 2)

3-(4-(8-oxa-3-azabicyclo[3.2.1]octan-3-yl)-6-chloro-1H-pyrazolo[3,4-d]pyrimidin-1-yl)propanenitrile (1.75 mmol)

was dissolved in toluene (32 mL) and ethanol (19 mL). 4-Aminophenylboronic acid, pinacol ester (858 mg, 3.9 mmol) was added followed by the addition of a 2M aqueous solution of Na2CO3 (7.1 mL). The mixture was degassed by bubbling a stream of nitrogen through the solution and tetrakis(triphenylphosphine)palladium (53 mg) was added. The mixture was heated under reflux for 4 h, cooled to room temperature and concentrated. The mixture was dissolved in ethyl acetate and washed with brine. The organic phase was dried over MgSO4, filtered and concentrated. The crude product was applied to a silica gel column and eluted with ethyl acetate in hexanes (30-100%) to give 547 mg of the title compound.

General Procedure for the Formation of Urea or Carbamate Compounds from 3-(6-(4-aminophenyl)-4-(8-oxa-3-azabicyclo[3.2.1]octan-3-yl)-1H-pyrazolo[3,4-d]pyrimidin-1-yl)propanenitrile: (Scheme 2)

3-(6-(4-aminophenyl)-4-(8-oxa-3-azabicyclo[3.2.1]octan-3-yl)-1H-pyrazolo[3,4-d]pyrimidin-1-yl)propanenitrile (425 mg, 1.25 mmol) was dissolved in dichloromethane (20 mL) and triethylamine was added (650 uL). The mixture was added dropwise to a solution of triphosgene (178 mg, 0.6 mmol) in dichloromethane (10 mL). The mixture was stirred at room temperature for 10 minutes and was then divided over 10 vials containing amine or alcohol as specified below. The mixtures were stirred for 2 h. The mixtures were concentrated and purified by HPLC (NH4OH buffers).
The Following Compounds were Prepared Following the General Procedure for Formation or Urea or Carbamate Compounds:

2-hydroxyethyl{4-[1-(2-cyanoethyl)-4-(8-oxa-3-azabicyclo[3.2.1]oct-3-yl)-1H-pyrazolo[3,4-d]pyrimidin-6-yl]phenyl}carbamate using ethylene glycol (56 uL) in 1 mL dichloromethane, the title compound was obtained. MS: 464.2 [M+H], RT 1.93.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-methylurea using 1 mL of a 2N solution of methylamine in THF, the title compound was obtained. MS: 433.2 [M+H], RT 1.91.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-cyclopropylurea using cyclopropylamine (70 uL) in 1 mL dichloromethane, the title compound was obtained. MS: 459.2 [M+H], RT 2.00.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-3-ylurea using 3-aminopyridine (94 mg) in 1 mL dichloromethane, the title compound was obtained. MS: 496.2 [M+H], RT 1.81.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-4-ylurea using 4-aminopyridine (94 mg) in 1 mL dichloromethane, the title compound was obtained. MS: 496.2 [M+H], RT 1.79.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea using 4-aminobenzyl alcohol (62 mg) in 1 mL dichloromethane, the title compound was obtained. MS: 525.2 [M+H], RT 2.03.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea using 4-aminophenethyl alcohol (69 mg) in 1 mL dichloromethane, the title compound was obtained. MS: 539.2 [M+H], RT 2.07.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea using 4-(4-methylpiperazino)aniline (96 mg) in 1 mL dichloromethane, the title compound was obtained. MS: 593.3 [M+H], RT 1.86.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea using 4-morpholinoaniline (89 mg) in 1 mL dichloromethane, the title compound was obtained. MS: 580.3 [M+H], RT 2.09.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea Using 6-(4-methylpiperazino)-3-pyridinamine (96 mg) in 1 mL dichloromethane, the title compound was obtained. MS: 594.3 [M+H], RT 1.80.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea using 3-amino-6-morpholinopyridine (90 mg) in 1 mL dichloromethane, the title compound was obtained. MS: 581.3 [M+H], RT 1.88.

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-{4-[2-(dimethylamino)ethoxy]phenyl}urea using 4-(2-(dimethylamino)ethoxy)aniline.2HCl (100 mg) in 1 mL dichloromethane, the title compound was obtained. MS: 582.3 [M+H], RT 1.86

4-(8-oxa-3-azabicyclo[3.2.1]octan-3-yl)-2-chlorothieno[3,2-d]pyrimidine-6-carbaldehyde: (Scheme 45)

In a dried 250 mL round-bottomed flask was placed 3-(2-chlorothieno[3,2-d]pyrimidin-4-yl)-8-oxa-3-azabicyclo[3.2.1]octane (0.5 g, 1.775 mmol) in THF (20 ml) to give a colorless solution. The mixture was cooled to −78 C and butyllithium (1.6N in hexane) (1.331 ml, 2.129 mmol) was added. After stirring for 1 h at −78 C, N,N-dimethylformamide (0.205 ml, 2.66 mmol) was added to the now yellow solution and the mixture was stirred for an additional hour at −78 C. The mixture was slowly warmed to RT.

The mixture was diluted with sat. NaHCO3 and extracted with EtOAc. The organic phase was dried over MgSO4 and concentrated. The crude product was added to a silica gel column and was eluted with ethyl acetate in hexanes (20-40%) to give 498 mg of the title compound as a yellow solid.

3-(2-chloro-6-((4-methylpiperazin-1-yl)methyl) thieno[3,2-d]pyrimidin-4-yl)-8-oxa-3-azabicyclo [3.2.1]octane: (Scheme 45)

In a 250 mL round-bottomed flask was placed 4-(8-oxa-3-azabicyclo[3.2.1]octan-3-yl)-2-chlorothieno[3,2-d]pyrimidine-6-carbaldehyde (222 mg, 0.717 mmol), 1-methylpiperazine (0.119 ml, 1.075 mmol), and acetic acid (0.043 ml, 0.752 mmol) in 1,2-dichloroethane (6 ml) to give a yellow solution. Sodium triacetoxyborohydride (167 mg, 0.788 mmol) was added and the resulting fine suspension was stirred at room temperature for 1 h.

The reaction mixture was diluted with DCM and washed with saturated NaHCO$_3$. The organic phase was dried over MgSO$_4$, filtered and concentrated. The crude product was added to a silica gel column and was eluted with methanol in dichloromethane (0-5%, containing 1% NEt3) to give 177 mg of a tan solid. HRMS: 394.1468 [M+H]. For [M+H]+ mass error=0.5 mDa or 1.22 ppm.

3-(6-((4-methylpiperazin-1-yl)methyl)-2-(4-nitrophenyl)thieno[3,2-d]pyrimidin-4-yl)-8-oxa-3-azabicyclo[3.2.1]octane: (Scheme 45)

In a 100 mL microwave vial was placed 3-(2-chloro-6-((4-methylpiperazin-1-yl)methyl)thieno[3,2-d]pyrimidin-4-yl)-8-oxa-3-azabicyclo[3.2.1]octane (168 mg, 0.426 mmol) and 4,4,5,5-tetramethyl-2-(4-nitrophenyl)-1,3,2-dioxaborolane (127 mg, 0.512 mmol) in DME (5 ml) to give a yellow solution. Na2CO3 (2M solution in water) (0.853 ml, 1.706 mmol) was added. The mixture was degassed by bubbling N2 through the solution. Pd(PPh3)4 (49.3 mg, 0.043 mmol) was added. The mixture was heated under reflux (oil bath at 95 C). LC MS (RT 2.8, M+H=481) showed complete conversion after 7.5 h. The reaction mixture was diluted with ethyl acetate and washed with a sat. solution of NaHCO3. A precipitate remained that was insoluble in either organic or aqueous phase. LCMS showed that both the precipitate and the organic phase contained product.

The precipitate was dissolved in DCM and MeOH, filtered and concentrated. The ethyl acetate layer was dried (MgSO4) and added to the DCM/MeOH filtrate. The crude product was added to a silica gel column and was eluted with methanol in dichloromethane (0-5%, containing 1% NEt3). Collected fractions were concentrated to give 170 mg of a yellow solid (0.35 mmol, 83%). HRMS: 481.2019 [M+H]. For [M+H]+ mass error=0.3 mDa or 0.64 ppm.

4-(4-(8-oxa-3-azabicyclo[3.2.1]octan-3-yl)-6-((4-methylpiperazin-1-yl)methyl)thieno[3,2-d]pyrimidin-2-yl)aniline: (Scheme 45)

In a 250 mL round-bottomed flask was placed 3-(6-((4-methylpiperazin-1-yl)methyl)-2-(4-nitrophenyl)thieno[3,2-d]pyrimidin-4-yl)-8-oxa-3-azabicyclo[3.2.1]octane (170 mg, 0.354 mmol) in isopropanol (3 mL) and DCM (3.00 mL) to give a nearly colorless solution. A catalytic amount of Pd on charcoal (wet) was added and the mixture was stirred under a hydrogen atmosphere for 4 h. LCMS showed complete conversion, along with some minor impurities. The mixture was filtered over Celite, rinsed with DCM and concentrated. The product was used in the next step without further purification.

General Procedure for the Formation of Urea and Carbamate Compounds from 4-(4-(8-oxa-3-azabicyclo[3.2.1]octan-3-yl)-6-((4-methylpiperazin-1-yl) methyl)thieno[3,2-d]pyrimidin-2-yl)aniline: (Scheme 45)

In a round-bottomed flask was placed 4-(4-(8-oxa-3-azabicyclo[3.2.1]octan-3-yl)-6-((4-methylpiperazin-1-yl)methyl) thieno[3,2-d]pyrimidin-2-yl)aniline (0.160 g, 0.354 mmol) and triethylamine (0.197 ml, 1.416 mmol) in DCM (6 ml). The mixture was added dropwise to a solution of triphosgene (0.053 g, 0.177 mmol) in 2 mL DCM in a scintillation vial. Another 3 mL of DCM was used to rinse the round-bottomed flask and transfer any remaining material to the scintillation vial. The mixture was stirred at room temperature for 5 min.

The mixture was divided over 6 vials (~2 mL in each vial), each vial containing amine or alcohol as specified below. The mixture was stirred at room temperature for 16 h. The crude material was concentrated and purified by HPLC (Gilson, trifluoroacetic acid buffers).

The following compounds were made following the general procedure for formation of urea or carbamate compounds:

1-methyl-3-(4-{6-[(4-methylpiperazin-1-yl)methyl]-4-(8-oxa-3-azabicyclo[3.2.1]oct-3-yl)thieno[3,2-d] pyrimidin-2-yl}phenyl)urea using 1 mL of a 2N solution of methylamine in THF, the title compound was obtained. MS: 508.2 [M+H], RT 1.53.

1-cyclopropyl-3-(4-{6-[(4-methylpiperazin-1-yl) methyl]-4-(8-oxa-3-azabicyclo[3.2.1]oct-3-yl)thieno [3,2-d]pyrimidin-2-yl}phenyl)urea:

using cyclopropylamine (35 uL) in dichloromethane (1 mL), the title compound was obtained. MS: 534.3 [M+H], RT 1.59.

2,2-dimethyl-N-(4-{6-[(4-methylpiperazin-1-yl)methyl]-4-(8-oxa-3-azabicyclo[3.2.1]oct-3-yl)thieno[3, 2-d]pyrimidin-2-yl}phenyl)hydrazinecarboxamide using 1,1-dimethylhydrazine (38 uL) in dichloromethane (1 mL), the title compound was obtained. MS: 537.3 [M+H], RT 1.61.

1-(4-{6-[(4-methylpiperazin-1-yl)methyl]-4-(8-oxa-3-azabicyclo[3.2.1]oct-3-yl)thieno[3,2-d]pyrimidin-2-yl}phenyl)-3-pyridin-3-ylurea using 3-aminopyridine (19 mg) in dichloromethane (1 mL), the title compound was obtained. MS: 571.3 [M+H], RT 1.53.

1-(4-{6-[(4-methylpiperazin-1-yl)methyl]-4-(8-oxa-3-azabicyclo[3.2.1]oct-3-yl)thieno[3,2-d]pyrimidin-2-yl}phenyl)-3-pyridin-4-ylurea using 4-aminopyridine (19 mg) in dichloromethane (1 mL), the title compound was obtained. MS: 571.3 [M+H], RT 1.52.

4-{[(4-{6-[(4-methylpiperazin-1-yl)methyl]-4-(8-oxa-3-azabicyclo[3.2.1]oct-3-yl)thieno[3,2-d]pyrimidin-2-yl}phenyl)carbamoyl]amino}benzamide using 4-aminobenzamide (27 mg) in dichloromethane (1 mL), the title compound was obtained. MS: 613.3 [M+H], RT 1.66.

tert-butyl 4-(methylsulfonyl)piperazine-1-carboxylate

In a 250 mL round-bottomed flask was placed tert-butyl piperazine-1-carboxylate (1 g, 5.37 mmol) and triethylamine (1.488 ml, 10.74 mmol) in DCM (30 ml) to give a colorless solution. Methanesulfonyl chloride (0.458 ml, 5.91 mmol) was added slowly. The mixture was stirred at room temperature for 16 h.

The reaction mixture was diluted with DCM, washed with 0.1M HCl, sat NaHCO3 and 0.1N NaOH and the organic phase was dried over MgSO4 and concentrated to give 1.34 g of a light yellow solid. HRMS: 287.10349 [M+H]. Exptl–Calc'd=–0.11 mmu.

1-(methylsulfonyl)piperazine

In a 250 mL round-bottomed flask was placed tert-butyl 4-(methylsulfonyl)piperazine-1-carboxylate (1.34 g, 5.07 mmol) in DCM (10 mL) to give a light yellow solution. TFA (5 mL) was added and the solution was stirred at room temperature for 2 h. The mixture was concentrated under reduced pressure to give 1.39 g of a tan solid (quant. yield). HRMS: 165.0695 [M+H]. For [M+H]+ mass error=0.3 mDa or 1.63 ppm.

4-(8-oxa-3-azabicyclo[3.2.1]octan-3-yl)-2-(4-nitrophenyl)thieno[3,2-d]pyrimidine-6-carbaldehyde (Scheme 45)

In a 250 mL round-bottomed flask was placed 4-(8-oxa-3-azabicyclo[3.2.1]octan-3-yl)-2-chlorothieno[3,2-d]pyrimidine-6-carbaldehyde (276 mg, 0.891 mmol) and 4,4,5,5-tetramethyl-2-(4-nitrophenyl)-1,3,2-dioxaborolane (266 mg, 1.069 mmol) in dimethoxyethane (10 ml) to give an orange suspension (which dissolved when heated). Na2CO3 (2M solution in water) (1.782 ml, 3.56 mmol) was added. The mixture was degassed by bubbling nitrogen through the solution. Pd(PPh3)4 (103 mg, 0.089 mmol) was added.

The mixture was heated under reflux (oil bath at 95 C) for 2 h. The reaction mixture was diluted with ethyl acetate and washed with a sat. solution of NaHCO3. The precipitate that was not dissolved in either the organic or aqueous phase was collected by filtration. The precipitate was dissolved in DCM and MeOH, filtered and concentrated. The ethyl acetate layer is dried (MgSO4) and concentrated and added to the DCM/MeOH filtrate. The crude product was added to a silica gel column and was eluted with methanol in dichloromethane (0-3%). Collected fractions were concentrated to give 181 mg of a yellow solid (0.46 mmol, 51%). HRMS: 397.0969 [M+H]. For [M+H]+ mass error=0.4 mDa or 1.02 ppm.

3-(6-((4-(methylsulfonyl)piperazin-1-yl)methyl)-2-(4-nitrophenyl)thieno[3,2-d]pyrimidin-4-yl)-8-oxa-3-azabicyclo[3.2.1]octane (Scheme 45)

In a 250 mL round-bottomed flask was placed 4-(8-oxa-3-azabicyclo[3.2.1]octan-3-yl)-2-(4-nitrophenyl)thieno[3,2-d]pyrimidine-6-carbaldehyde (170 mg, 0.429 mmol) and 1-(methylsulfonyl)piperazine, TFA (179 mg, 0.643 mmol) in 1,2-dichloroethane (6 ml) to give a yellow suspension. Sodium triacetoxyborohydride (100 mg, 0.472 mmol) was added and the resulting fine suspension was stirred at room temperature for 4 h.

Stirring was continued overnight. Additional methylsulfonylpiperazine (60 mg) and NaHB(OAc)3 (40 mg) were added and the mixture was diluted with 4 mL dichloroethane and stirred overnight.

The reaction mixture was diluted with dichloromethane and washed with saturated NaHCO3. The aqueous phase was extracted with dichloromethane. The combined organic phases were dried over MgSO4, filtered and concentrated. The crude product was added to a silica gel column and was eluted with ethyl acetate in hexanes (50-100% EtOAc in hexanes, 1% NEt3) to give 125 mg of the title compound as a light yellow solid. HRMS: 545.1633 [M+H]. For [M+H]+ mass error=–0.2 mDa or –0.40 ppm.

4-(4-(8-oxa-3-azabicyclo[3.2.1]octan-3-yl)-6-((4-(methylsulfonyl)piperazin-1-yl)methyl)thieno[3,2-d]pyrimidin-2-yl)aniline (Scheme 45)

In a 250 mL round-bottomed flask was placed 3-(6-((4-(methylsulfonyl)piperazin-1-yl)methyl)-2-(4-nitrophenyl)thieno[3,2-d]pyrimidin-4-yl)-8-oxa-3-azabicyclo[3.2.1]octane (115 mg, 0.211 mmol) in isopropanol (10 ml) and DCM (10.00 ml) to give a yellow solution.

A catalytic amount of Pd on charcoal (wet) was added and the mixture was stirred under a hydrogen atmosphere for 5 h. The mixture was filtered over Celite, rinsed with DCM and concentrated to give a light yellow solid (92 mg, 85%). HRMS: 515.1893 [M+H]. For [M+H]+ mass error=–0.1 mDa or –0.18 ppm.

General Procedure for the Formation of Urea or Carbamate Compounds from 4-(4-(8-Oxa-3-azabicyclo[3.2.1]octan-3-yl)-6-((4-(methylsulfonyl)piperazin-1-yl)methyl)thieno[3,2-d]pyrimidin-2-yl)aniline (Scheme 45)

In a round-bottomed flask was placed 4-(4-(8-oxa-3-azabicyclo[3.2.1]octan-3-yl)-6-((4-(methylsulfonyl)piperazin-1-yl)methyl)thieno[3,2-d]pyrimidin-2-yl)aniline (80 mg, 0.155 mmol) and triethylamine (0.087 ml, 0.622 mmol) in DCM (3 ml) to give a yellow solution. The mixture was added dropwise to a solution of triphosgene (23.06 mg, 0.078 mmol) in 3 mL DCM in a scintillation vial. Another 3 mL of DCM was used to rinse the round-bottomed flask and transfer any remaining material to the scintillation vial. The mixture was stirred at room temperature for 5 min.

The mixture was divided over 6 vials (~1.5 mL in each vial), each vial containing amine or alcohol as specified below. The mixture was stirred at room temperature for 16 h. The crude material was concentrated and purified by HPLC (Gilson, trifluoroacetic acid buffers).

The Following Compounds were Made According to the General Procedure for Formation of Urea or Carbamate Compounds.

1-methyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea using 1 mL of a 2N solution of methylamine in THF, the title compound was obtained. MS: 572.2 [M+H], RT 1.77.

1-ethyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea:

using 1 mL of a 2N solution of ethylamine in THF, the title compound was obtained. MS: 586.2 [M+H], RT 1.83.

1-cyclopropyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea:

using cyclopropylamine (35 uL) in dichloromethane (1 mL), the title compound was obtained. MS: 598.2 [M+H], RT 1.84.

1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-phenylurea using aniline (18 uL) in dichloromethane (1 mL), the title compound was obtained. MS: 634.2 [M+H], RT 2.05.

1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-3-ylurea using 3-aminopyridine (19 mg) in dichloromethane (1 mL), the title compound was obtained. MS: 635.2 [M+H], RT 1.77.

1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-4-ylurea using 4-aminopyridine (19 mg) in dichloromethane (1 mL), the title compound was obtained. MS: 635.2 [M+H], RT 1.68.

Methyl 4-(4-(3-oxa-8-azabicyclo[3.2.1]octan-8-yl)-6-chloro-1H-pyrazolo[3,4-d]pyrimidin-1-yl)piperidine-1-carboxylate (Scheme 30)

In a 100 mL round-bottomed flask was placed 8-(1-(1-benzylpiperidin-4-yl)-6-chloro-1H-pyrazolo[3,4-d]pyrimidin-4-yl)-3-oxa-8-azabicyclo[3.2.1]octane (1.5 g, 3.42 mmol) in DCM (5 ml) to give a very fine red suspension. methyl chloroformate (1.323 ml, 17.09 mmol) was added and the mixture was stirred at room temperature for 3 h. The mixture was concentrated under reduced pressure, dissolved in DCM and washed with sat NaHCO3. The organic phase was dried over MgSO4, filtered and concentrated. The crude product was added to a silica gel column and was eluted with ethyl acetate in hexanes (40-80%). Collected fractions were concentrated to give 605 mg of a yellow solid (1.5 mmol, 44%). HRMS: 407.1596 [M+H]. For [M+H]+ mass error=0.75 ppm.

Methyl 4-(6-(4-aminophenyl)-4-(3-oxa-8-azabicyclo[3.2.1]octan-8-yl)-1H-pyrazolo[3,4-d]pyrimidin-1-yl)piperidine-1-carboxylate (Scheme 30)

In a 250 mL round-bottomed flask was placed methyl 4-(4-(3-oxa-8-azabicyclo[3.2.1]octan-8-yl)-6-chloro-1H-pyrazolo[3,4-d]pyrimidin-1-yl)piperidine-1-carboxylate (738 mg, 1.814 mmol) and 4-(4,4,5,5-tetramethyl-1,3,2-dioxaborolan-2-yl)aniline (477 mg, 2.177 mmol) in DME (20 mL) to give a yellow suspension. Na2CO3 (2M solution in water) (3.63 mL, 7.26 mmol) was added. The mixture was degassed by bubbling N2 through the solution. Pd(PPh3)4 (105 mg, 0.091 mmol) was added. The reaction was heated under reflux for 24 h. The mixture was diluted with ethyl acetate, filtered over celite and washed with a sat. solution of NaHCO3. The organic phase was dried (MgSO4) and concentrated.

The crude product was added to a silica gel column and was eluted with ethyl acetate in hexanes (55-80%) to give 514 mg of the title compound. HRMS: 464.2402. For [M+H]+ mass error=−0.2 mDa or −0.48 ppm.

General Procedure for Formation of Urea or Carbamate Compounds from methyl 4-(6-(4-aminophenyl)-4-(3-oxa-8-azabicyclo[3.2.1]octan-8-yl)-1H-pyrazolo[3,4-d]pyrimidin-1-yl)piperidine-1-carboxylate (Scheme 30)

In a round-bottomed flask was placed methyl 4-(6-(4-aminophenyl)-4-(3-oxa-8-azabicyclo[3.2.1]octan-8-yl)-1H-pyrazolo[3,4-d]pyrimidin-1-yl)piperidine-1-carboxylate (0.834 g, 1.8 mmol) and triethylamine (1.004 mL, 7.20 mmol) in DCM (7 mL) to give a brown solution. The mixture was added dropwise to a solution of triphosgene (0.267 g, 0.900 mmol) in DCM (7 mL) in a scintillation vial. Another 7 mL of DCM was used to rinse the round-bottomed flask and transfer any remaining material to the scintillation vial. The mixture was stirred at room temperature for 15 min. The mixture was divided over 14 vial, each vial containing amine or alcohol as specified below. The mixture was stirred at room temperature for 16 h. Where appropriate, Boc protective groups were removed by addition of TFA (1 mL) and stirring at room temperature for 1 h. The crude material was concentrated and purified by HPLC (Gilson, trifluoroacetic acid buffers).

The Following Compounds were Made According to the General Procedure for Formation of Urea or Carbamate Compounds:

Methyl 4-[6-(4-{[(2-hydroxyethoxy)carbonyl]amino}phenyl)-4-(3-oxa-8-azabicyclo[3.2.1]oct-8-yl)-1H-pyrazolo[3,4-d]pyrimidin-1-yl]piperidine-1-carboxylate using ethylene glycol (56 uL) in 1 mL dichloromethane, the title compound was obtained. MS: 552.2 [M+H], RT 2.13.

Methyl 4-[6-[4-[(methylcarbamoyl)amino]phenyl]-4-(3-oxa-8-azabicyclo[3.2.1]oct-8-yl)-1H-pyrazolo[3,4-d]pyrimidin-1-yl]piperidine-1-carboxylate using 1 mL of a 2N solution of methylamine in THF, the title compound was obtained. MS: 521.3 [M+H], RT 2.11.

Methyl 4-[6-[4-[(ethylcarbamoyl)amino]phenyl]-4-(3-oxa-8-azabicyclo[3.2.1]oct-8-yl)-1H-pyrazolo[3,4-d]pyrimidin-1-yl]piperidine-1-carboxylate using 1 mL of a 2N solution of ethylamine in THF, the title compound was obtained. MS: 535.3 [M+H], RT 2.17.

Methyl 4-[6-(4-{[(2-fluoroethyl)carbamoyl]amino}phenyl)-4-(3-oxa-8-azabicyclo[3.2.1]oct-8-yl)-1H-pyrazolo[3,4-d]pyrimidin-1-yl]piperidine-1-carboxylate using 2-fluoroethylamine.HCl (100 mg) in 1 mL 1N NaOH, the title compound was obtained. MS: 553.2 [M+H], RT 2.15.

Methyl 4-[6-{4-[(cyclopropylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate using cyclopropylamine (70 uL) in 1 mL dichloromethane, the title compound was obtained. MS: 547.3 [M+H], RT 2.19.

Methyl 4-[4-(3-oxa-8-azabicyclo[3.2.1]oct-8-yl)-6-{4-[(phenylcarbamoyl)amino]phenyl}-1H-pyrazolo[3,4-d]pyrimidin-1-yl]piperidine-1-carboxylate using aniline (46 uL) in 1 mL dichloromethane, the title compound was obtained. MS: 583.3 [M+H], RT 2.24.

Methyl 4-[4-(3-oxa-8-azabicyclo[3.2.1]oct-8-yl)-6-{4-[(pyridin-3-ylcarbamoyl)amino]phenyl}-1H-pyrazolo[3,4-d]pyrimidin-1-yl]piperidine-1-carboxylate using 3-aminopyridine (47 mg) in 1 mL dichloromethane, the title compound was obtained. MS: 584.3 [M+H], RT 2.00.

Methyl 4-[4-(3-oxa-8-azabicyclo[3.2.1]oct-8-yl)-6-{4-[(pyridin-4-ylcarbamoyl)amino]phenyl}-1H-pyrazolo[3,4-d]pyrimidin-1-yl]piperidine-1-carboxylate using 4-aminopyridine (47 mg) in 1 mL dichloromethane, the title compound was obtained. MS: 584.3 [M+H], RT 1.97.

Methyl 4-{6-[4-({[4-(4-methylpiperazin-1-yl)phenyl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate using 4-(4-methylpiperazin-1-yl)aniline (57 mg) in 1 mL dichloromethane, the title compound was obtained. MS: 681.4 [M+H], RT 2.03.

Methyl 4-[4-(3-oxa-8-azabicyclo[3.2.1]oct-8-yl)-6-(4-{[(4-piperazin-1-ylphenyl)carbamoyl]amino}phenyl)-1H-pyrazolo[3,4-d]pyrimidin-1-yl]piperidine-1-carboxylate using tert-butyl 4-(4-aminophenyl)piperazine-1-carboxylate (83 mg) in 1 mL dichloromethane, the title compound was obtained. MS: 667.3 [M+H], RT 2.00.

Methyl 4-{6-[4-({[6-(4-methylpiperazin-1-yl)pyridin-3-yl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate using 6-(4-methylpiperazin-1-yl)pyridin-3-amine (58 mg) in 1 mL dichloromethane, the title compound was obtained. MS: 682.4 [M+H], RT 1.97.

Methyl 4-[6-{4-[({4-[(dimethylamino)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate using 4-((dimethylamino)methyl)aniline (45 mg) in 1 mL dichloromethane, the title compound was obtained. MS: 640.3 [M+H], RT 2.03.

Methyl 4-[6-{4-[({4-[(4-methylpiperazin-1-yl)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate using 4-((4-methylpiperazin-1-yl)methyl)aniline (62 mg) in 1 mL dichloromethane, the title compound was obtained. MS: 695.4 [M+H], RT 1.98.

Methyl 4-[6-{4-[({4-[2-(dimethylamino)ethoxy]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate using 4-(2-(dimethylamino)ethoxy)aniline in 0.6 mL 1N NaOH, the title compound was obtained. MS: 670.3 [M+H], RT 2.03.

The Following Compounds can be Made by Adaptation of the Procedures Described Above:

2-hydroxyethyl 4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenylcarbamate 1-methyl-3-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)urea 1-(4-(2-(dimethylamino)ethoxy)phenyl)-3-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)urea 1-cyclopropyl-3-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)urea 1-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(4-(4-methylpiperazin-1-yl)phenyl)urea 1-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(pyridin-4-yl)urea 1-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(pyridin-3-yl)urea 1-(4-(2,2-dimethylhydrazinecarbonyl)phenyl)-3-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)urea 4-(3-(4-(4-(7-methyl-3-oxa-7,9-diazabicyclo[3.3.1]nonan-9-yl)-1-(2,2,2-trifluoroethyl)-1H-pyrazolo[3,4-d]pyrimidin-6-yl)phenyl)ureido)benzamide 1-(4-(4-(6-fluoro-8-oxa-3-azabicyclo[3.2.1]octan-3-yl)-1-(2,2,2-trifluoroethyl)-1H-pyrazolo[3,4-d]pyrimidin-6-yl)phenyl)-3-methylurea 1-(4-(4-(6-fluoro-8-oxa-3-azabicyclo[3.2.1]octan-3-yl)-1-(2,2,2-trifluoroethyl)-1H-pyrazolo[3,4-d]pyrimidin-6-yl)phenyl)-3-(4-(4-methylpiperazin-1-yl)phenyl)urea 1-(4-(2-(dimethylamino)ethoxy)phenyl)-3-(4-(4-(6-fluoro-8-oxa-3-azabicyclo[3.2.1]octan-3-yl)-1-(2,2,2-trifluoroethyl)-1H-pyrazolo[3,4-d]pyrimidin-6-yl)phenyl)urea 1-(4-(4-(6-fluoro-8-oxa-3-azabicyclo[3.2.1]octan-3-yl)-1-(2,2,2-trifluoroethyl)-1H-pyrazolo[3,4-d]pyrimidin-6-yl)phenyl)-3-(pyridin-4-yl)urea 1-(4-(4-(6-fluoro-8-oxa-3-azabicyclo[3.2.1]octan-3-yl)-1-(2,2,2-trifluoroethyl)-1H-pyrazolo[3,4-d]pyrimidin-6-yl)phenyl)-3-(pyridin-3-yl)urea 2-hydroxyethyl 4-(4-(6-fluoro-8-oxa-3-azabicyclo[3.2.1]octan-3-yl)-1-(2,2,2-trifluoroethyl)-1H-pyrazolo[3,4-d]pyrimidin-6-yl)phenylcarbamate 1-cyclopropyl-3-(4-(4-(6-fluoro-8-oxa-3-azabicyclo[3.2.1]
 octan-3-yl)-1-(2,2,2-trifluoroethyl)-1H-pyrazolo[3,4-d]
 pyrimidin-6-yl)phenyl)urea
1-(4-(4-(6-fluoro-8-oxa-3-azabicyclo[3.2.1]octan-3-yl)-1-
 (2,2,2-trifluoroethyl)-1H-pyrazolo[3,4-d]pyrimidin-6-yl)
 phenyl)-3-methylurea
1-(4-(4-(6-fluoro-8-oxa-3-azabicyclo[3.2.1]octan-3-yl)-1-
 (2,2,2-trifluoroethyl)-1H-pyrazolo[3,4-d]pyrimidin-6-yl)
 phenyl)-3-(4-(4-methylpiperazin-1-yl)phenyl)urea
1-(4-(2-(dimethylamino)ethoxy)phenyl)-3-(4-(4-(6-fluoro-
 8-oxa-3-azabicyclo[3.2.1]octan-3-yl)-1-(2,2,2-trifluoro-
 ethyl)-1H-pyrazolo[3,4-d]pyrimidin-6-yl)phenyl)urea
1-(4-(4-(6-fluoro-8-oxa-3-azabicyclo[3.2.1]octan-3-yl)-1-
 (2,2,2-trifluoroethyl)-1H-pyrazolo[3,4-d]pyrimidin-6-yl)
 phenyl)-3-(pyridin-4-yl)urea
1-(4-(4-(6-fluoro-8-oxa-3-azabicyclo[3.2.1]octan-3-yl)-1-
 (2,2,2-trifluoroethyl)-1H-pyrazolo[3,4-d]pyrimidin-6-yl)
 phenyl)-3-(pyridin-3-yl)urea
2-hydroxyethyl 4-(4-(6-fluoro-8-oxa-3-azabicyclo[3.2.1]oc-
 tan-3-yl)-1-(2,2,2-trifluoroethyl)-1H-pyrazolo[3,4-d]py-
 rimidin-6-yl)phenylcarbamate
1-cyclopropyl-3-(4-(4-(6-fluoro-8-oxa-3-azabicyclo[3.2.1]
 octan-3-yl)-1-(2,2,2-trifluoroethyl)-1H-pyrazolo[3,4-d]
 pyrimidin-6-yl)phenyl)urea
1-(4-(4-(6-fluoro-3-oxa-8-azabicyclo[3.2.1]octan-8-yl)-1-
 (2,2,2-trifluoroethyl)-1H-pyrazolo[3,4-d]pyrimidin-6-yl)
 phenyl)-3-(4-(4-methylpiperazin-1-yl)phenyl)urea
1-(4-(4-(6-fluoro-3-oxa-8-azabicyclo[3.2.1]octan-8-yl)-1-
 (2,2,2-trifluoroethyl)-1H-pyrazolo[3,4-d]pyrimidin-6-yl)
 phenyl)-3-methylurea
1-(4-(2-(dimethylamino)ethoxy)phenyl)-3-(4-(4-(6-fluoro-
 3-oxa-8-azabicyclo[3.2.1]octan-8-yl)-1-(2,2,2-trifluoro-
 ethyl)-1H-pyrazolo[3,4-d]pyrimidin-6-yl)phenyl)urea
1-(4-(4-(6-fluoro-3-oxa-8-azabicyclo[3.2.1]octan-8-yl)-1-
 (2,2,2-trifluoroethyl)-1H-pyrazolo[3,4-d]pyrimidin-6-yl)
 phenyl)-3-(pyridin-4-yl)urea
1-(4-(4-(6-fluoro-3-oxa-8-azabicyclo[3.2.1]octan-8-yl)-1-
 (2,2,2-trifluoroethyl)-1H-pyrazolo[3,4-d]pyrimidin-6-yl)
 phenyl)-3-(pyridin-3-yl)urea
2-hydroxyethyl 4-(4-(6-fluoro-3-oxa-8-azabicyclo[3.2.1]oc-
 tan-8-yl)-1-(2,2,2-trifluoroethyl)-1H-pyrazolo[3,4-d]py-
 rimidin-6-yl)phenylcarbamate
1-cyclopropyl-3-(4-(4-(6-fluoro-3-oxa-8-azabicyclo[3.2.1]
 octan-8-yl)-1-(2,2,2-trifluoroethyl)-1H-pyrazolo[3,4-d]
 pyrimidin-6-yl)phenyl)urea
1-(4-(4-(8-oxa-3-azabicyclo[3.2.1]octan-3-yl)-1-(2,2-dif-
 luoroethyl)-1H-pyrazolo[3,4-d]pyrimidin-6-yl)phenyl)-3-
 (4-(4-methylpiperazin-1-yl)phenyl)urea
1-(4-(4-(8-oxa-3-azabicyclo[3.2.1]octan-3-yl)-1-(2,2-dif-
 luoroethyl)-1H-pyrazolo[3,4-d]pyrimidin-6-yl)phenyl)-3-
 (4-(2-(dimethylamino)ethoxy)phenyl)urea
1-(4-(4-(8-oxa-3-azabicyclo[3.2.1]octan-3-yl)-1-(2,2-dif-
 luoroethyl)-1H-pyrazolo[3,4-d]pyrimidin-6-yl)phenyl)-3-
 (pyridin-4-yl)urea
1-(4-(4-(8-oxa-3-azabicyclo[3.2.1]octan-3-yl)-1-(2,2-dif-
 luoroethyl)-1H-pyrazolo[3,4-d]pyrimidin-6-yl)phenyl)-3-
 (pyridin-3-yl)urea
2-hydroxyethyl 4-(4-(8-oxa-3-azabicyclo[3.2.1]octan-3-yl)-
 1-(2,2-difluoroethyl)-1H-pyrazolo[3,4-d]pyrimidin-6-yl)
 phenylcarbamate
1-(4-(4-(8-oxa-3-azabicyclo[3.2.1]octan-3-yl)-1-(2,2-dif-
 luoroethyl)-1H-pyrazolo[3,4-d]pyrimidin-6-yl)phenyl)-3-
 cyclopropylurea
1-(4-(4-(8-oxa-3-azabicyclo[3.2.1]octan-3-yl)-1-(2,2-dif-
 luoroethyl)-1H-pyrazolo[3,4-d]pyrimidin-6-yl)phenyl)-3-
 methylurea
1-(4-(4-(3-oxa-9-azabicyclo[3.3.1]nonan-9-yl)-1-(2,2,2-trif-
 luoroethyl)-1H-pyrazolo[3,4-d]pyrimidin-6-yl)phenyl)-3-
 cyclopropylurea
1-(4-(4-(3-oxa-9-azabicyclo[3.3.1]nonan-9-yl)-1-(2,2,2-trif-
 luoroethyl)-1H-pyrazolo[3,4-d]pyrimidin-6-yl)phenyl)-3-
 (4-(4-methylpiperazin-1-yl)phenyl)urea
1-(4-(4-(3-oxa-9-azabicyclo[3.3.1]nonan-9-yl)-1-(2,2,2-trif-
 luoroethyl)-1H-pyrazolo[3,4-d]pyrimidin-6-yl)phenyl)-3-
 (pyridin-4-yl)urea
1-(4-(4-(3-oxa-9-azabicyclo[3.3.1]nonan-9-yl)-1-(2,2,2-trif-
 luoroethyl)-1H-pyrazolo[3,4-d]pyrimidin-6-yl)phenyl)-3-
 (pyridin-3-yl)urea
1-(4-(4-(3-oxa-9-azabicyclo[3.3.1]nonan-9-yl)-1-(2,2,2-trif-
 luoroethyl)-1H-pyrazolo[3,4-d]pyrimidin-6-yl)phenyl)-3-
 (4-(2,2-dimethylhydrazinecarbonyl)phenyl)urea
4-(3-(4-(4-(3-oxa-9-azabicyclo[3.3.1]nonan-9-yl)-1-(2,2,2-
 trifluoroethyl)-1H-pyrazolo[3,4-d]pyrimidin-6-yl)phe-
 nyl)ureido)benzamide
1-(4-(4-(3,7-dioxa-9-azabicyclo[3.3.1]nonan-9-yl)-1-(2,2,2-
 trifluoroethyl)-1H-pyrazolo[3,4-d]pyrimidin-6-yl)phe-
 nyl)-3-cyclopropylurea
1-(4-(4-(3,7-dioxa-9-azabicyclo[3.3.1]nonan-9-yl)-1-(2,2,2-
 trifluoroethyl)-1H-pyrazolo[3,4-d]pyrimidin-6-yl)phe-
 nyl)-3-(4-(4-methylpiperazin-1-yl)phenyl)urea
1-(4-(4-(3,7-dioxa-9-azabicyclo[3.3.1]nonan-9-yl)-1-(2,2,2-
 trifluoroethyl)-1H-pyrazolo[3,4-d]pyrimidin-6-yl)phe-
 nyl)-3-(pyridin-4-yl)urea
1-(4-(4-(3,7-dioxa-9-azabicyclo[3.3.1]nonan-9-yl)-1-(2,2,2-
 trifluoroethyl)-1H-pyrazolo[3,4-d]pyrimidin-6-yl)phe-
 nyl)-3-(pyridin-3-yl)urea
1-(4-(4-(3,7-dioxa-9-azabicyclo[3.3.1]nonan-9-yl)-1-(2,2,2-
 trifluoroethyl)-1H-pyrazolo[3,4-d]pyrimidin-6-yl)phe-
 nyl)-3-(4-(2,2-dimethylhydrazinecarbonyl)phenyl)urea
4-(3-(4-(4-(3,7-dioxa-9-azabicyclo[3.3.1]nonan-9-yl)-1-(2,
 2,2-trifluoroethyl)-1H-pyrazolo[3,4-d]pyrimidin-6-yl)
 phenyl)ureido)benzamide
tert-butyl 9-(6-(4-(3-cyclopropylureido)phenyl)-1-(2,2,2-tri-
 fluoroethyl)-1H-pyrazolo[3,4-d]pyrimidin-4-yl)-3-oxa-7,
 9-diazabicyclo[3.3.1]nonane-7-carboxylate
tert-butyl 9-(6-(4-(3-(4-(4-methylpiperazin-1-yl)phenyl)ure-
 ido)phenyl)-1-(2,2,2-trifluoroethyl)-1H-pyrazolo[3,4-d]
 pyrimidin-4-yl)-3-oxa-7,9-diazabicyclo[3.3.1]nonane-7-
 carboxylate
tert-butyl 9-(6-(4-(3-pyridin-4-ylureido)phenyl)-1-(2,2,2-tri-
 fluoroethyl)-1H-pyrazolo[3,4-d]pyrimidin-4-yl)-3-oxa-7,
 9-diazabicyclo[3.3.1]nonane-7-carboxylate
tert-butyl 9-(6-(4-(3-pyridin-3-ylureido)phenyl)-1-(2,2,2-tri-
 fluoroethyl)-1H-pyrazolo[3,4-d]pyrimidin-4-yl)-3-oxa-7,
 9-diazabicyclo[3.3.1]nonane-7-carboxylate
tert-butyl 9-(6-(4-(3-(4-(2,2-dimethylhydrazinecarbonyl)
 phenyl)ureido)phenyl)-1-(2,2,2-trifluoroethyl)-1H-pyra-
 zolo[3,4-d]pyrimidin-4-yl)-3-oxa-7,9-diazabicyclo[3.3.1]
 nonane-7-carboxylate
tert-butyl 9-(6-(4-(3-(4-carbamoylphenyl)ureido)phenyl)-1-
 (2,2,2-trifluoroethyl)-1H-pyrazolo[3,4-d]pyrimidin-4-yl)-
 3-oxa-7,9-diazabicyclo[3.3.1]nonane-7-carboxylate
1-(4-(4-(3-oxa-7,9-diazabicyclo[3.3.1]nonan-9-yl)-1-(2,2,2-
 trifluoroethyl)-1H-pyrazolo[3,4-d]pyrimidin-6-yl)phe-
 nyl)-3-cyclopropylurea
1-(4-(4-(3-oxa-7,9-diazabicyclo[3.3.1]nonan-9-yl)-1-(2,2,2-
 trifluoroethyl)-1H-pyrazolo[3,4-d]pyrimidin-6-yl)phe-
 nyl)-3-(4-(4-methylpiperazin-1-yl)phenyl)urea
1-(4-(4-(3-oxa-7,9-diazabicyclo[3.3.1]nonan-9-yl)-1-(2,2,2-
 trifluoroethyl)-1H-pyrazolo[3,4-d]pyrimidin-6-yl)phe-
 nyl)-3-(pyridin-4-yl)urea 1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(pyridin-3-yl)urea
1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(4-(2,2-dimethylhydrazinecarbonyl)phenyl)urea
4-(3-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)ureido)benzamide
1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-cyclopropylurea
1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(4-(4-methylpiperazin-1-yl)phenyl)urea
1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(pyridin-4-yl)urea
1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(pyridin-3-yl)urea
1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(4-(2,2-dimethylhydrazinecarbonyl)phenyl)urea
4-(3-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)ureido)benzamide
N-(4-(4-(8-oxa-3-azabicyclo[3.2.1]octan-3-yl)-1-(2,2,2-trifluoroethyl)-1H-pyrazolo[3,4-d]pyrimidin-6-yl)phenyl)-4-hydroxybutanamide
N-(4-(4-(8-oxa-3-azabicyclo[3.2.1]octan-3-yl)-1-(2,2-difluoroethyl)-1H-pyrazolo[3,4-d]pyrimidin-6-yl)phenyl)-4-hydroxybutanamide
N-(4-(4-(8-oxa-3-azabicyclo[3.2.1]octan-3-yl)-1-(2-fluoroethyl)-1H-pyrazolo[3,4-d]pyrimidin-6-yl)phenyl)-4-hydroxybutanamide
N-(4-(4-(8-oxa-3-azabicyclo[3.2.1]octan-3-yl)-1-ethyl-1H-pyrazolo[3,4-d]pyrimidin-6-yl)phenyl)-4-hydroxybutanamide
N-(4-(4-(3-oxa-8-azabicyclo[3.2.1]octan-8-yl)-1-ethyl-1H-pyrazolo[3,4-d]pyrimidin-6-yl)phenyl)-4-hydroxybutanamide
N-(4-(4-(3-oxa-8-azabicyclo[3.2.1]octan-8-yl)-1-(2-fluoroethyl)-1H-pyrazolo[3,4-d]pyrimidin-6-yl)phenyl)-4-hydroxybutanamide
N-(4-(4-(3-oxa-8-azabicyclo[3.2.1]octan-8-yl)-1-(2,2-difluoroethyl)-1H-pyrazolo[3,4-d]pyrimidin-6-yl)phenyl)-4-hydroxybutanamide
N-(4-(4-(3-oxa-8-azabicyclo[3.2.1]octan-8-yl)-1-(2,2,2-trifluoroethyl)-1H-pyrazolo[3,4-d]pyrimidin-6-yl)phenyl)-4-hydroxybutanamide The following compounds can be prepared according to the general procedure for formation of urea or carbamate compounds, starting from 4-(4-(3-oxa-8-azabicyclo[3.2.1]octan-8-yl)-6-((4-(methylsulfonyl)piperazin-1-yl)methyl)thieno[3,2-d]pyrimidin-2-yl)aniline instead of 4-(4-(8-oxa-3-azabicyclo[3.2.1]octan-3-yl)-6-((4-(methylsulfonyl)piperazin-1-yl)methyl)thieno[3,2-d]pyrimidin-2-yl)aniline:

1-methyl-3-{4-[6-{[4-(methylsulfonyl)piperazin-1-yl]methyl}-4-(3-oxa-8-azabicyclo[3.2.1]octan-8-yl)thieno[3,2-d]pyrimidin-2-yl]phenyl}urea using 1 mL of a 2N solution of methylamine in THF, the title compound is obtained.

1-ethyl-3-{4-[6-{[4-(methylsulfonyl)piperazin-1-yl]methyl}-4-(3-oxa-8-azabicyclo[3.2.1]octan-8-yl)thieno[3,2-d]pyrimidin-2-yl]phenyl}urea:

using 1 mL of a 2N solution of ethylamine in THF, the title compound is obtained.

1-cyclopropyl-3-{4-[6-{[4-(methylsulfonyl)piperazin-1-yl]methyl}-4-(3-oxa-8-azabicyclo[3.2.1]octan-8-yl)thieno[3,2-d]pyrimidin-2-yl]phenyl}urea:

using cyclopropylamine (35 uL) in dichloromethane (1 mL), the title compound is obtained.

1-{4-[6-{[4-(methylsulfonyl)piperazin-1-yl]methyl}-4-(3-oxa-8-azabicyclo[3.2.1]octan-8-yl)thieno[3,2-d]pyrimidin-2-yl]phenyl}-3-phenylurea using aniline (18 uL) in dichloromethane (1 mL), the title compound is obtained.

1-{4-[6-{[4-(methylsulfonyl)piperazin-1-yl]methyl}-4-(3-oxa-8-azabicyclo[3.2.1]octan-8-yl)thieno[3,2-d]pyrimidin-2-yl]phenyl}-3-pyridin-3-ylurea using 3-aminopyridine (19 mg) in dichloromethane (1 mL), the title compound is obtained.

1-{4-[6-{[4-(methylsulfonyl)piperazin-1-yl]methyl}-4-(3-oxa-8-azabicyclo[3.2.1]octan-8-yl)thieno[3,2-d]pyrimidin-2-yl]phenyl}-3-pyridin-4-ylurea using 4-aminopyridine (19 mg) in dichloromethane (1 mL), the title compound is obtained.

The compounds shown in Table 1, below, were prepared according to the above procedures:

TABLE 1

| | 1H-Pyrazolo[3,4-d]pyrimidine compounds | | |
|---|---|---|---|
| Example | Name | m/z (M + H) | LC/MS (RT min) |
| 1 | 1-methyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 462.2 | 2.23 |
| 2 | methyl {4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate | 463.2 | 2.42 |
| 3 | 1-ethyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 476.2 | 2.31 |

TABLE 1-continued

1H-Pyrazolo[3,4-d]pyrimidine compounds

| Example | Name | m/z (M + H) | LC/MS (RT min) |
|---|---|---|---|
| 4 | 1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-3-ylurea | 525.2 | 2.16 |
| 5 | 1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea | 525.2 | 2.08 |
| 6 | 1-(2-fluoroethyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 494.2 | 2.27 |
| 7 | methyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 521.3 | 2.17 |
| 8 | tert-butyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 563.3 | 2.4 |
| 9 | methyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 535.3 | 2.24 |
| 10 | methyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 553.3 | 2.21 |
| 11 | methyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate | 583.3 | 2.47 |
| 12 | methyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 547.3 | 2.26 |
| 13 | methyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate | 584.3 | 2.03 |
| 14 | methyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate | 584.3 | 1.97 |
| 15 | 1-ethyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea | 568.3 | 1.8 |
| 16 | 1-(2-fluoroethyl)-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea | 586.3 | 1.79 |
| 17 | 1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-phenylurea | 616.3 | 2.01 |
| 18 | 1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-3-ylurea | 617.3 | 1.68 |
| 19 | 1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-4-ylurea | 617.3 | 1.64 |
| 20 | tert-butyl4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 577.3 | 2.44 |
| 21 | tert-butyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 595.3 | 2.41 |
| 22 | tert-butyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 589.3 | 2.46 |
| 23 | tert-butyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate | 625.3 | 2.63 |
| 24 | tert-butyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate | 626.3 | 2.27 |
| 25 | tert-butyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate | 626.3 | 2.16 |
| 26 | 1-methyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea | 545.2 | 2.2 |
| 27 | 1-methyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea | 554.3 | 1.75 |
| 28 | 1-ethyl-3-{4-[4-(8-oxa-3-azabicyclo[3.2.1]oct-3-yl)-1-piperidin-4-yl-1H-pyrazolo[3,4-d]pyrimidin-6-yl]phenyl}urea | 477.3 | 1.73 |

TABLE 1-continued

1H-Pyrazolo[3,4-d]pyrimidine compounds

| Example | Name | m/z (M + H) | LC/MS (RT min) |
|---|---|---|---|
| 29 | 1-{4-[4-(8-oxa-3-azabicyclo[3.2.1]oct-3-yl)-1-piperidin-4-yl-1H-pyrazolo[3,4-d]pyrimidin-6-yl]phenyl}-3-phenylurea | 525.3 | 1.93 |
| 30 | 4-{[1-(1-benzylpiperidin-4-yl)-4-(8-oxa-3-azabicyclo[3.2.1]oct-3-yl)-1H-pyrazolo[3,4-d]pyrimidin-6-yl]amino}phenol | 512.3 | 1.8 |
| 31 | ethyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 549.3 | 2.3 |
| 32 | ethyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 567.3 | 2.27 |
| 33 | ethyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate | 597.3 | 2.51 |
| 34 | ethyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate | 598.3 | 2.15 |
| 35 | ethyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate | 598.3 | 2.05 |
| 36 | ethyl 4-[6-(4-{[(1-methylpiperidin-4-yl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 618.3 | 1.97 |
| 37 | ethyl 4-{6-[4-({[1-(tert-butoxycarbonyl)piperidin-4-yl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 704.4 | 2.53 |
| 38 | ethyl 4-{6-[4-({[3-(methylamino)propyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 592.3 | 1.93 |
| 39 | ethyl 4-[4-(8-oxa-3-azabicyclo[3.2.1]oct-3-yl)-6-{4-[(1H-pyrazol-5-ylcarbamoyl)amino]phenyl}-1H-pyrazolo[3,4-d]pyrimidin-1-yl]piperidine-1-carboxylate | 587.3 | 2.44 |
| 40 | 1-{4-[1-ethyl-4-(8-oxa-3-azabicyclo[3.2.1]oct-3-yl)-1H-pyrazolo[3,4-d]pyrimidin-6-yl]phenyl}-3-methylurea | 408.2 | 2.07 |
| 41 | 1-ethyl-3-{4-[1-ethyl-4-(8-oxa-3-azabicyclo[3.2.1]oct-3-yl)-1H-pyrazolo[3,4-d]pyrimidin-6-yl]phenyl}urea | 422.2 | 2.15 |
| 42 | 1-{4-[1-ethyl-4-(8-oxa-3-azabicyclo[3.2.1]oct-3-yl)-1H-pyrazolo[3,4-d]pyrimidin-6-yl]phenyl}-3-(2-fluoroethyl)urea | 440.2 | 2.12 |
| 43 | 1-cyclopropyl-3-{4-[1-ethyl-4-(8-oxa-3-azabicyclo[3.2.1]oct-3-yl)-1H-pyrazolo[3,4-d]pyrimidin-6-yl]phenyl}urea | 434.2 | 2.18 |
| 44 | 1-{4-[1-ethyl-4-(8-oxa-3-azabicyclo[3.2.1]oct-3-yl)-1H-pyrazolo[3,4-d]pyrimidin-6-yl]phenyl}-3-(2-hydroxyethyl)urea | 438.2 | 1.97 |
| 45 | 2-hydroxyethyl {4-[1-ethyl-4-(8-oxa-3-azabicyclo[3.2.1]oct-3-yl)-1H-pyrazolo[3,4-d]pyrimidin-6-yl]phenyl}carbamate | 439.2 | 2.1 |
| 46 | 1-{4-[1-ethyl-4-(8-oxa-3-azabicyclo[3.2.1]oct-3-yl)-1H-pyrazolo[3,4-d]pyrimidin-6-yl]phenyl}-3-phenylurea | 470.2 | 2.41 |
| 47 | 1-{4-[1-ethyl-4-(8-oxa-3-azabicyclo[3.2.1]oct-3-yl)-1H-pyrazolo[3,4-d]pyrimidin-6-yl]phenyl}-3-pyridin-3-ylurea | 471.2 | 1.94 |
| 48 | 1-{4-[1-ethyl-4-(8-oxa-3-azabicyclo[3.2.1]oct-3-yl)-1H-pyrazolo[3,4-d]pyrimidin-6-yl]phenyl}-3-pyridin-4-ylurea | 471.2 | 1.89 |
| 49 | 1-{4-[1-ethyl-4-(8-oxa-3-azabicyclo[3.2.1]oct-3-yl)-1H-pyrazolo[3,4-d]pyrimidin-6-yl]phenyl}-3-[3-(methylamino)propyl]urea | 465.3 | 1.77 |
| 50 | 1-methyl-3-{4-[1-methyl-4-(8-oxa-3-azabicyclo[3.2.1]oct-3-yl)-1H-pyrazolo[3,4-d]pyrimidin-6-yl]phenyl}urea | 394.2 | 1.98 |
| 51 | 1-ethyl-3-{4-[1-methyl-4-(8-oxa-3-azabicyclo[3.2.1]oct-3-yl)-1H-pyrazolo[3,4-d]pyrimidin-6-yl]phenyl}urea | 408.2 | 2.07 |
| 52 | 1-(2-fluoroethyl)-3-{4-[1-methyl-4-(8-oxa-3-azabicyclo[3.2.1]oct-3-yl)-1H-pyrazolo[3,4-d]pyrimidin-6-yl]phenyl}urea | 426.2 | 2.03 |
| 53 | 1-cyclopropyl-3-{4-[1-methyl-4-(8-oxa-3-azabicyclo[3.2.1]oct-3-yl)-1H-pyrazolo[3,4-d]pyrimidin-6-yl]phenyl}urea | 420.2 | 2.09 |
| 54 | 1-(2-hydroxyethyl)-3-{4-[1-methyl-4-(8-oxa-3-azabicyclo[3.2.1]oct-3-yl)-1H-pyrazolo[3,4-d]pyrimidin-6-yl]phenyl}urea | 424.2 | 1.88 |
| 55 | 1-{4-[1-methyl-4-(8-oxa-3-azabicyclo[3.2.1]oct-3-yl)-1H-pyrazolo[3,4-d]pyrimidin-6-yl]phenyl}-3-phenylurea | 456.2 | 2.35 |
| 56 | 1-{4-[1-methyl-4-(8-oxa-3-azabicyclo[3.2.1]oct-3-yl)-1H-pyrazolo[3,4-d]pyrimidin-6-yl]phenyl}-3-pyridin-3-ylurea | 457.2 | 1.86 |
| 57 | 1-{4-[1-methyl-4-(8-oxa-3-azabicyclo[3.2.1]oct-3-yl)-1H-pyrazolo[3,4-d]pyrimidin-6-yl]phenyl}-3-pyridin-4-ylurea | 457.2 | 1.82 |

TABLE 1-continued

1H-Pyrazolo[3,4-d]pyrimidine compounds

| Example | Name | m/z (M + H) | LC/MS (RT min) |
|---|---|---|---|
| 58 | 1-[2-(dimethylamino)ethyl]-3-{4-[1-methyl-4-(8-oxa-3-azabicyclo[3.2.1]oct-3-yl)-1H-pyrazolo[3,4-d]pyrimidin-6-yl]phenyl}urea | 451.2 | 1.7 |
| 59 | 1-[3-(dimethylamino)propyl]-3-{4-[1-methyl-4-(8-oxa-3-azabicyclo[3.2.1]oct-3-yl)-1H-pyrazolo[3,4-d]pyrimidin-6-yl]phenyl}urea | 465.3 | 1.72 |
| 60 | methyl {4-[1-methyl-4-(8-oxa-3-azabicyclo[3.2.1]oct-3-yl)-1H-pyrazolo[3,4-d]pyrimidin-6-yl]phenyl}carbamate | 395.2 | 2.21 |
| 61 | 3-[1-methyl-4-(8-oxa-3-azabicyclo[3.2.1]oct-3-yl)-1H-pyrazolo[3,4-d]pyrimidin-6-yl]phenol | 338.2 | 2.04 |
| 62 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-methylurea | 520.3 | 2.19 |
| 63 | 1-methyl-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea | 476.2 | 2.06 |
| 64 | 1-{4-[1-(4-hydroxycyclohexyl)-4-(8-oxa-3-azabicyclo[3.2.1]oct-3-yl)-1H-pyrazolo[3,4-d]pyrimidin-6-yl]phenyl}-3-methylurea | 478.2 | 2 |
| 65 | isopropyl 4-[6-(4-aminophenyl)-4-(8-oxa-3-azabicyclo[3.2.1]oct-3-yl)-1H-pyrazolo[3,4-d]pyrimidin-1-yl]piperidine-1-carboxylate | 492.3 | 2.31 |
| 66 | isopropyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 549.3 | 2.33 |
| 67 | isopropyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 563.3 | 2.37 |
| 68 | isopropyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 581.3 | 2.35 |
| 69 | isopropyl 4-[6-(4-{[(2-hydroxyethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 579.3 | 2.21 |
| 70 | isopropyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate | 575.3 | 2.39 |
| 71 | isopropyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate | 611.3 | 2.59 |
| 72 | isopropyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate | 612.3 | 2.18 |
| 73 | isopropyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate | 612.3 | 2.1 |
| 74 | isopropyl 4-[6-{4-[(methoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate | 550.3 | 2.51 |
| 75 | 3-[1-ethyl-4-(8-oxa-3-azabicyclo[3.2.1]oct-3-yl)-1H-pyrazolo[3,4-d]pyrimidin-6-yl]phenol | 352.2 | 2.11 |
| 76 | 1-ethyl-6-(1H-indol-5-yl)-4-(8-oxa-3-azabicyclo[3.2.1]oct-3-yl)-1H-pyrazolo[3,4-d]pyrimidine | 375.1 | 2.21 |
| 77 | 1-{4-[1-benzyl-4-(8-oxa-3-azabicyclo[3.2.1]oct-3-yl)-1H-pyrazolo[3,4-d]pyrimidin-6-yl]phenyl}-3-methylurea | 470.2 | 2.25 |
| 78 | 1-{4-[1-benzyl-4-(8-oxa-3-azabicyclo[3.2.1]oct-3-yl)-1H-pyrazolo[3,4-d]pyrimidin-6-yl]phenyl}-3-ethylurea | 484.2 | 2.31 |
| 79 | 1-{4-[1-benzyl-4-(8-oxa-3-azabicyclo[3.2.1]oct-3-yl)-1H-pyrazolo[3,4-d]pyrimidin-6-yl]phenyl}-3-pyridin-4-ylurea | 533.2 | 2.04 |
| 80 | 4-[1-(1-isobutyrylpiperidin-4-yl)-4-(8-oxa-3-azabicyclo[3.2.1]oct-3-yl)-1H-pyrazolo[3,4-d]pyrimidin-6-yl]aniline | 476.3 | 2.09 |
| 81 | 4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]aniline | 463.2 | 2.09 |
| 82 | 1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-methylurea | 533.3 | 2.13 |
| 83 | 1-ethyl-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea | 547.3 | 2.2 |
| 84 | 1-(2-hydroxyethyl)-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea | 563.3 | 2.04 |

TABLE 1-continued

1H-Pyrazolo[3,4-d]pyrimidine compounds

| Example | Name | m/z (M + H) | LC/MS (RT min) |
|---|---|---|---|
| 85 | 1-(2-fluoroethyl)-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea | 565.3 | 2.17 |
| 86 | 1-cyclopropyl-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea | 559.3 | 2.22 |
| 87 | 1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-phenylurea | 595.3 | 2.41 |
| 88 | 1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-3-ylurea | 596.3 | 2.02 |
| 89 | 1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-4-ylurea | 596.3 | 1.98 |
| 90 | 1-{4-[4-(8-oxa-3-azabicyclo[3.2.1]oct-3-yl)-1-(tetrahydro-2H-pyran-2-yl)-1H-pyrazolo[3,4-d]pyrimidin-6-yl]phenyl}-3-pyridin-3-ylurea | 527.2 | 1.94 |
| 91 | 1-{4-[4-(8-oxa-3-azabicyclo[3.2.1]oct-3-yl)-1H-pyrazolo[3,4-d]pyrimidin-6-yl]phenyl}-3-pyridin-3-ylurea | 443.2 | 1.65 |
| 92 | {4-[1-tert-butyl-4-(8-oxa-3-aza-bicyclo[3.2.1]oct-3-yl)-1H-pyrazolo[3,4-d]pyrimidin-6-yl]-phenyl}-carbamic acid methyl ester | 437.2 | 2.44 |
| 93 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-methyl-urea | 436.2 | 2.25 |
| 94 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-ethyl-urea | 450.3 | 2.30 |
| 95 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-(2-fluoro-ethyl)-urea | 468.2 | 2.28 |
| 96 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-cyclopropyl-urea | 462.3 | 2.32 |
| 97 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-(2-hydroxy-ethyl)-urea | 466.2 | 2.15 |
| 98 | {4-[1-tert-butyl-4-(8-oxa-3-aza-bicyclo[3.2.1]oct-3-yl)-1H-pyrazolo[3,4-d]pyrimidin-6-yl]-phenyl}-carbamic acid 2-hydroxy-ethyl ester | 467.2 | 2.26 |
| 99 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-phenyl-urea | 498.3 | 2.51 |
| 100 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-pyridin-3-yl-urea | 499.2 | 2.13 |
| 101 | 1-{4-[1-tert-butyl-4-(8-oxa-3-aza-bicyclo[3.2.1]oct-3-yl)-1H-pyrazolo[3,4-d]pyrimidin-6-yl]-phenyl}-3-pyridin-4-yl-urea | 499.2 | 2.06 |
| 102 | 3-[4-(8-oxa-3-azabicyclo[3.2.1]oct-3-yl)-1-phenyl-1H-pyrazolo[3,4-d]pyrimidin-6-yl]phenol | 400.1777 | |
| 103 | ethyl 4-[4-(8-oxa-3-azabicyclo[3.2.1]oct-3-yl)-6-{4-[(piperidin-4-ylcarbamoyl)amino]phenyl}-1H-pyrazolo[3,4-d]pyrimidin-1-yl]piperidine-1-carboxylate | 604.3356 | |
| 104 | 1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea | 525.2 | 2.08 |
| 105 | 1-(4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea | 520.3 | 2.19 |
| 106 | 1-(4-(4-(8-oxa-3-azabicyclo[3.2.1]octan-3-yl)-1-(4-oxocyclohexyl)-1H-pyrazolo[3,4-d]pyrimidin-6-yl)phenyl)-3-methylurea | 476.2 | 2.06 |
| 107 | 1-(4-(4-(8-oxa-3-azabicyclo[3.2.1]octan-3-yl)-1-(4-hydroxycyclohexyl)-1H-pyrazolo[3,4-d]pyrimidin-6-yl)phenyl)-3-methylurea | 478.2 | 2.00 |
| 108 | 1-(4-(4-(8-oxa-3-azabicyclo[3.2.1]octan-3-yl)-1-((1r,4r)-4-hydroxycyclohexyl)-1H-pyrazolo[3,4-d]pyrimidin-6-yl)phenyl)-3-methylurea | 478.3 | — |
| 109 | 1-(4-(4-(8-oxa-3-azabicyclo[3.2.1]octan-3-yl)-1-((1s,4s)-4-hydroxycyclohexyl)-1H-pyrazolo[3,4-d]pyrimidin-6-yl)phenyl)-3-methylurea | 478.3 | — |
| 110 | 2-hydroxyethyl {4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate | 493.4 | — |
| 111 | methyl 4-[6-{4-[(ethoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate | 536.3 | 2.52 |

TABLE 1-continued

1H-Pyrazolo[3,4-d]pyrimidine compounds

| Example | Name | m/z (M + H) | LC/MS (RT min) |
|---|---|---|---|
| 112 | methyl 4-[6-(4-{[(2-hydroxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate | 552.2 | 2.22 |
| 113 | methyl 4-[6-(4-{[(2-methoxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate | 566.3 | 2.42 |
| 114 | methyl 4-[6-(4-{[(2-aminoethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate | 551.3 | 1.88 |
| 115 | methyl 4-{6-[4-({[2-(dimethylamino)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate | 579.3 | 1.94 |
| 116 | methyl 4-[4-(8-oxa-3-azabicyclo[3.2.1]oct-3-yl)-6-(4-{[(2-pyrrolidin-1-ylethoxy)carbonyl]amino}phenyl)-1H-pyrazolo[3,4-d]pyrimidin-1-yl]piperidine-1-carboxylate | 605.3 | 1.99 |
| 117 | methyl 4-[6-(4-{[(2-morpholin-4-ylethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate | 621.3 | 1.95 |
| 118 | methyl 4-{6-[4-({[2-(4-methylpiperazin-1-yl)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate | 634.3 | 1.96 |
| 119 | methyl 4-[6-{4-[(methoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate | 522.2 | 2.42 |
| 120 | methyl 4-[6-(4-aminophenyl)-4-8-oxa-3-azabicyclo[3.2.1]oct-3-yl)-1H-pyrazolo[3,4-d]pyrimidin-1-yl]piperidine-1-carboxylate | 464.2 | 2.18 |
| 121 | 2-hydroxyethyl {4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate | 551.3 | 2.21 |
| 122 | 3-hydroxypropyl {4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate | 565.3 | 2.28 |
| 123 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-ethylurea | 534.3 | 2.26 |
| 124 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-fluoroethyl)urea | 552.3 | 2.24 |
| 125 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-hydroxyethyl)urea | 550.3 | 2.09 |
| 126 | 1-cyclopropyl-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea | 546.3 | 2.29 |
| 127 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-phenylurea | 582.3 | 2.49 |
| 128 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-4-ylurea | 583.3 | 1.99 |
| 129 | 2,2,2-trifluoroethyl {4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate | 589.2 | 2.56 |
| 130 | 2-fluoroethyl {4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate | 553.2 | 2.42 |
| 131 | 3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-1,3-oxazolidin-2-one | 533.2 | 2.33 |
| 132 | 2-({4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}amino)ethanol | 507.3 | 2.13 |
| 133 | 1-[2-(dimethylamino)ethyl]-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea | 577.3 | 1.90 |
| 134 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea | 632.4 | 1.86 |

TABLE 1-continued

1H-Pyrazolo[3,4-d]pyrimidine compounds

| Example | Name | m/z (M + H) | LC/MS (RT min) |
|---|---|---|---|
| 135 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 680.4 | 2.06 |
| 136 | methyl {4-[4-(8-oxa-3-azabicyclo[3.2.1]oct-3-yl)-1-(4-oxocyclohexyl)-1H-pyrazolo[3,4-d]pyrimidin-6-yl]phenyl}carbamate | 477.2 | 2.26 |
| 137 | methyl {4-[1-(4-hydroxycyclohexyl)-4-(8-oxa-3-azabicyclo[3.2.1]oct-3-yl)-1H-pyrazolo[3,4-d]pyrimidin-6-yl]phenyl}carbamate | 479.2 | 2.20 |
| 138 | methyl {4-[1-isopropyl-4-(8-oxa-3-azabicyclo[3.2.1]oct-3-yl)-1H-pyrazolo[3,4-d]pyrimidin-6-yl]phenyl}carbamate | 423.2 | 2.40 |
| 139 | 1-{4-[1-isopropyl-4-(8-oxa-3-azabicyclo[3.2.1]oct-3-yl)-1H-pyrazolo[3,4-d]pyrimidin-6-yl]phenyl}-3-methylurea | 422.2 | 2.17 |
| 140 | 1-ethyl-3-{4-[1-isopropyl-4-(8-oxa-3-azabicyclo[3.2.1]oct-3-yl)-1H-pyrazolo[3,4-d]pyrimidin-6-yl]phenyl}urea | 436.2 | 2.25 |
| 141 | 1-(2-fluoroethyl)-3-{4-[1-isopropyl-4-(8-oxa-3-azabicyclo[3.2.1]oct-3-yl)-1H-pyrazolo[3,4-d]pyrimidin-6-yl]phenyl}urea | 454.2 | 2.22 |
| 142 | 1-cyclopropyl-3-{4-[1-isopropyl-4-(8-oxa-3-azabicyclo[3.2.1]oct-3-yl)-1H-pyrazolo[3,4-d]pyrimidin-6-yl]phenyl}urea | 448.2 | 2.27 |
| 143 | 1-(2-hydroxyethyl)-3-{4-[1-isopropyl-4-(8-oxa-3-azabicyclo[3.2.1]oct-3-yl)-1H-pyrazolo[3,4-d]pyrimidin-6-yl]phenyl}urea | 452.2 | 2.07 |
| 144 | 2-hydroxyethyl {4-[1-isopropyl-4-(8-oxa-3-azabicyclo[3.2.1]oct-3-yl)-1H-pyrazolo[3,4-d]pyrimidin-6-yl]phenyl}carbamate | 453.2 | 2.20 |
| 145 | 3-hydroxypropyl {4-[1-isopropyl-4-(8-oxa-3-azabicyclo[3.2.1]oct-3-yl)-1H-pyrazolo[3,4-d]pyrimidin-6-yl]phenyl}carbamate | 467.2 | 2.27 |
| 146 | 2,3-dihydroxypropyl {4-[1-isopropyl-4-(8-oxa-3-azabicyclo[3.2.1]oct-3-yl)-1H-pyrazolo[3,4-d]pyrimidin-6-yl]phenyl}carbamate | 483.2 | 2.09 |
| 147 | 1-{4-[1-isopropyl-4-(8-oxa-3-azabicyclo[3.2.1]oct-3-yl)-1H-pyrazolo[3,4-d]pyrimidin-6-yl]phenyl}-3-phenylurea | 484.2 | 2.49 |
| 148 | 1-{4-[1-isopropyl-4-(8-oxa-3-azabicyclo[3.2.1]oct-3-yl)-1H-pyrazolo[3,4-d]pyrimidin-6-yl]phenyl}-3-pyridin-3-ylurea | 485.2 | 2.01 |
| 149 | 1-{4-[1-isopropyl-4-(8-oxa-3-azabicyclo[3.2.1]oct-3-yl)-1H-pyrazolo[3,4-d]pyrimidin-6-yl]phenyl}-3-pyridin-4-ylurea | 485.2 | 1.97 |
| 150 | 1-{4-[1-(4,4-dimethoxycyclohexyl)-4-(8-oxa-3-azabicyclo[3.2.1]oct-3-yl)-1H-pyrazolo[3,4-d]pyrimidin-6-yl]phenyl}-3-methylurea | 522.3 | 2.25 |
| 151 | 1-{4-[1-(1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea | 534.3 | 2.21 |
| 152 | 1-{4-[1-(3,3-dimethyl-1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea | 562.3 | 2.39 |
| 153 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-methylurea | 451.2 | 1.66 |
| 154 | methyl (4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate | 452.2 | 1.78 |
| 155 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(2-hydroxyethyl)phenyl]urea | 557.3 | 1.83 |
| 156 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-phenylurea | 513.3 | 1.93 |
| 157 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-pyridin-3-ylurea | 514.3 | 1.59 |
| 158 | 2-hydroxyethyl (4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate | 482.2 | 1.69 |
| 159 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea | 611.3 | 1.64 |
| 160 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-ethylurea | 465.3 | 1.72 |

TABLE 1-continued

1H-Pyrazolo[3,4-d]pyrimidine compounds

| Example | Name | m/z (M + H) | LC/MS (RT min) |
|---|---|---|---|
| 161 | 1-cyclopropyl-3-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)urea | 477.3 | 1.74 |
| 162 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-pyridin-4-ylurea | 514.3 | 1.57 |
| 163 | 1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(hydroxymethyl)phenyl]urea | 543.3 | 1.79 |
| 164 | methyl 4-{6-[4-({[4-(hydroxymethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 613.3 | 2.27 |
| 165 | methyl 4-{6-[4-({[4-(2-hydroxyethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 627.3 | 2.28 |
| 166 | methyl 4-{6-[4-({[4-(4-methylpiperazin-1-yl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 681.4 | 2.03 |
| 167 | methyl 4-{6-[4-({[6-(4-methylpiperazin-1-yl)pyridin-3-yl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 682.4 | 1.97 |
| 168 | methyl 4-[6-(4-{[(2-aminoethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate | 550.3 | 1.84 |
| 169 | methyl 4-{6-[4-({[2-(dimethylamino)ethyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 578.3 | 1.89 |
| 170 | methyl 4-{6-[4-({[2-(4-methylpiperazin-1-yl)ethyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 633.4 | 1.84 |
| 171 | methyl 4-{6-[4-({[3-(hydroxymethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 613.3 | 2.27 |
| 172 | methyl 4-{6-[4-({[2-(hydroxymethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate | 613.3 | 2.32 |
| 173 | 1-(2-aminoethyl)-3-{4-[1-ethyl-4-(8-oxa-3-azabicyclo[3.2.1]oct-3-yl)-1H-pyrazolo[3,4-d]pyrimidin-6-yl]phenyl}urea | 437.2 | 1.71 |
| 174 | 1-{4-[1-ethyl-4-(8-oxa-3-azabicyclo[3.2.1]oct-3-yl)-1H-pyrazolo[3,4-d]pyrimidin-6-yl]phenyl}-3-[2-(methylamino)ethyl]urea | 451.2 | 1.74 |
| 175 | 1-[2-(dimethylamino)ethyl]-3-{4-[1-ethyl-4-(8-oxa-3-azabicyclo[3.2.1]oct-3-yl)-1H-pyrazolo[3,4-d]pyrimidin-6-yl]phenyl}urea | 465.3 | 1.77 |
| 176 | 1-(3-aminopropyl)-3-{4-[1-ethyl-4-(8-oxa-3-azabicyclo[3.2.1]oct-3-yl)-1H-pyrazolo[3,4-d]pyrimidin-6-yl]phenyl}urea | 451.2 | 1.73 |
| 177 | 1-[3-(dimethylamino)propyl]-3-{4-[1-ethyl-4-(8-oxa-3-azabicyclo[3.2.1]oct-3-yl)-1H-pyrazolo[3,4-d]pyrimidin-6-yl]phenyl}urea | 479.3 | 1.79 |
| 178 | 1-{4-[1-ethyl-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea | 520.3 | 1.73 |
| 179 | 1-{4-[1-ethyl-4-(8-oxa-3-azabicyclo[3.2.1]oct-3-yl)-1H-pyrazolo[3,4-d]pyrimidin-6-yl]phenyl}-3-(2-morpholin-4-ylethyl)urea | 507.3 | 1.78 |
| 180 | 1-{4-[1-ethyl-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 568.3 | 1.96 |
| 181 | 1-{4-[1-ethyl-4-(8-oxa-3-azabicyclo[3.2.1]oct-3-yl)-1H-pyrazolo[3,4-d]pyrimidin-6-yl]phenyl}-3-(4-morpholin-4-ylphenyl)urea | 555.3 | 2.27 |
| 182 | 1-{4-[1-ethyl-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea | 500.2 | 2.17 |

TABLE 1-continued

1H-Pyrazolo[3,4-d]pyrimidine compounds

| Example | Name | m/z (M + H) | LC/MS (RT min) |
|---|---|---|---|
| 183 | 1-{4-[1-ethyl-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea | 514.2 | 2.22 |
| 184 | 1-{4-[1-ethyl-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea | 556.3 | 1.98 |
| 185 | 1-{4-[1-ethyl-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea | 569.3 | 1.87 |
| 186 | 1-{4-[2-(dimethylamino)ethoxy]phenyl}-3-{4-[1-ethyl-4-(8-oxa-3-azabicyclo[3.2.1]oct-3-yl)-1H-pyrazolo[3,4-d]pyrimidin-6-yl]phenyl}urea | 557.3 | 1.93 |
| 187 | 1-{4-[1-ethyl-4-(8-oxa-3-azabicyclo[3.2.1]oct-3-yl)-1H-pyrazolo[3,4-d]pyrimidin-6-yl]phenyl}-3-(4-methoxyphenyl)urea | 500.2 | 2.35 |
| 188 | 1-(4-chlorophenyl)-3-{4-[1-ethyl-4-(8-oxa-3-azabicyclo[3.2.1]oct-3-yl)-1H-pyrazolo[3,4-d]pyrimidin-6-yl]phenyl}urea | 504.2 | 2.51 |
| 189 | 1-{4-[1-ethyl-4-(8-oxa-3-azabicyclo[3.2.1]oct-3-yl)-1H-pyrazolo[3,4-d]pyrimidin-6-yl]phenyl}-3-(4-methylphenyl)urea | 484.2 | 2.45 |
| 190 | 1-(4-cyanophenyl)-3-{4-[1-ethyl-4-(8-oxa-3-azabicyclo[3.2.1]oct-3-yl)-1H-pyrazolo[3,4-d]pyrimidin-6-yl]phenyl}urea | 495.2 | 2.41 |
| 191 | 2-hydroxypropyl {4-[1-ethyl-4-(8-oxa-3-azabicyclo[3.2.1]oct-3-yl)-1H-pyrazolo[3,4-d]pyrimidin-6-yl]phenyl}carbamate | 453.2 | 2.14 |
| 192 | methyl {4-[1-(2-hydroxyethyl)-4-(8-oxa-3-azabicyclo[3.2.1]oct-3-yl)-1H-pyrazolo[3,4-d]pyrimidin-6-yl]phenyl}carbamate | 425.2 | 2.00 |
| 193 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-methylurea | 424.2 | 1.83 |
| 194 | 1-ethyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea | 438.2 | 1.90 |
| 195 | 2-hydroxyethyl {4-[1-(2-hydroxyethyl)-4-(8-oxa-3-azabicyclo[3.2.1]oct-3-yl)-1H-pyrazolo[3,4-d]pyrimidin-6-yl]phenyl}carbamate | 455.2 | 1.85 |
| 196 | 1-(2-hydroxyethyl)-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea | 454.2 | 1.75 |
| 197 | 1-cyclopropyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea | 450.2 | 1.92 |
| 198 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-phenylurea | 486.2 | 2.16 |
| 199 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-3-ylurea | 487.2 | 1.73 |
| 200 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-4-ylurea | 487.2 | 1.71 |
| 201 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea | 516.2 | 1.97 |
| 202 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea | 530.2 | 2.01 |
| 203 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 584.3 | 1.78 |
| 204 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea | 571.3 | 2.03 |
| 205 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea | 585.3 | 1.72 |
| 206 | 1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea | 572.3 | 1.80 |
| 207 | 2-[6-(4-aminophenyl)-4-(8-oxa-3-azabicyclo[3.2.1]oct-3-yl)-1H-pyrazolo[3,4-d]pyrimidin-1-yl]ethanol | 367.2 | 1.70 |
| 208 | ethyl {4-[1-(2-hydroxyethyl)-4-(8-oxa-3-azabicyclo[3.2.1]oct-3-yl)-1H-pyrazolo[3,4-d]pyrimidin-6-yl]phenyl}carbamate | 439.2 | 2.10 |

TABLE 1-continued

1H-Pyrazolo[3,4-d]pyrimidine compounds

| Example | Name | m/z (M + H) | LC/MS (RT min) |
|---|---|---|---|
| 209 | 2-hydroxyethyl (4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)carbamate | 576.2 | 2.18 |
| 210 | 2-hydroxyethyl (4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)carbamate | 585.3 | 1.75 |
| 211 | 2-hydroxyethyl {4-[4-(8-oxa-3-azabicyclo[3.2.1]oct-3-yl)-1-(4-oxocyclohexyl)-1H-pyrazolo[3,4-d]pyrimidin-6-yl]phenyl}carbamate | 507.2 | 2.04 |
| 212 | 2-hydroxyethyl {4-[1-(4-hydroxycyclohexyl)-4-(8-oxa-3-azabicyclo[3.2.1]oct-3-yl)-1H-pyrazolo[3,4-d]pyrimidin-6-yl]phenyl}carbamate | 509.2 | 1.99 |
| 213 | 2-hydroxyethyl {4-[1-(2-cyanoethyl)-4-(8-oxa-3-azabicyclo[3.2.1]oct-3-yl)-1H-pyrazolo[3,4-d]pyrimidin-6-yl]phenyl}carbamate | 464.2 | 1.93 |
| 214 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-methylurea | 433.2 | 1.91 |
| 215 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-cyclopropylurea | 459.2 | 2.00 |
| 216 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-3-ylurea | 496.2 | 1.81 |
| 217 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-4-ylurea | 496.2 | 1.79 |
| 218 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea | 525.2 | 2.03 |
| 219 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea | 539.2 | 2.07 |
| 220 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 593.3 | 1.86 |
| 221 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea | 580.3 | 2.09 |
| 222 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea | 594.3 | 1.80 |
| 223 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea | 581.3 | 1.88 |
| 224 | 1-{4-[1-(2-cyanoethyl)-4-(8-oxa-3-azabicyclo[3.2.1]oct-3-yl)-1H-pyrazolo[3,4-d]pyrimidin-6-yl]phenyl}-3-{4-[2-(dimethylamino)ethoxy]phenyl}urea | 582.3 | 1.86 |
| 225 | 1-[2-(2-aminoethoxy)ethyl]-3-{4-[1-ethyl-4-(8-oxa-3-azabicyclo[3.2.1]oct-3-yl)-1H-pyrazolo[3,4-d]pyrimidin-6-yl]phenyl}urea | 481.3 | 1.74 |
| 226 | 1-{4-[1-ethyl-4-(8-oxa-3-azabicyclo[3.2.1]oct-3-yl)-1H-pyrazolo[3,4-d]pyrimidin-6-yl]phenyl}-3-[(1-methylpiperidin-4-yl)methyl]urea | 505.3 | 1.80 |
| 227 | 1-cyclohexyl-3-{4-[1-ethyl-4-(8-oxa-3-azabicyclo[3.2.1]oct-3-yl)-1H-pyrazolo[3,4-d]pyrimidin-6-yl]phenyl}urea | 476.3 | 2.36 |
| 228 | 1-{4-[1-ethyl-4-(8-oxa-3-azabicyclo[3.2.1]oct-3-yl)-1H-pyrazolo[3,4-d]pyrimidin-6-yl]phenyl}-3-(1-methylpiperidin-4-yl)urea | 491.3 | 1.78 |
| 229 | 1-(cis-4-aminocyclohexyl)-3-{4-[1-ethyl-4-(8-oxa-3-azabicyclo[3.2.1]oct-3-yl)-1H-pyrazolo[3,4-d]pyrimidin-6-yl]phenyl}urea | 491.3 | 1.78 |
| 230 | 1-(trans-4-aminocyclohexyl)-3-{4-[1-ethyl-4-(8-oxa-3-azabicyclo[3.2.1]oct-3-yl)-1H-pyrazolo[3,4-d]pyrimidin-6-yl]phenyl}urea | 491.3 | 1.79 |
| 231 | 1-[4-(hydroxymethyl)phenyl]-3-{4-[1-methyl-4-(8-oxa-3-azabicyclo[3.2.1]oct-3-yl)-1H-pyrazolo[3,4-d]pyrimidin-6-yl]phenyl}urea | 486.2 | 2.07 |
| 232 | 1-[4-(2-hydroxyethyl)phenyl]-3-{4-[1-methyl-4-(8-oxa-3-azabicyclo[3.2.1]oct-3-yl)-1H-pyrazolo[3,4-d]pyrimidin-6-yl]phenyl}urea | 500.2 | 2.12 |
| 233 | 1-[4-(dimethylamino)phenyl]-3-{4-[1-methyl-4-(8-oxa-3-azabicyclo[3.2.1]oct-3-yl)-1H-pyrazolo[3,4-d]pyrimidin-6-yl]phenyl}urea | 499.2 | 1.90 |
| 234 | 1-(4-aminophenyl)-3-{4-[1-methyl-4-(8-oxa-3-azabicyclo[3.2.1]oct-3-yl)-1H-pyrazolo[3,4-d]pyrimidin-6-yl]phenyl}urea | 471.2 | 1.80 |

TABLE 1-continued

1H-Pyrazolo[3,4-d]pyrimidine compounds

| Example | Name | m/z (M + H) | LC/MS (RT min) |
|---|---|---|---|
| 235 | 1-{4-[1-methyl-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea | 555.3 | 1.82 |
| 236 | 1-{4-[1-methyl-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 554.3 | 1.89 |
| 237 | 1-{4-[1-methyl-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea | 542.3 | 1.91 |
| 238 | 1-{4-[1-methyl-4-(8-oxa-3-azabicyclo[3.2.1]oct-3-yl)-1H-pyrazolo[3,4-d]pyrimidin-6-yl]phenyl}-3-(4-morpholin-4-ylphenyl)urea | 541.3 | 2.14 |
| 239 | 1-{4-[1-methyl-4-(8-oxa-3-azabicyclo[3.2.1]oct-3-yl)-1H-pyrazolo[3,4-d]pyrimidin-6-yl]phenyl}-3-[4-(methylsulfonyl)phenyl]urea | 534.2 | 2.16 |
| 240 | 1-{4-[1-methyl-4-(8-oxa-3-azabicyclo[3.2.1]oct-3-yl)-1H-pyrazolo[3,4-d]pyrimidin-6-yl]phenyl}-3-{4-[(2-piperidin-1-ylethyl)sulfonyl]phenyl}urea | 631.3 | 1.97 |
| 241 | 1-{4-[1-(2-fluoroethyl)-4-(8-oxa-3-azabicyclo[3.2.1]oct-3-yl)-1H-pyrazolo[3,4-d]pyrimidin-6-yl]phenyl}-3-methylurea | 426.2 | 2.13 |
| 242 | 1-[4-(dimethylamino)phenyl]-3-{4-[1-(2-fluoroethyl)-4-(8-oxa-3-azabicyclo[3.2.1]oct-3-yl)-1H-pyrazolo[3,4-d]pyrimidin-6-yl]phenyl}urea | 531.3 | 2.04 |
| 243 | 1-{4-[2-(dimethylamino)ethoxy]phenyl}-3-{4-[1-(2-fluoroethyl)-4-(8-oxa-3-azabicyclo[3.2.1]oct-3-yl)-1H-pyrazolo[3,4-d]pyrimidin-6-yl]phenyl}urea | 575.3 | 2.00 |
| 244 | 1-{4-[1-(2-fluoroethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea | 573.3 | 2.36 |
| 245 | 2-hydroxyethyl {4-[1-(2-fluoroethyl)-4-(8-oxa-3-azabicyclo[3.2.1]oct-3-yl)-1H-pyrazolo[3,4-d]pyrimidin-6-yl]phenyl}carbamate | 457.2 | 2.13 |
| 246 | 1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 586.3 | 2.00 |
| 247 | 1-ethyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea | 440.2 | 2.22 |
| 248 | 1-cyclopropyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea | 452.2 | 2.24 |
| 249 | 1-{4-[1-(2-fluoroethyl)-4-(8-oxa-3-azabicyclo[3.2.1]oct-3-yl)-1H-pyrazolo[3,4-d]pyrimidin-6-yl]phenyl}-3-pyridin-4-ylurea | 489.2 | 1.91 |
| 250 | 1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea | 518.2 | 2.24 |
| 251 | 1-(4-morpholin-4-ylphenyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 609.2 | 2.49 |
| 252 | 1-(6-morpholin-4-ylpyridin-3-yl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 610.2 | 2.19 |
| 253 | 1-[4-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 554.2 | 2.36 |
| 254 | 3-aminobenzyl {4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate | 554.2 | 2.45 |
| 255 | 1-[3-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 554.2 | 2.38 |
| 256 | 3-(dimethylamino)phenyl {4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate | 568.2 | 2.73 |
| 257 | 1-[3-(dimethylamino)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 567.2 | 2.17 |
| 258 | N~2~,N~2~-dimethyl-N-{4-[({4-[1-methyl-4-(8-oxa-3-azabicyclo[3.2.1]oct-3-yl)-1H-pyrazolo[3,4-d]pyrimidin-6-yl]phenyl}carbamoyl)amino]phenyl}glycinamide | 585.2 | 2.06 |
| 259 | N-{4-[({4-[1-methyl-4-(8-oxa-3-azabicyclo[3.2.1]oct-3-yl)-1H-pyrazolo[3,4-d]pyrimidin-6-yl]phenyl}carbamoyl)amino]phenyl}acetamide | 542.2 | 2.38 |

TABLE 1-continued

1H-Pyrazolo[3,4-d]pyrimidine compounds

| Example | Name | m/z (M + H) | LC/MS (RT min) |
|---|---|---|---|
| 260 | 1-[4-(2-hydroxyethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 568.2 | 2.36 |
| 261 | 1-[4-(4-methylpiperazin-1-yl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 622.3 | 2.04 |
| 262 | 1-[6-(4-methylpiperazin-1-yl)pyridin-3-yl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 623.3 | 1.98 |
| 263 | 1-[4-(2-hydroxyethoxy)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 584.2 | 2.32 |
| 264 | 2-hydroxyethyl {4-[1-(1-benzylpiperidin-4-yl)-4-(8-oxa-3-azabicyclo[3.2.1]oct-3-yl)-1H-pyrazolo[3,4-d]pyrimidin-6-yl]phenyl}carbamate | 584.3 | 1.90 |
| 265 | 1-cyclopropyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea | 571.3 | 2.35 |
| 266 | 2-hydroxyethyl {4-[4-(3-oxa-8-azabicyclo[3.2.1]oct-8-yl)-1-(2,2,2-trifluoroethyl)-1H-pyrazolo[3,4-d]pyrimidin-6-yl]phenyl}carbamate | 493.2 | 2.20 |
| 267 | 1-methyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 462.2 | 2.20 |
| 268 | 1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-pyridin-3-ylurea | 525.2 | 2.05 |
| 269 | 1-[4-(hydroxymethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 554.2 | 2.29 |
| 270 | 1-[4-(4-methylpiperazin-1-yl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 622.3 | 2.04 |
| 271 | 1-cyclopropyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 488.2 | 2.28 |
| 272 | 1-[4-(2-hydroxyethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 568.2 | 2.33 |
| 273 | 1-(4-morpholin-4-ylphenyl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 609.2 | 2.38 |
| 274 | 1-(6-morpholin-4-ylpyridin-3-yl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 610.2 | 2.11 |
| 275 | 1-{4-[2-(dimethylamino)ethoxy]phenyl}-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea | 611.3 | 2.04 |
| 276 | 1-{4-[1-ethyl-4-(8-oxa-3-azabicyclo[3.2.1]oct-3-yl)-1H-pyrazolo[3,4-d]pyrimidin-6-yl]phenyl}-3-[2-(4-methylpiperazin-1-yl)-2-oxoethyl]urea | 534.3 | 1.82 |
| 277 | 1-{4-[1-ethyl-4-(8-oxa-3-azabicyclo[3.2.1]oct-3-yl)-1H-pyrazolo[3,4-d]pyrimidin-6-yl]phenyl}-3-[3-(4-methylpiperazin-1-yl)-3-oxopropyl]urea | 548.3 | 1.83 |
| 278 | N-[2-(dimethylamino)ethyl]-N~2~-({4-[1-ethyl-4-(8-oxa-3-azabicyclo[3.2.1]oct-3-yl)-1H-pyrazolo[3,4-d]pyrimidin-6-yl]phenyl}carbamoyl)glycinamide | 522.3 | 1.80 |
| 279 | N-[2-(dimethylamino)ethyl]-N~3~-({4-[1-ethyl-4-(8-oxa-3-azabicyclo[3.2.1]oct-3-yl)-1H-pyrazolo[3,4-d]pyrimidin-6-yl]phenyl}carbamoyl)-beta-alaninamide | 536.3 | 1.88 |
| 280 | 1-{4-[1-ethyl-4-(8-oxa-3-azabicyclo[3.2.1]oct-3-yl)-1H-pyrazolo[3,4-d]pyrimidin-6-yl]phenyl}-3-(4-pyrrolidin-1-ylphenyl)urea | 539.3 | 2.28 |
| 281 | 1-{4-[1-ethyl-4-(8-oxa-3-azabicyclo[3.2.1]oct-3-yl)-1H-pyrazolo[3,4-d]pyrimidin-6-yl]phenyl}-3-[4-(2-hydroxyethoxy)phenyl]urea | | |
| 282 | 1-{4-[1-ethyl-4-(8-oxa-3-azabicyclo[3.2.1]oct-3-yl)-1H-pyrazolo[3,4-d]pyrimidin-6-yl]phenyl}-3-[6-(2-hydroxyethoxy)pyridin-3-yl]urea | 531.2 | 2.14 |
| 283 | 1-{4-[1-ethyl-4-(8-oxa-3-azabicyclo[3.2.1]oct-3-yl)-1H-pyrazolo[3,4-d]pyrimidin-6-yl]phenyl}-3-[6-(2-morpholin-4-ylethoxy)pyridin-3-yl]urea | 600.3 | 1.96 |
| 284 | 1-[6-(dimethylamino)pyridin-3-yl]-3-{4-[1-ethyl-4-(8-oxa-3-azabicyclo[3.2.1]oct-3-yl)-1H-pyrazolo[3,4-d]pyrimidin-6-yl]phenyl}urea | 514.3 | 1.94 |

TABLE 1-continued

1H-Pyrazolo[3,4-d]pyrimidine compounds

| Example | Name | m/z (M + H) | LC/MS (RT min) |
|---|---|---|---|
| 285 | 4-[({4-[1-ethyl-4-(8-oxa-3-azabicyclo[3.2.1]oct-3-yl)-1H-pyrazolo[3,4-d]pyrimidin-6-yl]phenyl}carbamoyl)amino]benzamide | 513.2 | 2.18 |
| 286 | 1-{4-[1-ethyl-4-(8-oxa-3-azabicyclo[3.2.1]oct-3-yl)-1H-pyrazolo[3,4-d]pyrimidin-6-yl]phenyl}-3-[6-(methylamino)pyridin-3-yl]urea | 500.2 | 1.90 |
| 287 | 1-(6-aminopyridin-3-yl)-3-{4-[1-ethyl-4-(8-oxa-3-azabicyclo[3.2.1]oct-3-yl)-1H-pyrazolo[3,4-d]pyrimidin-6-yl]phenyl}urea | 486.2 | 1.87 |
| 288 | 1-{4-[1-ethyl-4-(8-oxa-3-azabicyclo[3.2.1]oct-3-yl)-1H-pyrazolo[3,4-d]pyrimidin-6-yl]phenyl}-3-(4-piperazin-1-ylphenyl)urea | 554.3 | 1.96 |
| 289 | 1-{4-[(2,2-dimethylhydrazino)carbonyl]phenyl}-3-{4-[1-ethyl-4-(8-oxa-3-azabicyclo[3.2.1]oct-3-yl)-1H-pyrazolo[3,4-d]pyrimidin-6-yl]phenyl}urea | 556.3 | 2.16 |
| 290 | 4-[({4-[1-ethyl-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-ylbenzamide | 582.3 | 2.12 |
| 291 | 2-hydroxyethyl (4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)carbamate | 479.2 | 2.05 |
| 292 | 1-methyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 448.2 | 2.03 |
| 293 | 1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea | 511.2 | 1.91 |
| 294 | 1-[4-(hydroxymethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 540.2 | 2.15 |
| 295 | 1-[4-(4-methylpiperazin-1-yl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 608.3 | 1.93 |
| 296 | 1-cyclopropyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 474.2 | 2.12 |
| 297 | 1-[4-(2-hydroxyethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | | |
| 298 | 1-(4-morpholin-4-ylphenyl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 595.2 | 2.22 |
| 299 | 1-(6-morpholin-4-ylpyridin-3-yl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 596.2 | 1.98 |
| 300 | 1-{4-[2-(dimethylamino)ethoxy]phenyl}-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea | 597.2 | 1.96 |
| 301 | 1-ethyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea | 506.3 | 2.46 |
| 302 | 1-cyclopropyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea | 518.3 | 2.48 |
| 303 | 1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-4-ylurea | 555.3 | 2.04 |
| 304 | 1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 652.4 | 2.11 |
| 305 | 1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-(4-piperazin-1-ylphenyl)urea | 638.3 | 2.08 |
| 306 | 4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]benzamide | 597.3 | 2.41 |
| 307 | 4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-ylbenzamide | 666.3 | 2.34 |
| 308 | 1-[4-(hydroxymethyl)phenyl]-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea | 584.3 | 2.46 |

TABLE 1-continued

1H-Pyrazolo[3,4-d]pyrimidine compounds

| Example | Name | m/z (M + H) | LC/MS (RT min) |
|---|---|---|---|
| 309 | 1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea | 653.4 | 2.03 |
| 310 | 1-{4-[2-(dimethylamino)ethoxy]phenyl}-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea | 641.3 | 2.12 |
| 311 | 2-hydroxyethyl {4-[1-(4-methoxycyclohexyl)-4-(8-oxa-3-azabicyclo[3.2.1]oct-3-yl)-1H-pyrazolo[3,4-d]pyrimidin-6-yl]phenyl}carbamate | 523.3 | 2.37 |
| 312 | 1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-pyridin-4-ylurea | 581.3 | 2.11 |
| 313 | 1-[4-(4-methylpiperazin-1-yl)phenyl]-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea | 678.4 | 2.18 |
| 314 | 1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-(4-piperazin-1-ylphenyl)urea | 664.4 | 2.14 |
| 315 | 2-hydroxyethyl (4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)carbamate | 549.3 | 2.35 |
| 316 | 1-cyclopropyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea | 544.3 | 2.44 |
| 317 | 1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-(4-piperazin-1-ylphenyl)urea | 608.3 | 1.95 |
| 318 | 1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-(4-piperazin-1-ylphenyl)urea | 608.3 | 1.94 |
| 319 | 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-methylurea | 482.2 | 2.15 |
| 320 | 1-ethyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea | 496.3 | 2.09 |
| 321 | 1-cyclopropyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea | 508.3 | 2.26 |
| 322 | 1-(2-hydroxyethyl)-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea | 512.3 | 2.02 |
| 323 | 2-hydroxyethyl (4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate | 513.2 | 2.03 |
| 324 | 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-phenylurea | 544.3 | 2.50 |
| 325 | 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-4-ylurea | 545.3 | 1.91 |
| 326 | 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-3-ylurea | 545.3 | 1.88 |
| 327 | 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea | 642.3 | 1.89 |
| 328 | methyl (4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate | 483.2 | 2.38 |
| 329 | 1-methyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea | 560.3 | 1.74 |
| 330 | 1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-pyridin-3-ylurea | 623.3 | 1.70 |
| 331 | 1-methyl-3-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}urea | 531.3 | 1.88 |
| 332 | 1-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}-3-pyridin-3-ylurea | 594.3 | 1.84 |

TABLE 1-continued

1H-Pyrazolo[3,4-d]pyrimidine compounds

| Example | Name | m/z (M + H) | LC/MS (RT min) |
|---|---|---|---|
| 333 | 1-(4-{1-[4-(2,2-dimethylhydrazino)cyclohexyl]-4-(8-oxa-3-azabicyclo[3.2.1]oct-3-yl)-1H-pyrazolo[3,4-d]pyrimidin-6-yl}phenyl)-3-methylurea | 520.3 | 1.82 |
| 334 | 1-{4-[1-{4-[(2-hydroxyethyl)amino]cyclohexyl}-4-(8-oxa-3-azabicyclo[3.2.1]oct-3-yl)-1H-pyrazolo[3,4-d]pyrimidin-6-yl]phenyl}-3-methylurea | 521.3 | 1.77 |
| 335 | 1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-(4-piperazin-1-ylphenyl)urea | 628.3 | 1.96 |
| 336 | 1-{4-[(2,2-dimethylhydrazino)carbonyl]phenyl}-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea | 630.3 | 2.15 |
| 337 | 1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea | 540.2 | 1.64 |
| 338 | 1-{4-[4-(7-formyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea | 568.2 | 1.82 |
| 339 | 1-{4-[4-(7-acetyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea | 582.2 | 1.83 |
| 340 | tert-butyl 7-[6-{4-[(pyridin-4-ylcarbamoyl)amino]phenyl}-1-(2,2,2-trifluoroethyl)-1H-pyrazolo[3,4-d]pyrimidin-4-yl]-9-oxa-3,7-diazabicyclo[3.3.1]nonane-3-carboxylate | 640.3 | 2.00 |
| 341 | 1-methyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea | 448.2 | 1.99 |
| 342 | 1-cyclopropyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea | 474.2 | 2.08 |
| 343 | 2-hydroxyethyl (4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)carbamate | 479.2 | 2.01 |
| 344 | 1-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea | 511.2 | 1.89 |
| 345 | 1-[4-(4-methylpiperazin-1-yl)phenyl]-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea | 608.3 | 1.92 |
| 346 | 1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-pyridin-3-ylurea | | |
| 347 | 1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-methylurea | 477.3 | 2.28 |
| 348 | 1-{4-[1-ethyl-3-(4-methylpiperazin-1-yl)-4-(8-oxa-3-azabicyclo[3.2.1]oct-3-yl)-1H-pyrazolo[3,4-d]pyrimidin-6-yl]phenyl}-3-methylurea | 506.3 | 1.77 |
| 349 | 1-{4-[1-ethyl-4-(8-oxa-3-azabicyclo[3.2.1]oct-3-yl)-3-pyridin-3-yl-1H-pyrazolo[3,4-d]pyrimidin-6-yl]phenyl}-3-methylurea | 485.2 | 2.05 |
| 350 | 1-{4-[1-ethyl-4-(8-oxa-3-azabicyclo[3.2.1]oct-3-yl)-3-vinyl-1H-pyrazolo[3,4-d]pyrimidin-6-yl]phenyl}-3-methylurea | 434.2 | 2.21 |
| 351 | 1-{4-[3-(1,2-dihydroxyethyl)-1-ethyl-4-(8-oxa-3-azabicyclo[3.2.1]oct-3-yl)-1H-pyrazolo[3,4-d]pyrimidin-6-yl]phenyl}-3-methylurea | 468.2 | 1.80 |
| 352 | 1-{4-[1-ethyl-3-formyl-4-(8-oxa-3-azabicyclo[3.2.1]oct-3-yl)-1H-pyrazolo[3,4-d]pyrimidin-6-yl]phenyl}-3-methylurea | 436.2 | 2.19 |
| 353 | 1-(4-{1-ethyl-3-[(4-methylpiperazin-1-yl)methyl]-4-(8-oxa-3-azabicyclo[3.2.1]oct-3-yl)-1H-pyrazolo[3,4-d]pyrimidin-6-yl}phenyl)-3-methylurea | 520.3 | 1.72 |
| 354 | 1-{4-[1-ethyl-4-(8-oxa-3-azabicyclo[3.2.1]oct-3-yl)-3-(pyrrolidin-1-ylmethyl)-1H-pyrazolo[3,4-d]pyrimidin-6-yl]phenyl}-3-methylurea | 491.3 | 1.72 |
| 355 | methyl 4-[6-(4-{[(2-hydroxyethoxy)carbonyl]amino}phenyl)-4-(3-oxa-8-azabicyclo[3.2.1]oct-8-yl)-1H-pyrazolo[3,4-d]pyrimidin-1-yl]piperidine-1-carboxylate | 552.2 | 2.13 |
| 356 | methyl 4-[6-{4-[(methylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate | 521.3 | 2.11 |
| 357 | methyl 4-[6-{4-[(ethylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate | 535.3 | 2.17 |

TABLE 1-continued

1H-Pyrazolo[3,4-d]pyrimidine compounds

| Example | Name | m/z (M + H) | LC/MS (RT min) |
|---|---|---|---|
| 358 | methyl 4-[6-(4-{[(2-fluoroethyl)carbamoyl]amino}phenyl)-4-(3-oxa-8-azabicyclol[3.2.1]oct-8-yl)-1H-pyrazolo[3,4-d]pyrimidin-1-yl]piperidine-1-carboxylate | 553.3 | 2.15 |
| 359 | methyl 4-[6-{4-[(cyclopropylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate | 547.3 | 2.19 |
| 360 | methyl 4-[4-(3-oxa-8-azabicyclo[3.2.1]oct-8-yl)-6-{4-[(phenylcarbamoyl)amino]phenyl}-1H-pyrazolo[3,4-d]pyrimidin-1-yl]piperidine-1-carboxylate | 583.3 | 2.24 |
| 361 | methyl 4-[4-(3-oxa-8-azabicyclo[3.2.1]oct-8-yl)-6-{4-[(pyridin-3-ylcarbamoyl)amino]phenyl}-1H-pyrazolo[3,4-d]pyrimidin-1-yl]piperidine-1-carboxylate | 584.3 | 2.00 |
| 362 | methyl 4-[4-(3-oxa-8-azabicyclo[3.2.1]oct-8-yl)-6-{4-[(pyridin-4-ylcarbamoyl)amino]phenyl}-1H-pyrazolo[3,4-d]pyrimidin-1-yl]piperidine-1-carboxylate | 584.3 | 1.97 |
| 363 | methyl 4-{6-[4-({[4-(4-methylpiperazin-1-yl)phenyl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate | 681.4 | 2.03 |
| 364 | methyl 4-[4-(3-oxa-8-azabicyclo[3.2.1]oct-8-yl)-6-(4-{[(4-piperazin-1-ylphenyl)carbamoyl]amino}phenyl)-1H-pyrazolo[3,4-d]pyrimidin-1-yl]piperidine-1-carboxylate | 667.3 | 2.00 |
| 365 | methyl 4-{6-[4-({[6-(4-methylpiperazin-1-yl)pyridin-3-yl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate | 682.4 | 1.97 |
| 366 | methyl 4-[6-{4-[-({4-[(dimethylamino)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate | 640.3 | 2.03 |
| 367 | methyl 4-[6-{4-[({4-[(4-methylpiperazin-1-yl)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate | 695.4 | 1.98 |
| 368 | methyl 4-[6-{4-[({4-[2-(dimethylamino)ethoxy]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate | 670.3 | 2.03 |
| 369 | 2-hydroxyethyl (4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)carbamate | 591.3 | 1.75 |
| 370 | 1-ethyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea | 574.4 | 1.78 |
| 371 | 1-(2-fluoroethyl)-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea | 592.3 | 1.77 |
| 372 | 1-cyclopropyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea | 586.4 | 1.79 |
| 373 | 1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-phenylurea | 622.4 | 2.00 |
| 374 | 4-[4-(8-oxa-3-azabicyclo[3.2.1]oct-3-yl)-1-(2,2,2-trifluoroethyl)-1H-pyrazolo[3,4-d]pyrimidin-6-yl]aniline | 405.2 | |
| 375 | methyl {4-[1-ethyl-4-(8-oxa-3-azabicyclo[3.2.1]oct-3-yl)-1H-pyrazolo[3,4-d]pyrimidin-6-yl]phenyl}carbamate | 409.3 | |
| 376 | 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-3-ylurea | 583.1 | |
| 377 | methyl {4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate | 521.2513 | |
| 378 | 3-[4-(3-oxa-8-azabicyclo[3.2.1]oct-8-yl)-1-phenyl-1H-pyrazolo[3,4-d]pyrimidin-6-yl]phenol | 400.3 | |
| 379 | 2-hydroxyethyl (4-{4-[(6R)-6-hydroxy-8-oxa-3-azabicyclo[3.2.1]oct-3-yl]-1-(2,2,2-trifluoroethyl)-1H-pyrazolo[3,4-d]pyrimidin-6-yl}phenyl)carbamate | | |
| 380 | 1-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}-3-methylurea | 478.3 | |
| 381 | 1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-methylurea | 478.3 | |

TABLE 1-continued

1H-Pyrazolo[3,4-d]pyrimidine compounds

| Example | Name | m/z (M + H) | LC/MS (RT min) |
|---|---|---|---|
| 382 | 3-{4-[(1S,4S)-2-oxa-5-azabicyclo[2.2.1]hept-5-yl]-1-phenyl-1H-pyrazolo[3,4-d]pyrimidin-6-yl}phenol | 386.3 | |
| 383 | 1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-methylurea | 492.2721 | |
| 384 | 1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-3-ylurea | 555.2831 | |
| 385 | 1-{4-[1-(1,3-dioxan-5-yl)-4-(8-oxa-3-azabicyclo[3.2.1]oct-3-yl)-1H-pyrazolo[3,4-d]pyrimidin-6-yl]phenyl}-3-methylurea | 466.2201 | |
| 386 | 1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-methylurea | 492.3 | |
| 387 | 1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-methylurea | 492.2 | 2.25 |
| 388 | 1-(1,4-dioxaspiro[4.5]dec-8-yl)-6-(1H-indol-5-yl)-4-(8-oxa-3-azabicyclo[3.2.1]oct-3-yl)-1H-pyrazolo[3,4-d]pyrimidine | 487.2 | 2.47 |
| 389 | 1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea | 518.2 | |
| 390 | 1-{4-[4-(6-hydroxy-3-oxa-8-azabicyclo[3.2.1]oct-8-yl)-1-(2,2,2-trifluoroethyl)-1H-pyrazolo[3,4-d]pyrimidin-6-yl]phenyl}-3-methylurea | | |
| 391 | 1-{4-[4-(6,8-dioxa-3-azabicyclo[3.2.1]oct-3-yl)-1-methyl-1H-pyrazolo[3,4-d]pyrimidin-6-yl]phenyl}-3-pyridin-3-ylurea | 459.1894 | |
| 392 | 1-{4-[4-(6,8-dioxa-3-azabicyclo[3.2.1]oct-3-yl)-1-methyl-1H-pyrazolo[3,4-d]pyrimidin-6-yl]phenyl}-3-methylurea | | |
| 393 | 1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-(4-piperazin-1-ylphenyl)urea | 594.4 | |
| 394 | 6-(1H-indol-5-yl)-4-(8-oxa-3-azabicyclo[3.2.1]oct-3-yl)-1-[1-(pyridin-3-ylmethyl)piperidin-4-yl]-1H-pyrazolo[3,4-d]pyrimidine | 521.7 | 1.89 |
| 395 | 1-cyclopropyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea | 488.1 | |
| 396 | 1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 652.5 | |
| 397 | 1-{4-[3-bromo-1-ethyl-4-(8-oxa-3-azabicyclo[3.2.1]oct-3-yl)-1H-pyrazolo[3,4-d]pyrimidin-6-yl]phenyl}-3-methylurea | 486.3 | |
| 398 | 1-cyclopropyl-3-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}urea | 518.4 | |
| 399 | 1-cyclopropyl-3-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}urea | 518.4 | |
| 400 | 1-[4-(4-methylpiperazin-1-yl)phenyl]-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea | 636.3406 | |
| 401 | 1-cyclopropyl-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea | 502.2559 | |
| 402 | 1-cyclopropyl-3-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}urea | 504.2719 | |
| 403 | 1-cyclopropyl-3-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}urea | 504.2718 | |
| 404 | 1-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 638.3562 | |
| 405 | 1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea | 638.3557 | |

The compounds shown in Table 2, below, were prepared according to the above procedures:

TABLE 2

| | Thieno[3,4-d]pyrimidine compounds | | |
|---|---|---|---|
| Example | Name | m/z | LC/MS (min) |
| 406 | 1-methyl-3-{4-[4-(8-oxa-3-azabicyclo[3.2.1]oct-3-yl)thieno[3,2-d]pyrimidin-2-yl]phenyl}urea | 396.1 | 1.69 |
| 407 | 1-ethyl-3-{4-[4-(8-oxa-3-azabicyclo[3.2.1]oct-3-yl)thieno[3,2-d]pyrimidin-2-yl]phenyl}urea | 410.2 | 1.75 |
| 408 | 1-(2-fluoroethyl)-3-{4-[4-(8-oxa-3-azabicyclo[3.2.1]oct-3-yl)thieno[3,2-d]pyrimidin-2-yl]phenyl}urea | 428.1 | 1.73 |
| 409 | 1-(2-hydroxyethyl)-3-{4-[4-(8-oxa-3-azabicyclo[3.2.1]oct-3-yl)thieno[3,2-d]pyrimidin-2-yl]phenyl}urea | 426.2 | 1.64 |
| 410 | 1-cyclopropyl-3-{4-[4-(8-oxa-3-azabicyclo[3.2.1]oct-3-yl)thieno[3,2-d]pyrimidin-2-yl]phenyl}urea | 422.2 | 1.76 |
| 411 | 1-{4-[4-(8-oxa-3-azabicyclo[3.2.1]oct-3-yl)thieno[3,2-d]pyrimidin-2-yl]phenyl}-3-phenylurea | 458.2 | 1.99 |
| 412 | 1-{4-[4-(8-oxa-3-azabicyclo[3.2.1]oct-3-yl)thieno[3,2-d]pyrimidin-2-yl]phenyl}-3-pyridin-3-ylurea | 459.2 | 1.64 |
| 413 | 1-{4-[4-(8-oxa-3-azabicyclo[3.2.1]oct-3-yl)thieno[3,2-d]pyrimidin-2-yl]phenyl}-3-pyridin-4-ylurea | 459.2 | 1.61 |
| 414 | 4-[4-(8-oxa-3-azabicyclo[3.2.1]oct-3-yl)thieno[3,2-d]pyrimidin-2-yl]aniline | 339.1 | 1.67 |
| 415 | N-{4-[4-(8-oxa-3-azabicyclo[3.2.1]oct-3-yl)thieno[3,2-d]pyrimidin-2-yl]phenyl}acetamide | 381.1 | 1.72 |
| 416 | methyl {4-[4-(8-oxa-3-azabicyclo[3.2.1]oct-3-yl)thieno[3,2-d]pyrimidin-2-yl]phenyl}carbamate | 397.1 | 1.8 |
| 417 | 3-[4-(8-oxa-3-azabicyclo[3.2.1]oct-3-yl)thieno[3,2-d]pyrimidin-2-yl]phenol | 340.1 | 1.69 |
| 418 | 4-[4-(8-oxa-3-azabicyclo[3.2.1]oct-3-yl)thieno[3,2-d]pyrimidin-2-yl]phenol | 340.1 | 1.65 |
| 419 | 2-(1H-indol-5-yl)-4-(8-oxa-3-azabicyclo[3.2.1]oct-3-yl)thieno[3,2-d]pyrimidine | 363.1 | 1.81 |
| 420 | 5-[4-(8-oxa-3-azabicyclo[3.2.1]oct-3-yl)thieno[3,2-d]pyrimidin-2-yl]pyridin-2-amine | 340.1 | 1.63 |
| 421 | 5-[4-(8-oxa-3-azabicyclo[3.2.1]oct-3-yl)thieno[3,2-d]pyrimidin-2-yl]pyrimidin-2-amine | 341.1 | 1.72 |
| 422 | 4-{[4-(8-oxa-3-azabicyclo[3.2.1]oct-3-yl)thieno[3,2-d]pyrimidin-2-yl]amino}phenol | 355.1223 | — |
| 423 | 1-methyl-3-(4-{6-[(4-methylpiperazin-1-yl)methyl]-4-(8-oxa-3-azabicyclo[3.2.1]oct-3-yl)thieno[3,2-d]pyrimidin-2-yl}phenyl)urea | 508.2 | 1.53 |
| 424 | 1-cyclopropyl-3-(4-{6-[(4-methylpiperazin-1-yl)methyl]-4-(8-oxa-3-azabicyclo[3.2.1]oct-3-yl)thieno[3,2-d]pyrimidin-2-yl}phenyl)urea | 534.3 | 1.59 |
| 425 | 2,2-dimethyl-N-(4-{6-[(4-methylpiperazin-1-yl)methyl]-4-(8-oxa-3-azabicyclo[3.2.1]oct-3-yl)thieno[3,2-d]pyrimidin-2-yl}phenyl)hydrazinecarboxamide | 537.3 | 1.61 |
| 426 | 1-(4-{6-[(4-methylpiperazin-1-yl)methyl]-4-(8-oxa-3-azabicyclo[3.2.1]oct-3-yl)thieno[3,2-d]pyrimidin-2-yl}phenyl)-3-pyridin-3-ylurea | 571.3 | 1.53 |
| 427 | 1-(4-{6-[(4-methylpiperazin-1-yl)methyl]-4-(8-oxa-3-azabicyclo[3.2.1]oct-3-yl)thieno[3,2-d]pyrimidin-2-yl}phenyl)-3-pyridin-4-ylurea | 571.3 | 1.52 |
| 428 | 4-{[(4-{6-[(4-methylpiperazin-1-yl)methyl]-4-(8-oxa-3-azabicyclo[3.2.1]oct-3-yl)thieno[3,2-d]pyrimidin-2-yl}phenyl)carbamoyl]amino}benzamide | 613.3 | 1.66 |
| 429 | 1-methyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea | 572.2 | 1.77 |
| 430 | 1-ethyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea | 586.2 | 1.83 |
| 431 | 1-cyclopropyl-3-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}urea | 598.2 | 1.84 |
| 432 | 1-{4-[6-{[4-(methylsulfonyl)piperazin-1-yl]methyl}-4-(8-oxa-3-azabicyclo[3.2.1]oct-3- | 634.2 | 2.05 |

TABLE 2-continued

Thieno[3,4-d]pyrimidine compounds

| Example | Name | m/z | LC/MS (min) |
|---|---|---|---|
| | yl)thieno[3,2-d]pyrimidin-2-yl]phenyl}-3-phenylurea | | |
| 433 | 1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-3-ylurea | 635.2 | 1.77 |
| 434 | 1-{4-[6-{[4-(methylsulfonyl)piperazin-1-yl]methyl}-4-(8-oxa-3-azabicyclo[3.2.1]oct-3-yl)thieno[3,2-d]pyrimidin-2-yl]phenyl}-3-pyridin-4-ylurea | 635.2 | 1.68 |

Biological Evaluation

MTOR Kinase Assay Methods

Human mTOR assays (See Toral-Barza, et al. *Biochem Biophys. Res. Commun.* 2005 Jun. 24; 332(1):304-10) with purified enzyme are performed in 96-well plates by DELFIA format as follows. Enzymes are first diluted in kinase assay buffer (10 mM HEPES (pH 7.4), 50 mM NaCl, 50 mM β-glycerophosphate, 10 mM $MnCl_2$, 0.5 mM DTT, 0.25 mM microcystin LR, and 100 mg/mL BSA). To each well, 12 μL of the diluted enzyme is mixed briefly with 0.5 μL test inhibitor or control vehicle dimethylsulfoxide (DMSO). The kinase reaction is initiated by adding 12.5 μL kinase assay buffer containing ATP and His6-S6K to give a final reaction volume of 25 μL containing 800 ng/mL FLAG-TOR, 100 mM ATP and 1.25 mM His6-S6K. The reaction plate is incubated for 2 hours (linear at 1-6 hours) at room temperature with gentle shaking and then terminated by adding 25 μL Stop buffer (20 mM HEPES (pH 7.4), 20 mM EDTA, 20 mM EGTA). The DELFIA detection of the phosphorylated (Thr-389) His6-S6K is performed at room temperature using a monoclonal anti-P(T389)-p70S6K antibody (1A5, Cell Signaling) labeled with Europium-N1-ITC (Eu) (10.4 Eu per antibody, PerkinElmer). The DELFIA Assay buffer and Enhancement solution can be purchased from PerkinElmer. 45 μL of the terminated kinase reaction mixture is transferred to a Maxi-iSorp plate (Nunc) containing 55 μL PBS. The His6-S6K is allowed to attach for 2 hours after which the wells are aspirated and washed once with PBS. 100 μL of DELFIA Assay buffer with 40 ng/mL Eu—P(T389)-S6K antibody is added. The antibody binding is continued for 1 hour with gentle agitation. The wells are then aspirated and washed 4 times with PBS containing 0.05% Tween-20 (PBST). 100 μL of DELFIA Enhancement solution is added to each well and the plates are read in a PerkinElmer Victor model plate reader. Data obtained is used to calculate enzymatic activity and enzyme inhibition by potential inhibitors.

Fluorescence Polarization Assay for PI3K

This assay is used to determine the $IC_{50}$ of compounds of the present invention as it identifies inhibitors of PI3 kinase by measuring inhibition.

Materials

Reaction Buffer: 20 mM HEPES, pH 7.5, 2 mM $MgCl_2$, 0.05% CHAPS; and 0.01% BME (added fresh) Stop/Detection Buffer: 100 mM HEPES, pH 7.5, 4 mM EDTA, 0.05% CHAPS; ATP 20 mM in water; PIP2 (diC8, cat# P-4508) 1 mM in water (MW=856.5); GST-GRP 1.75 mg/mL or 1.4 mg/mL in 10% glycerol; Red detector (TAMRA) 2.5 μM; Plate: Nunc 384 well black polypropylene fluorescence plate.

Methods

The assay is run by placing 5 μL of diluted enzyme per well, then 5 μL of diluted compound (or 9.5 μL enzyme then 0.5 μL compound in DMSO) is added and mixed. Then, 10 μL substrate is added to start the reaction. The samples are incubated 30-60 minutes, then the reaction is stopped by adding 20 μL stop/detector mix. PI3K is diluted with reaction buffer (e.g., 5 μL or 7.5 μL PI3K into 620 μL reaction buffer), and 5 μL of diluted enzyme is used per well. 5 μL reaction buffer or drug diluted in buffer (e.g., 4 μL/100 so final DMSO is 1% in reaction) is added to each. Pipetting up and down mixes the samples. Alternatively, the enzyme can be diluted to 1215 μL. In this case 9.8 μL is added per well and 0.2 μL compound is added in DMSO. To prepare 1 mL of substrate solution, 955 μL reaction buffer, 40 μL PIP2, and 2.5 μL ATP are mixed. 10 μL of substrate is added to each well to start the reaction. This results in 20 μM PIP2, and 25 μM ATP per reaction.

Stop/detector mix is prepared by mixing 4 μL Red detector and 1.6 μL or 2.0 μL GST-GRP with 1 mL Stop buffer, which results in 10 nM probe and 70 nM GST-GRP). 20 μL of the stop/detector mix is added to each well to stop the reaction. The plates are read after 30-90 minutes keeping the red probe solutions dark. For the zero time point, stop/detector mix is added to the enzyme just before adding substrate. For an extra control, stop/detector mix is added to buffer (no enzyme) and substrate or to just buffer (no substrate). Pooled PI3K preparations had a protein concentration of 0.25 mg/mL. The recommended reaction has 0.06 μL per 20 μL (0.015 μg/20 μL) or 0.01125 μg/15 μL or 0.75 μg/mL. Plates are read on machines with filters for Tamra. The units are mP with no enzyme controls reading app 190-220 mP units. Fully active enzyme reduces fluorescence polarization down to 70-100 mP after 30 minutes. An active compound raises the mP values halfway to control or to 120-150 mP units.

In Vitro Cell Culture Growth Assay Methods:

Human tumor cell lines used include prostate lines LNCap and PC3MM2, breast lines MDA468, MCF7, renal line HTB44 (A498), colon line HCT116, and ovarian line OVCAR3. Cells were plated in 96-well culture plates. One day following plating, the inhibitors were added to cells. Three days after drug treatment, viable cell densities were determined by metabolic conversion (by viable cells) of the dye MTS, a well-established cell proliferation assay. The assays were performed using an assay kit purchased from Promega Corp. (Madison, Wis.) following the protocol supplied with the kit. The MTS assay results were read in a 96-well plate reader by measuring absorbance at 490 nm. The effect of each treatment was calculated as percent of control growth relative to the vehicle-treated cells grown in the same culture plate. The drug concentration that conferred 50% inhibition of growth was determined as $IC_{50}$ (μg/ml).

Table 3 shows the results of the described biological assays.

TABLE 3

| Example | TOR Kinase IC$_{50}$ (nM) | PI3 Kinase α IC$_{50}$ (nM) | PI3 Kinase β IC$_{50}$ (nM) | PI3 Kinase γ IC$_{50}$ (nM) | PI3 Kinase δ IC$_{50}$ (nM) | LNCap IC$_{50}$ (μM) | MDA468 IC$_{50}$ (μM) |
|---|---|---|---|---|---|---|---|
| 1 | 0.63 | 1616.00 | | >10000 | | 0.038 | 0.046 |
| 2 | 8 | >10000 | | >10000 | | 0.65 | 0.68 |
| 3 | 0.38 | 3748.00 | | >10000 | | <0.0270 | <0.0270 |
| 4 | 0.18 | 345.00 | | 2138 | | <0.0270 | <0.0270 |
| 5 | 0.19 | 168 | | 1030 | | 0.0019 | 0.0115 |
| 6 | 0.22 | 2746.00 | | 6574 | | <0.0270 | <0.0270 |
| 7 | 0.21 | 1803.00 | | >10000 | | 0.026 | 0.08 |
| 8 | 0.28 | 1475.00 | | >10000 | | <0.0270 | 0.18 |
| 9 | 0.22 | 5333.00 | | >10000 | | 0.009 | 0.18 |
| 10 | 0.34 | 4927.00 | | 6586 | | 0.012 | 0.22 |
| 11 | 0.37 | 272.00 | | 6815 | | 0.01 | 0.12 |
| 12 | 0.52 | 6662.00 | | >10000 | | 0.023 | 0.3 |
| 13 | 0.1 | 613.00 | | 6845 | | 0.015 | 0.075 |
| 14 | 0.16 | 487.00 | | 2048 | | 0.0009 | 0.019 |
| 15 | 0.31 | 2275.00 | | >10000 | | 0.004 | 0.085 |
| 16 | 0.5 | 2633.00 | | >10000 | | 0.006 | 0.08 |
| 17 | 0.61 | 222.00 | | 1864 | | 0.0008 | 0.01 |
| 18 | 0.25 | 326.00 | | 3475 | | <0.0008 | <0.0008 |
| 19 | 0.14 | 223.00 | | 391 | | <0.0008 | <0.0008 |
| 20 | 0.47 | 2352.00 | | >10000 | | 0.027 | 0.098 |
| 21 | 0.24 | 3955.00 | | 11000 | | 0.012 | 0.12 |
| 22 | 0.56 | 3852.00 | | >10000 | | 0.027 | 0.15 |
| 23 | 0.7 | 888.00 | | >10000 | | 0.04 | 0.18 |
| 24 | 0.39 | 629.00 | | 6297 | | 0.007 | 0.018 |
| 25 | 0.47 | 595.00 | | 1644 | | 0.038 | 0.07 |
| 26 | 1.1 | 1281 | | >10000 | | 0.027 | 0.19 |
| 27 | 0.47 | 677 | | >10000 | | 0.0008 | 0.027 |
| 28 | 1.8 | 2155 | | 9000 | | 0.79 | 1.3 |
| 29 | 2.3 | 273 | | 2306 | | 0.1 | 0.28 |
| 30 | 260 | 2451 | | >10000 | | 2.8 | 7.6 |
| 31 | 0.36 | 1889 | | 11000 | | 0.0008 | 0.07 |
| 32 | 0.33 | 3322 | | 9500 | | 0.009 | 0.21 |
| 33 | 0.36 | 215 | | 4284 | | 0.0009 | 0.018 |
| 34 | 0.12 | 314 | | 2614 | | <0.0008 | 0.025 |
| 35 | 0.34 | 291 | | 1804 | | <0.0008 | 0.009 |
| 36 | 26 | 6206 | | 7616 | | 1.2 | 4.5 |
| 37 | 37 | 8621 | | 7393 | | 1 | >60 |
| 38 | 5.3 | 1761 | | 11000 | | 4.4 | 7 |
| 39 | 96 | 5700 | | 8881 | | 2.6 | 8 |
| 40 | 0.58 | 270 | | >10000 | | 0.07 | 0.3 |
| 41 | 0.47 | 1249 | | 12000 | | 0.016 | 0.08 |
| 42 | 0.31 | 973 | | >10000 | | 0.031 | 0.12 |
| 43 | 0.4 | 1758 | | >10000 | | 0.052 | 0.25 |
| 44 | 0.34 | 416 | | 12000 | | 0.22 | 0.37 |
| 45 | 1.2 | 1613 | | >10000 | | 0.1 | 0.27 |
| 46 | 0.3 | 68 | | 1613 | | 0.0008 | 0.012 |
| 47 | 0.11 | 160 | | 2719 | | <0.0008 | 0.0012 |
| 48 | 0.16 | 134 | | 1124 | | <0.0008 | <0.0008 |
| 49 | 14 | 968 | | >10000 | | 1.8 | 3 |
| 50 | 2 | 247 | | 6294 | | 0.17 | 0.7 |
| 51 | 1.6 | 799 | | 7909 | | 0.046 | 0.39 |
| 52 | 1 | 877 | | 9500 | | 0.1 | 0.5 |
| 53 | 1.4 | 845 | | 8821 | | 0.072 | 0.8 |
| 54 | 1.1 | 437 | | 5790 | | 0.41 | 1.2 |
| 55 | 0.66 | 74 | | 648 | | 0.0008 | 0.032 |
| 56 | 0.27 | 227 | | 579 | | 0.0007 | 0.005 |
| 57 | 0.18 | 162 | | 782 | | 0.0008 | 0.009 |
| 58 | 99 | 307 | | 1124 | | 0.7 | 2.8 |
| 59 | 100 | 1696 | | >10000 | | 2.9 | 8.8 |
| 60 | 28 | 3316 | | >10000 | | 1.05 | 6.8 |
| 61 | 90 | 903 | | 1837 | | 1.8 | 7.6 |
| 62 | 0.16 | 2011 | | >10000 | | 0.005 | 0.035 |
| 63 | 0.23 | 1301 | | >10000 | | 0.032 | 0.11 |
| 64 | 0.21 | 1309 | | 5000 | | 0.048 | 0.19 |
| 65 | 46 | 4626 | | >10000 | | 1.2 | 7 |
| 66 | 0.22 | 2021 | | >10000 | | 0.006 | 0.084 |
| 67 | 0.23 | 2464 | | 9500 | | 0.017 | 0.15 |
| 68 | 0.27 | 3153 | | >10000 | | 0.018 | 0.18 |
| 69 | 0.17 | 1531 | | 11000 | | 0.1 | 0.195 |
| 70 | 0.44 | 924 | | 9500 | | 0.003 | 0.14 |
| 71 | 0.62 | 594 | | 4911 | | 0.02 | 0.17 |
| 72 | 0.2 | 324 | | 2692 | | 0.0017 | 0.036 |
| 73 | 0.23 | 460 | | 672 | | 0.0009 | 0.009 |

TABLE 3-continued

| Example | TOR Kinase IC$_{50}$ (nM) | PI3 Kinase α IC$_{50}$ (nM) | PI3 Kinase β IC$_{50}$ (nM) | PI3 Kinase γ IC$_{50}$ (nM) | PI3 Kinase δ IC$_{50}$ (nM) | LNCap IC$_{50}$ (μM) | MDA468 IC$_{50}$ (μM) |
|---|---|---|---|---|---|---|---|
| 74 | 4.5 | 4479 | | 9500 | | 0.2 | 6 |
| 75 | 27 | 1057 | | >10000 | | 0.35 | 1.3 |
| 76 | 29 | 6692 | | >10000 | | 1.7 | 7 |
| 77 | 2.2 | 2095 | | >10000 | | 0.12 | 0.7 |
| 78 | 2.6 | >10000 | | >10000 | | 0.17 | 1.05 |
| 79 | 1.9 | 1975 | | >10000 | | 0.02 | 0.15 |
| 80 | 100 | >10000 | | >10000 | | | |
| 81 | 54 | >10000 | | >10000 | | 1.05 | 5.8 |
| 82 | 0.58 | 1710 | | >10000 | | 0.06 | 0.23 |
| 83 | 0.76 | 2351 | | >10000 | | 0.04 | 0.24 |
| 84 | 0.56 | 1975 | | >10000 | | 1.01 | 1.2 |
| 85 | 0.47 | 2636 | | >10000 | | 0.09 | 0.3 |
| 86 | 0.66 | 4237 | | >10000 | | 0.08 | 0.35 |
| 87 | 0.8 | 396 | | 7022 | | 0.03 | 0.12 |
| 88 | 0.3 | 454 | | 3816 | | 0.06 | 0.13 |
| 89 | 0.26 | 301 | | 2378 | | 0.015 | 0.063 |
| 90 | 0.39 | 412 | | 4330 | | 0.012 | 0.06 |
| 91 | 0.49 | 306 | | 2640 | | 0.5 | 0.12 |
| 92 | 11.7 | >10000 | | >10000 | | 1.8 | 30 |
| 93 | 0.41 | 202 | | >10000 | | 0.023 | 0.17 |
| 94 | 0.51 | 804 | | >10000 | | 0.05 | 0.49 |
| 95 | 0.61 | 1059 | | >10000 | | 0.017 | 0.28 |
| 96 | 0.40 | 1142 | | >10000 | | 1.7 | >60 |
| 97 | 0.34 | 282 | | 9500 | | 0.02 | 0.18 |
| 98 | 0.98 | 1415 | | >10000 | | 0.09 | 0.62 |
| 99 | 1.8 | 130 | | 577 | | 0.068 | 0.28 |
| 100 | 0.63 | 149 | | 794 | | 0.02 | 0.13 |
| 101 | 0.53 | 178 | | 727 | | 0.019 | 0.11 |
| 102 | 16 | 1174 | | 7825 | | 1.3 | 5 |
| 103 | 6.8 | 874 | | 1098 | | 5 | 11 |
| 104 | 0.16 | 201 | | 695 | | 0.0008 | 0.004 |
| 105 | 0.21 | 1179 | >10000 | >10000 | 2380 | 0.0024 | 0.026 |
| 106 | 0.22 | 1301 | | >10000 | | 0.032 | 0.11 |
| 107 | 0.24 | 1309 | | 5000 | | 0.048 | 0.19 |
| 108 | 0.24 | 882 | | >10000 | | 0.02 | 0.07 |
| 109 | 0.3 | 227 | | >10000 | | 0.02 | 0.051 |
| 110 | 0.6 | 1051 | >10000 | 12000 | 12000 | 0.0023 | 0.042 |
| 111 | 8.500 | 3345 | | 12000 | | 0.7000 | 6.0000 |
| 112 | 0.750 | 1260 | | >10000 | | 0.0400 | 1.0500 |
| 113 | 225.000 | 7510 | | >10000 | | 2.7000 | 30.0000 |
| 114 | 36.500 | 1428 | | 7481 | | 4.0000 | 6.0000 |
| 115 | 360.000 | 5057 | | 8930 | | 1.6000 | 4.6000 |
| 116 | 335.000 | 2664 | | 6738 | | 1.7000 | 4.0000 |
| 117 | >800.000 | >10000 | | >10000 | | 4.4000 | 22.0000 |
| 118 | >800.000 | 8037 | | >10000 | | 2.8000 | 4.7000 |
| 119 | 3.600 | 4671 | | >10000 | | 0.1800 | 1.2000 |
| 120 | 69.000 | 7916 | | >10000 | | 0.9500 | 6.9000 |
| 121 | 0.500 | 7652 | | >10000 | | 0.0020 | 0.0630 |
| 122 | 4.000 | >10000 | | >10000 | | 0.1900 | 1.8000 |
| 123 | 0.260 | 4577 | | >10000 | | 0.0010 | 0.0090 |
| 124 | 0.225 | 5129 | | >10000 | | 0.0010 | 0.0200 |
| 125 | 0.235 | 1350 | | >10000 | | 0.0080 | 0.0400 |
| 126 | 0.220 | 12000 | | >10000 | | 0.0020 | 0.0580 |
| 127 | 0.155 | 353 | | >10000 | | 0.0040 | 0.0180 |
| 128 | 0.125 | 220 | | 1934 | | <0.0010 | 0.0010 |
| 129 | 10.400 | >10000 | | >10000 | | 0.8000 | 4.9000 |
| 130 | 1.500 | >10000 | | >10000 | | 0.0450 | 0.8000 |
| 131 | 635.000 | >10000 | | >10000 | | >60.0000 | >60.0000 |
| 132 | 15.500 | >10000 | | >10000 | | 0.5800 | 5.0000 |
| 133 | 18.500 | 905 | | 7637 | | 0.0900 | 0.7000 |
| 134 | 17.500 | 2441 | | >10000 | | 0.3900 | 4.0000 |
| 135 | 0.268 | 146 | | 1710 | | 0.0010 | 0.0010 |
| 136 | 6.250 | 3900 | | >10000 | | 0.0400 | 1.1000 |
| 137 | 3.750 | 6662 | | >10000 | | 0.2000 | 1.7000 |
| 138 | 1.275 | 1036 | | 3781 | | 0.0800 | 0.5100 |
| 139 | 0.115 | 234 | | 6166 | | 0.0050 | 0.0500 |
| 140 | 0.140 | 740 | | 5896 | | 0.0010 | 0.0320 |
| 141 | 0.155 | 648 | | 6374 | | 0.0010 | 0.0400 |
| 142 | 0.200 | 953 | | 5379 | | 0.0010 | 0.0480 |
| 143 | 0.076 | 246 | | 4581 | | 0.0100 | 0.0700 |
| 144 | 0.270 | 831 | | 11000 | | 0.0230 | 0.2700 |
| 145 | 2.750 | 3358 | | >10000 | | 0.2500 | 12.0000 |
| 146 | 2.900 | 2146 | | 7638 | | 0.1100 | 0.5800 |
| 147 | 0.185 | 30 | | 475 | | <0.0010 | 0.0180 |
| 148 | 0.064 | 49 | | 781 | | <0.0010 | 0.0090 |
| 149 | 0.125 | 40 | | 342 | | <0.0010 | 0.0040 |

TABLE 3-continued

| Example | TOR Kinase IC$_{50}$ (nM) | PI3 Kinase α IC$_{50}$ (nM) | PI3 Kinase β IC$_{50}$ (nM) | PI3 Kinase γ IC$_{50}$ (nM) | PI3 Kinase δ IC$_{50}$ (nM) | LNCap IC$_{50}$ (μM) | MDA468 IC$_{50}$ (μM) |
|---|---|---|---|---|---|---|---|
| 150 | 0.745 | 648 | | >10000 | | 0.0020 | 0.0350 |
| 151 | 1.190 | 363 | | >10000 | | 0.0080 | 0.1300 |
| 152 | 0.600 | 566 | | >10000 | | 0.0030 | 0.1800 |
| 153 | 14.500 | 966 | | 4239 | | 0.4000 | 2.2000 |
| 154 | 85.000 | 4285 | | >10000 | | 2.9000 | 19.0000 |
| 155 | 1.750 | 82 | | 1171 | | 0.0010 | 0.1100 |
| 156 | 2.650 | 160 | | 1534 | | 0.0010 | 0.0680 |
| 157 | 2.700 | 235 | | 3119 | | 0.0500 | 0.2200 |
| 158 | 27.000 | 3519 | | >10000 | | 0.6800 | 5.0000 |
| 159 | 4.850 | 188 | | 3822 | | 0.0180 | 0.0900 |
| 160 | 13.000 | 3125 | | >10000 | | 0.2800 | 1.8000 |
| 161 | 8.400 | 3597 | | >10000 | | 0.2100 | 2.2000 |
| 162 | 1.200 | 173 | | 482 | | 0.0500 | 0.2000 |
| 163 | 0.880 | 43 | | 1292 | | 0.0280 | 0.0900 |
| 164 | 0.080 | 29 | | 1822 | | <0.0010 | <0.0010 |
| 165 | 0.095 | 54 | | 2488 | | <0.0010 | <0.0010 |
| 166 | 0.480 | 117 | | 867 | | <0.0010 | 0.0020 |
| 167 | 0.425 | 234 | | 1220 | | <0.0010 | 0.0040 |
| 168 | 3.150 | 218 | | 3223 | | 1.5000 | 9.0000 |
| 169 | 40.500 | 422 | | 5454 | | 0.5000 | 2.2000 |
| 170 | 51.000 | 705 | | 4417 | | 1.3000 | 6.0000 |
| 171 | 0.215 | 54 | | 1830 | | 0.0050 | 0.0080 |
| 172 | 3.050 | 1374 | | 1732 | | 0.2000 | 1.3000 |
| 173 | 2.250 | 270 | | 3133 | | 0.2700 | 0.6500 |
| 174 | 4.700 | 232 | | 4975 | | 0.1900 | 0.7000 |
| 175 | 52.000 | 836 | | 668 | | 0.3500 | 1.2500 |
| 176 | 3.550 | 386 | | 9500 | | 5.5000 | 28.00 |
| 177 | 69.500 | 1644 | | >10000 | | 1.2000 | 4.5000 |
| 178 | 87.000 | 959 | | >10000 | | 1.9000 | 5.8000 |
| 179 | 66.500 | 482 | | 9982 | | 1.7000 | 5.0000 |
| 180 | 0.275 | 56 | | 1338 | | <0.0010 | <0.0010 |
| 181 | 0.180 | 175 | | 3672 | | <0.0010 | <0.0010 |
| 182 | 0.120 | 40 | | 1273 | | <0.0010 | <0.0010 |
| 183 | 0.120 | 68 | | 1499 | | <0.0010 | <0.0010 |
| 184 | 0.295 | 2154 | | 7764 | | 0.0010 | 0.0080 |
| 185 | 0.735 | 196 | | 2271 | | <0.0010 | 0.0010 |
| 186 | 0.835 | 136 | | 1784 | | <0.0010 | 0.0080 |
| 187 | 0.405 | 199 | | 3800 | | 0.0010 | 0.0190 |
| 188 | 1.100 | 464 | | 2980 | | 0.0100 | 0.1900 |
| 189 | 0.885 | 849 | | 11000 | | 0.0050 | 0.0200 |
| 190 | 0.505 | 542 | | 3047 | | 0.0040 | 0.0330 |
| 191 | 3.550 | 6637 | | >10000 | | 0.2100 | 0.7800 |
| 192 | 26.000 | 2098 | | >10000 | | 1.0200 | 5.0000 |
| 193 | 2.850 | 375 | | >10000 | | 0.6500 | 0.9800 |
| 194 | 2.700 | 1499 | | >10000 | | 0.2800 | 0.8000 |
| 195 | 4.900 | 1879 | | >10000 | | 0.6400 | 1.5000 |
| 196 | 2.200 | 607 | | 7331 | | 10.0000 | 13.0000 |
| 197 | 2.850 | 1345 | | 12000 | | 0.4000 | 1.4000 |
| 198 | 0.685 | 68 | | 1926 | | 0.0280 | 0.1900 |
| 199 | 0.460 | 174 | | 3992 | | 0.0900 | 0.1100 |
| 200 | 0.390 | 92 | | 2196 | | 0.0500 | 0.0500 |
| 201 | 0.265 | 50 | | 1762 | | 0.0130 | 0.0120 |
| 202 | 0.215 | 44 | | 2162 | | 0.0010 | 0.0040 |
| 203 | 1.075 | 104 | | 1144 | | 0.0010 | 0.0020 |
| 204 | 0.490 | 274 | | 11280 | | 0.0060 | 0.0350 |
| 205 | 1.700 | 202 | | 3573 | | 0.0900 | 0.0800 |
| 206 | 0.700 | 469 | | 11783 | | 0.1900 | 0.1200 |
| 207 | 145.000 | 3590 | | >10000 | | 14.0000 | 38.0000 |
| 208 | 8.200 | 1855 | | >10000 | | 0.2200 | 0.9000 |
| 209 | 2.250 | 3712 | | 4950 | | 0.0400 | 0.6000 |
| 210 | 0.930 | 1749 | | >10000 | | 0.0040 | 0.1100 |
| 211 | 0.885 | 2117 | | >10000 | | 0.0170 | 0.1200 |
| 212 | 0.565 | 3964 | | >10000 | | 0.0420 | 0.1900 |
| 213 | 1.250 | 4527 | | >10000 | | 0.1500 | 1.0000 |
| 214 | 1.500 | 726 | | >10000 | | 0.2100 | 0.5700 |
| 215 | 1.350 | 3595 | | >10000 | | 0.0780 | 0.8000 |
| 216 | 0.255 | 124 | | 3324 | | 0.0040 | 0.0550 |
| 217 | 0.170 | 112 | | 348 | | <0.0010 | 0.0010 |
| 218 | 0.122 | 40 | | 2202 | | <0.0010 | <0.0010 |
| 219 | 0.082 | 44 | | 1375 | | <0.0010 | <0.0010 |
| 220 | 0.480 | 74 | | 1678 | | 0.0040 | 0.0100 |
| 221 | 0.235 | 444 | | 4791 | | <0.0010 | 0.0030 |
| 222 | 0.405 | 143 | | 2609 | | 0.0010 | 0.0080 |
| 223 | 0.265 | 1663 | | >10000 | | 0.0100 | 0.0210 |
| 224 | 0.745 | 155 | | 2602 | | 0.0030 | 0.0120 |
| 225 | 26.500 | 1388 | | >10000 | | 2.4000 | 4.0000 |

TABLE 3-continued

| Example | TOR Kinase IC$_{50}$ (nM) | PI3 Kinase α IC$_{50}$ (nM) | PI3 Kinase β IC$_{50}$ (nM) | PI3 Kinase γ IC$_{50}$ (nM) | PI3 Kinase δ IC$_{50}$ (nM) | LNCap IC$_{50}$ (μM) | MDA468 IC$_{50}$ (μM) |
|---|---|---|---|---|---|---|---|
| 226 | 230.000 | 4149 | | >10000 | | 0.7000 | 1.3000 |
| 227 | 15.000 | 5936 | | >10000 | | 1.2000 | 3.2000 |
| 228 | 31.500 | 4498 | | >10000 | | 0.4900 | 0.9000 |
| 229 | 245.000 | 2850 | | >10000 | | 4.9000 | 4.0000 |
| 230 | 15.500 | 2889 | | >10000 | | 1.3000 | 1.5000 |
| 231 | 0.130 | 47 | | 468 | | <0.0010 | <0.0010 |
| 232 | 0.105 | 60 | | 524 | | <0.0010 | 0.0020 |
| 233 | 0.865 | 604 | | >10000 | | 0.0400 | 0.1400 |
| 234 | 0.355 | 162 | | 1100 | | 0.0020 | 0.0110 |
| 235 | 0.625 | 187 | | 1064 | | 0.0030 | 0.0680 |
| 236 | 0.445 | 70 | | 260 | | 0.0040 | 0.0430 |
| 237 | 0.370 | 1351 | | >10000 | | 0.0070 | 0.0520 |
| 238 | 0.245 | 371 | | >10000 | | 0.0010 | 0.0080 |
| 239 | 0.108 | 64 | | 440 | | 0.0010 | 0.0040 |
| 240 | 0.305 | 116 | | 916 | | 0.0010 | 0.0080 |
| 241 | 0.950 | 551 | | >10000 | | 0.1100 | 0.2300 |
| 242 | 0.655 | 869 | | >10000 | | 0.0040 | 0.0190 |
| 243 | 0.835 | 116 | | 1302 | | 0.0040 | 0.0090 |
| 244 | 0.185 | 739 | | >10000 | | 0.0010 | 0.0070 |
| 245 | 1.200 | 2903 | | >10000 | | 0.1300 | 0.9000 |
| 246 | 0.698 | 96 | | 1561 | | <0.0010 | 0.0070 |
| 247 | 0.700 | 1365 | | >10000 | | 0.0900 | 0.4000 |
| 248 | 0.765 | 1825 | | >10000 | | 0.0900 | 0.5000 |
| 249 | 0.185 | 102 | | 1197 | | <0.0010 | 0.0080 |
| 250 | 0.086 | 34 | | 952 | | <0.0010 | 0.0040 |
| 251 | 0.340 | 1004 | | >10000 | | <0.0010 | <0.0010 |
| 252 | 0.465 | 9500 | | >10000 | | 0.0010 | 0.0080 |
| 253 | 0.150 | 56 | | 780 | | 0.0010 | <0.0010 |
| 254 | 1625.000 | 9650 | | 12000 | | 6.2000 | 0.2000 |
| 255 | 0.595 | 105 | | 730 | | 0.0060 | 0.0300 |
| 256 | 195.000 | >10000 | | >10000 | | 3.5000 | 18.0000 |
| 257 | 1.800 | 344 | | 4245 | | <0.0010 | 0.0030 |
| 258 | 3.950 | 346 | | 1409 | | <0.0010 | 0.0050 |
| 259 | 2.400 | 1051 | | 2723 | | <0.0010 | 0.0010 |
| 260 | 0.111 | 98 | | 440 | | <0.0010 | <0.0010 |
| 261 | 0.776 | 142 | >10000 | >10000 | 945 | 0.0010 | 0.0020 |
| 262 | 0.515 | 191 | | 1357 | | 0.0010 | 0.0050 |
| 263 | 0.215 | 147 | | 10436 | | <0.0010 | 0.0050 |
| 264 | 2.900 | 1689 | | 8837 | | 0.0380 | 0.7000 |
| 265 | 1.200 | 3473 | | >10000 | | 0.0180 | 0.7000 |
| 266 | 0.615 | 2718 | | >10000 | | 0.0270 | 0.1800 |
| 267 | 0.565 | 1367 | | 9000 | | 0.0090 | 0.0400 |
| 268 | 0.200 | 227 | | 3012 | | <0.0010 | 0.0030 |
| 269 | 0.079 | 117 | | 2127 | | <0.0010 | <0.0010 |
| 270 | 0.520 | 371 | | 9500 | | <0.0010 | 0.0010 |
| 271 | 0.355 | 3681 | | 9000 | | 0.0070 | 0.0800 |
| 272 | 0.106 | 132 | | 1149 | | <0.0010 | 0.0010 |
| 273 | 0.240 | 618 | | >10000 | | 0.0010 | 0.0100 |
| 274 | 0.245 | 1209 | | 7306 | | <0.0010 | 0.0200 |
| 275 | 0.575 | 275 | | 3113 | | <0.0010 | <0.0010 |
| 276 | 93.000 | 3978 | | 9000 | | 7.5000 | 30.0000 |
| 277 | 110.000 | 2952 | | >10000 | | 3.5000 | 8.0000 |
| 278 | 42.000 | 311 | | 494 | | 2.2000 | 5.2000 |
| 279 | 23.500 | 1832 | | 8111 | | 3.2000 | 6.0000 |
| 280 | 6.000 | 1436 | | 8212 | | 0.0550 | 0.1200 |
| 281 | 1.075 | 173 | | 1104 | | 0.0040 | 0.0190 |
| 282 | 0.300 | 166 | | 1161 | | 0.0050 | 0.0210 |
| 283 | 0.975 | 373 | | 4748 | | <0.0010 | 0.0080 |
| 284 | 1.500 | 419 | | >10000 | | 0.0060 | 0.0800 |
| 285 | 0.105 | 23 | | 524 | | <0.0010 | 0.0010 |
| 286 | 0.900 | 270 | | 14868 | | 0.0170 | 0.2000 |
| 287 | 0.410 | 164 | | 1459 | | 0.0370 | 0.2000 |
| 288 | 0.575 | 53 | | 534 | | <0.0010 | 0.0500 |
| 289 | 0.330 | 109 | | 706 | | <0.0010 | <0.0010 |
| 290 | 0.175 | 102 | | 757 | | <0.0010 | 0.0040 |
| 291 | 9.000 | 6138 | | >10000 | | 0.1700 | 0.3000 |
| 292 | 5.500 | 2092 | | >10000 | | 0.0800 | 0.3000 |
| 293 | 1.250 | 602 | | >10000 | | 0.0170 | 0.0500 |
| 294 | 0.775 | 220 | | 3021 | | <0.0010 | 0.0010 |
| 295 | 2.325 | 410 | | 4672 | | 0.0010 | 0.0130 |
| 296 | 1.867 | 4052 | >10000 | 1070 | 6822 | 0.0670 | 0.1380 |
| 297 | 0.550 | 275 | | 3576 | | <0.0010 | 0.0040 |
| 298 | 1.250 | 1218 | | 10426 | | <0.0010 | 0.0010 |
| 299 | 2.850 | 10250 | | >10000 | | 0.0100 | 0.0420 |
| 300 | 5.500 | 572 | | 5282 | | 0.0010 | 0.0120 |
| 301 | 0.335 | 2032 | | >10000 | | | |

TABLE 3-continued

| Example | TOR Kinase IC$_{50}$ (nM) | PI3 Kinase α IC$_{50}$ (nM) | PI3 Kinase β IC$_{50}$ (nM) | PI3 Kinase γ IC$_{50}$ (nM) | PI3 Kinase δ IC$_{50}$ (nM) | LNCap IC$_{50}$ (μM) | MDA468 IC$_{50}$ (μM) |
|---|---|---|---|---|---|---|---|
| 302 | 0.300 | 3917 | >10000 | 8018 | 1742 | 0.0020 | 0.0070 |
| 303 | 0.145 | 164 | | 845 | | <0.0010 | 0.0010 |
| 304 | 0.265 | 239 | 2843 | 720 | 200 | <0.0010 | 0.0010 |
| 305 | 0.250 | 182 | | 1523 | | <0.0010 | 0.0010 |
| 306 | 0.079 | 88 | | 1272 | | <0.0010 | 0.0080 |
| 307 | 0.145 | 404 | | 4957 | | <0.0010 | 0.0020 |
| 308 | 0.080 | 80 | | 2718 | | <0.0010 | <0.0010 |
| 309 | 0.385 | 336 | | 2674 | | <0.0010 | 0.0020 |
| 310 | 0.495 | 221 | | 2427 | | <0.0010 | 0.0010 |
| 311 | 0.860 | 3840 | | >10000 | | 0.0020 | 0.1200 |
| 312 | 0.203 | 353 | | 2216 | | 0.0010 | 0.0120 |
| 313 | 0.365 | 581 | | 1451 | | 0.0010 | 0.0150 |
| 314 | 0.455 | 511 | | 2016 | | 0.0010 | 0.0150 |
| 315 | 0.800 | 5604 | | 2064 | | 0.0100 | 0.2200 |
| 316 | 0.495 | 4564 | | >10000 | | 0.0070 | 0.1600 |
| 317 | 0.255 | 77 | | >10000 | | <0.0010 | 0.0010 |
| 318 | 0.190 | 173 | | 2267 | | <0.0010 | 0.0010 |
| 319 | 13.500 | 628 | | >10000 | | 0.2400 | 0.9000 |
| 320 | 9.100 | 1950 | | >10000 | | 0.1600 | 0.5900 |
| 321 | 10.450 | 3809 | | >10000 | | 0.1700 | 1.0500 |
| 322 | 6.450 | 1246 | | >10000 | | 1.0000 | 2.8000 |
| 323 | 16.500 | 6625 | | >10000 | | 0.4700 | 2.0000 |
| 324 | 3.400 | 382 | | 5205 | | 0.0080 | 0.0580 |
| 325 | 1.600 | 601 | | 4976 | | 0.0020 | 0.0190 |
| 326 | 2.650 | 1178 | | 9532 | | 0.0300 | 0.1500 |
| 327 | 3.750 | 764 | | 3492 | | 0.0030 | 0.0500 |
| 328 | 125.000 | 5772 | | >10000 | | 2.3500 | 9.2000 |
| 329 | 1.750 | 357 | | 4348 | | | |
| 330 | 0.405 | 238 | | 1849 | | 0.0070 | 0.0600 |
| 331 | 8.050 | 606 | | 5315 | | 0.3800 | 1.2000 |
| 332 | 2.450 | 351 | | 2764 | | 0.3700 | 0.9000 |
| 333 | 0.580 | 276 | | 4590 | | 0.0680 | 0.3800 |
| 334 | 4.500 | 434 | | 3944 | | 2.9600 | 5.2000 |
| 335 | 2.350 | 273 | | 4477 | | 0.0280 | 0.2100 |
| 336 | 2.750 | 666 | | >10000 | | <0.0010 | 0.0040 |
| 337 | 31.500 | 1790 | | 7929 | | 2.2000 | 1.9000 |
| 338 | 786.667 | 9500 | | >10000 | | 2.9500 | 1.8700 |
| 339 | >6333 | 9415 | | >10000 | | >60.0000 | >60.0000 |
| 340 | 305.000 | 5084 | | 5761 | | 5.2000 | 5.2000 |
| 341 | 91.000 | 4632 | | >10000 | | 2.5000 | 5.0000 |
| 342 | 53.000 | 9500 | | >10000 | | 0.6700 | 1.0000 |
| 343 | 81.000 | 5170 | | >10000 | | 1.2000 | 1.5000 |
| 344 | 17.000 | 1935 | | >10000 | | 0.6600 | 1.0000 |
| 345 | 38.500 | 1917 | | >10000 | | 0.1900 | 0.4500 |
| 346 | 10.900 | 448 | | 372 | | 0.2900 | 0.9500 |
| 347 | 5.600 | 1101 | | 7131 | | 0.3100 | 1.3000 |
| 348 | 7.500 | 1011 | | 8590 | | 0.2800 | 1.0000 |
| 349 | 8.900 | 596 | | 4962 | | 0.2100 | 0.8000 |
| 350 | 1.950 | 565 | | 6583 | | 0.1300 | 0.4800 |
| 351 | 9.000 | 2456 | | >10000 | | 1.0500 | 1.6000 |
| 352 | 17.500 | 1082 | | 6103 | | 0.2000 | 0.7000 |
| 353 | 15.000 | 1562 | | >10000 | | 0.7000 | 1.2000 |
| 354 | 66.500 | 2386 | | >10000 | | 1.2000 | 2.9000 |
| 355 | 0.775 | 7452 | | 6801 | | 0.0580 | 0.2200 |
| 356 | 0.220 | 4271 | | 6735 | | 0.0300 | 0.0500 |
| 357 | 0.625 | 5554 | | 9160 | | 0.0090 | 0.0700 |
| 358 | 0.495 | 7697 | | 7933 | | 0.0060 | 0.0350 |
| 359 | 0.705 | 5639 | | 7786 | | 0.0060 | 0.0360 |
| 360 | 0.425 | 1463 | | 2148 | | 0.0100 | 0.0400 |
| 361 | 0.165 | 1827 | | 4074 | | 0.0020 | 0.0200 |
| 362 | 0.260 | 1928 | | 2004 | | 0.0030 | 0.0100 |
| 363 | 0.545 | 1590 | | 3239 | | <0.0010 | 0.0010 |
| 364 | 0.440 | 1233 | | 947 | | 0.0010 | 0.0040 |
| 365 | 0.795 | 2590 | | 4527 | | 0.0040 | 0.0120 |
| 366 | 0.795 | 2067 | | 1500 | | 0.0100 | 0.0200 |
| 367 | 0.880 | 2392 | | 1822 | | 0.0010 | 0.0130 |
| 368 | 0.885 | 1162 | | 2000 | | 0.0010 | 0.0040 |
| 369 | 1.600 | 3136 | | 11857 | | 0.2200 | 0.7500 |
| 370 | 0.985 | 2151 | | 6508 | | 0.1300 | 0.4000 |
| 371 | 1.300 | 2494 | | 8927 | | 0.1900 | 0.4600 |
| 372 | 0.395 | 2975 | | 5338 | | 0.1100 | 0.4200 |
| 373 | 0.385 | 217 | | 1124 | | 0.2200 | 0.2000 |
| 374 | 57.000 | | | | | 1.0000 | 5.5000 |
| 375 | 15.500 | 4791 | | >10000 | | 0.7000 | 1.7000 |
| 376 | 0.125 | 270 | | 4055 | | 0.0010 | 0.0050 |
| 377 | 2.500 | 7355 | | >10000 | | 0.1400 | 1.2000 |

TABLE 3-continued

| Example | TOR Kinase IC$_{50}$ (nM) | PI3 Kinase α IC$_{50}$ (nM) | PI3 Kinase β IC$_{50}$ (nM) | PI3 Kinase γ IC$_{50}$ (nM) | PI3 Kinase δ IC$_{50}$ (nM) | LNCap IC$_{50}$ (μM) | MDA468 IC$_{50}$ (μM) |
|---|---|---|---|---|---|---|---|
| 378 | 11.500 | 407 | | 1965 | | 0.8200 | 5.8000 |
| 379 | 245.000 | >10000 | | >10000 | | 6.8000 | 5.0000 |
| 380 | 0.245 | 882 | | >10000 | | 0.0200 | 0.0700 |
| 381 | 0.300 | 227 | | >10000 | | 0.0200 | 0.0510 |
| 382 | 49.500 | 1913 | | 11621 | | 1.2000 | 5.5000 |
| 383 | 0.530 | 793 | | >10000 | | 0.0070 | 0.0300 |
| 384 | 0.175 | 297 | | 2166 | | 0.0020 | 0.0220 |
| 385 | 9.950 | 4029 | | >10000 | | 1.0000 | 4.7000 |
| 386 | 0.375 | 1170 | | 7444 | | 0.0020 | 0.0370 |
| 387 | 0.330 | 705 | | 404 | | 0.0010 | 0.0190 |
| 388 | 12.500 | 10495 | | >10000 | | 0.3300 | 2.0000 |
| 389 | 0.285 | 909 | | >10000 | | 0.0020 | 0.0170 |
| 390 | 540.000 | | | | | 12.0000 | 10.0000 |
| 391 | 4.200 | 101 | | 919 | | 0.1850 | 0.5800 |
| 392 | 39.500 | 582 | | 10950 | | 1.2000 | 4.8000 |
| 393 | 1.750 | 330 | | 3090 | | 0.0010 | 0.0140 |
| 394 | 14.500 | 2920 | | 9500 | | 0.3200 | 2.0000 |
| 395 | 0.480 | 1457 | | 8002 | | 0.0040 | 0.0600 |
| 396 | 0.335 | 145 | | 1794 | | <0.0010 | 0.0040 |
| 397 | 3.100 | 317 | | 5626 | | 0.2100 | 1.5000 |
| 398 | 0.520 | 1151 | | 5649 | | 0.0010 | 0.0200 |
| 399 | 0.520 | 1500 | | 6599 | | 0.0010 | 0.0410 |
| 400 | 0.335 | 165 | | 1990 | | <0.0010 | <0.0010 |
| 401 | 0.445 | 2114 | | >10000 | | 0.0010 | 0.0100 |
| 402 | 0.410 | 2969 | | >10000 | | 0.0020 | 0.0400 |
| 403 | 0.400 | 3632 | | >10000 | | 0.0050 | 0.1800 |
| 404 | 0.190 | 93 | | 1140 | | <0.0010 | 0.0180 |
| 405 | 0.330 | 107 | | 1359 | | <0.0010 | 0.0200 |
| 406 | 0.94 | 423 | | >10000 | | 0.085 | 0.4 |
| 407 | 0.76 | 1262 | | >10000 | | 0.012 | 0.25 |
| 408 | 0.61 | 825 | | >10000 | | 0.087 | 0.53 |
| 409 | 0.31 | 324 | | 10000 | | 0.18 | 0.475 |
| 410 | 0.71 | 1359 | | 10000 | | 0.04 | 0.78 |
| 411 | 1.3 | 82 | | 2188 | | 0.14 | 0.38 |
| 412 | 0.28 | 119 | | 2358 | | 0.027 | 0.072 |
| 413 | 0.39 | 80 | | 1384 | | 0.01 | 0.048 |
| 414 | 100 | >10000 | | >10000 | | 4.3 | 30 |
| 415 | 26 | 4372 | | >10000 | | 1.7 | 8.5 |
| 416 | 8.6 | 6199 | | >10000 | | 1.85 | 9.1 |
| 417 | 61 | 399 | | >10000 | | 2.8 | 7.8 |
| 418 | 34 | 6270 | | >10000 | | 2.8 | 17 |
| 419 | 22 | 8619 | | >10000 | | 1.35 | 7.9 |
| 420 | 32 | 1767 | | >10000 | | 1.25 | 4.8 |
| 421 | 51 | 246 | | 9181 | | 1.2 | 3.9 |
| 422 | 270 | 4434 | | >10000 | | 7.2 | 31 |
| 423 | 19.500 | 322 | | 5722 | | 0.5000 | 1.0000 |
| 424 | 15.500 | 874 | | 3667 | | 0.4000 | 2.0000 |
| 425 | 545.000 | 5530 | | >10000 | | 19.0000 | 23.0000 |
| 426 | 4.700 | 148 | | 2609 | | 0.1800 | 0.3800 |
| 427 | 3.700 | 86 | | 1270 | | 0.2000 | 0.3900 |
| 428 | 1.500 | 34 | | 815 | | 0.2400 | 0.1100 |
| 429 | 1.405 | 46 | | 3712 | | 0.1200 | 0.0900 |
| 430 | 1.290 | 113 | | 1626 | | 0.0360 | 0.0900 |
| 431 | 1.015 | 179 | | 1531 | | 0.0320 | 0.2000 |
| 432 | 1.300 | 6 | | 522 | | 0.0040 | 0.0370 |
| 433 | 0.560 | 12 | | 286 | | 0.0220 | 0.0600 |
| 434 | 0.445 | 8 | | 330 | | 0.1200 | 0.1800 |

While particular embodiments of the present invention have been illustrated and described, it would be understood by those skilled in the art that various other changes and modifications can be made without departing from the spirit and scope of the invention. Therefore, the invention is not limited to the embodiments illustrated and described, but includes the entire subject matter encompassed by the appended claims.

It is intended that each of the patents, applications, and printed publications, including books, mentioned in this patent document be hereby incorporated by reference in their entirety.

What is claimed is:

1. A compound of the Formula (Ia):

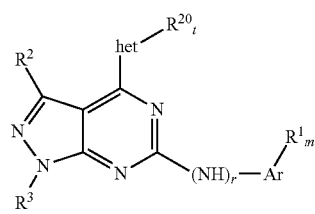

(Ia)

or pharmaceutically acceptable salts thereof, wherein:
het is a 5-10-membered bridged heterobicyclyl-group containing at least one oxygen atom, at least one nitrogen atom, and optionally additional heteroatoms selected from oxygen, sulfur and nitrogen, and is connected to the pyrazolopyrimidinyl group through one of the nitrogen atoms;

$R^{20}$ is independently selected from hydrogen, halogen, hydroxyl, $C_1$-$C_2$alkoxy, $NH_2$, $NH(C_1$-$C_2$alkyl), $N(C_1$-$C_2$alkyl)($C_1$-$C_2$alkyl), NHC(O)($C_1$-$C_2$alkyl), $N(C_1$-$C_2$alkyl)C(O)($C_1$-$C_2$alkyl), NHC(O)H, C(O)$NH_2$, C(O)NH($C_1$-$C_2$alkyl), C(O)N($C_1$-$C_2$alkyl)($C_1$-$C_2$alkyl), CN, C(O)OH, and $C_1$-$C_4$alkoxycarbonyl;

t is 0-16;

each $R^1$ is independently halogen; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_8$alkoxycarbonyl, —$C_1$-$C_8$acyl, $C_6$-$C_{14}$aryl, heteroaryl, and $C_3$-$C_8$-carbocycle; $C_1$-$C_6$alkoxy optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_2$-$C_6$alkenyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_2$-$C_6$alkynyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$carbocycle; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$;

heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; $C_1$-$C_8$acyl; $C_1$-$C_8$alkoxycarbonyl; $C_1$-$C_8$alkylcarboxy; —N—($C_1$-$C_6$)alkylamido; hydroxyl; $NR^4R^5$; —NHC(O)$NR^4R^5$; —NHC(O)NHN$R^4R^5$; —NHC(O)O$R^6$; —NH(SO$_2$)NH—$C_1$-$C_6$alkyl; —NH(SO$_2$)NH—$C_6$-$C_{14}$aryl; —NHC(S)—$NR^4R^5$; —NHC(=N—CN)—$NR^4R^5$; —NHC(=$NR^4$)—$NR^4R^5$; —N=C(S—$C_1$-$C_6$alkyl)(NH—$C_1$-$C_6$alkyl); or —N(H)—C(=N—(CN))-(O—$C_6$-$C_{14}$aryl);

m is 0, 1, 2, 3, or 4;

r is 0 or 1;

each $R^4$ and $R^5$ is independently —H; a 4- to 7-membered monocyclic heterocycle optionally substituted with from 1 to 3 substituents independently selected from $C_1$-$C_6$alkyl, heterocyclylalkyl, $C_7$-$C_{24}$arylalkyl, $C_1$-$C_8$acyl, $C_1$-$C_8$alkoxycarbonyl, $C_1$-$C_8$alkylcarboxy, halo, —$C_1$-$C_8$haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; $C_6$-$C_{14}$aryl optionally substituted with from 1 to 3 substituents independently selected from $C_1$-$C_6$alkyl optionally substituted with —$NH_2$, -alkylamino, or -dialkylamino, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido optionally substituted with —$NH_2$, -alkylamino, or -dialkylamino, —C(O)$NH_2$, -alkylcarboxamido, heterocycle optionally substituted with $C_1$-$C_6$alkyl, —S(O)$_2$-heterocyclylalkyl optionally substituted with $C_1$-$C_6$alkyl, heterocyclylalkyl optionally substituted with $C_1$-$C_6$alkyl, $C_1$-$C_6$alkoxy optionally substituted with —$NH_2$, -alkylamino, -dialkylamino, heterocycle, or hydroxyl, —C(O)NH—$NH_2$, —C(O)NH—NH($C_1$-$C_6$alkyl), —C(O)NH—N($C_1$-$C_6$alkyl)($C_1$-$C_6$alkyl), —C(O)NH-heterocycle, —SO$_2$($C_1$-$C_6$alkyl), —CN, and —$NO_2$; heteroaryl optionally substituted with from 1 to 3 substituents independently selected from $C_1$-$C_6$alkyl optionally substituted with —$NH_2$, -alkylamino, or -dialkylamino, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —($C_1$-$C_6$alkyl)carboxyl, —N—($C_1$-$C_6$)alkylamido optionally substituted with —$NH_2$, -alkylamino, or -dialkylamino, —C(O)$NH_2$, -alkylcarboxamido, heterocycle optionally substituted with $C_1$-$C_6$alkyl, —S(O)$_2$-heterocyclylalkyl optionally substituted with $C_1$-$C_6$alkyl, heterocyclylalkyl optionally substituted with $C_1$-$C_6$alkyl, $C_1$-$C_6$alkoxy optionally substituted with —$NH_2$, -alkylamino, -dialkylamino, heterocycle optionally substituted with $C_1$-$C_6$alkyl, or hydroxyl, —C(O)NH—$NH_2$, —C(O)NH—NH($C_1$-$C_6$alkyl), —C(O)NH—N($C_1$-$C_6$alkyl)($C_1$-$C_6$alkyl), —C(O)NH-heterocycle, —SO$_2$($C_1$-$C_6$alkyl), —CN, and —$NO_2$; —$C_3$-$C_8$-carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$, wherein any two hydrogen atoms on the same carbon atom of the carbocyclic ring can be replaced by an oxygen atom to form an oxo (=O) substituent, and wherein any two hydrogen atoms on the same carbon atom of the carbocyclic ring can be replaced by an alkylenedioxy group so that the alkylenedioxy group, when taken together with the carbon atom to which it is attached, forms a 5- to 7-membered heterocycle containing two oxygen atoms; heterocyclylalkyl optionally substituted with $C_1$-$C_6$alkyl; $C_6$-$C_{10}$carbocycle; bicyclic heterocycle; or $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-

$C_6$alkyl), —CN, hydroxyl, —$C_1$-$C_6$alkoxy optionally substituted with —$NH_2$, $C_1$-$C_6$alkyl, —C(O)OH, —$C_1$-$C_6$alkoxycarbonyl, —$C_1$-$C_8$acyl, $C_6$-$C_{14}$aryl, heteroaryl, -alkylcarboxamido optionally substituted with —$NH_2$, -alkylamino, or -dialkylamino, —C(O)-heterocycle optionally substituted with $C_1$-$C_6$alkyl, and $C_3$-$C_8$-carbocycle;

or $R^4$ and $R^5$ when taken together with the nitrogen to which they are attached can form a 3- to 7-membered heterocycle wherein up to two of the carbon atoms of the heterocycle can be independently replaced with —N($R^7$)—, —O—, —C(O)—, or —S(=O)$_s$—;

each s is independently 1 or 2;

$R^6$ is $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl optionally substituted with —$NH_2$, -alkylamino, or -dialkylamino, heteroaryl, and $C_3$-$C_8$-carbocycle; heterocyclylalkyl optionally substituted with $C_1$-$C_6$alkyl; $C_6$-$C_{10}$-carbocycle; bicyclic heterocycle; or $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$;

$R^7$ is hydrogen; $C_1$-$C_8$acyl; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_3$-$C_8$-carbocycle optionally substituted with from 1 to 3 substituents independently selected from $C_1$-$C_6$alkyl, halo, -haloalkyl, hydroxyl, $C_1$-$C_6$alkoxy, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, alkylcarboxyamido, and —$NO_2$; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; alkylamino; or arylamino optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle;

with the proviso that when m>1, two $R^1$ groups attached to adjacent carbon atoms can be taken together with the two carbons to which they are attached to form a fused 5- to 7-membered aromatic ring wherein up to 2 of the carbon atoms of the fused ring can be replaced with —N=, —N($R^7$)—, —O—, or —S(=O)$_s$—;

$R^2$ is hydrogen; halogen; $C_1$-$C_8$acyl; heterocycle; heterocyclylalkyl; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_2$-$C_6$alkenyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_2$-$C_6$alkynyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_6$-$C_{14}$aryl optionally substituted with from 1 to 3 substituents independently selected from $C_1$-$C_6$alkyl, halo, haloalkyl, hydroxyl, $C_1$-$C_6$hydroxyalkyl, —$NH_2$, -alkylamino, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$; or heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -aminoalkyl, -dialkylamino, —COOH, —$C_1$-$C_6$alkoxycarbonyl, —($C_1$-$C_6$alkyl)carboxyl, —N—($C_1$-$C_6$)alkylamido, —C(O)$NH_2$, -alkylcarboxamido and —$NO_2$;

$R^3$ is hydrogen; $C_1$-$C_6$alkyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_2$-$C_6$alkenyl optionally substituted with from 1 to 3 substituents independently selected from halogen, —$NH_2$, -alkylamino, -dialkylamino, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —$C_1$-$C_8$acyl, $C_6$-$C_{14}$aryl, heteroaryl, and $C_3$-$C_8$-carbocycle; $C_2$-$C_6$alkynyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$-carbocycle; C$_1$-C$_8$acyl; C$_6$-C$_{14}$aryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; heteroaryl optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; C$_7$-C$_{24}$arylalkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$-carbocycle; heterocyclylalkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, and C$_3$-C$_8$carbocycle; C$_1$-C$_6$hydroxyalkyl-; alkylcarboxy; alkoxycarbonyl;

C$_1$-C$_6$ perfluoroalkyl; —S(O)$_S$—C$_1$-C$_6$alkyl wherein the C$_1$-C$_6$alkyl of —S(O)$_S$—C$_1$-C$_6$alkyl is optionally substituted with from 1 to 3 substituents independently selected from C$_1$-C$_6$alkyl, halo, -haloalkyl, hydroxyl, C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$; —S(O)$_S$-aryl wherein the aryl of —S(O)$_S$-aryl is optionally substituted with from 1 to 3 substituents independently selected from C$_1$-C$_6$alkyl, halo, -haloalkyl, hydroxyl, C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$; C$_3$-C$_8$-carbocycle optionally substituted with from 1 to 3 substituents independently selected from C$_1$-C$_6$alkyl, halo, -haloalkyl, hydroxyl, C$_1$-C$_6$alkoxy, —NH$_2$, -alkylamino optionally substituted by hydroxyl, -dialkylamino, heterocycle optionally substituted with C$_1$-C$_6$alkyl, —NH—N(C$_1$-C$_6$alkyl)$_2$, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$, wherein any two hydrogen atoms on the same carbon atom of the C$_3$-C$_8$-carbocycle ring can be replaced by an oxygen atom to form an oxo (═O) substituent, and wherein any two hydrogen atoms on the same carbon atom of the C$_3$-C$_8$-carbocycle ring can be replaced by an alkyleneoxy group so that the alkyleneoxy group, when taken together with the carbon atom to which it is attached, forms a spiro-fused 5- to 7-membered heterocycle containing an oxygen atom, and wherein any two hydrogen atoms on the same carbon atom of the C$_3$-C$_8$-carbocycle ring can be replaced by an alkylenedioxy group so that the alkylenedioxy group, when taken together with the carbon atom to which it is attached, forms a 5- to 7-membered heterocycle containing two oxygen atoms wherein the 5- to 7-membered heterocycle containing two oxygen atoms is optionally substituted with from 1 to 3 C$_1$-C$_6$alkyl substituents; a 6- to 10-membered bicyclic carbocycle optionally substituted with from 1 to 3 substituents independently selected from C$_1$-C$_6$alkyl, halo, -haloalkyl, hydroxyl, C$_1$-C$_6$alkoxy, —NH$_2$, -aminoalkyl, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, alkylcarboxyamido, and —NO$_2$, wherein any two hydrogen atoms on the same carbon atom of the bicyclic carbocycle rings can be replaced by an oxygen atom to form an oxo (═O) substituent, and wherein any two hydrogen atoms on the same carbon atom of the bicyclic carbocycle rings can be replaced by an alkylenedioxy group so that the alkylenedioxy group, when taken together with the carbon atom to which it is attached, forms a 5- to 7-membered heterocycle containing two oxygen atoms; a 4- to 7-membered monocyclic heterocycle optionally substituted with from 1 to 3 substituents independently selected from C$_1$-C$_6$alkyl, heterocyclylalkyl, arylalkyl, (C$_1$-C$_9$heteroaryl)alkyl-, C$_1$-C$_8$acyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, S(O)$_S$—C$_1$-C$_6$alkyl, —S(O)$_S$-aryl, -alkylcarboxamido, and —NO$_2$; or a 6- to 10-membered bicyclic heterocycle optionally substituted with from 1 to 3 substituents independently selected from C$_1$-C$_6$alkyl, heterocyclylalkyl, arylalkyl, (C$_1$-C$_9$heteroaryl)alkyl-, C$_1$-C$_8$acyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$; and R$^8$ is hydrogen; halogen; C$_1$-C$_8$acyl; C$_1$-C$_6$alkyl; C$_2$-C$_6$alkenyl; C$_2$-C$_6$alkynyl; C$_6$-C$_{14}$aryl; heterocyclylalkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C$_1$-C$_8$acyl, C$_6$-C$_{14}$aryl, heteroaryl, —S(O)$_2$—C$_1$-C$_6$alkyl, and C$_3$-C$_8$-carbocycle; or heteroaryl; and Ar is phenyl, naphthyl, or a monocyclic or bicyclic ring system having from 5 to 14 ring members, and containing at least one ring nitrogen atom, wherein the phenyl, naphthyl, and monocyclic or bicyclic ring system is optionally substituted with from 1 to 3 substituents independently selected from C$_1$-C$_6$alkyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, -alkylcarboxamido and —NO$_2$.

2. A compound of claim 1 of the Formula (Ib):

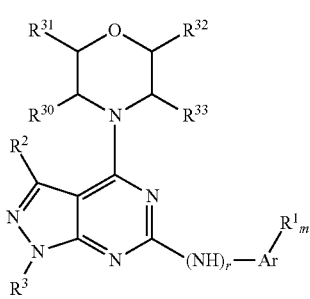

(Ib)

or pharmaceutically acceptable salts thereof, wherein:
wherein one of $R^{30}$ and $R^{32}$, $R^{30}$ and $R^{33}$, or $R^{31}$ and $R^{32}$ together are —$CH_2$—, —$CH_2CH_2$—, —$CH_2CH_2CH_2$—, —$CH_2$—O—, —$CH_2CH_2$—O—, —$CH_2OCH_2$—, —$CH_2$—NH—, —$CH_2CH_2$—NH—, —$CH_2NHCH_2$—, —$CH_2$—N($CH_3$)—, —$CH_2CH_2$—N($CH_3$)—, or —$CH_2N(CH_3)CH_2$—, and with the two carbon atoms to which they are attached form a bridged ring;
wherein the bridging ring formed by $R^{30}$ and $R^{32}$, $R^{30}$ and $R^{33}$, or $R^{31}$ and $R^{32}$ is optionally substituted with halogen, or hydroxyl;
wherein the remaining $R^{30}$, $R^{31}$, $R^{32}$ and $R^{33}$ are each independently selected from hydrogen, halogen, hydroxyl, $C_1$-$C_2$alkoxy, C(O)$NH_2$, C(O)NH($C_1$-$C_2$alkyl), C(O)N($C_1$-$C_2$alkyl)($C_1$-$C_2$alkyl), CN, C(O)OH, and $C_1$-$C_4$alkoxycarbonyl;
wherein the remaining constituent variables are as defined in claim 1.

3. A compound of claim 1 of the Formula (I):

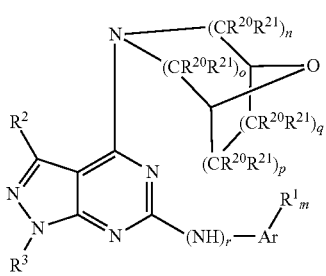

(I)

or pharmaceutically acceptable salts thereof, wherein:
each $R^1$ is independently halogen; $C_1$-$C_6$alkyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, —$C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_1$-$C_6$alkoxy optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_2$-$C_6$alkenyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —ON, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_2$-$C_6$alkynyl optionally substituted with from 1 to 3 substituents independently selected from halogen, —$NH_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkyl carboxyl, —N—($C_1$-$C_6$)alkylamido, —C(O)$NH_2$, -alkylcarboxamido and —$NO_2$; $C_1$-$C_8$acyl; $C_1$-$C_8$alkoxycarbonyl; $C_1$-$C_8$alkylcarboxy; —N—($C_1$-$C_6$)alkylamido; hydroxyl; $NR^4R^5$; —NHC(O)$NR^4R^5$; —NHC(O)$OR^6$; —NH($SO_2$)NH—$C_1$-$C_6$alkyl; —NH($SO_2$)NH—$C_6$-$C_{14}$aryl; —NHC(S)—NH—$C_1$-$C_6$alkyl; —N═C(S—$C_1$-$C_6$alkyl)(NH—$C_1$-$C_6$alkyl); or —N(H)—C(═N—(CN))—(O—$C_6$-$C_{14}$aryl);
m is 0, 1 or 2;
n is 1 or 2;
o is 1 or 2;
p and q are each independently 0, 1, or 2;
with the two provisos that at least one of n and o must be 1; and the sum of p and q must be greater than zero;
r is 0 or 1;
each $R^{20}$ and $R^{21}$ is independently selected from halogen, hydroxyl, $C_1$-$C_2$alkoxy, $NH_2$, NH($C_1$-$C_2$alkyl), N($C_1$-$C_2$alkyl)($C_1$-$C_2$alkyl), NHC(O)($C_1$-$C_2$alkyl), N($C_1$-$C_2$alkyl)C(O)($C_1$-$C_2$alkyl), NHC(O)H, C(O)$NH_2$, C(O)NH($C_1$-$C_2$alkyl), C(O)N($C_1$-$C_2$alkyl)($C_1$-$C_2$alkyl), CN, C(O)OH, and C(O)O$C_1$-$C_2$alkyl;
each $R^4$ and $R^5$ is independently —H; a 4- to 7-membered monocyclic heterocycle optionally substituted with from 1 to 3 substituents independently selected from $C_1$-$C_6$alkyl, heterocyclylalkyl, $C_7$-$C_{24}$arylalkyl, $C_1$-$C_8$acyl, $C_1$-$C_8$alkoxycarbonyl, $C_1$-$C_8$alkylcarboxy, halo, —$C_1$-$C_8$haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —NO₂; heteroaryl optionally substituted with from 1 to 3 substituents independently selected from $C_1$-$C_6$alkyl, halo, -haloalkyl, hydroxyl, $C_1$-$C_6$hydroxyalkyl, —NH₂, -aminoalkyl, -dialkylamino, —COOH, —$C_1$-$C_6$alkoxycarbonyl, —$C_1$-$C_8$alkylcarboxyl, —N—($C_1$-$C_6$)alkylamido, —C(O)NH₂, -alkylcarboxamido and —NO₂; —$C_3$-$C_8$-carbocycle optionally substituted with from 1 to 3 substituents independently selected from $C_1$-$C_6$alkyl, halo, -haloalkyl, hydroxyl, —$C_1$-$C_6$alkoxy, —NH₂, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH₂, and —NO₂, wherein any two hydrogen atoms on the same carbon atom of the carbocyclic ring can be replaced by an oxygen atom to form an oxo (=O) substituent, and wherein any two hydrogen atoms on the same carbon atom of the carbocyclic ring can be replaced by an alkylenedioxy group so that the alkylenedioxy group, when taken together with the carbon atom to which it is attached, forms a 5- to 7-membered heterocycle containing two oxygen atoms; or $C_1$-$C_6$alkyl optionally substituted with from 1 to 3 substituents independently selected from halogen, —NH₂, —NH($C_1$-$C_8$alkyl), —N($C_1$-$C_8$alkyl)($C_1$-$C_8$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle;

or $R^4$ and $R^5$ when taken together with the nitrogen to which they are attached can form a 3- to 7-membered heterocycle wherein up to two of the carbon atoms of the heterocycle can be independently replaced with —N($R^7$)—, —O—, or —S(=O)$_s$;

each s is independently 1 or 2;

$R^6$ is $C_1$-$C_6$alkyl optionally substituted with from 1 to 3 substituents independently selected from halogen, —NH₂, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_6$-carbocycle; or $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —NH₂, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH₂, -alkylcarboxamido and —NO₂;

$R^7$ is hydrogen; $C_1$-$C_8$acyl; $C_1$-$C_6$alkyl optionally substituted with from 1 to 3 substituents independently selected from halogen, —NH₂, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_3$-$C_8$-carbocycle optionally substituted with from 1 to 3 substituents independently selected from $C_1$-$C_6$alkyl, halo, -haloalkyl, hydroxyl, —$C_1$-$C_6$alkoxy, —NH₂, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH₂, and —NO₂; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —NH₂, -alkylamino, -dialkylamino, —COOH, —$C_1$-$C_6$alkoxycarbonyl, -$C_1$-$C_6$alkyl carboxyl, —N—($C_1$-$C_6$)alkylamido, —C(O)NH₂, -alkylcarboxamido and —NO₂; heteroaryl optionally substituted with from 1 to 3 substituents independently selected from $C_1$-$C_6$alkyl, halo, -haloalkyl, hydroxyl, $C_1$-$C_6$hydroxyalkyl, —NH₂, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)NH₂, -alkylcarboxamido and —NO₂; alkylamino; or aminoaryl optionally substituted with from 1 to 3 substituents independently selected from halogen, —NH₂, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, -$C_1$-$C_6$alkoxycarbonyl, —C(O)$C_1$-$C_6$alkyl, $C_6$-$C_{14}$aryl, heteroaryl, and $C_3$-$C_8$-carbocycle;

with the proviso that when m=2, any two adjacent $R^1$ groups can be taken together with the two carbons to which they are attached to form a 5- to 7-membered aromatic ring wherein up to 2 of the carbon atoms of the fused ring can be replaced with —N=, —N($R^7$)—, —O—, or —S(=O)$_s$;

$R^2$ is hydrogen; halogen; $C_1$-$C_8$acyl; $C_1$-$C_6$alkyl optionally substituted with from 1 to 3 substituents independently selected from halogen, —NH₂, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, -$C_1$-$C_6$alkoxycarbonyl, —C(O)$C_1$-$C_6$alkyl, $C_6$-$C_{14}$aryl, heteroaryl, and $C_3$-$C_8$-carbocycle; $C_2$-$C_6$alkenyl optionally substituted with from 1 to 3 substituents independently selected from halogen, —NH₂, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, -$C_1$-$C_6$alkoxycarbonyl, —C(O)$C_1$-$C_6$alkyl, $C_6$-$C_{14}$aryl, heteroaryl, and $C_3$-$C_8$-carbocycle; $C_2$-$C_6$alkynyl optionally substituted with from 1 to 3 substituents independently selected from halogen, —NH₂, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH₂, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_6$-$C_{14}$aryl optionally substituted with from 1 to 3 substituents independently selected from $C_1$-$C_6$alkyl, halo, haloalkyl, hydroxyl, $C_1$-$C_6$hydroxyalkyl, —NH₂, -alkylamino, -dialkylamino, —COOH, —$C_1$-$C_6$alkoxycarbonyl, —$C_1$-$C_6$alkyl carboxyl, —N—($C_1$-$C_6$)alkylamido, —C(O)NH₂, -alkylcarboxamido and —NO₂; or heteroaryl optionally substituted with from 1 to 3 substituents independently selected from $C_1$-$C_6$alkyl, halo, -haloalkyl, hydroxyl, $C_1$-$C_6$hydroxyalkyl, —NH₂, -aminoalkyl, -dialkylamino, —COOH, —$C_1$-$C_6$alkoxycarbonyl, —$C_1$-$C_6$alkylcarboxyl, —N—($C_1$-$C_6$)alkylamido, —C(O)NH₂, -alkylcarboxamido and —NO₂;

$R^3$ is hydrogen; $C_1$-$C_6$alkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_2$-$C_6$alkenyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; $C_2$-$C_6$alkynyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, -$C_1$-$C_6$alkoxycarbonyl, —C(O)$C_1$-$C_6$alkyl, $C_6$-$C_{14}$aryl, heteroaryl, and $C_3$-$C_8$-carbocycle; $C_1$-$C_8$acyl; $C_6$-$C_{14}$aryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkyl carboxyl, —N—($C_1$-C6)alkylamido, —C(O)$NH_2$, -alkylcarboxamido and —$NO_2$; heteroaryl optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; $C_7$-$C_{24}$arylalkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; heterocyclylalkyl optionally substituted with from 1 to 3 substituents independently selected from halogen, —$NH_2$, —$NH(C_1$-$C_6$alkyl), —$N(C_1$-$C_6$alkyl)($C_1$-$C_6$alkyl), —$N(C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —$C_1$-$C_6$alkoxycarbonyl, —C(O)$C_1$-$C_6$alkyl, $C_6$-$C_{14}$aryl, heteroaryl, and $C_3$-$C_8$-carbocycle; hydroxyl ($C_1$-$C_6$alkyl)-; alkylcarboxy; alkoxycarbonyl; $C_1$-$C_6$ perfluoroalkyl; —S(O)$_S$—$C_1$-$C_6$alkyl wherein the $C_1$-$C_6$alkyl of —S(O)$_S$—$C_1$-$C_6$alkyl is optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$; —S(O)$_S$-aryl wherein the aryl of —S(O)$_S$-aryl is optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-$C_6$alkyl carboxyl, —N—($C_1$-$C_6$)alkylamido, —C(O)$NH_2$, and —$NO_2$; a $C_3$-$C_8$carbocycle optionally substituted with from 1 to 3 substituents independently selected from $C_1$-$C_6$alkyl, halo, -haloalkyl, hydroxyl, —$C_1$-$C_6$alkoxy, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$, wherein any two hydrogen atoms on the same carbon atom of the carbocycle ring can be replaced by an oxygen atom to form an oxo (=O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms; a 6- to 10-membered bicyclic carbocycle optionally substituted with from 1 to 3 substituents independently selected from $C_1$-$C_6$alkyl, halo, -haloalkyl, hydroxyl, —$C_1$-$C_6$alkoxy, —$NH_2$, -aminoalkyl, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, and —$NO_2$, wherein any two hydrogen atoms on the same carbon atom of the bicyclic carbocycle rings can be replaced by an oxygen atom to form an oxo (=O) substituent, and wherein any two hydrogen atoms on the same carbon atom of the bicyclic carbocycle rings can be replaced by an alkylenedioxy group so that the alkylenedioxy group, when taken together with the carbon atom to which it is attached, forms a 5- to 7-membered heterocycle containing two oxygen atoms; a 4- to 7-membered monocyclic heterocycle optionally substituted with from 1 to 3 substituents independently selected from $C_1$-$C_6$alkyl, heterocyclylalkyl, arylalkyl, $C_1$-$C_8$acyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; or a 6- to 10-membered bicyclic heterocycle optionally substituted with from 1 to 3 substituents independently selected from $C_1$-$C_6$alkyl, heterocyclylalkyl, arylalkyl, $C_1$-$C_8$acyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$; and Ar is phenyl, naphthyl, or a monocyclic or bicyclic ring system having from 5 to 14 ring members, and containing at least one ring nitrogen atom, wherein the phenyl, naphthyl, and monocyclic or bicyclic ring system is optionally substituted with from 1 to 3 substituents independently selected from $C_1$-$C_6$alkyl, halo, -haloalkyl, hydroxyl, $C_1$-$C_6$hydroxyalkyl, —$NH_2$, -alkylamino, -dialkylamino, —COOH, —$C_1$-$C_6$alkoxycarbonyl, —$C_1$-$C_6$alkylcarboxyl, —N—($C_1$-$C_6$)alkylamido, —C(O)$NH_2$, -alkylcarboxamido and —$NO_2$.

4. A compound of claim 3 or pharmaceutically acceptable salts thereof.

5. A compound of claim 1 wherein Ar is phenyl.

6. A compound of claim 1 wherein m is 1.

7. A compound of claim 1 wherein $R^1$ is —NHC(O)$NR^4R^5$, —NHC(O)$OR^6$, —NH(SO$_2$)NH—($C_1$-$C_6$alkyl) or —NH(SO$_2$)NH—$C_6$-$C_{14}$aryl.

8. A compound of claim 7 wherein $R^1$ is —NHC(O)NR$^4$R$^5$.

9. A compound of claim 8 wherein $R^5$ is H.

10. A compound of claim 9 wherein the —NHC(O)NR$^4$R$^5$ group is attached to the C4 of the phenyl ring.

11. A compound of claim 1 wherein $R^3$ is hydrogen.

12. A compound of claim 1 wherein $R^3$ is $C_1$-$C_6$alkyl optionally substituted with from 1 to 3 substituents independently selected from halogen, —NH$_2$, -alkylamino, -dialkylamino, —N(C$_1$-C$_3$alkyl)C(O)(C$_1$-C$_6$alkyl), —NHC(O)(C$_1$-C$_6$alkyl), —NHC(O)H, —C(O)NH$_2$, —C(O)NH(C$_1$-C$_6$alkyl), —C(O)N(C$_1$-C$_6$alkyl)(C$_1$-C$_6$alkyl), —CN, hydroxyl, —C$_1$-C$_6$alkoxy, C$_1$-C$_6$alkyl, —C(O)OH, —C$_1$-C$_6$alkoxycarbonyl, —C(O)C$_1$-C$_6$alkyl, C$_6$-C$_{14}$aryl, heteroaryl, and C$_3$-C$_8$-carbocycle.

13. A compound of claim 12 wherein $R^3$ is $C_1$-$C_6$alkyl optionally substituted with from 1 to 3 independently selected halogens.

14. A compound of claim 13 wherein $R^3$ is 2,2,2-trifluoroethyl.

15. A compound of claim 1 wherein $R^3$ is a 4- to 7-membered monocyclic heterocycle optionally substituted with from 1 to 3 substituents independently selected from C$_1$-C$_6$alkyl, heterocyclylalkyl, arylalkyl, (C$_1$-C$_9$heteroaryl)alkyl-, C$_1$-C$_8$acyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, S(O)$_S$—C$_1$-C$_6$alkyl, —S(O)$_S$-aryl, -alkylcarboxamido, and —NO$_2$.

16. A compound of claim 15 wherein $R^3$ is an optionally substituted piperidinyl.

17. A compound of claim 16 wherein $R^3$ is optionally substituted piperidin-4-yl.

18. A compound of claim 17 wherein the piperidinyl nitrogen is substituted with C$_1$-C$_6$alkyl, heterocyclylalkyl, arylalkyl, (C$_1$-C$_9$heteroaryl)alkyl-, C$_1$-C$_8$acyl, halo, -haloalkyl, hydroxyl, C$_1$-C$_6$hydroxyalkyl, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, S(O)$_S$—C$_1$-C$_6$alkyl, —S(O)$_S$-aryl, or -alkylcarboxamido.

19. A compound of claim 1 wherein $R^3$ is $C_7$-$C_{14}$arylalkyl.

20. A compound of claim 1 wherein $R^3$ is a 4- to 7-membered monocyclic heterocycle containing at least one ring oxygen atom.

21. A compound of claim 1 wherein $R^3$ is a $C_3$-$C_8$-carbocycle optionally substituted with from 1 to 3 substituents independently selected from C$_1$-C$_6$alkyl, halo, -haloalkyl, hydroxyl, —C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, and —NO$_2$, wherein any two hydrogen atoms on the same carbon atom of the carbocycle ring can be replaced by an oxygen atom to form an oxo (═O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms.

22. A compound of claim 1 wherein het is selected from 8-oxa-3-azabicyclo[3.2.1]oct-3-yl, 3-oxa-8-azabicyclo[3.2.1]oct-8-yl, and 2-oxa-5-azabicyclo[2.2.1]hept-5-yl.

23. A compound of claim 22 wherein t is 0.

24. A compound of claim 3 wherein n, o, p, and q are each 1.

25. A compound of claim 4 wherein $R^3$ is a $C_3$-$C_8$-carbocycle, which can be optionally substituted with from 1 to 3 substituents independently selected from C$_1$-C$_6$alkyl, halo, -haloalkyl, hydroxyl, —C$_1$-C$_6$alkoxy, —NH$_2$, -alkylamino, -dialkylamino, —COON, —C$_1$-C$_6$alkoxycarbonyl, —(C$_1$-C$_6$alkyl)carboxyl, —N—(C$_1$-C$_6$)alkylamido, —C(O)NH$_2$, and —NO$_2$, wherein any two hydrogen atoms on the same carbon atom of the carbocycle ring can optionally be replaced by an oxygen atom to form an oxo (═O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms.

26. A compound of claim 25 wherein $R^3$ is a $C_6$-carbocycle, wherein two hydrogen atoms on one of the carbon atoms of the carbocycle ring have been replaced by an alkylenedioxy group so that the alkylenedioxy group, when taken together with the carbon atom to which it is attached, forms a 5- to 7-membered heterocycle containing two oxygen atoms.

27. A compound of claim 4 wherein n, o, p, and q are each 1; r is 0; $R^3$ is a $C_5$-$C_7$ carbocycle, which can be optionally substituted with from 1 to 3 substituents independently selected from C$_1$-C$_6$alkyl, halo, -haloalkyl, hydroxyl, —C$_1$-C$_6$alkoxy, —NH$_2$, -alkylamino, -dialkylamino, —COOH, —C$_1$-C$_6$alkoxycarbonyl, —(C$_1$-C$_6$alkyl)carboxyl, —N—(C$_1$-C$_6$)alkylamido, —C(O)NH$_2$, and —NO$_2$, wherein any two hydrogen atoms on the same carbon atom of the carbocycle ring can optionally be replaced by an oxygen atom to form an oxo (═O) substituent, and wherein any two hydrogen atoms on the same carbon atom of the carbocycle ring can be replaced by an alkylenedioxy group so that the alkylenedioxy group, when taken together with the carbon atom to which it is attached, forms a 5- to 7-membered heterocycle containing two oxygen atoms; $R^1$ is —NHC(O)NR$^4$R$^5$, —NHC(O)OR$^6$, —NH(SO$_2$)NH—C$_1$-C$_6$alkyl or —NH(SO$_2$)NH—C$_6$-C$_{14}$aryl, and Ar is phenyl.

28. A compound of claim 3 wherein n, o, p, and q are each 1; r is 0; $R^3$ is a $C_6$-carbocycle, wherein two hydrogen atoms on one of the carbon atoms of the carbocycle ring have been replaced by an alkylenedioxy group so that the alkylenedioxy group, when taken together with the carbon atom to which it is attached, forms a 5- to 7-membered heterocycle containing two oxygen atoms; $R^1$ is —NHC(O)NR$^4$R$^5$ and Ar is phenyl.

29. A compound selected from the group consisting of:
3-[4-(8-oxa-3-azabicyclo[3.2.1]oct-3-yl)-1-phenyl-1H-pyrazolo[3,4-d]pyrimidin-6-yl]phenol;
1-methyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
methyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate;
1-ethyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-3-ylurea;
1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea;
1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-pyridin-4-ylurea;
1-(2-fluoroethyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;

methyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

tert-butyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

methyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;

methyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate;

methyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;

1-ethyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea;

1-(2-fluoroethyl)-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea;

1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-phenylurea;

1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-3-ylurea;

1-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)-3-pyridin-4-ylurea;

tert-butyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

tert-butyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

tert-butyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

tert-butyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;

tert-butyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate.

tert-butyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;

1-methyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea;

1-ethyl-3-(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)urea;

1-ethyl-3-{4-[4-(8-oxa-3-azabicyclo[3.2.1]oct-3-yl)-1-piperidin-4-yl-1H-pyrazolo[3,4-d]pyrimidin-6-yl]phenyl}urea;

1-{4-[4-(8-oxa-3-azabicyclo[3.2.1]oct-3-yl)-1-piperidin-4-yl-1H-pyrazolo[3,4-d]pyrimidin-6-yl]phenyl}-3-phenylurea;

4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]aniline;

4-{[1-(1-benzylpiperidin-4-yl)-4-(8-oxa-3-azabicyclo[3.2.1]oct-3-yl)-1H-pyrazolo[3,4-d]pyrimidin-6-yl]amino}phenol;

ethyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;

ethyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

ethyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;

ethyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate;

ethyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;

ethyl 4-[6-(4-{[(1-methylpiperidin-4-yl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;

ethyl 4-{6-[4-({[1-(tert-butoxycarbonyl)piperidin-4-yl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;

ethyl 4-{6-[4-({[3-(methylamino)propyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;

ethyl 4-[4-(8-oxa-3-azabicyclo[3.2.1]oct-3-yl)-6-{4-[(1H-pyrazol-5-ylcarbamoyl)amino]phenyl}-1H-pyrazolo[3,4-d]pyrimidin-1-yl]piperidine-1-carboxylate;

1-{4-[1-ethyl-4-(8-oxa-3-azabicyclo[3.2.1]oct-3-yl)-1H-pyrazolo[3,4-d]pyrimidin-6-yl]phenyl}-3-methylurea;

1-ethyl-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(2-fluoroethyl)urea;

1-cyclopropyl-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(2-hydroxyethyl)urea;

2-hydroxyethyl{4-[1-ethyl-4-(8-oxa-3-azabicyclo[3.2.1]oct-3-yl)-1H-pyrazolo[3,4-d]pyrimidin-6-yl]phenyl}carbamate;

1-{4-[1-ethyl-4-(8-oxa-3-azabicyclo[3.2.1]oct-3-yl)-1H-pyrazolo[3,4-d]pyrimidin-6-yl]phenyl}-3-phenylurea;

1-{4-[1-ethyl-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-ethyl-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-ethyl-4-(8-oxa-3-azabicyclo[3.2.1]oct-3-yl)-1H-pyrazolo[3,4-d]pyrimidin-6-yl]phenyl}-3-[3-(methylamino)propyl]urea;
1-methyl-3-{4-[1-methyl-4-(8-oxa-3-azabicyclo[3.2.1]oct-3-yl)-1H-pyrazolo[3,4-d]pyrimidin-6-yl]phenyl}urea;
1-ethyl-3-{4-[1-methyl-4-(8-oxa-3-azabicyclo[3.2.1]oct-3-yl)-1H-pyrazolo[3,4-d]pyrimidin-6-yl]phenyl}urea.
1-(2-fluoroethyl)-3-{4-[1-methyl-4-(8-oxa-3-azabicyclo[3.2.1]oct-3-yl)-1H-pyrazolo[3,4-d]pyrimidin-6-yl]phenyl}urea;
1-cyclopropyl-3-{4-[1-methyl-4-(8-oxa-3-azabicyclo[3.2.1]oct-3-yl)-1H-pyrazolo[3,4-d]pyrimidin-6-yl]phenyl}urea;
1-(2-hydroxyethyl)-3-{4-[1-methyl-4-(8-oxa-3-azabicyclo[3.2.1]oct-3-yl)-1H-pyrazolo[3,4-d]pyrimidin-6-yl]phenyl}urea;
1-{4-[1-methyl-4-(8-oxa-3-azabicyclo[3.2.1]oct-3-yl)-1H-pyrazolo[3,4-d]pyrimidin-6-yl]phenyl}-3-phenylurea;
1-{4-[1-methyl-4-(8-oxa-3-azabicyclo[3.2.1]oct-3-yl)-1H-pyrazolo[3,4-d]pyrimidin-6-yl]phenyl}-3-pyridin-3-yl urea;
1-{4-[1-methyl-4-(8-oxa-3-azabicyclo[3.2.1]oct-3-yl)-1H-pyrazolo[3,4-d]pyrimidin-6-yl]phenyl}-3-pyridin-4-ylurea;
1-[2-(dimethylamino)ethyl]-3-{4-[1-methyl-4-(8-oxa-3-azabicyclo[3.2.1]oct-3-yl)-1H-pyrazolo[3,4-d]pyrimidin-6-yl]phenyl}urea;
1-[3-(dimethylamino)propyl]-3-{4-[1-methyl-4-(8-oxa-3-azabicyclo[3.2.1]oct-3-yl)-1H-pyrazolo[3,4-d]pyrimidin-6-yl]phenyl}urea;
methyl{4-[1-methyl-4-(8-oxa-3-azabicyclo[3.2.1]oct-3-yl)-1H-pyrazolo[3,4-d]pyrimidin-6-yl]phenyl}carbamate;
3-[1-methyl-4-(8-oxa-3-azabicyclo[3.2.1]oct-3-yl)-1H-pyrazolo[3,4-d]pyrimidin-6-yl]phenol;
1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-methylurea;
1-methyl-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea;
1-{4-[1-(4-hydroxycyclohexyl)-4-(8-oxa-3-azabicyclo[3.2.1]oct-3-yl)-1H-pyrazolo[3,4-d]pyrimidin-6-yl]phenyl}-3-methylurea;
ethyl 4-[4-(8-oxa-3-azabicyclo[3.2.1]oct-3-yl)-6-{4-[(piperidin-4-ylcarbamoyl)amino]phenyl}-1H-pyrazolo[3,4-d]pyrimidin-1-yl]piperidine-1-carboxylate;
isopropyl 4-[6-(4-aminophenyl)-4-(8-oxa-3-azabicyclo[3.2.1]oct-3-yl)-1H-pyrazolo[3,4-d]pyrimidin-1-yl]piperidine-1-carboxylate;
isopropyl 4-[6-{4-[(methylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;
1-[4-(1-{1-[(6-bromopyridin-3-yl)methyl]piperidin-4-yl}-4-morpholin-4-yl-1H-pyrazolo[3,4-d]pyrimidin-6-yl)phenyl]-3-methylurea;
1-methyl-3-(4-{4-morpholin-4-yl-1-[1-(pyridin-3-ylmethyl)piperidin-4-yl]-1H-pyrazolo[3,4-d]pyrimidin-6-yl}phenyl)urea;
1-methyl-3-[4-(1-{1-[(2-methylpyridin-3-yl)carbonyl]piperidin-4-yl}-4-morpholin-4-yl-1H-pyrazolo[3,4-d]pyrimidin-6-yl)phenyl]urea;
1-methyl-3-[4-(1-{1-[(4-methylpyridin-3-yl)carbonyl]piperidin-4-yl}-4-morpholin-4-yl-1H-pyrazolo[3,4-d]pyrimidin-6-yl)phenyl]urea;
1-methyl-3-(4-{4-morpholin-4-yl-1-[1-(pyridin-2-ylmethyl)piperidin-4-yl]-1H-pyrazolo[3,4-d]pyrimidin-6-yl}phenyl)urea;
1-(4-{1-[1-(2-methoxybenzoyl)piperidin-4-yl]-4-morpholin-4-yl-1H-pyrazolo[3,4-d]pyrimidin-6-yl}phenyl)-3-methylurea;
1-(4-{1-[1-(3-acetylbenzoyl)piperidin-4-yl]-4-morpholin-4-yl-1H-pyrazolo[3,4-d]pyrimidin-6-yl}phenyl)-3-methylurea;
1-(2-fluoro-4-{4-morpholin-4-yl-1-[1-(pyridin-3-ylmethyl)piperidin-4-yl]-1H-pyrazolo[3,4-d]pyrimidin-6-yl}phenyl)-3-pyridin-3-ylurea;
2-[4-(6-{4-[(methylcarbamoyl)amino]phenyl}-4-morpholin-4-yl-1H-pyrazolo[3,4-d]pyrimidin-1-yl)piperidin-1-yl]acetamide;
Methyl 4-(6-{4-[(methylcarbamoyl)amino]phenyl}-4-morpholin-4-yl-1H-pyrazolo[3,4-d]pyrimidin-1-yl)piperidine-1-carboxylate;
isopropyl 4-[6-{4-[(ethylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;
isopropyl 4-[6-(4-{[(2-fluoroethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;
isopropyl 4-[6-(4-{[(2-hydroxyethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;
isopropyl 4-[6-{4-[(cyclopropylcarbamoyl)amino]phenyl}-4-(8-oxa-3-azabicyclo[3.2.1]oct-3-yl)-1H-pyrazolo[3,4-d]pyrimidin-1-yl]piperidine-1-carboxylate;
isopropyl 4-[4-(8-oxa-3-azabicyclo[3.2.1]oct-3-yl)-6-{4-[(phenylcarbamoyl)amino]phenyl}-1H-pyrazolo[3,4-d]pyrimidin-1-yl]piperidine-1-carboxylate;
isopropyl 4-[4-(8-oxa-3-azabicyclo[3.2.1]oct-3-yl)-6-{4-[(pyridin-3-ylcarbamoyl)amino]phenyl}-1H-pyrazolo[3,4-d]pyrimidin-1-yl]piperidine-1-carboxylate;
isopropyl 4-[4-(8-oxa-3-azabicyclo[3.2.1]oct-3-yl)-6-{4-[(pyridin-4-ylcarbamoyl)amino]phenyl}-1H-pyrazolo[3,4-d]pyrimidin-1-yl]piperidine-1-carboxylate;
isopropyl 4-[6-{4-[(methoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate;
3-[1-ethyl-4-(8-oxa-3-azabicyclo[3.2.1]oct-3-yl)-1H-pyrazolo[3,4-d]pyrimidin-6-yl]phenol;
1-ethyl-6-(1H-indol-5-yl)-4-(8-oxa-3-azabicyclo[3.2.1]oct-3-yl)-1H-pyrazolo[3,4-d]pyrimidine;
1-{4-[1-benzyl-4-(8-oxa-3-azabicyclo[3.2.1]oct-3-yl)-1H-pyrazolo[3,4-d]pyrimidin-6-yl]phenyl}-3-methylurea;
1-{4-[1-benzyl-4-(8-oxa-3-azabicyclo[3.2.1]oct-3-yl)-1H-pyrazolo[3,4-d]pyrimidin-6-yl]phenyl}-3-ethylurea;
1-{4-[1-benzyl-4-(8-oxa-3-azabicyclo[3.2.1]oct-3-yl)-1H-pyrazolo[3,4-d]pyrimidin-6-yl]phenyl}-3-pyridin-4-yl urea;
4-[1-(1-isobutyrylpiperidin-4-yl)-4-(8-oxa-3-azabicyclo[3.2.1]oct-3-yl)-1H-pyrazolo[3,4-d]pyrimidin-6-yl]aniline.
1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-methylurea;
1-ethyl-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea;

1-(2-hydroxyethyl)-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea;

1-(2-fluoroethyl)-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}urea;

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-phenylurea;

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-(1-isobutyrylpiperidin-4-yl)-4-(8-oxa-3-azabicyclo[3.2.1]oct-3-yl)-1H-pyrazolo[3,4-d]pyrimidin-6-yl]phenyl}-3-pyridin-4-ylurea;

1-{4-[4-(8-oxa-3-azabicyclo[3.2.1]oct-3-yl)-1-(tetrahydro-2H-pyran-2-yl)-1H-pyrazolo[3,4-d]pyrimidin-6-yl]phenyl}-3-pyridin-3-ylurea;

1-{4-[4-(8-oxa-3-azabicyclo[3.2.1]oct-3-yl)-1H-pyrazolo[3,4-d]pyrimidin-6-yl]phenyl}-3-pyridin-3-ylurea;

1-(4-(4-(8-oxa-3-azabicyclo[3.2.1]octan-3-yl)-1-(1,4-dioxaspiro[4.5]decan-8-yl)-1H-pyrazolo[3,4-d]pyrimidin-6-yl)phenyl)-3-methylurea;

1-(4-(4-(8-oxa-3-azabicyclo[3.2.1]octan-3-yl)-1-(4-oxocyclohexyl)-1H-pyrazolo[3,4-d]pyrimidin-6-yl)phenyl)-3-methylurea;

1-(4-(4-(8-oxa-3-azabicyclo[3.2.1]octan-3-yl)-1-(4-hydroxycyclohexyl)-1H-pyrazolo[3,4-d]pyrimidin-6-yl)phenyl)-3-methylurea;

1-(4-(4-(8-oxa-3-azabicyclo[3.2.1]octan-3-yl)-1-((1r,4r)-4-hydroxycyclohexyl)-1H-pyrazolo[3,4-d]pyrimidin-6-yl)phenyl)-3-methylurea; and 1-(4-(4-(8-oxa-3-azabicyclo[3.2.1]octan-3-yl)-1-((1s,4s)-4-hydroxycyclohexyl)-1H-pyrazolo[3,4-d]pyrimidin-6-yl)phenyl)-3-methylurea; and 2-hydroxyethyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate.

30. A compound selected from the group consisting of:

methyl 4-[6-{4-[(ethoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[6-(4-{[(2-hydroxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;

methyl 4-[6-(4-{[(2-methoxyethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;

methyl 4-[6-(4-{[(2-aminoethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;

methyl 4-{6-[4-({[2-(dimethylamino)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate;

methyl 4-[4-(8-oxa-3-azabicyclo[3.2.1]oct-3-yl)-6-(4-{[(2-pyrrolidin-1-ylethoxy)carbonyl]amino}phenyl)-1H-pyrazolo[3,4-d]pyrimidin-1-yl]piperidine-1-carboxylate;

methyl 4-[6-(4-{[(2-morpholin-4-ylethoxy)carbonyl]amino}phenyl)-4-(8-oxa-3-azabicyclo[3.2.1]oct-3-yl)-1H-pyrazolo[3,4-d]pyrimidin-1-yl]piperidine-1-carboxylate;

methyl 4-{6-[4-({[2-(4-methylpiperazin-1-yl)ethoxy]carbonyl}amino)phenyl]-4-(8-oxa-3-azabicyclo[3.2.1]oct-3-yl)-1H-pyrazolo[3,4-d]pyrimidin-1-yl}piperidine-1-carboxylate;

methyl 4-[6-{4-[(methoxycarbonyl)amino]phenyl}-4-(8-oxa-3-azabicyclo[3.2.1]oct-3-yl)-1H-pyrazolo[3,4-d]pyrimidin-1-yl]piperidine-1-carboxylate;

methyl 4-[6-(4-aminophenyl)-4-(8-oxa-3-azabicyclo[3.2.1]oct-3-yl)-1H-pyrazolo[3,4-d]pyrimidin-1-yl]piperidine-1-carboxylate;

2-hydroxyethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;

3-hydroxypropyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-ethylurea;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-fluoroethyl)urea;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-(2-hydroxyethyl)urea;

1-cyclopropyl-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-phenylurea;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-4-ylurea;

2,2,2-trifluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;

2-fluoroethyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;

3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-1,3-oxazolidin-2-one;

2-({4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}amino)ethanol;

1-[2-(dimethylamino)ethyl]-3-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}urea;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

methyl{4-[4-(8-oxa-3-azabicyclo[3.2.1]oct-3-yl)-1-(4-oxocyclohexyl)-1H-pyrazolo[3,4-d]pyrimidin-6-yl]phenyl}carbamate;

methyl{4-[1-(4-hydroxycyclohexyl)-4-(8-oxa-3-azabicyclo[3.2.1]oct-3-yl)-1H-pyrazolo[3,4-d]pyrimidin-6-yl]phenyl}carbamate;

methyl{4-[1-isopropyl-4-(8-oxa-3-azabicyclo[3.2.1]oct-3-yl)-1H-pyrazolo[3,4-d]pyrimidin-6-yl]phenyl}carbamate;
1-{4-[1-isopropyl-4-(8-oxa-3-azabicyclo[3.2.1]oct-3-yl)-1H-pyrazolo[3,4-d]pyrimidin-6-yl]phenyl}-3-methylurea;
1-ethyl-3-{4-[1-isopropyl-4-(8-oxa-3-azabicyclo[3.2.1]oct-3-yl)-1H-pyrazolo[3,4-d]pyrimidin-6-yl]phenyl}urea;
1-(2-fluoroethyl)-3-{4-[1-isopropyl-4-(8-oxa-3-azabicyclo[3.2.1]oct-3-yl)-1H-pyrazolo[3,4-d]pyrimidin-6-yl]phenyl}urea;
1-cyclopropyl-3-{4-[1-isopropyl-4-(8-oxa-3-azabicyclo[3.2.1]oct-3-yl)-1H-pyrazolo[3,4-d]pyrimidin-6-yl]phenyl}urea;
1-(2-hydroxyethyl)-3-{4-[1-isopropyl-4-(8-oxa-3-azabicyclo[3.2.1]oct-3-yl)-1H-pyrazolo[3,4-d]pyrimidin-6-yl]phenyl}urea;
2-hydroxyethyl{4-[1-isopropyl-4-(8-oxa-3-azabicyclo[3.2.1]oct-3-yl)-1H-pyrazolo[3,4-d]pyrimidin-6-yl]phenyl}carbamate;
3-hydroxypropyl{4-[1-isopropyl-4-(8-oxa-3-azabicyclo[3.2.1]oct-3-yl)-1H-pyrazolo[3,4-d]pyrimidin-6-yl]phenyl}carbamate;
2,3-dihydroxypropyl{4-[1-isopropyl-4-(8-oxa-3-azabicyclo[3.2.1]oct-3-yl)-1H-pyrazolo[3,4-d]pyrimidin-6-yl]phenyl}carbamate;
1-{4-[1-isopropyl-4-(8-oxa-3-azabicyclo[3.2.1]oct-3-yl)-1H-pyrazolo[3,4-d]pyrimidin-6-yl]phenyl}-3-phenylurea;
1-{4-[1-isopropyl-4-(8-oxa-3-azabicyclo[3.2.1]oct-3-yl)-1H-pyrazolo[3,4-d]pyrimidin-6-yl]phenyl}-3-pyridin-3-yl urea;
1-{4-[1-isopropyl-4-(8-oxa-3-azabicyclo[3.2.1]oct-3-yl)-1H-pyrazolo[3,4-d]pyrimidin-6-yl]phenyl}-3-pyridin-4-ylurea;
1-{4-[1-(4,4-dimethoxycyclohexyl)-4-(8-oxa-3-azabicyclo[3.2.1]oct-3-yl)-1H-pyrazolo[3,4-d]pyrimidin-6-yl]phenyl}-3-methylurea;
1-{4-[1-(1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea;
1-{4-[1-(3,3-dimethyl-1,5-dioxaspiro[5.5]undec-9-yl)-4-(8-oxa-3-azabicyclo[3.2.1]oct-3-yl)-1H-pyrazolo[3,4-d]pyrimidin-6-yl]phenyl}-3-methylurea;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-methylurea;
methyl (4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(2-hydroxyethyl)phenyl]urea;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-phenylurea;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-pyridin-3-ylurea;
2-hydroxyethyl(4-{1-[2-(dimethylamino)ethyl]-4-(8-oxa-3-azabicyclo[3.2.1]oct-3-yl)-1H-pyrazolo[3,4-d]pyrimidin-6-yl}phenyl)carbamate;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-ethylurea;
1-cyclopropyl-3-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)urea;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-pyridin-4-ylurea;
1-(4-{1-[2-(dimethylamino)ethyl]-4-(8-oxa-3-azabicyclo[3.2.1]oct-3-yl)-1H-pyrazolo[3,4-d]pyrimidin-6-yl}phenyl)-3-[4-(hydroxymethyl)phenyl]urea;
methyl 4-{6-[4-({[4-(hydroxymethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-{6-[4-({[4-(2-hydroxyethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-{6-[4-({[4-(4-methylpiperazin-1-yl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-{6-[4-({[6-(4-methylpiperazin-1-yl)pyridin-3-yl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-[6-(4-{[(2-aminoethyl)carbamoyl]amino}phenyl)-4-(8-oxa-3-azabicyclo[3.2.1]oct-3-yl)-1H-pyrazolo[3,4-d]pyrimidin-1-yl]piperidine-1-carboxylate;
methyl 4-{6-[4-({[2-(dimethylamino)ethyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-{6-[4-({[2-(4-methylpiperazin-1-yl)ethyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-{6-[4-({[3-(hydroxymethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
methyl 4-{6-[4-({[2-(hydroxymethyl)phenyl]carbamoyl}amino)phenyl]-4-(8-oxa-3-azabicyclo[3.2.1]oct-3-yl)-1H-pyrazolo[3,4-d]pyrimidin-1-yl}piperidine-1-carboxylate;
1-(2-aminoethyl)-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[2-(methylamino)ethyl]urea;
1-[2-(dimethylamino)ethyl]-3-{4-[1-ethyl-4-(8-oxa-3-azabicyclo[3.2.1]oct-3-yl)-1H-pyrazolo[3,4-d]pyrimidin-6-yl]phenyl}urea;
1-(3-aminopropyl)-3-{4-[1-ethyl-4-(8-oxa-3-azabicyclo[3.2.1]oct-3-yl)-1H-pyrazolo[3,4-d]pyrimidin-6-yl]phenyl}urea;
1-[3-(dimethylamino)propyl]-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[2-(4-methylpiperazin-1-yl)ethyl]urea;

1-{4-[1-ethyl-4-(8-oxa-3-azabicyclo[3.2.1]oct-3-yl)-1H-pyrazolo[3,4-d]pyrimidin-6-yl]phenyl}-3-(2-morpholin-4-ylethyl)urea;

1-{4-[1-ethyl-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[1-ethyl-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;

1-{4-[1-ethyl-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;

1-{4-[1-ethyl-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea;

1-{4-[1-ethyl-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;

1-{4-[1-ethyl-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;

1-{4-[2-(dimethylamino)ethoxy]phenyl}-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(4-methoxyphenyl)urea;

1-(4-chlorophenyl)-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(4-methylphenyl)urea;

1-(4-cyanophenyl)-3-{4-[1-ethyl-4-(8-oxa-3-azabicyclo[3.2.1]oct-3-yl)-1H-pyrazolo[3,4-d]pyrimidin-6-yl]phenyl}urea;

2-hydroxypropyl{4-[1-ethyl-4-(8-oxa-3-azabicyclo[3.2.1]oct-3-yl)-1H-pyrazolo[3,4-d]pyrimidin-6-yl]phenyl}carbamate;

methyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-methylurea;

1-ethyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea;

2-hydroxyethyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate;

1-(2-hydroxyethyl)-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(2-hydroxyethyl)-4-(8-oxa-3-azabicyclo[3.2.1]oct-3-yl)-1H-pyrazolo[3,4-d]pyrimidin-6-yl]phenyl}urea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-phenylurea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;

1-{4-[1-(2-hydroxyethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;

2-[6-(4-aminophenyl)-4-(8-oxa-3-azabicyclo[3.2.1]oct-3-yl)-1H-pyrazolo[3,4-d]pyrimidin-1-yl]ethanol;

ethyl{4-[1-(2-hydroxyethyl)-4-(8-oxa-3-azabicyclo[3.2.1]oct-3-yl)-1H-pyrazolo[3,4-d]pyrimidin-6-yl]phenyl}carbamate;

2-hydroxyethyl(4-{4-(8-oxa-3-azabicyclo[3.2.1]oct-3-yl)-1-[(2,2,2-trifluoroethyl)piperidin-4-yl]-1H-pyrazolo[3,4-d]pyrimidin-6-yl}phenyl)carbamate;

2-hydroxyethyl(4-{4-(8-oxa-3-azabicyclo[3.2.1]oct-3-yl)-1-[1-(pyridin-3-ylmethyl)piperidin-4-yl]-1H-pyrazolo[3,4-d]pyrimidin-6-yl}phenyl)carbamate;

2-hydroxyethyl{4-[4-(8-oxa-3-azabicyclo[3.2.1]oct-3-yl)-1-(4-oxocyclohexyl)-1H-pyrazolo[3,4-d]pyrimidin-6-yl]phenyl}carbamate;

2-hydroxyethyl{4-[1-(4-hydroxycyclohexyl)-4-(8-oxa-3-azabicyclo[3.2.1]oct-3-yl)-1H-pyrazolo[3,4-d]pyrimidin-6-yl]phenyl}carbamate;

2-hydroxyethyl{4-[1-(2-cyanoethyl)-4-(8-oxa-3-azabicyclo[3.2.1]oct-3-yl)-1H-pyrazolo[3,4-d]pyrimidin-6-yl]phenyl}carbamate;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-methylurea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-cyclopropylurea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(2-hydroxyethyl)phenyl]urea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;

1-{4-[1-(2-cyanoethyl)-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;
1-{4-[1-(2-cyanoethyl)-4-(8-oxa-3-azabicyclo[3.2.1]oct-3-yl)-1H-pyrazolo[3,4-d]pyrimidin-6-yl]phenyl}-3-{4-[2-(dimethylamino)ethoxy]phenyl}urea;
1-[2-(2-aminoethoxy)ethyl]-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[(1-methylpiperidin-4-yl)methyl]urea;
1-cyclohexyl-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-(1-methylpiperidin-4-yl)urea;
1-(cis-4-aminocyclohexyl)-3-{4-[1-ethyl-4-(8-oxa-3-azabicyclo[3.2.1]oct-3-yl)-1H-pyrazolo[3,4-d]pyrimidin-6-yl]phenyl}urea;
1-(trans-4-aminocyclohexyl)-3-{4-[1-ethyl-4-(8-oxa-3-azabicyclo[3.2.1]oct-3-yl)-1H-pyrazolo[3,4-d]pyrimidin-6-yl]phenyl}urea;
1-[4-(hydroxymethyl)phenyl]-3-{4-[1-methyl-4-(8-oxa-3-azabicyclo[3.2.1]oct-3-yl)-1H-pyrazolo[3,4-d]pyrimidin-6-yl]phenyl}urea;
1-[4-(2-hydroxyethyl)phenyl]-3-{4-[1-methyl-4-(8-oxa-3-azabicyclo[3.2.1]oct-3-yl)-1H-pyrazolo[3,4-d]pyrimidin-6-yl]phenyl}urea;
1-[4-(dimethylamino)phenyl]-3-{4-[1-methyl-4-(8-oxa-3-azabicyclo[3.2.1]oct-3-yl)-1H-pyrazolo[3,4-d]pyrimidin-6-yl]phenyl}urea;
1-(4-aminophenyl)-3-{4-[1-methyl-4-(8-oxa-3-azabicyclo[3.2.1]oct-3-yl)-1H-pyrazolo[3,4-d]pyrimidin-6-yl]phenyl}urea;
1-{4-[1-methyl-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;
1-{4-[1-methyl-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-{4-[1-methyl-4-(8-oxa-3-azabicyclo[3.2.1]oct-3-yl)-1H-pyrazolo[3,4-d]pyrimidin-6-yl]phenyl}-3-(6-morpholin-4-ylpyridin-3-yl)urea;
1-{4-[1-methyl-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;
1-{4-[1-methyl-4-(8-oxa-3-azabicyclo[3.2.1]oct-3-yl)-1H-pyrazolo[3,4-d]pyrimidin-6-yl]phenyl}-3-[4-(methylsulfonyl)phenyl]urea;
1-{4-[1-methyl-4-(8-oxa-3-azabicyclo[3.2.1]oct-3-yl)-1H-pyrazolo[3,4-d]pyrimidin-6-yl]phenyl}-3-{4-[(2-piperidin-1-ylethyl)sulfonyl]phenyl}urea;
1-{4-[1-(2-fluoroethyl)-4-(8-oxa-3-azabicyclo[3.2.1]oct-3-yl)-1H-pyrazolo[3,4-d]pyrimidin-6-yl]phenyl}-3-methylurea;
1-[4-(dimethylamino)phenyl]-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;
1-{4-[2-(dimethylamino)ethoxy]phenyl}-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;
1-{4-[1-(2-fluoroethyl)-4-(8-oxa-3-azabicyclo[3.2.1]oct-3-yl)-1H-pyrazolo[3,4-d]pyrimidin-6-yl]phenyl}-3-(4-morpholin-4-ylphenyl)urea;
2-hydroxyethyl{4-[1-(2-fluoroethyl)-4-(8-oxa-3-azabicyclo[3.2.1]oct-3-yl)-1H-pyrazolo[3,4-d]pyrimidin-6-yl]phenyl}carbamate;
1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-ethyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;
1-cyclopropyl-3-{4-[1-(2-fluoroethyl)-4-(8-oxa-3-azabicyclo[3.2.1]oct-3-yl)-1H-pyrazolo[3,4-d]pyrimidin-6-yl]phenyl}urea;
1-{4-[1-(2-fluoroethyl)-4-(8-oxa-3-azabicyclo[3.2.1]oct-3-yl)-1H-pyrazolo[3,4-d]pyrimidin-6-yl]phenyl}-3-pyridin-4-ylurea;
1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(hydroxymethyl)phenyl]urea;
1-(4-morpholin-4-ylphenyl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-(6-morpholin-4-ylpyridin-3-yl)-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-[4-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
3-aminobenzyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate;
1-[3-(hydroxymethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
3-(dimethylamino)phenyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate;
1-[3-(dimethylamino)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
N~2~,N~2~-dimethyl-N-{4-[({4-[1-methyl-4-(8-oxa-3-azabicyclo[3.2.1]oct-3-yl)-1H-pyrazolo[3,4-d]pyrimidin-6-yl]phenyl}carbamoyl)amino]phenyl}glycinamide;
N-{4-[({4-[1-methyl-4-(8-oxa-3-azabicyclo[3.2.1]oct-3-yl)-1H-pyrazolo[3,4-d]pyrimidin-6-yl]phenyl}carbamoyl)amino]phenyl}acetamide;
1-[4-(2-hydroxyethyl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-[4-(4-methylpiperazin-1-yl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-[6-(4-methylpiperazin-1-yl)pyridin-3-yl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-[4-(2-hydroxyethoxy)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
2-hydroxyethyl{4-[1-(1-benzylpiperidin-4-yl)-4-(8-oxa-3-azabicyclo[3.2.1]oct-3-yl)-1H-pyrazolo[3,4-d]pyrimidin-6-yl]phenyl}carbamate;
1-cyclopropyl-3-(4-{4-(8-oxa-3-azabicyclo[3.2.1]oct-3-yl)-1-[1-(2,2,2-trifluoroethyl)piperidin-4-yl]-1H-pyrazolo[3,4-d]pyrimidin-6-yl}phenyl)urea;
2-hydroxyethyl{4-[4-(3-oxa-8-azabicyclo[3.2.1]oct-8-yl)-1-(2,2,2-trifluoroethyl)-1H-pyrazolo[3,4-d]pyrimidin-6-yl]phenyl}carbamate;

1-methyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-pyridin-3-ylurea;

1-[4-(hydroxymethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-[4-(4-methylpiperazin-1-yl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-cyclopropyl-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-[4-(2-hydroxyethyl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-(4-morpholin-4-ylphenyl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-(6-morpholin-4-ylpyridin-3-yl)-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-{4-[2-(dimethylamino)ethoxy]phenyl}-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-[2-(4-methylpiperazin-1-yl)-2-oxoethyl]urea;

1-{4-[1-ethyl-4-(8-oxa-3-azabicyclo[3.2.1]oct-3-yl)-1H-pyrazolo[3,4-d]pyrimidin-6-yl]phenyl}-3-[3-(4-methylpiperazin-1-yl)-3-oxopropyl]urea;

N-[2-(dimethylamino)ethyl]-N~2~-({4-[1-ethyl-4-(8-oxa-3-azabicyclo[3.2.1]oct-3-yl)-1H-pyrazolo[3,4-d]pyrimidin-6-yl]phenyl}carbamoyl)glycinamide;

N-[2-(dimethylamino)ethyl]-N~3~-({4-[1-ethyl-4-(8-oxa-3-azabicyclo[3.2.1]oct-3-yl)-1H-pyrazolo[3,4-d]pyrimidin-6-yl]phenyl}carbamoyl)-beta-alaninamide;

1-{4-[1-ethyl-4-(8-oxa-3-azabicyclo[3.2.1]oct-3-yl)-1H-pyrazolo[3,4-d]pyrimidin-6-yl]phenyl}-3-(4-pyrrolidin-1-ylphenyl)urea;

1-{4-[1-ethyl-4-(8-oxa-3-azabicyclo[3.2.1]oct-3-yl)-1H-pyrazolo[3,4-d]pyrimidin-6-yl]phenyl}-3-[4-(2-hydroxyethoxy)phenyl]urea;

1-{4-[1-ethyl-4-(8-oxa-3-azabicyclo[3.2.1]oct-3-yl)-1H-pyrazolo[3,4-d]pyrimidin-6-yl]phenyl}-3-[6-(2-hydroxyethoxy)pyridin-3-yl]urea;

1-{4-[1-ethyl-4-(8-oxa-3-azabicyclo[3.2.1]oct-3-yl)-1H-pyrazolo[3,4-d]pyrimidin-6-yl]phenyl}-3-[6-(2-morpholin-4-ylethoxy)pyridin-3-yl]urea;

1-[6-(dimethylamino)pyridin-3-yl]-3-{4-[1-ethyl-4-(8-oxa-3-azabicyclo[3.2.1]oct-3-yl)-1H-pyrazolo[3,4-d]pyrimidin-6-yl]phenyl}urea;

4-[({4-[1-ethyl-4-(8-oxa-3-azabicyclo[3.2.1]oct-3-yl)-1H-pyrazolo[3,4-d]pyrimidin-6-yl]phenyl}carbamoyl)amino]benzamide;

1-{4-[1-ethyl-4-(8-oxa-3-azabicyclo[3.2.1]oct-3-yl)-1H-pyrazolo[3,4-d]pyrimidin-6-yl]phenyl}-3-[6-(methylamino)pyridin-3-yl]urea;

1-(6-aminopyridin-3-yl)-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(8-oxa-3-azabicyclo[3.2.1]oct-3-yl)-1H-pyrazolo[3,4-d]pyrimidin-6-yl]phenyl}-3-(4-piperazin-1-ylphenyl)urea;

1-{4-[(2,2-dimethylhydrazino)carbonyl]phenyl}-3-{4-[1-ethyl-4-(8-oxa-3-azabicyclo[3.2.1]oct-3-yl)-1H-pyrazolo[3,4-d]pyrimidin-6-yl]phenyl}urea;

4-[({4-[1-ethyl-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-ylbenzamide;

2-hydroxyethyl(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)carbamate;

1-methyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea;

1-[4-(hydroxymethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-[4-(4-methylpiperazin-1-yl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-cyclopropyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-[4-(2-hydroxyethyl)phenyl]-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-(4-morpholin-4-ylphenyl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-(6-morpholin-4-ylpyridin-3-yl)-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-{4-[2-(dimethylamino)ethoxy]phenyl}-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea;

1-ethyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

1-cyclopropyl-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-4-ylurea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-(4-piperazin-1-ylphenyl)urea;

4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]benzamide;

4-[({4-[1-(4-methoxycyclohexyl)-4-(8-oxa-3-azabicyclo[3.2.1]oct-3-yl)-1H-pyrazolo[3,4-d]pyrimidin-6-yl]phenyl}carbamoyl)amino]-N-pyrrolidin-1-ylbenzamide;

1-[4-(hydroxymethyl)phenyl]-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-[6-(4-methylpiperazin-1-yl)pyridin-3-yl]urea;

1-{4-[2-(dimethylamino)ethoxy]phenyl}-3-{4-[1-(4-methoxycyclohexyl)-4-(8-oxa-3-azabicyclo[3.2.1]oct-3-yl)-1H-pyrazolo[3,4-d]pyrimidin-6-yl]phenyl}urea;
2-hydroxyethyl{4-[1-(4-methoxycyclohexyl)-4-(8-oxa-3-azabicyclo[3.2.1]oct-3-yl)-1H-pyrazolo[3,4-d]pyrimidin-6-yl]phenyl}carbamate;
1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-pyridin-4-ylurea;
1-[4-(4-methylpiperazin-1-yl)phenyl]-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea;
1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-(4-piperazin-1-ylphenyl)urea;
2-hydroxyethyl(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)carbamate;
1-cyclopropyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea;
1-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}-3-(4-piperazin-1-ylphenyl)urea;
1-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}-3-(4-piperazin-1-ylphenyl)urea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-methylurea;
1-ethyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
1-cyclopropyl-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
1-(2-hydroxyethyl)-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
2-hydroxyethyl(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-phenylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-4-ylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-pyridin-3-ylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-[4-(4-methylpiperazin-1-yl)phenyl]urea;
methyl (4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)carbamate;
1-methyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;
1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-pyridin-3-ylurea;
1-methyl-3-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}urea;
1-{4-[4-(8-oxa-3-azabicyclo[3.2.1]oct-3-yl)-1-(4-pyrrolidin-1-ylcyclohexyl)-1H-pyrazolo[3,4-d]pyrimidin-6-yl]phenyl}-3-pyridin-3-ylurea;
1-(4-{1-[4-(2,2-dimethylhydrazino)cyclohexyl]-4-(8-oxa-3-azabicyclo[3.2.1]oct-3-yl)-1H-pyrazolo[3,4-d]pyrimidin-6-yl}phenyl)-3-methylurea;
1-{4-[1-{4-[(2-hydroxyethyl)amino]cyclohexyl}-4-(8-oxa-3-azabicyclo[3.2.1]oct-3-yl)-1H-pyrazolo[3,4-d]pyrimidin-6-yl]phenyl}-3-methylurea;
1-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)-3-(4-piperazin-1-ylphenyl)urea;
1-{4-[(2,2-dimethylhydrazino)carbonyl]phenyl}-3-(4-{1-[2-methoxy-1-(methoxymethyl)ethyl]-4-(8-oxa-3-azabicyclo[3.2.1]oct-3-yl)-1H-pyrazolo[3,4-d]pyrimidin-6-yl}phenyl)urea;
1-{4-[4-(9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea;
1-{4-[4-(7-formyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea;
1-{4-[4-(7-acetyl-9-oxa-3,7-diazabicyclo[3.3.1]non-3-yl)-1-(2,2,2-trifluoroethyl)-1H-pyrazolo[3,4-d]pyrimidin-6-yl]phenyl}-3-pyridin-4-ylurea;
tert-butyl 7-[6-{4-[(pyridin-4-ylcarbamoyl)amino]phenyl}-1-(2,2,2-trifluoroethyl)-1H-pyrazolo[3,4-d]pyrimidin-4-yl]-9-oxa-3,7-diazabicyclo[3.3.1]nonane-3-carboxylate;
1-methyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea;
1-cyclopropyl-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea;
2-hydroxyethyl(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)carbamate;
1-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)-3-pyridin-3-ylurea;
1-[4-(4-methylpiperazin-1-yl)phenyl]-3-(4-{4-[(1R,4R)-2-oxa-5-azabicyclo[2.2.1]hept-5-yl]-1-(2,2,2-trifluoroethyl)-1H-pyrazolo[3,4-d]pyrimidin-6-yl}phenyl)urea;
1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-pyridin-3-ylurea;
1-{4-[1-ethyl-4-(8-oxa-3-azabicyclo[3.2.1]oct-3-yl)-3-pyrrolidin-1-yl-1H-pyrazolo[3,4-d]pyrimidin-6-yl]phenyl}-3-methylurea;
1-{4-[1-ethyl-3-(4-methylpiperazin-1-yl)-4-(8-oxa-3-azabicyclo[3.2.1]oct-3-yl)-1H-pyrazolo[3,4-d]pyrimidin-6-yl]phenyl}-3-methylurea;
1-{4-[1-ethyl-4-(8-oxa-3-azabicyclo[3.2.1]oct-3-yl)-3-pyridin-3-yl-1H-pyrazolo[3,4-d]pyrimidin-6-yl]phenyl}-3-methylurea;
1-{4-[1-ethyl-4-(8-oxa-3-azabicyclo[3.2.1]oct-3-yl)-3-vinyl-1H-pyrazolo[3,4-d]pyrimidin-6-yl]phenyl}-3-methylurea;
1-{4-[3-(1,2-dihydroxyethyl)-1-ethyl-4-(8-oxa-3-azabicyclo[3.2.1]oct-3-yl)-1H-pyrazolo[3,4-d]pyrimidin-6-yl]phenyl}-3-methylurea;

1-{4-[1-ethyl-3-formyl-4-(8-oxa-3-azabicyclo[3.2.1]oct-3-yl)-1H-pyrazolo[3,4-d]pyrimidin-6-yl]phenyl}-3-methylurea;

1-(4-{1-ethyl-3-[(4-methylpiperazin-1-yl)methyl]-4-(8-oxa-3-azabicyclo[3.2.1]oct-3-yl)-1H-pyrazolo[3,4-d]pyrimidin-6-yl}phenyl)-3-methylurea;

1-{4-[1-ethyl-4-(8-oxa-3-azabicyclo[3.2.1]oct-3-yl)-3-(pyrrolidin-1-ylmethyl)-1H-pyrazolo[3,4-d]pyrimidin-6-yl]phenyl}-3-methylurea;

methyl 4-[6-(4-{[(2-hydroxyethoxy)carbonyl]amino}phenyl)-4-(3-oxa-8-azabicyclo[3.2.1]oct-8-yl)-1H-pyrazolo[3,4-d]pyrimidin-1-yl]piperidine-1-carboxylate;

methyl 4-[6-{4-[(methylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[6-{4-[(ethylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[6-(4-{[(2-fluoroethyl)carbamoyl]amino}phenyl)-4-(3-oxa-8-azabicyclo[3.2.1]oct-8-yl)-1H-pyrazolo[3,4-d]pyrimidin-1-yl]piperidine-1-carboxylate;

methyl 4-[6-{4-[(cyclopropylcarbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[4-(3-oxa-8-azabicyclo[3.2.1]oct-8-yl)-6-{4-[(phenylcarbamoyl)amino]phenyl}-1H-pyrazolo[3,4-d]pyrimidin-1-yl]piperidine-1-carboxylate;

methyl 4-[4-(3-oxa-8-azabicyclo[3.2.1]oct-8-yl)-6-{4-[(pyridin-3-ylcarbamoyl)amino]phenyl}-1H-pyrazolo[3,4-d]pyrimidin-1-yl]piperidine-1-carboxylate;

methyl 4-[4-(3-oxa-8-azabicyclo[3.2.1]oct-8-yl)-6-{4-[(pyridin-4-ylcarbamoyl)amino]phenyl}-1H-pyrazolo[3,4-d]pyrimidin-1-yl]piperidine-1-carboxylate;

methyl 4-{6-[4-({[4-(4-methylpiperazin-1-yl)phenyl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate;

methyl 4-[4-(3-oxa-8-azabicyclo[3.2.1]oct-8-yl)-6-(4-{[(4-piperazin-1-ylphenyl)carbamoyl]amino}phenyl)-1H-pyrazolo[3,4-d]pyrimidin-1-yl]piperidine-1-carboxylate;

methyl 4-{6-[4-({[6-(4-methylpiperazin-1-yl)pyridin-3-yl]carbamoyl}amino)phenyl]-4-(3-oxa-8-azabicyclo[3.2.1]oct-8-yl)-1H-pyrazolo[3,4-d]pyrimidin-1-yl}piperidine-1-carboxylate;

methyl 4-[6-{4-[({4-[(dimethylamino)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[6-{4-[({4-[(4-methylpiperazin-1-yl)methyl]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

methyl 4-[6-{4-[({4-[2-(dimethylamino)ethoxy]phenyl}carbamoyl)amino]phenyl}-4-(3-oxa-8-azabicyclo[3.2.1]oct-8-yl)-1H-pyrazolo[3,4-d]pyrimidin-1-yl]piperidine-1-carboxylate;

2-hydroxyethyl(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)carbamate;

1-ethyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;

1-(2-fluoroethyl)-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;

1-cyclopropyl-3-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)urea;

1-(4-{1-[4-(4-methylpiperazin-1-yl)cyclohexyl]-4-(8-oxa-3-azabicyclo[3.2.1]oct-3-yl)-1H-pyrazolo[3,4-d]pyrimidin-6-yl}phenyl)-3-phenylurea;

4-[4-(8-oxa-3-azabicyclo[3.2.1]oct-3-yl)-1-(2,2,2-trifluoroethyl)-1H-pyrazolo[3,4-d]pyrimidin-6-yl]aniline;

methyl{4-[1-ethyl-4-(8-oxa-3-azabicyclo[3.2.1]oct-3-yl)-1H-pyrazolo[3,4-d]pyrimidin-6-yl]phenyl}carbamate;

1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-pyridin-3-ylurea;

methyl{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}carbamate;

3-[4-(3-oxa-8-azabicyclo[3.2.1]oct-8-yl)-1-phenyl-1H-pyrazolo[3,4-d]pyrimidin-6-yl]phenol;

2-hydroxyethyl(4-{4-[(6R)-6-hydroxy-8-oxa-3-azabicyclo[3.2.1]oct-3-yl]-1-(2,2,2-trifluoroethyl)-1H-pyrazolo[3,4-d]pyrimidin-6-yl}phenyl)carbamate;

1-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}-3-methylurea;

1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-methylurea;

3-{4-[(1S,4S)-2-oxa-5-azabicyclo[2.2.1]hept-5-yl]-1-phenyl-1H-pyrazolo[3,4-d]pyrimidin-6-yl}phenol;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-methylurea;

1-{4-[1-(4-methoxycyclohexyl)-4-(8-oxa-3-azabicyclo[3.2.1]oct-3-yl)-1H-pyrazolo[3,4-d]pyrimidin-6-yl]phenyl}-3-pyridin-3-ylurea;

1-{4-[1-(1,3-dioxan-5-yl)-4-(8-oxa-3-azabicyclo[3.2.1]oct-3-yl)-1H-pyrazolo[3,4-d]pyrimidin-6-yl]phenyl}-3-methylurea;

1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-methylurea;

1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-methylurea;

1-(1,4-dioxaspiro[4.5]dec-8-yl)-6-(1H-indol-5-yl)-4-(8-oxa-3-azabicyclo[3.2.1]oct-3-yl)-1H-pyrazolo[3,4-d]pyrimidine;

1-methyl-3-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)urea;

1-{4-[4-(6-hydroxy-3-oxa-8-azabicyclo[3.2.1]oct-8-yl)-1-(2,2,2-trifluoroethyl)-1H-pyrazolo[3,4-d]pyrimidin-6-yl]phenyl}-3-methylurea;

1-{4-[4-(6,8-dioxa-3-azabicyclo[3.2.1]oct-3-yl)-1-methyl-1H-pyrazolo[3,4-d]pyrimidin-6-yl]phenyl}-3-pyridin-3-ylurea;

1-{4-[4-(6,8-dioxa-3-azabicyclo[3.2.1]oct-3-yl)-1-methyl-1H-pyrazolo[3,4-d]pyrimidin-6-yl]phenyl}-3-methylurea;

1-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)-3-(4-piperazin-1-ylphenyl)urea;

6-(1H-indol-5-yl)-4-(8-oxa-3-azabicyclo[3.2.1]oct-3-yl)-1-[1-(pyridin-3-ylmethyl)piperidin-4-yl]-1H-pyrazolo[3,4-d]pyrimidine;
1-cyclopropyl-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea;
1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-{4-[3-bromo-1-ethyl-4-(8-oxa-3-azabicyclo[3.2.1]oct-3-yl)-1H-pyrazolo[3,4-d]pyrimidin-6-yl]phenyl}-3-methylurea;
1-cyclopropyl-3-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}urea;
1-cyclopropyl-3-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}urea;
1-[4-(4-methylpiperazin-1-yl)phenyl]-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea;
1-cyclopropyl-3-{4-[4-(8-oxa-3-azabicyclo[3.2.1]oct-3-yl)-1-(4-oxocyclohexyl)-1H-pyrazolo[3,4-d]pyrimidin-6-yl]phenyl}urea;
1-cyclopropyl-3-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}urea;
1-cyclopropyl-3-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}urea;
1-{4-[1-(trans-4-hydroxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea; and
1-{4-[1-(cis-4-hydroxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea.

31. A compound selected from the group consisting of:
1-{4-[1-ethyl-4-(8-oxa-3-azabicyclo[3.2.1]oct-3-yl)-1H-pyrazolo[3,4-d]pyrimidin-6-yl]phenyl}-3-{4-[(4-methylpiperazin-1-yl)methyl]phenyl}urea;
1-[4-(aminomethyl)phenyl]-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(8-oxa-3-azabicyclo[3.2.1]oct-3-yl)-1H-pyrazolo[3,4-d]pyrimidin-6-yl]phenyl}-3-[4-(pyrrolidin-1-ylmethyl)phenyl]urea;
1-{4-[(dimethylamino)methyl]phenyl}-3-{4-[1-ethyl-4-(8-oxa-3-azabicyclo[3.2.1]oct-3-yl)-1H-pyrazolo[3,4-d]pyrimidin-6-yl]phenyl}urea;
1-cyclopropyl-3-{4-[1-(4-ethoxycyclohexyl)-4-(8-oxa-3-azabicyclo[3.2.1]oct-3-yl)-1H-pyrazolo[3,4-d]pyrimidin-6-yl]phenyl}urea;
1-cyclopropyl-3-{4-[4-(8-oxa-3-azabicyclo[3.2.1]oct-3-yl)-1-(4-propoxycyclohexyl)-1H-pyrazolo[3,4-d]pyrimidin-6-yl]phenyl}urea;
1-[4-(4-methylpiperazin-1-yl)phenyl]-3-{4-[4-(8-oxa-3-azabicyclo[3.2.1]oct-3-yl)-1-(4-propoxycyclohexyl)-1H-pyrazolo[3,4-d]pyrimidin-6-yl]phenyl}urea;
1-{4-[1-(4-ethoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-cyclobutyl-3-{4-[1-ethyl-4-(8-oxa-3-azabicyclo[3.2.1]oct-3-yl)-1H-pyrazolo[3,4-d]pyrimidin-6-yl]phenyl}urea;
1-{4-[1-ethyl-4-(3-oxa-8-azabicyclo[3.2.1]oct-8-yl)-1H-pyrazolo[3,4-d]pyrimidin-6-yl]phenyl}-3-methylurea;
1-cyclopentyl-3-{4-[1-ethyl-4-(3-oxa-8-azabicyclo[3.2.1]oct-8-yl)-1H-pyrazolo[3,4-d]pyrimidin-6-yl]phenyl}urea;
1-ethyl-3-{4-[1-ethyl-4-(3-oxa-8-azabicyclo[3.2.1]oct-8-yl)-1H-pyrazolo[3,4-d]pyrimidin-6-yl]phenyl}urea;
1-{4-[1-ethyl-4-(3-oxa-8-azabicyclo[3.2.1]oct-8-yl)-1H-pyrazolo[3,4-d]pyrimidin-6-yl]phenyl}-3-phenylurea;
tert-butyl 9-(6-(4-((2-hydroxyethoxy)carbonylamino)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate;
2-hydroxyethyl 4-(4-(3-oxa-7,9-diazabicyclo[3.3.1]nonan-9-yl)-1-(2,2,2-trifluoroethyl)-1H-pyrazolo[3,4-d]pyrimidin-6-yl)phenylcarbamate;
1-(4-{[2-(dimethylamino)ethyl](methyl)amino}phenyl)-3-{4-[1-ethyl-4-(8-oxa-3-azabicyclo[3.2.1]oct-3-yl)-1H-pyrazolo[3,4-d]pyrimidin-6-yl]phenyl}urea;
2-hydroxyethyl{4-[1-ethyl-4-(3-oxa-8-azabicyclo[3.2.1]oct-8-yl)-1H-pyrazolo[3,4-d]pyrimidin-6-yl]phenyl}carbamate;
1-{4-[1-ethyl-4-(3-oxa-8-azabicyclo[3.2.1]oct-8-yl)-1H-pyrazolo[3,4-d]pyrimidin-6-yl]phenyl}-3-{4-[(4-methylpiperazin-1-yl)methyl]phenyl}urea;
1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-methylurea;
1-{4-[1-(cis-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea;
1-cyclopentyl-3-{4-[1-ethyl-4-(8-oxa-3-azabicyclo[3.2.1]oct-3-yl)-1H-pyrazolo[3,4-d]pyrimidin-6-yl]phenyl}urea;
1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea;
1-(4-(4-(3-oxa-7,9-diazabicyclo[3.3.1]nonan-9-yl)-1-(2,2,2-trifluoroethyl)-1H-pyrazolo[3,4-d]pyrimidin-6-yl)phenyl)-3-methylurea;
1-{4-[1-ethyl-4-(3-oxa-8-azabicyclo[3.2.1]oct-8-yl)-1H-pyrazolo[3,4-d]pyrimidin-6-yl]phenyl}-3-[4-(pyrrolidin-1-ylmethyl)phenyl]urea;
1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-methylurea;
1-{4-[1-ethyl-4-(3-oxa-8-azabicyclo[3.2.1]oct-8-yl)-1H-pyrazolo[3,4-d]pyrimidin-6-yl]phenyl}-3-pyridin-3-ylurea;
1-{4-[2-(dimethylamino)ethoxy]phenyl}-3-{4-[1-ethyl-4-(3-oxa-8-azabicyclo[3.2.1]oct-8-yl)-1H-pyrazolo[3,4-d]pyrimidin-6-yl]phenyl}urea;
1-(4-{[2-(dimethylamino)ethyl](methyl)amino}phenyl)-3-{4-[1-ethyl-4-(3-oxa-8-azabicyclo[3.2.1]oct-8-yl)-1H-pyrazolo[3,4-d]pyrimidin-6-yl]phenyl}urea;
1-{4-[1-ethyl-4-(3-oxa-8-azabicyclo[3.2.1]oct-8-yl)-1H-pyrazolo[3,4-d]pyrimidin-6-yl]phenyl}-3-[6-(4-methylpiperazin-1-yl)pyridin-3-yl]urea;
2-hydroxyethyl 4-(4-(2-oxa-5-azabicyclo[2.2.2]octan-5-yl)-1-(2,2,2-trifluoroethyl)-1H-pyrazolo[3,4-d]pyrimidin-6-yl)phenylcarbamate;
2-hydroxyethyl 4-(4-(3-oxa-9-azabicyclo[3.3.1]nonan-9-yl)-1-(2,2,2-trifluoroethyl)-1H-pyrazolo[3,4-d]pyrimidin-6-yl)phenylcarbamate;
1-(4-{[2-(dimethylamino)ethyl]amino}phenyl)-3-{4-[1-ethyl-4-(3-oxa-8-azabicyclo[3.2.1]oct-8-yl)-1H-pyrazolo[3,4-d]pyrimidin-6-yl]phenyl}urea;

1-{4-[(dimethylamino)methyl]phenyl}-3-{4-[1-ethyl-4-(3-oxa-8-azabicyclo[3.2.1]oct-8-yl)-1H-pyrazolo[3,4-d]pyrimidin-6-yl]phenyl}urea;

1-cyclopropyl-3-{4-[1-ethyl-4-(3-oxa-8-azabicyclo[3.2.1]oct-8-yl)-1H-pyrazolo[3,4-d]pyrimidin-6-yl]phenyl}urea;

2-hydroxyethyl 4-(4-(3,7-dioxa-9-azabicyclo[3.3.1]nonan-9-yl)-1-(2,2,2-trifluoroethyl)-1H-pyrazolo[3,4-d]pyrimidin-6-yl)phenylcarbamate;

tert-butyl 9-(6-(4-(3-methylureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate;

1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-methylurea;

1-(4-{[2-(dimethylamino)ethyl]amino}phenyl)-3-{4-[1-ethyl-4-(8-oxa-3-azabicyclo[3.2.1]oct-3-yl)-1H-pyrazolo[3,4-d]pyrimidin-6-yl]phenyl}urea;

1-{4-[1-ethyl-4-(3-oxa-8-azabicyclo[3.2.1]oct-8-yl)-1H-pyrazolo[3,4-d]pyrimidin-6-yl]phenyl}-3-[4-(2-pyrrolidin-1-ylethoxy)phenyl]urea;

1-{4-[1-ethyl-4-(3-oxa-8-azabicyclo[3.2.1]oct-8-yl)-1H-pyrazolo[3,4-d]pyrimidin-6-yl]phenyl}-3-[4-(4-methylpiperazin-1-yl)phenyl]urea;

1-cyclobutyl-3-{4-[1-ethyl-4-(3-oxa-8-azabicyclo[3.2.1]oct-8-yl)-1H-pyrazolo[3,4-d]pyrimidin-6-yl]phenyl}urea;

1-[4-(aminomethyl)phenyl]-3-{4-[1-ethyl-4-(3-oxa-8-azabicyclo[3.2.1]oct-8-yl)-1H-pyrazolo[3,4-d]pyrimidin-6-yl]phenyl}urea;

1-{4-[1-ethyl-4-(3-oxa-8-azabicyclo[3.2.1]oct-8-yl)-1H-pyrazolo[3,4-d]pyrimidin-6-yl]phenyl}-3-pyridin-4-ylurea;

1-(4-(4-(3-oxa-9-azabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea;

1-(4-(4-(2-oxa-5-azabicyclo[2.2.2]octan-5-yl)-1-(2,2,2-trifluoroethyl)-1H-pyrazolo[3,4-d]pyrimidin-6-yl)phenyl)-3-(4-(2-(dimethylamino)ethoxy)phenyl)urea;

1-(4-(4-(3,7-dioxa-9-azabicyclo[3.3.1]nonan-9-yl)-1-(2,2,2-trifluoroethyl)-1H-pyrazolo[3,4-d]pyrimidin-6-yl)phenyl)-3-(4-(2-(dimethylamino)ethoxy)phenyl)urea; and tert-butyl 9-(6-(4-(3-(4-(2-(dimethylamino)ethoxy)phenyl)ureido)phenyl)-1-(2,2,2-trifluoroethyl)-1H-pyrazolo[3,4-d]pyrimidin-4-yl)-3-oxa-7,9-diazabicyclo[3.3.1]nonane-7-carboxylate.

32. The compound 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-methylurea.

33. The compound 1-{4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea.

34. The compound 1-(4-{4-(8-oxa-3-azabicyclo[3.2.1]oct-3-yl)-1-[(5r,8r)-1-oxaspiro[4.5]dec-8-yl]-1H-pyrazolo[3,4-d]pyrimidin-6-yl}phenyl)-3-pyridin-4-ylurea.

35. The compound 1-cyclopropyl-3-(4-{4-[(1S,4S)-2-oxa-5-azabicyclo[2.2.1]hept-5-yl]-1-(2,2,2-trifluoroethyl)-1H-pyrazolo[3,4-d]pyrimidin-6-yl}phenyl)urea.

36. The compound 1-{4-[1-(2-fluoroethyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea.

37. The compound 1-[4-(4-methylpiperazin-1-yl)phenyl]-3-{4-[4-(8-oxa-3-azabicyclo[3.2.1]oct-3-yl)-1-(2,2,2-trifluoroethyl)-1H-pyrazolo[3,4-d]pyrimidin-6-yl]phenyl}urea.

38. The compound 1-[4-(4-methylpiperazin-1-yl)phenyl]-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea.

39. The compound 1-{4-[2-(dimethylamino)ethoxy]phenyl}-3-{4-[4-(3-oxa-8-azabicyclo[3.2.1]oct-8-yl)-1-(2,2,2-trifluoroethyl)-1H-pyrazolo[3,4-d]pyrimidin-6-yl]phenyl}urea.

40. The compound 2-hydroxyethyl{4-[4-(8-oxa-3-azabicyclo[3.2.1]oct-3-yl)-1-(2,2,2-trifluoroethyl)-1H-pyrazolo[3,4-d]pyrimidin-6-yl]phenyl}carbamate.

41. The compound 1-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}-3-[4-(4-methylpiperazin-1-yl)phenyl]urea.

42. The compound 1-cyclopropyl-3-{4-[1-(trans-4-methoxycyclohexyl)-4-(8-oxa-3-azabicyclo[3.2.1]oct-3-yl)-1H-pyrazolo[3,4-d]pyrimidin-6-yl]phenyl}urea.

43. A composition comprising a compound of claim 1 and a pharmaceutically acceptable carrier.

44. The composition of claim 43, wherein the pharmaceutically acceptable carrier suitable for oral administration and the composition comprises an oral dosage form.

45. A composition comprising a compound of claim 1; a second compound selected from the group consisting of a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, bis-chloroethylnitrosourea, carmustine, lomustine, vinblastine, vincristine, vinorelbine, cisplatin, carboplatin, oxaliplatin, imatinib mesylate, Avastin (bevacizumab), hexamethylmelamine, topotecan, tyrosine kinase inhibitors, tyrphostins, herbimycin A, genistein, erbstatin, lavendustin A, hydroxyzine, glatiramer acetate, interferon beta-1a, interferon beta-1b, natalizumab and lavendustin A; and a pharmaceutically acceptable carrier.

46. The composition of claim 45, wherein the second compound is bevacizumab.

* * * * *